(12) United States Patent
Yu et al.

(10) Patent No.: US 7,977,353 B2
(45) Date of Patent: Jul. 12, 2011

(54) HETEROCYCLIC AROMATIC COMPOUNDS USEFUL AS GROWTH HORMONE SECRETAGOGUES

(75) Inventors: Guixue Yu, Princeton Junction, NJ (US); Jun Li, Princeton, NJ (US); William R. Ewing, Yardley, PA (US); Richard B. Sulsky, West Trenton, NJ (US); James J. Li, Pennington, NJ (US); Joseph Anthony Tino, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/852,610

(22) Filed: Aug. 9, 2010

(65) Prior Publication Data

US 2010/0305114 A1    Dec. 2, 2010

Related U.S. Application Data

(60) Division of application No. 12/507,430, filed on Jul. 22, 2009, now Pat. No. 7,799,801, which is a division of application No. 11/273,169, filed on Nov. 14, 2005, now Pat. No. 7,592,354, which is a continuation of application No. 10/653,410, filed on Sep. 2, 2003, now Pat. No. 7,166,596.

(60) Provisional application No. 60/491,645, filed on Jul. 31, 2003, provisional application No. 60/408,099, filed on Sep. 4, 2002.

(51) Int. Cl.
*A61K 31/437* (2006.01)
*C07D 401/02* (2006.01)

(52) U.S. Cl. ........................ 514/303; 546/118
(58) Field of Classification Search .................. None
See application file for complete search history.

(56) References Cited

U.S. PATENT DOCUMENTS

| | | | |
|---|---|---|---|
| 3,050,525 A | 8/1962 | Bicking | |
| 3,239,345 A | 3/1966 | Hodge et al. | |
| 4,036,979 A | 7/1977 | Asato | |
| 4,411,890 A | 10/1983 | Momany | |
| 5,179,080 A | 1/1993 | Rothkopf | |
| 5,430,150 A | 7/1995 | Trova et al. | |
| 5,612,359 A | 3/1997 | Murugesan | |
| 5,939,387 A * | 8/1999 | Broderick et al. | 514/6.9 |
| 6,013,658 A | 1/2000 | Lau et al. | |
| 6,043,265 A | 3/2000 | Murugesan et al. | |
| 6,114,310 A | 9/2000 | Chamberland et al. | |
| 6,184,231 B1 | 2/2001 | Hewawasam et al. | |
| 6,514,989 B1 | 2/2003 | Nettekoven et al. | |
| 6,548,529 B1 | 4/2003 | Robl et al. | |

FOREIGN PATENT DOCUMENTS

| | | |
|---|---|---|
| WO | 89/07110 | 8/1989 |
| WO | 89/07111 | 8/1989 |
| WO | 95/14666 | 6/1995 |
| WO | 96/15148 | 5/1996 |
| WO | 96/22997 A1 | 8/1996 |
| WO | 99/12923 | 3/1999 |
| WO | 99/64401 | 12/1999 |
| WO | 00/01389 | 1/2000 |
| WO | 00/54729 | 9/2000 |
| WO | WO 2007113226 A1 * | 10/2007 |

OTHER PUBLICATIONS

D'Amario et al., European Commission, The Fight Against Obesity, (2005), pp. 1-25 (pp. 17, 19, and 21 are blank).
Svenson, J., "Growth Hormone Secretagogues", Exp. Opin. Ther. Patents, vol. 10, No. 7, pp. 1071-1080 (2000).
Johannsson, G. et al., "Growth Hormone Treatment of Abdominally Obese Men Reduces Abdominal Fat Mass, Improves Glucose and Lipoprotein Metabolism, and Reduces Diastolic Blood Pressure", J. Clin. Endocrinol. and Metab., vol. 82, No. 3, pp. 727-734 (1997).
Ankerson, M. et al., "Growth hormone secretagogues: recent advances and applications", Drug Discovery Today, vol. 4, No. 11, pp. 497-506 (1999).
Edwards, J.P. et al., Bio. Med. Chem. Let., vol. 9, pp. 1003-1008 (1999).
Hamann, L.G. et al., J. Med. Chem., vol. 42, pp. 210-212 (1999).
Lautens et al., J. Org. Chem., vol. 62, pp. 5246-5247 (1997).
Zhu et al., J. Org. Chem., vol. 56, pp. 1445-1453 (1991).
Rieke et al., Tetrahedron, vol. 53, No. 6, pp, 1925-1956 (1997).

* cited by examiner

*Primary Examiner* — Zinna Northington Davis
(74) *Attorney, Agent, or Firm* — Fitzpatrick, Cella, Harper & Scinto

(57) ABSTRACT

Novel heterocyclic aromatic compounds are provided that are useful in stimulating endogenous production or release of growth hormone, said compounds having the general structure of formula I

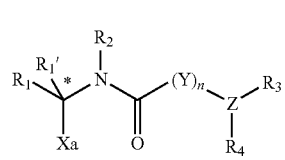

wherein $R_1$, $R_1'$, $R_2$, $R_3$, $R_4$, Xa, Y, Z and n are as described herein. The compounds provided herein are useful in treating obesity, osteoporosis (improving bone density) and in improving muscle mass and muscle strength.

6 Claims, No Drawings

HETEROCYCLIC AROMATIC COMPOUNDS USEFUL AS GROWTH HORMONE SECRETAGOGUES

RELATED APPLICATIONS

This application is a divisional of U.S. application Ser. No. 12/507,430, filed Jul. 22, 2009, now U.S. Pat. No. 7,799,801, which is a divisional of U.S. application Ser. No. 11/273,169, filed Nov. 14, 2005, now U.S. Pat. No. 7,592,354, which is a continuation of U.S. application Ser. No. 10/653,410, filed Sep. 2, 2003, now U.S. Pat. No. 7,166,596, which claims the benefit of U.S. Provisional Application Nos. 60/408,099, filed Sep. 4, 2002, and 60/491,645, filed Jul. 31, 2003. The entire contents of all of the above-mentioned applications are herein incorporated by reference.

FIELD OF THE INVENTION

The present invention relates to novel heterocyclic aromatic compounds which stimulate endogenous production and/or release of growth hormone. Further, the present invention relates to methods for using such compounds and to pharmaceutical compositions containing such compounds.

BACKGROUND OF THE INVENTION

Growth hormone is important not only for linear body growth, but is also important for the maintenance of body composition, metabolism and heart function in adult life. In fact, treatment with growth hormone is employed in both adults and children suffering from growth hormone deficiency. Treatment with growth hormone has been shown to reduce body fat, increase fat-free mass, increase muscle strength, improve bone mass and well-being. These beneficial effects associated with growth hormone treatment suggest that growth hormone treatment may further be useful for the treatment of osteoporosis, frailty in the elderly, complicated fracture, cardiomyopathy, obesity and some nitrogen-wasting conditions resulting from, for example, AIDS, chronic dialysis, catabolic disease and glucocorticoid treatment. Johan Svensson, *Exp. Opin. Ther. Patents,* 2000 10(7) 1071-1080; Ankersen et al., *DDT,* 1999, 4(11) 497-506. Moreover, growth hormone therapy is also been explored with a view towards reversing changes associated with aging.

Current methods for administering growth hormone are invasive in that synthetic growth hormone must be administered by daily injection. Therefore, if an orally administered secretagogue could be introduced that is safe, efficacious, well tolerated, it would provide an attractive treatment alternative to current growth hormone treatment.

Growth hormone secretagogues are synthetically produced peptides and non-peptides that stimulate the endogenous production and/or release of growth hormone by acting on one or more specific receptors at both pituitary and hypothalamic levels. Accordingly, orally active growth hormone secretagogues could offer attractive alternatives to traditional growth hormone therapy, thus providing a more convenient means to treat a wider array of diseases or disorders associated with growth hormone levels in patient circulation.

SUMMARY OF THE INVENTION

In accordance with the present invention, novel heterocyclic aromatic compounds are provided that have the general structure of formula I

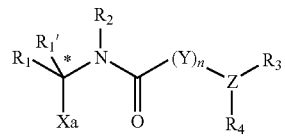

wherein
Xa is 2 to 4 fused or spiro cycloalkyl, heterocycle, aryl or heteroaryl rings, wherein one or more of said rings may optionally be substituted with one to five substituents selected from the group consisting of Ra and Rb;

$R_1$ is a substituted or unsubstituted functional group selected from the group consisting of alkyl, aryl, alkenyl, alkynyl, arylalkyl, cycloalkyl, heterocycle, alkoxyalkyl, arylallcyloxyalkyl, aryloxyalkyl, heteroaryl, cycloalkylalkoxyalkyl, heteroarylalkoxy, heteroarylalkyl, heterocycloalkyl and heterocycloalkyl;

$R_2$, $R_3$ and $R_4$ are each independently a substituted or unsubstituted functional group selected from the group consisting of hydrogen, alkyl, alkenyl, alkynyl, aryl, arylalkyl, cycloalkyl, heterocycle, alkoxyalkyl, arylalkyloxyalkyl, aryloxyalkyl, heteroaryl, cycloalkylalkoxyalkyl, heteroarylalkyl and heterocycloalkyl, or $R_3$ and $R_4$ taken together can form a 3 to 8 membered cycloalkyl or heterocyclic ring, or one or more of $R_3$ and $R_4$ can be taken together with one or more of Y and Z to form a mono- or bicyclic cycloalkyl or heterocyclic ring;

$R_1'$ is a substituted or unsubstituted functional group selected from the group consisting of hydrogen, alkyl, cycloalkyl, heterocycle, aryl and heteroaryl;

Y is a linking group selected from the group consisting of alkylene, alkenylene, alkynylene, arylene and heteroarylene, said linking group may optionally be substituted with one or more functional groups selected from the group consisting of alkyl, aryl, cycloalkyl, heterocycle, alkoxyalkyl, heteroaryl, arylalkyl, arylalkyloxyalkyl, aryloxyalkyl, cycloalkylalkoxyalkyl, heteroarylalkyl and heterocycloalkyl, halogen, —$OR_5$, —$OC(O)R_5$, —$CF_3$, —$OCF_3$, —$N(R_5)C(O)R_5'$ and —$NR_5R_5'$;

$R_5$ and $R_5'$ for each occurrence are each independently selected from the group consisting of hydrogen, alkyl, cycloalkyl, heterocycle and aryl, wherein $R_5$ and $R_5'$ for each occurrence may optionally be substituted with one or more Rb;

Ra and Rb for each occurrence are each independently selected from the group consisting of alkyl, alkenyl, alkenyl, halogen, cyano, carbonyl, —CN, aryl, arylalkyl, arylalkenyl, arylalkynyl, cycloalkyl, alkoxy, alkoxyalkyl, aryloxy, aryloxyalkyl, heterocycle, heteroaryl, heteroarylalkyl, —$OR_2$, —$NR_5R_5'$, —$CF_3$, —$SO_2NR_6R_6'$, —$(CH_2)_m R_8$ and $R_9$;

$R_6$ and $R_6'$ for each occurrence are each independently selected from the group consisting of hydrogen, alkyl, alkenyl, alkynyl, alkylthioalkyl, alkoxyalkyl, aryl, arylalkyl, heterocycle, heteroaryl, heteroarylalkyl, heterocycloalkyl and cycloalkyl, wherein $R_6$ and $R_6'$ for each occurrence may optionally be substituted with 1 to 3 substituents selected from the group consisting of halogen, —$OR_2$, alkoxy, heterocycloalkyl, —$NR_5C(O)NR_5R_5'$, —$C(O)NR_5R_5'$, —$NR_5C(O)R_5'$, —CN, —$NR_5SO_2R_5'$, —$OC(O)R_5$, —$SO_2NR_5R_5'$, —$SOR_7$, —COOH and —$C(O)OR_7$, or $R_6$ and $R_6'$ taken together can be cyclized to form —$(CH_2)_q X(CH_2)_s$—;

$R_7$ for each occurrence is independently selected from the group consisting of $C_1$ to $C_6$ alkyl, aryl and heteroaryl, wherein $R_7$ may optionally be substituted with —$(CH_2)_w OH$;

$R_8$ is selected from the group consisting of alkoxy, alkoxycarbonyl, —C(O)NR$_6$R$_6$', —NR$_5$R$_5$', —C(O)R$_6$, —NR$_5$C(O)NR$_5$R$_5$' and —N-heteroaryl;

$R_9$ is selected from the group consisting of heterocloalkyl, heteroaryl, —CN, —(CH$_2$)$_p$N(R$_6$)C(O)R$_6$', —(CH$_2$)$_p$CN, —(CH$_2$)$_p$N(R$_6$)C(O)OR$_6$', —(CH$_2$)$_p$N(R$_6$)C(O)NR$_6$R$_6$', —(CH$_2$)$_p$N(R$_6$)SO$_2$R$_6$, —(CH$_2$)$_p$C(O)NR$_6$R$_6$, —(CH$_2$)$_p$C(O)OR$_6$, —(CH$_2$)$_p$OC(O)OR$_6$, —(CH$_2$)$_p$OC(O)R$_6$, —(CH$_2$)$_p$OC(O)NR$_6$R$_6$', —(CH$_2$)$_p$N(R$_6$)SO$_2$NR$_6$R$_6$', —(CH$_2$)$_p$OR$_6$, —(CH$_2$)$_p$OC(O)N(R$_6$)(CH$_2$)$_m$OH— (CH$_2$)$_p$SOR$_6$ and —(CH$_2$)$_p$OCH$_2$C(O)N(R$_6$)(CH$_2$)$_m$OH;

X is selected from the group consisting of —CR$_5$R$_5$'—, —O—, —S—, —SO—, —SO$_2$—, —NC(O)OR$_7$—, —NC(O)NR$_5$— and —NR$_5$—;

Z is nitrogen;

m is an integer between 1 and 6;

n is an integer from 1 to 6;

p is an integer from 0 to 5;

w is an integer between 0 and 5; and q and s are each independently an integer between 1 and 3, with the proviso that R$_5$, R$_5$', R$_6$ or R$_6$' cannot be hydrogen when either is connected to a carbonyl group (e.g., —C(O)R$_6$) or sulfone group (e.g., —SO$_2$R$_s$).

The definition of formula I above is inclusive of all prodrugs, prodrug esters, stereoisomers and pharmaceutically acceptable salts of formula I.

Compounds of formula I demonstrate activity as growth hormone secretagogues, that is they stimulate endogenous production and/or release of growth hormone and are useful in the treatment of diseases or disorders associated with growth hormone levels, such as those diseases or disorders disclosed herein.

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Moreover, in accordance with the present invention, a method is provided for increasing levels of endogenous growth hormone or increasing the endogenous production or release of growth hormone, wherein a therapeutically effective amount of a compound of formula I is administered to a mammalian, e.g., human, patient in need of treatment.

Furthermore, in accordance with the present invention, a method is provided for preventing or treating diseases or disorders associated with mammalian growth hormone levels, such as described herein, wherein a therapeutically effective amount of a compound of formula I is administered to a mammalian, i.e., human, patient in need of treatment.

The compounds of the invention can be used alone, in combination with other compounds of the present invention, or in combination with one or more other agent(s) active in the therapeutic areas described herein.

Further, the present invention provides a method for preventing, inhibiting or treating the diseases as defined above and hereinafter, wherein a therapeutically effective amount of a combination of a compound of formula I and another compound of formula I and/or at least one other type of therapeutic agent, is administered to a mammalian, i.e., human patient in need of treatment.

Preferred are compounds of formula I wherein Xa has the structure

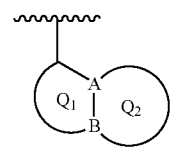

wherein $Q_1$ and $Q_2$ are each independently a cycloalkyl, heterocyclic, aryl or heteroaryl ring, wherein $Q_1$ may be substituted with 1 to four substituents selected from the group consisting of Ra and Rb, and $Q_2$ may be substituted with 1 to four substituents selected from the group consisting of Ra, Rb and $Q_3$;

$Q_3$ is a 3 to 8 membered fused or spiral cycloalkyl, heterocyclic, aryl or heteroaryl ring, wherein $Q_3$ may optionally be substituted with 1 to 5 substituents selected from the group consisting of Ra, Rb and $Q_4$; and $Q_4$ is a 3 to 8 membered fused or spiral cycloalkyl, heterocyclic, aryl or heteroaryl ring, wherein $Q_4$ may optionally be substituted with 1 to 5 substituents selected from the group consisting of Ra and Rb;

A is N or CR$_{11}$;

B is N or CR$_{11}$; and

R$_{11}$ is H or a bond.

Further embodiments include compounds of formula I wherein Xa has the structure

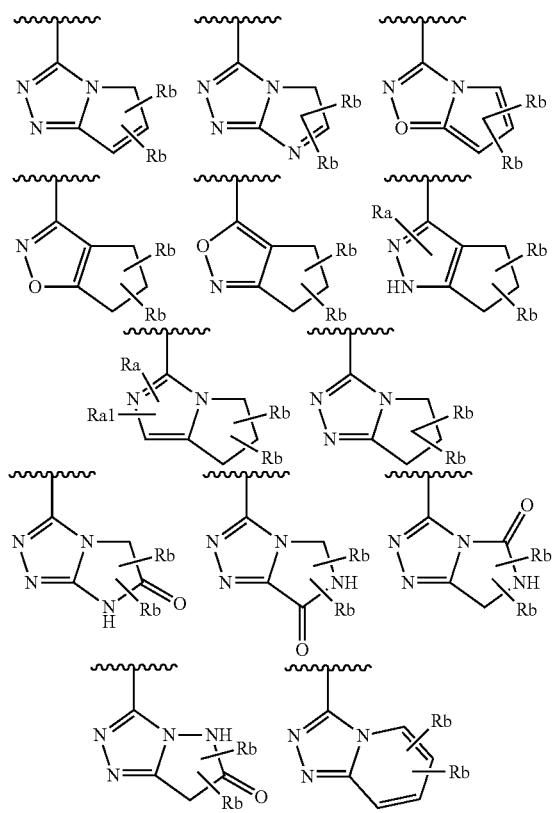

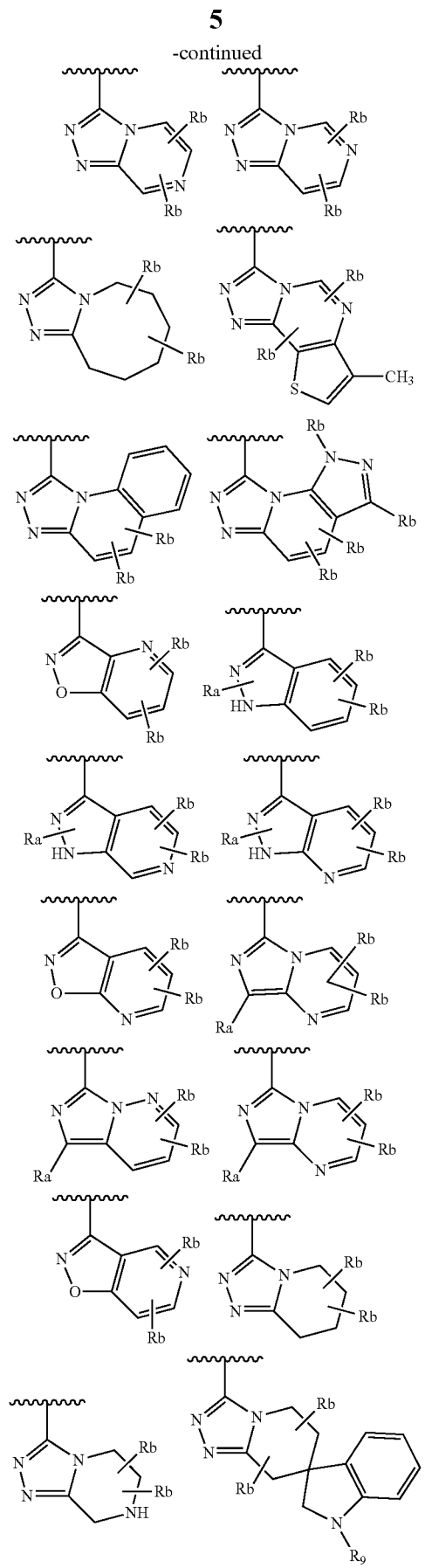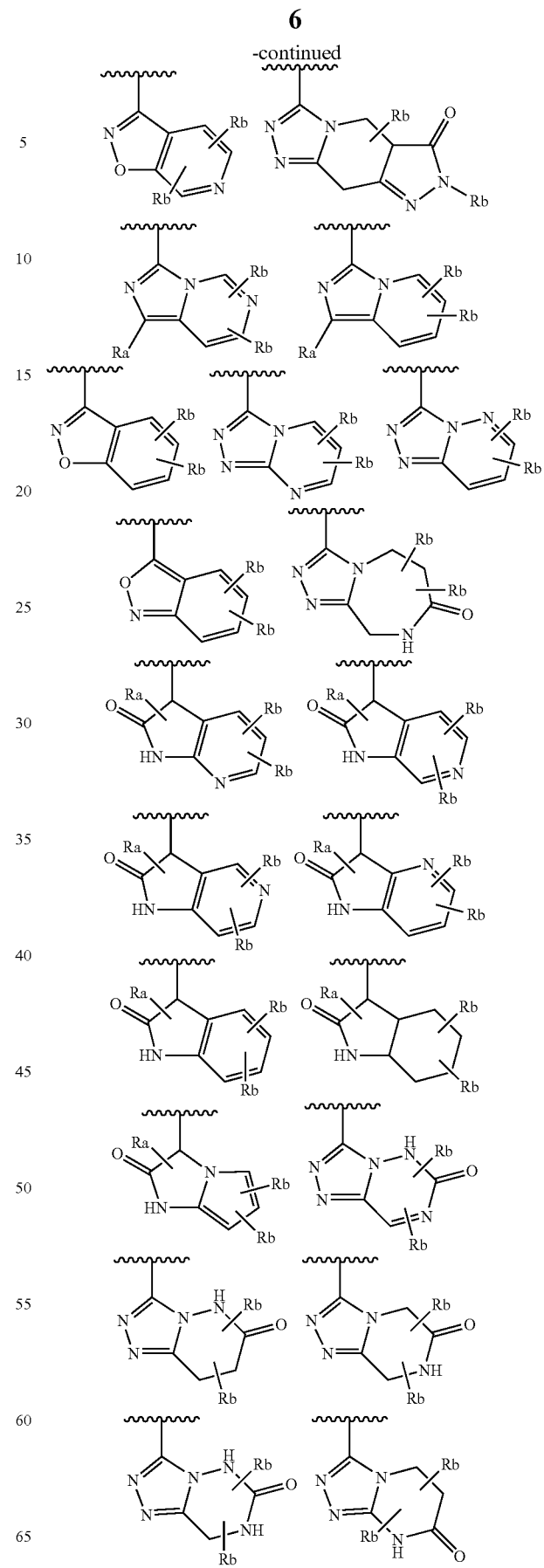

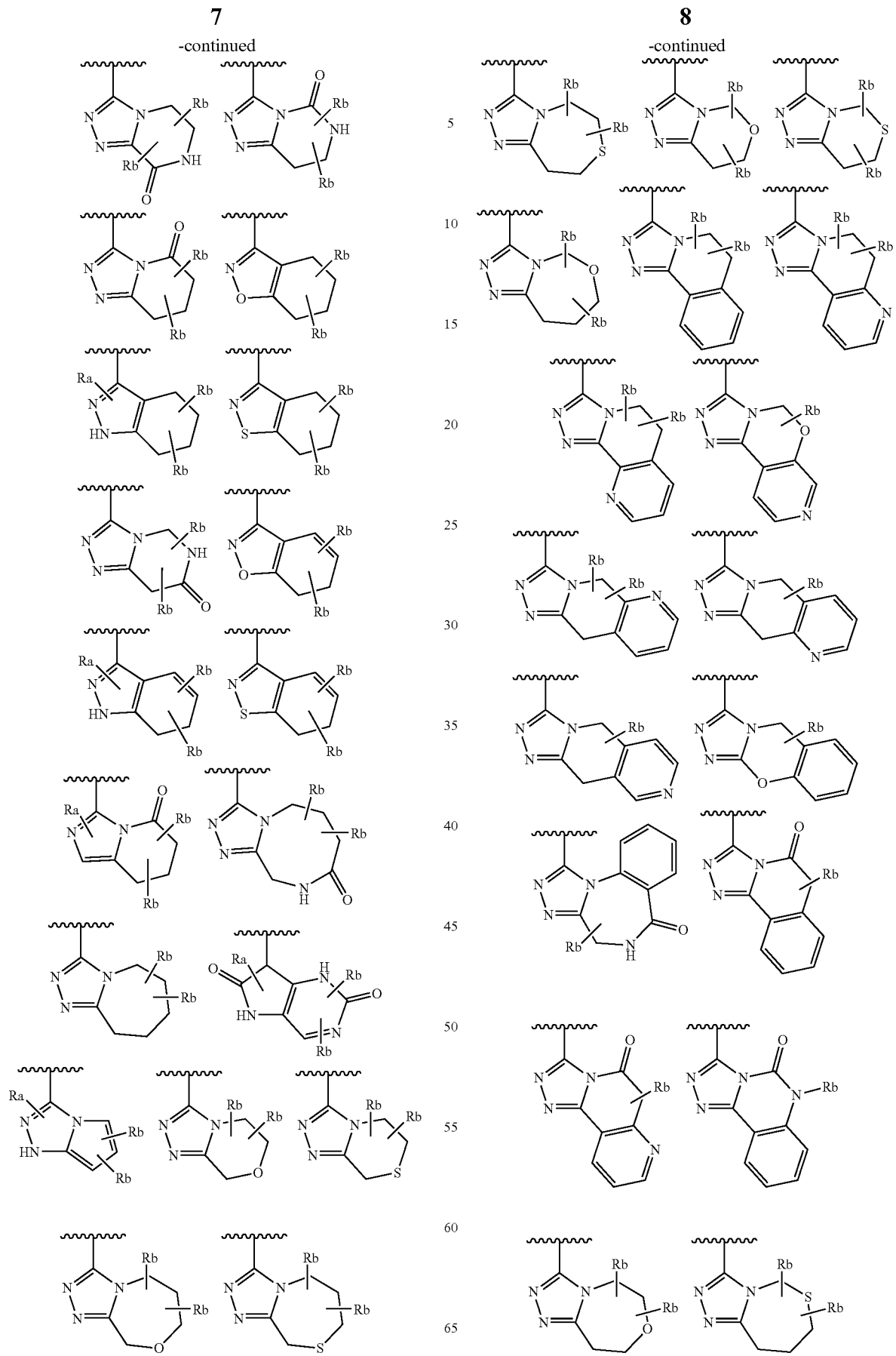

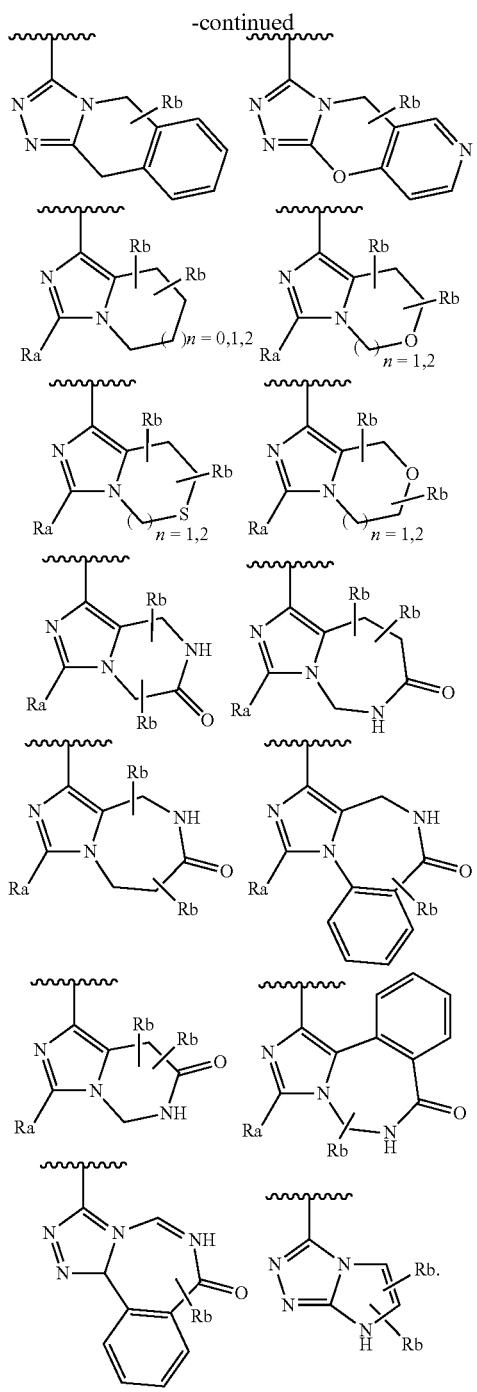

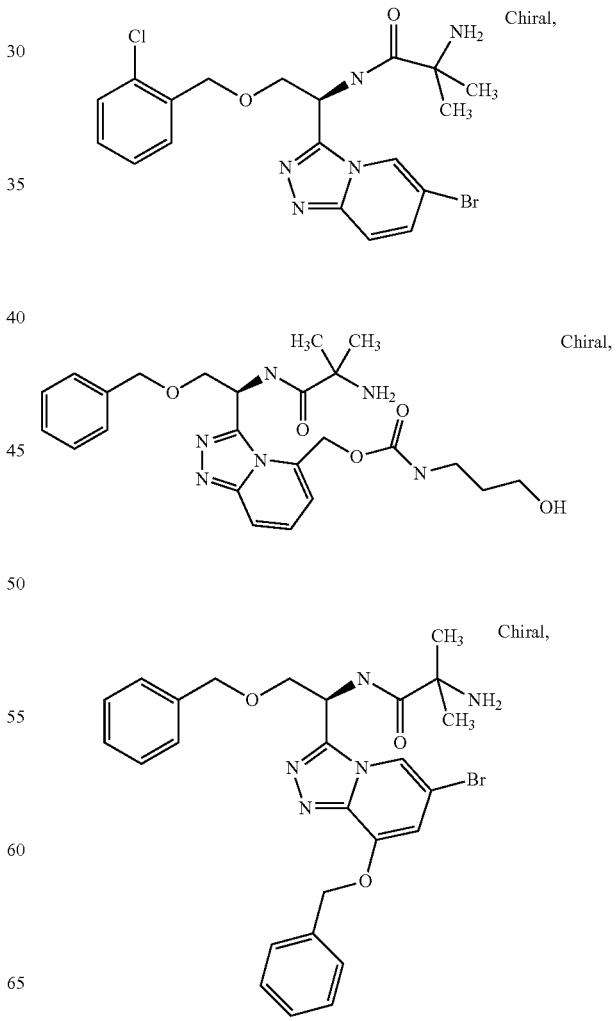

tions, such as the substitution of one or more Rb and/or Ra groups, or other modifications and therapeutically equivalent compounds known to those skilled in the art, may be employed within the scope and spirit of the compounds claimed herein Preferred are compounds of formula I wherein when Ra or Rb are $R_9$, $R_6$ is heterocycle or alkyl, optionally substituted with hydroxyl or halogen.

Preferred are compounds of formula I wherein when Ra or Rb are $R_9$, $R_6$ and are independently hydrogen, alkyl, or cycloalkyl, where the alkyl or cycloalkyl is optionally substituted with —C(O)OR$_7$ or —C(O)NR$_5$R$_5$', or $R_6$ and $R_6$' taken together can be cyclized to form —(CH$_2$)$_q$X(CH$_2$)$_s$—.

Also preferred are compounds of formula I wherein when Ra or Rb are $R_9$, $R_9$ is (CH$_2$)$_p$C(O)OR$_6$, (CH$_2$)$_p$OC(O)R$_6$, or (CH$_2$)$_p$OC(O)N(R$_6$)(CH$_2$)$_m$OH.

Also preferred are compounds of formula I wherein $R_9$ is —(CH$_2$)$_p$N(R$_6$)C(O)OR$_6$', —(CH$_2$)$_p$N(R$_6$)C(O)NR$_6$R$_6$', or (CH$_2$)$_p$OC(O)NR$_6$R$_6$', where $R_6$ and $R_6$' are independently hydrogen or alkyl, where the alkyl is optionally substituted with —C(O)NR$_5$R$_5$', where $R_5$ and $R_5$' are independently hydrogen or alkyl.

Further preferred embodiments include compounds of formula I having the structure:

Although the preferred Xa structures disclosed above illustrate one or more Ra and/or Rb substituents on any particular cycloalkyl, aryl, heteroaryl or heterocycle ring, the preferred Xa structures are not limited to the specific Ra/Rb substitution illustrated above, nor is an Ra and/or Rb group needed. Rather, the presence of the Rb and/or Ra substituents in the preferred Xa structures, the subsequent Schemes and the claims hereafter, indicate that one or more Ra/Rb group(s) may optionally be attached at any available position of attachment upon the ring to which an Rb/Rb group is associated. Therefore, even though the preferred Xa structures, Schemes and claims hereinafter may reference a particular embodiment, it should be understood that various other modifica-

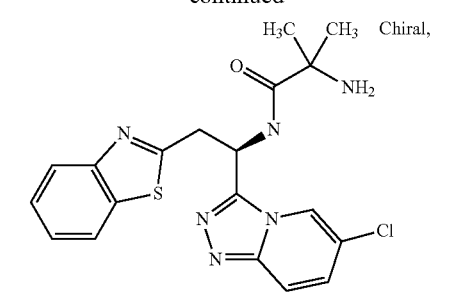
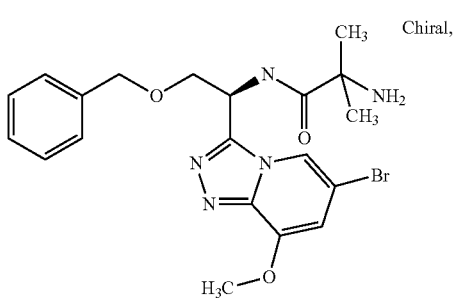
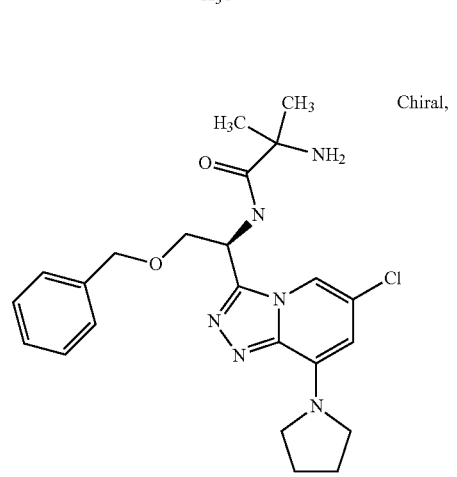
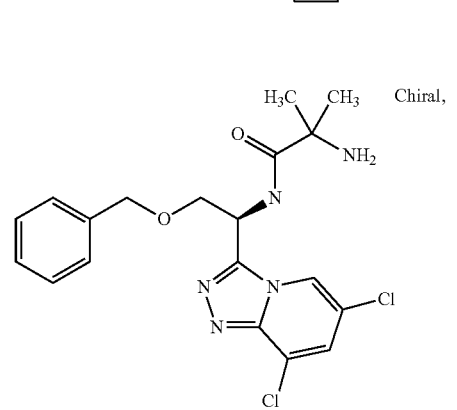
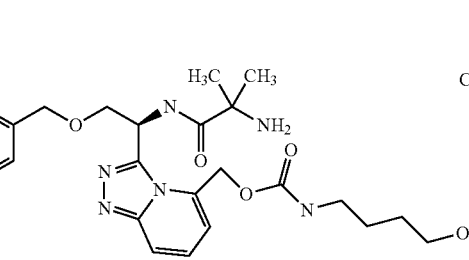
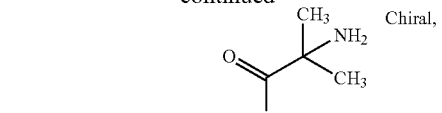
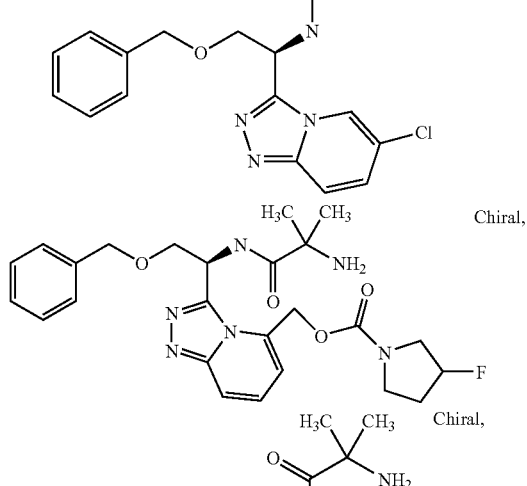
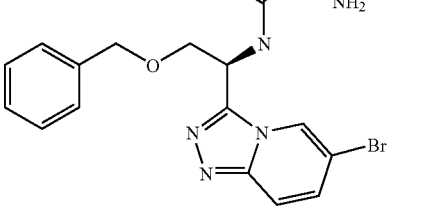
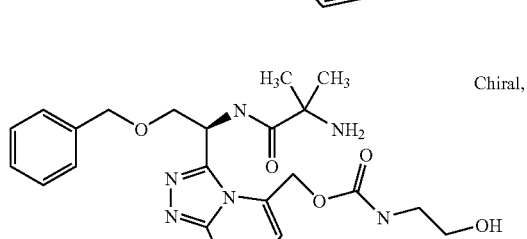
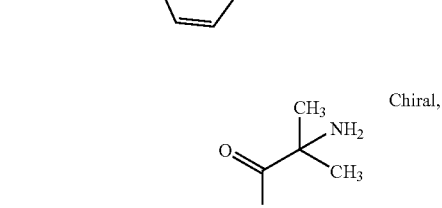
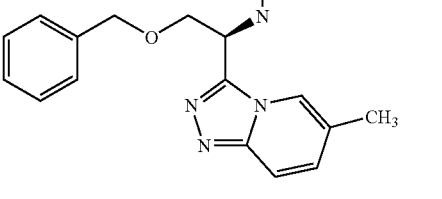
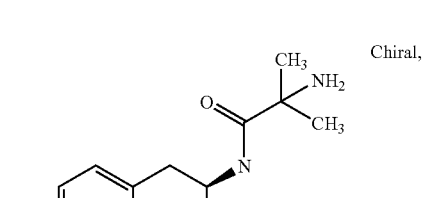
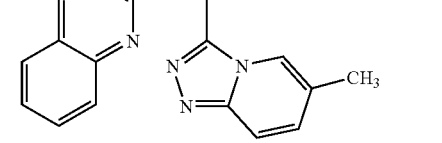

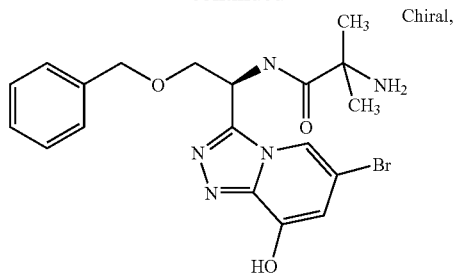
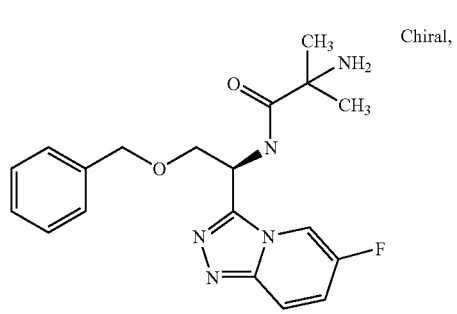
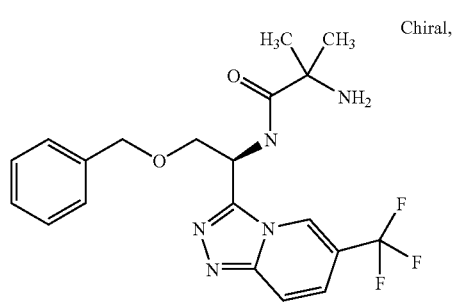
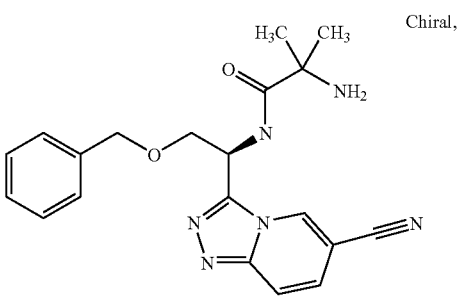
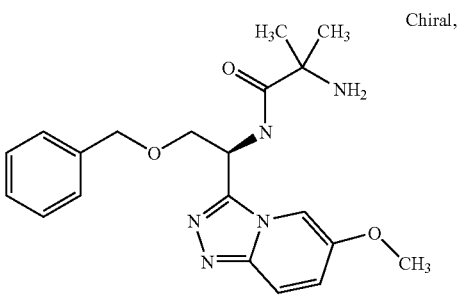
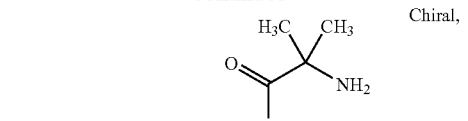
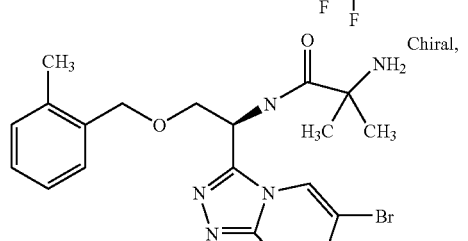
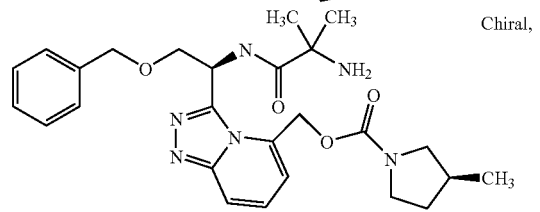
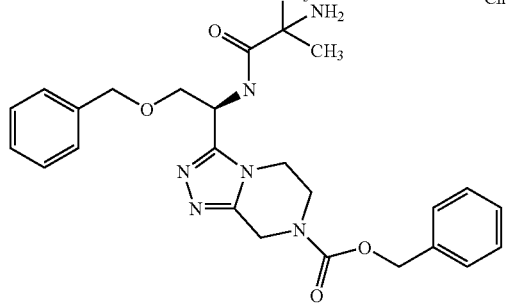
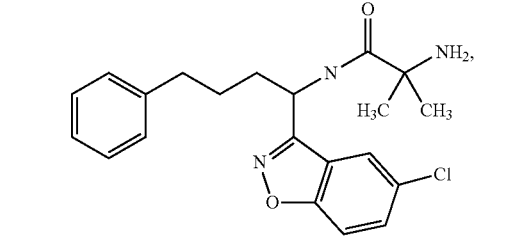
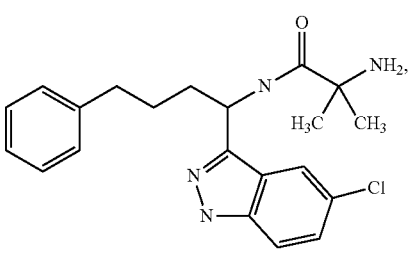

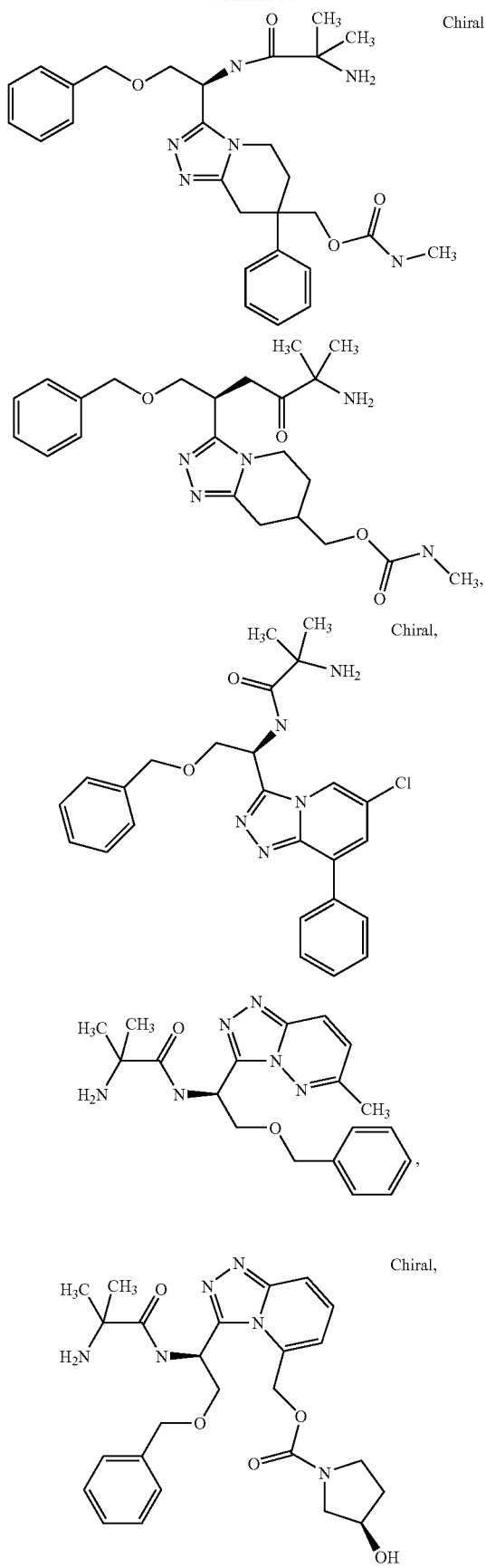
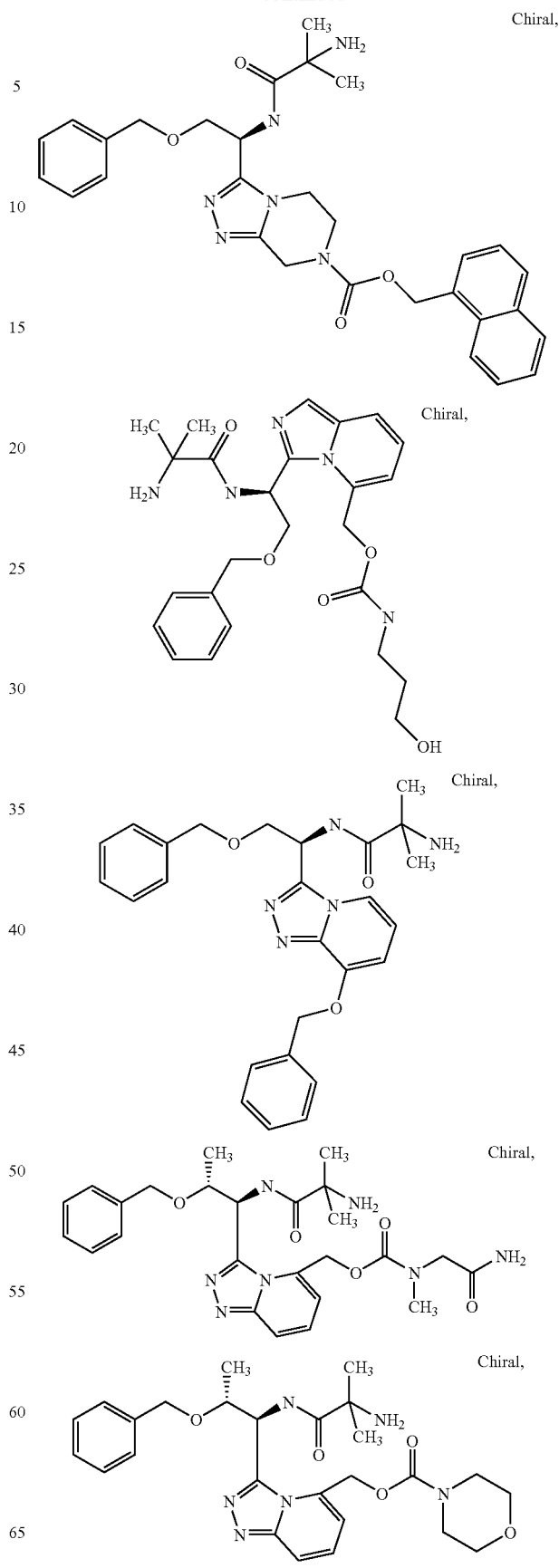

-continued
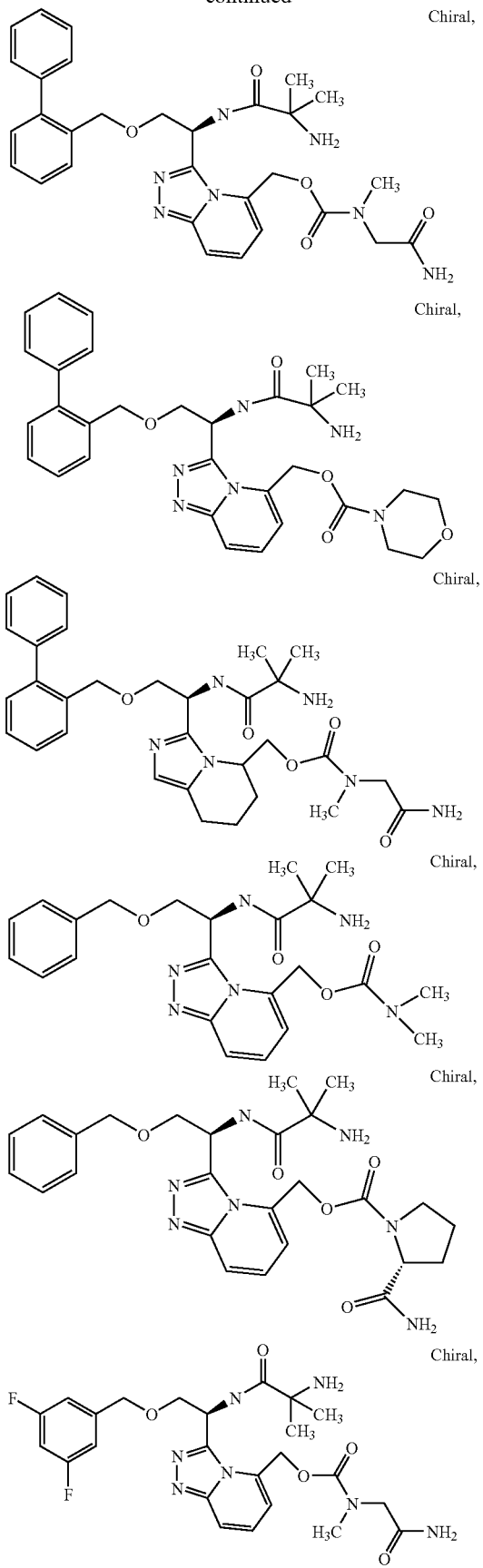
-continued
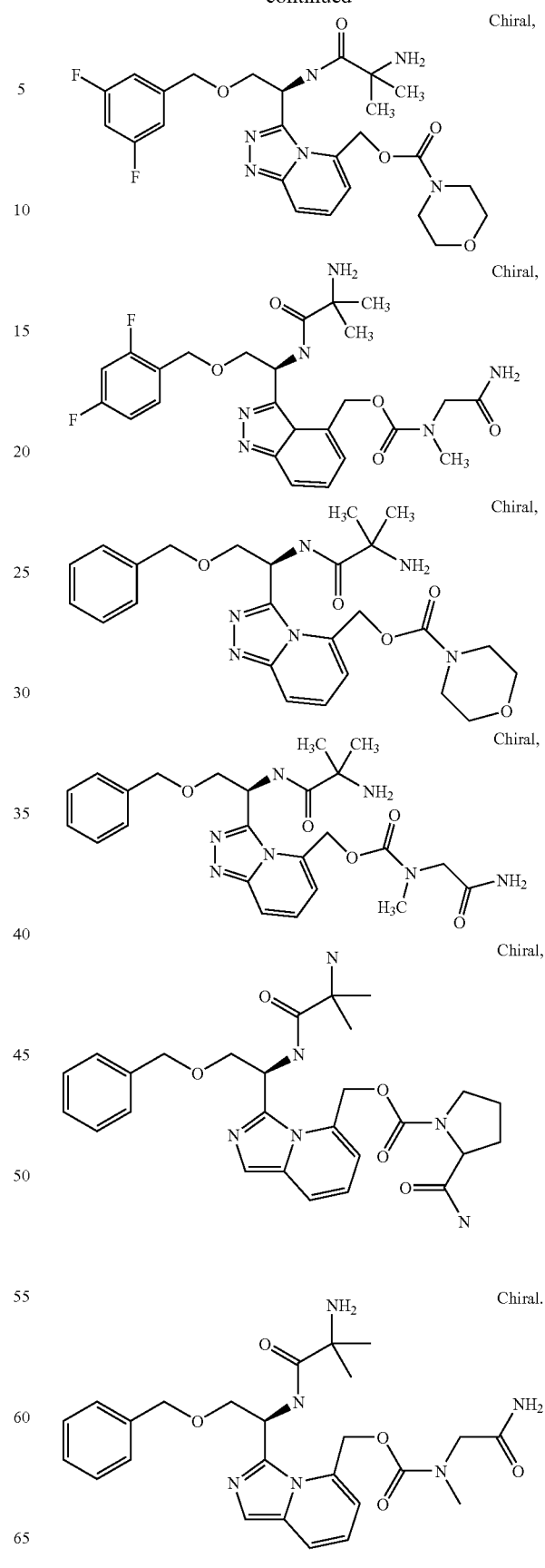

Additional preferred embodiments include compounds of formula I having the structure:
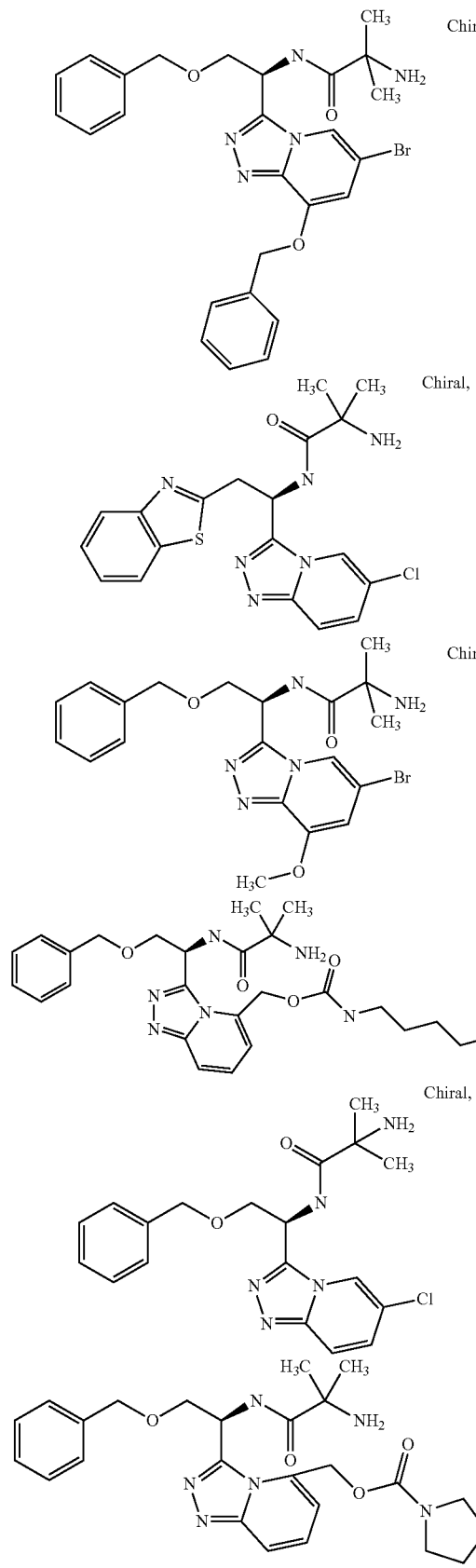
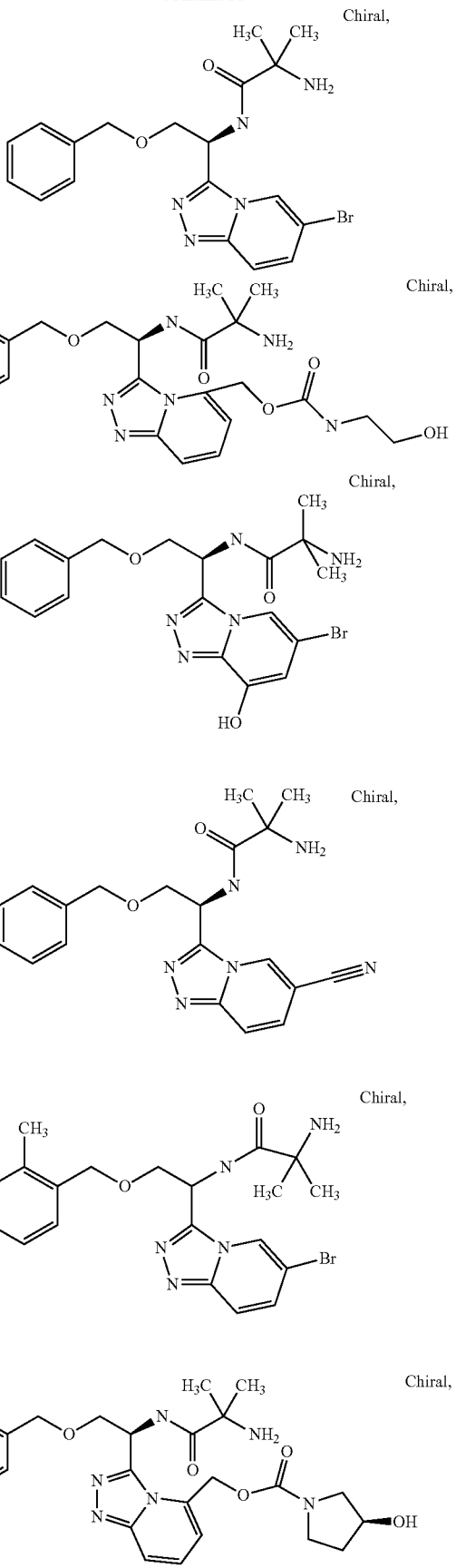

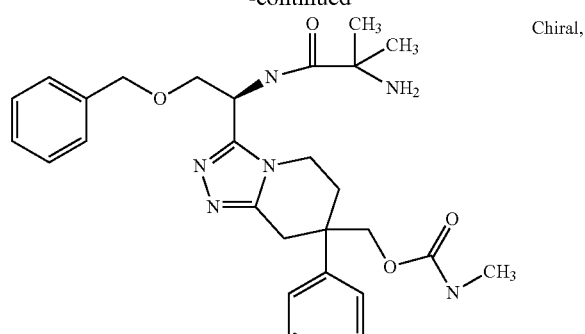
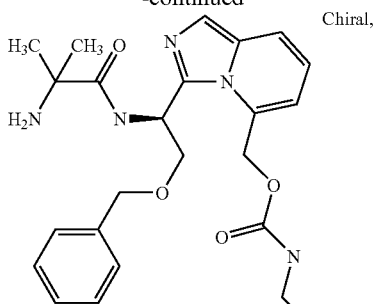
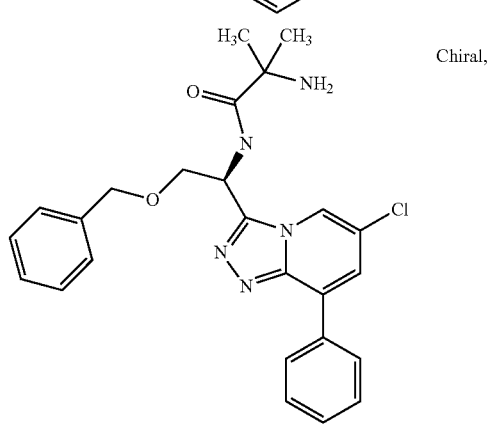
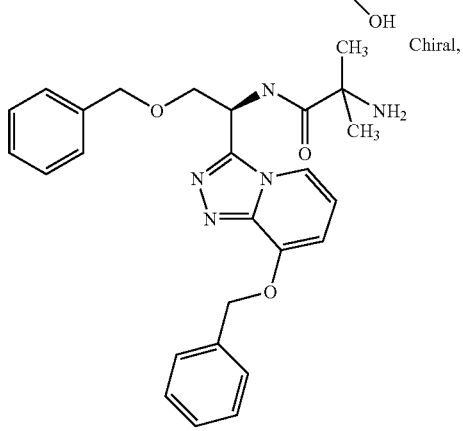
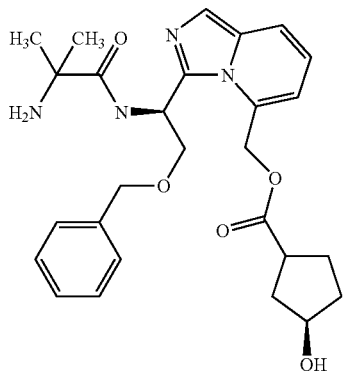
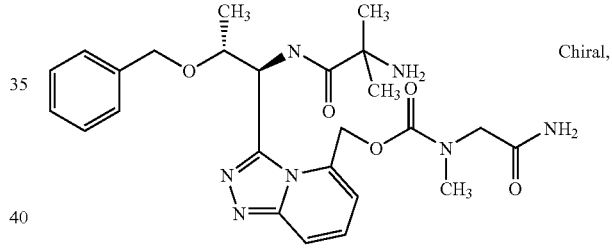
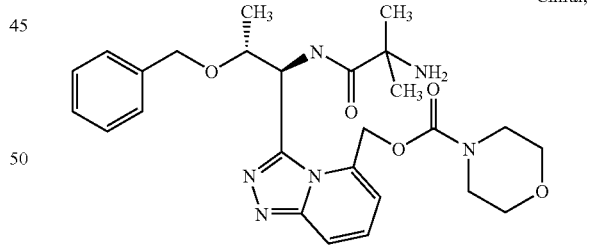
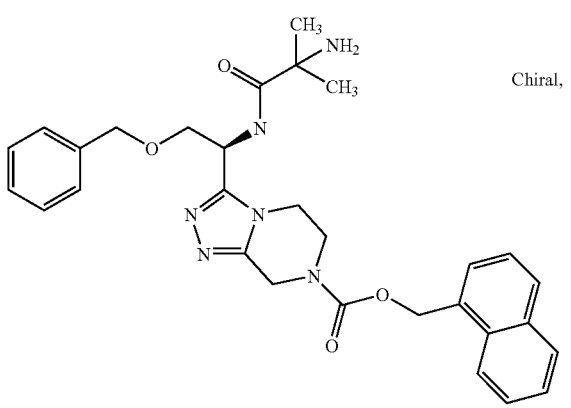
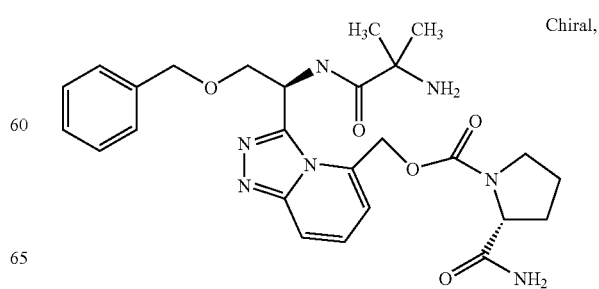

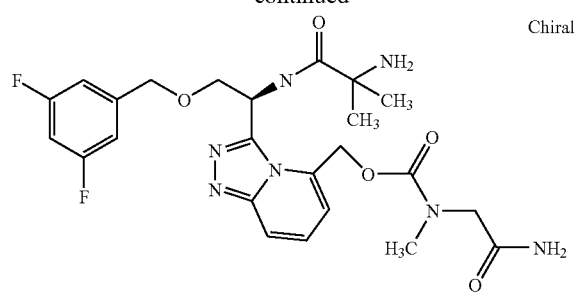
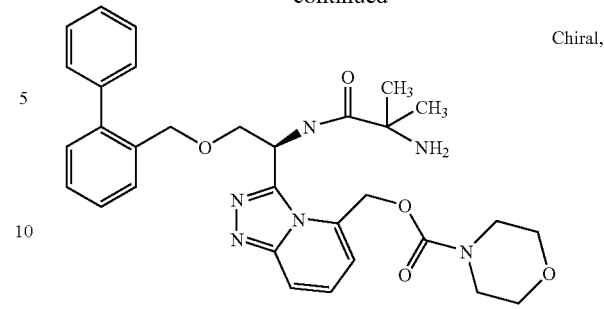
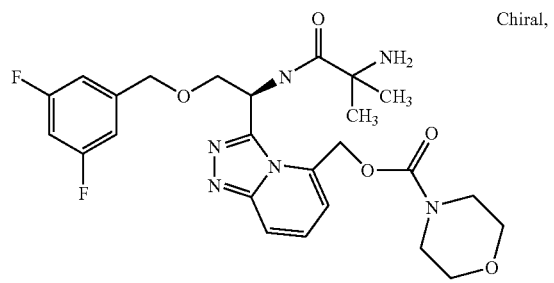
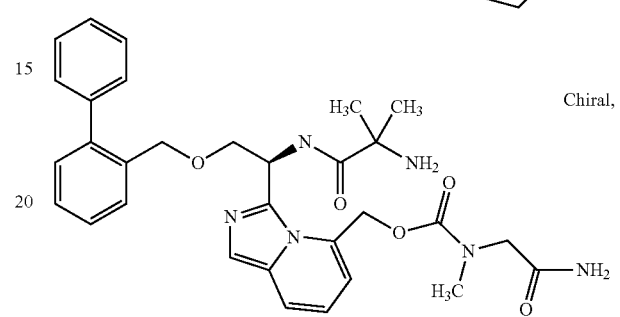
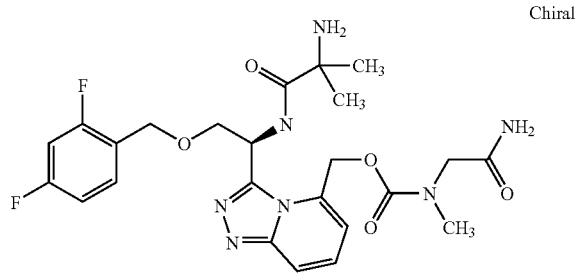
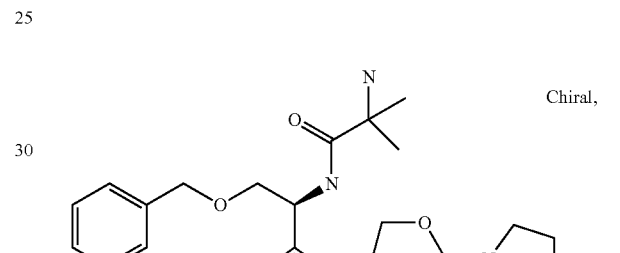
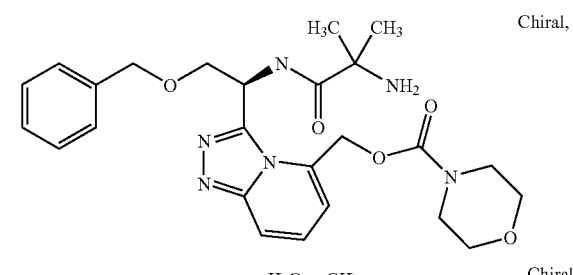
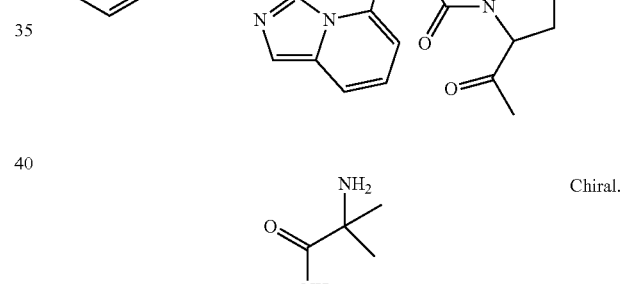
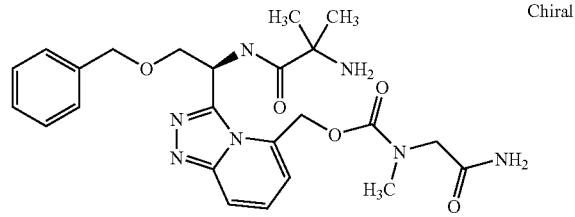
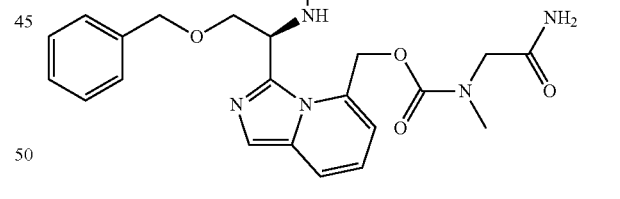
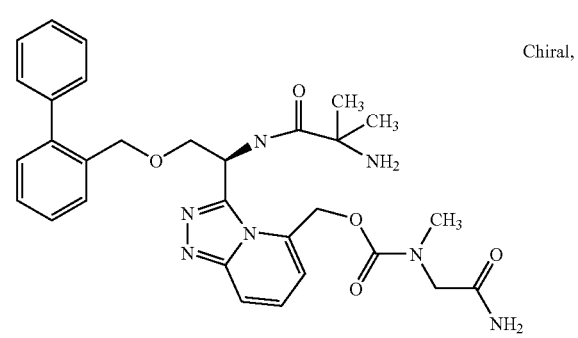

The compounds of this invention all have at least one asymmetric center as noted by the asterisk in structural formula I. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within spirit and scope of the present invention. In the case of the asymmetric center represented by the asterisk in formula I, the more active and thus more preferred configuration is R as determined by the R/S rules. Isomers may be separated by conventional methods, for example, chromatographic or fractional crystallization.

DETAILED DESCRIPTION OF THE INVENTION

The following abbreviations are employed herein:
Boc=tert-butoxycarbonyl
CBZ=benzyloxycarbonyl (or carbobenzoxy)
DIBAL=diisobutylaluminum hydride
DMAP=4-(dimethylamino)pyridine
DMF=N,N-dimethylformamide
EDAC=1-(3-dimethylaminopropyl)-3-ethylcarbodiimide hydrochloride
EtOAc=ethyl acetate
HOBT=hydroxybenztriazole
HPLC=high performance liquid chromatography
LC/MS=high performance liquid chromatography/mass spectrometry
MS or Mass Spec=mass spectrometry
Pd/C=palladium on activated charcoal
TFA=trifluoroacetic acid
YMC=trademark of YMC Co, Ltd., Kyoto, Japan
g=gram(s)
h or hr=hour(s)
min=minute(s)
ml=milliliter
mg=milligram(s)
mol=moles
mmol=millimole(s)
nM=nanomolar
r.t.=room temperature
Et=ethyl
i-Pr=isopropyl
Me=methyl The following definitions apply to the terms as used throughout this specification, unless otherwise limited in specific instances.

Unless otherwise indicated, the term "alkyl" as employed herein alone or as part of another group includes both straight and branched chain hydrocarbons, containing 1 to 40 carbons, preferably 1 to 20 carbons, more preferably 1 to 6 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Further, alkyl groups, as defined herein, may optionally be substituted on any available carbon atom with one or more functional groups commonly attached to such chains, such as, but not limited to alkyl, aryl, alkenyl, allynyl, hydroxy, arylalkyl, cycloalkyl, cycloalkylalkyl, alkoxy, arylalkyloxy, alkanoyl, amino, halo, thio, cyano, carboxyl, carbonyl

, amino, amido, haloaryl, $CF_3$, $OCF_3$, aryloxy, heteroaryl, cycloalkylalkoxyalkyl, cycloheteroalkyl and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl and tricyclic alkyl, containing a total of 3 to 20 carbons forming the rings, preferably 4 to 10 carbons, forming the ring and which may be fused to 1 aromatic ring as described for aryl, which include cyclopropyl, cyclobutyl, cyclopentyl, cyclohexyl, cycloheptyl, cyclooctyl, cyclodecyl, cyclododecyl, cyclohexenyl,

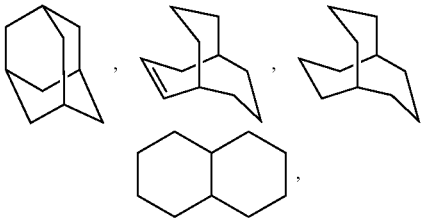

any of which groups may be optionally substituted with 1 to 3 substituents as defined above for alkyl.

The term "aryl" as employed herein alone or as part of another group refers to monocyclic and bicyclic aromatic groups containing 6 to 10 carbons in the ring portion (such as phenyl or naphthyl) and may optionally include one to three additional rings fused to "aryl" (such as aryl, cycloalkyl, heteroaryl or cycloheteroalkyl rings) and may be optionally substituted through any available carbon atoms with 1 or more groups selected from hydrogen, halo, alkyl, haloalkyl, alkoxy, haloalkoxy, alkenyl, trifluoromethyl, trifluoromethoxy, allynyl, cycloalkylalkyl, fluorenyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, oxo, cyano, amino, substituted amino wherein the amino includes 1 or 2 substituents (which are allyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylallyl, arylsulfonylamino or arylsulfonaminocarbonyl, or any of alkyl substituents as set out above.

The term "arylalkyl" as used herein alone or as part of another group refers to alkyl groups as defined above having an aryl substituent, such as benzyl, phenethyl or naphthylpropyl, wherein said aryl and/or alkyl groups may optionally be substituted as defined above.

The term "alkoxy" or "aryloxy" as employed herein alone or as part of another group includes an alkyl or aryl group as defined above linked through an oxygen atom.

Unless otherwise indicated, the term "alkenyl" as used herein by itself or as part of another group refers to straight or branched chain radicals of 2 to 20 carbons, preferably 3 to 12 carbons, and more preferably 2 to 6 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with one or more functional groups as defined above for alkyl.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with one or more functional groups as defined above for alkyl.

The term "alkylene" as employed herein alone or as part of another group refers to alkyl linking groups above having single bonds for attachment to other groups at two different carbon atoms and may optionally be substituted as defined above for "alkyl".

The terms "alkenylene" and "alkynylene" as employed herein alone or as part of another group refer to alkenyl and alkynyl linking groups, having single bonds for attachment at two different carbon atoms and may optionally be substituted as defined above for "alkyl". The term "halogen" or "halo" as used herein alone or as part of another group refers to chlorine, bromine, fluorine and iodine.

The term "heteroaryl" as used herein refers to a 5-, 6- or 7-membered aromatic heterocyclic ring which contains one or more heteroatoms selected from nitrogen, sulfur, oxygen and/or a SO or $SO_2$ group. Such rings may be fused to another cycloalkyl, cycloheteroalkyl, aryl or heteroaryl ring and include possible N-oxides. Optionally a heteroaryl group may be substituted with one or more functional groups commonly attached to such chains, such as those described for alkyl.

The term "heterocyclo", "heterocycle" or "heterocyclic", as used herein, represents an unsubstituted or substituted stable 4-, 5-, 6- or 7-membered monocyclic ring system which may be saturated or unsaturated, and which consists of carbon atoms and from one to four heteroatoms selected from N, O, S and or a SO or $SO_2$ group, wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl and oxadiazolyl. Optionally a heterocyclo group may be substituted with one or more functional groups, such as those described for alkyl.

The term "heterocycloalkyl" or "heteroarylalkyl" as used herein alone or as part of another group refers to a heterocyclo or heteroaryl group respectively, linked through an alkyl group.

The term "alkoxyalkyl" or "aryloxyalkyl" as used herein alone or as part of another group refers to a alkoxy or aryloxy group respectively, linked through an allyl group.

The term "heteroarylalkoxy" as used herein alone or as part of another group refers to a heteroaryl group linked through an alkoxy group.

As used herein alone or as part of another group, the term "cycloalkylalkoxyalkyl" and "arylalkyloxyalkyl" refers to a cycloalkyl group and an aryl group respectively, linked through an alkoxy group, that is in turn linked through an alkyl group.

The term "arylene" or "heteroarylene" as used herein alone or as part of another group, refers to a alkylene, alkenylene or alkynylene linking group as defined above, wherein said alkylene, alkenylene or alkynylene linking group contains an aryl (Ar) or heteroaryl (Het) group in the carbon chain. Examples include, but are not limited to —$(CH_2)_2$—Ar—$(CH_2)_2$— or —$(CH_2)_2$-Het-$(CH_2)_z$—.

The term "carbonyl," as used herein, refers to a —C(O)— group or when referred to as a possible substituent, refers to a (=O) group attached to any available carbon atom with in the functional group or linking group being substituted.

The term "phenoxy" as used herein, refers to a phenyl substituent linked through and oxygen atom. Optionally the phenyl ring porton a phenoxy group may be substituted with one or more functional groups, such as described for aryl.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

Any compound that can be converted in vivo to provide the bioactive agent (i.e., the compound of formula I) is a prodrug within the scope and spirit of the invention.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art and are described in:

a) *The Practice of Medicinal Chemistry*, Camille G. Wermuth et al., Ch. 31, (Academic Press, 1996);

b) *Design of Prodrugs*, edited by H. Bundgaard, (Elsevier, 1985); and c) *A Textbook of Drug Design and Development*, P. Krogsgaard-Larson and H. Bundgaard, eds. Ch 5, pgs 113-191 (Harwood Academic Publishers, 1991). Said references are incorporated herein by reference.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques or fractional crystallization.

The pharmaceutically acceptable salts of the compounds of formula I of the invention include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, stearate and salts of naturally occurring amino acids such as arginine, lysine, alanine and the like, and prodrug esters thereof.

General Synthetic Schemes

The compounds of the present invention may be prepared according to the following general synthetic reaction schemes as well as relevant published literature procedures that may be used by one skilled in the art. Exemplary reagents, procedures and conditions for these reactions appear hereinafter and in the working examples. Starting materials are commercially available or can be readily prepared by one of ordinary skill in the art using known methods. Unless otherwise specified the various substituents of the compounds are defined in the same manner as the formula I.

High Speed Analoging (HSA) may be employed in the preparation of compounds, for example, where the intermediates possess an amine position or activated aromatic position, such as the halogenated Q1 and Q2.

Scheme I

Scheme I describes a general synthetic sequence for the preparation of the compounds of formula I. During the preparation of compounds of formula I, one or more protecting groups might be used, reaction conditions for protection and deprotection may be found in the 'Protective Groups in Organic Synthesis" Greene et al., John Wiley and Sons Inc, 1991, or other methods used by one of ordinary skill in the art.

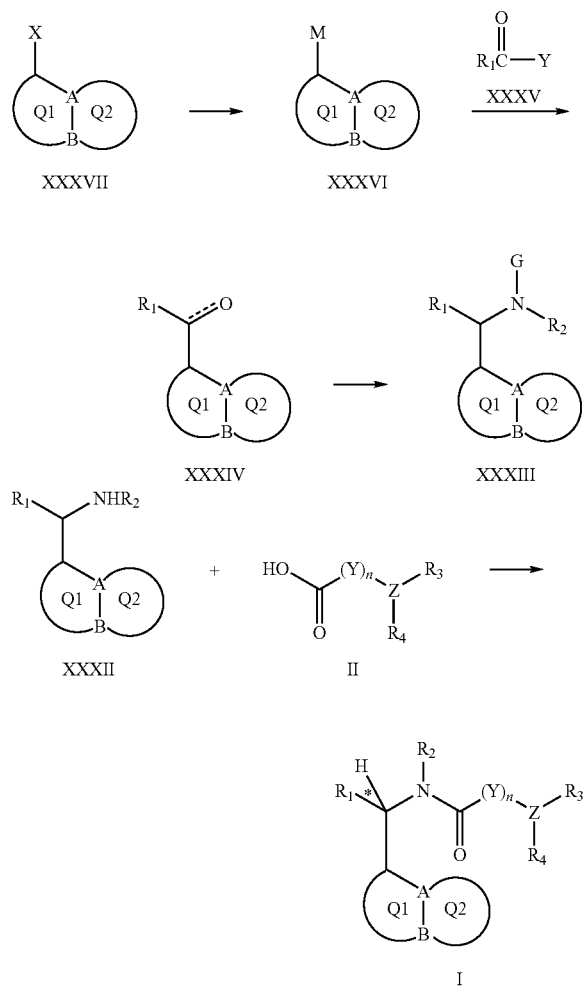

Compounds of formula I can be prepared from a compound of formula II and amine XXXII using an appropriate carboxylic acid activating reagent in an inert solvent. Exemplary carboxylic acid activating agents include isobutylchloroformate, carbonyldiimidazole, dicyclohexylcarbodiimide, pentofluorophenol trifluoroacetate, or 1-(3-dimethylaminopropyl)-3-ethylcarbodiimide. Exemplary inert solvents include ethers, dioxane, tetrahydrofuran, N,N-dimethylformamide, acetonitrile, or methylene chloride. If $R_3$ and/or $R_4$ are an amine protecting group, such as Boc-, CBZ or Trityl, they will be deprotected to afford the final products. Reaction conditions for deprotection may be founds in the 'Protective Groups in Organic Synthesis" Greene et al., John Wiley and Sons Inc, 1991, or other methods used by one of ordinary skill in the art.

Compound XXXII can be prepared by the deprotection of compound IV where PG is an appropriate amino protecting group such as Boc-, CBZ or Trityl, etc. Exemplary deprotection reagents for Boc- are hydrogen chloride in dioxane, TFA in dichloromethane, etc.; exemplary deprotection for CBZ is catalytic hydrogenation, exemplary deprotection for Trityl is hydrogen chloride in acetone or tetrahydrofuran.

Compound XXXIII can be prepared from compound XXXIV. When C═O is a hydroxyl group in compound XXXIV, it can be converted to an azide group followed by reduction to give the amino group in compound XXXIII. (for an example, see Lautens et al, *J. Org. Chem.* (1997) 62, 5246-5247). When C═O is a carbonyl group, it can be reduced to a hydroxyl group then converted to the amino group in compound XXXIII. Alternatively, it can be converted to an O-methyl oxime, then followed by reduction to give the amino group in compound XXXIII. Reduction of O-methyl oxime to amine can be carried out with borane tetrahydrofuran complex or other methods used by one of ordinary skill in the art.

Compound XXXIV can be prepared from reaction of compound XXXVI and compound XXXV. Compounds XXXV [Y═H, SPh, Cl, NMe(OMe)] can be prepared by one of the ordinary skill in the art. Compounds XXXVI (M═Li, MgBr, MgCl, ZnBr, ZnI) is an organometalic intermediate, which can be prepared from an appropriate precursor (X═B, I, Cl). or other methods used by one of ordinary skill in the art. Organic zinc reagents can be prepared via treatment of arylbromide or aryliodide with Rieke®zinc metal as described in. *J. Org. Chem.* (1991), 56, 1445 or *Tetrahedron* (1997), 53, 1925. Alternatively, it can also be prepared via treatment of arylbromide or aryliodide with n-BuLi or tert-BuLi followed by addition of zinc bromide or zinc iodide.

SCHEME IIa

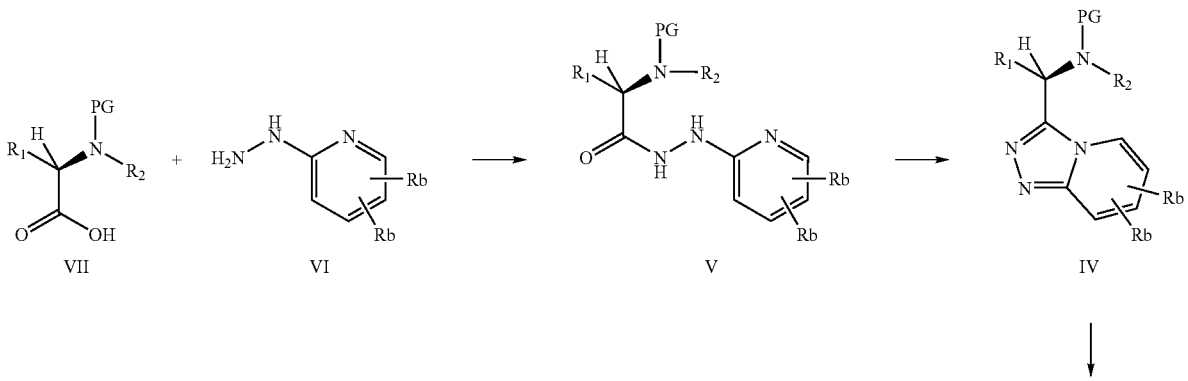

-continued

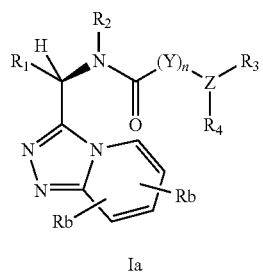 ← 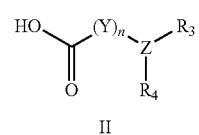 + 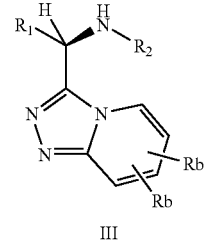

Ia   II   III

Compounds of the formula Ia can be prepared via the aminolysis of a compound of formula II using an appropriate carboxylic acid activating reagent and amine III in an inert solvent. Exemplary carboxylic acid activating agents include isobutylchloroformate, carbonyldiimidazole, dicyclohexylcarbodiimide, pentofluorophenol trifluoroacetate, or 1-(3-dimethylaminopropyl)-3-ethylcarbodiimide. Exemplary inert solvents include ethers, including tetrahydrofuran and dioxane, N,N-dimethylformamide, acetonitrile, or methylene chloride. If $R_3$ and/or $R_4$ are an amine-protecting group, such as Boc-, or CBZ, they will be deprotected to afford the final products. Deprotections are done by one of ordinary skill in the art as described in the following.

Compound III can be prepared by the deprotection of compound IV where G is an appropriate amino protecting group such as Boc-, CBZ, etc., as commonly used by one of ordinary skill in the art. Exemplary deprotection reagents for Boc- are hydrogen chloride in dioxane, TFA, etc; exemplary deprotection for CBZ is catalytic hydrogenation.

Compound IV can be prepared from compound V via a dehydrating process. Exemplary dehydrating agents include $POCl_3$, SOCK, HCl, HOAc and Mitsunobu reactions.

Compound V can be prepared from compounds VII via aminolysis using an appropriate carboxylic acid activating reagent and amine VI in an inert solvent. Exemplary carboxylic acid activating agents include isobutylchloroformate, carbonyldiimidazole, dicyclohexylcarbodiimide, pentofluorophenol trifluoroacetate, or 1-(3-dimethylaminopropyl)-3-ethylcarbodiimide. Exemplary inert solvents include ethers, including tetrahydrofuran and dioxane, N,N-dimethylformamide, acetonitrile, or methylene chloride.

Although compound VI discloses two Rb substituents on the pyridine ring, the schemes are not limited to a single Rb group, nor is an Rb group needed. Rather, the presence of the Rb substituents in Scheme Ha and the subsequent Schemes hereafter, indicate that one or more Rb groups may optionally be attached at any available position of attachment upon the ring to which the Rb group is associated. Therefore, even though Scheme Ha and the Schemes hereinafter may reference a particular embodiment, it should be understood that various other modifications, such as the substitution of one or more Rb groups, or other modifications known to those skilled in the art, may be employed within the scope and spirit of the general synthetic schemes herein.

SCHEME IIb

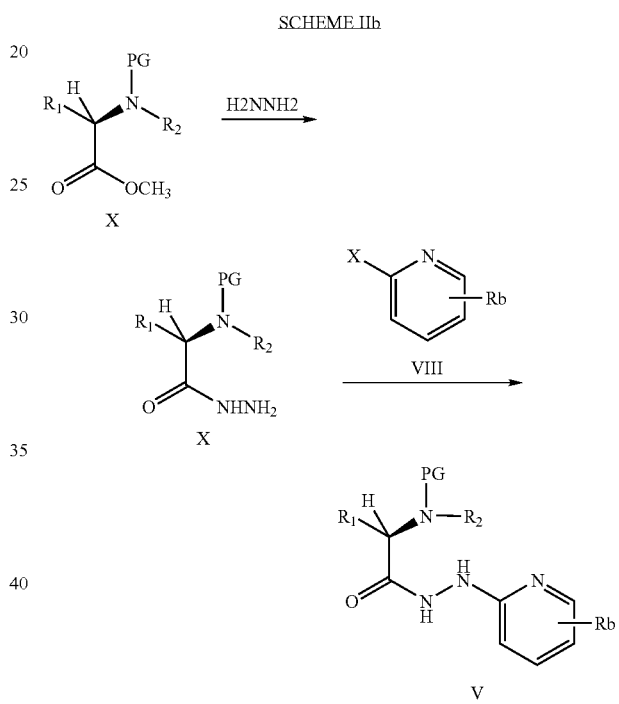

Alternately, compound V can be prepared by the condensation of 1x and VIII (where X is a leaving group such as a halogen) in an inert solvent at elevated temperatures. Exemplary inert solvents include DMF, THF, dioxane, acetonitrile, pyridine, and inert alcohol such as ethanol. Exemplary temperatures can range from 40 to 150° C.

Compound IX can be prepared by the hydrazinolysis of X via procedures used by one of ordinary skill in the art.

SCHEME IIc

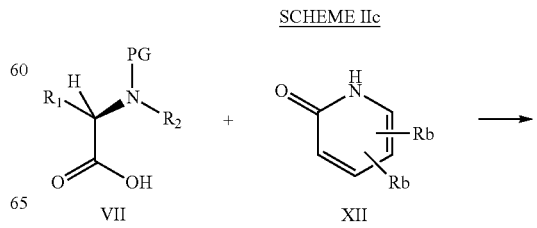

VII   XII

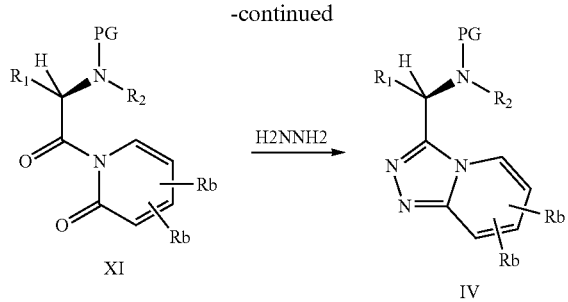

Alternately, compound N can be prepared by the hydrazinolysis of compound XI in an inert solvent at elevated temperature. Exemplary inert solvents include hydrazine, HOAc, THF, dioxane, pyridine and inert alcohol such as ethanol. Exemplary temperatures can range from 40 to 150° C.

Compound XI can be prepared by the condensation of XII and VII via an appropriate carboxylic acid activating agent in an inert solvent. Exemplary carboxylic acid activating agents include isobutylchloroformate, carbonyldiimidazole, dicyclohexylcarbodiimide, pentofluorophenol trifluoroacetate, or 1-(3-dimethylaminopropyl)-3-ethylcarbodiimide. Exemplary inert solvents include ethers, including tetrahydrofuran and dioxane, N,N-dimethylformamide, acetonitrile, or methylene chloride.

and m and n can independently be an integer from 0 to 6, with the caveat that m and n together form a 5-12 membered ring structure.

Compounds of formula XIII can be prepared via the aminolysis of a compound of formula II using an appropriate carboxylic acid activating reagent and amine XIV in an inert solvent. Exemplary carboxylic acid activating agents include isobutylchloroformate, carbonyldiimidazole, dicyclohexylcarbodiimide, pentofluorophenol trifluoroacetate, or 1-(3-dimethylaminopropyl)-3-ethylcarbodiimide. Exemplary inert solvents include ethers, including tetrahydrofuran and dioxane, N,N-dimethylformamide, acetonitrile, or methylene chloride. If $R_3$ and/or $R_4$ are an amine-protecting group, such as Boc-, or CBZ, they will be deprotected to afford the final products. Deprotections are done by one of ordinary skill in the art as described in the following.

Compound XIV can be prepared by the deprotection of compound XV where PG is an appropriate amino protecting group such as Boc-, CBZ, etc. used by one of ordinary skill in the art. Exemplary deprotection reagents for Boc- are hydrogen chloride in dioxane, TFA, etc; exemplary deprotection for CBZ is catalytic hydrogenation.

Compound XVI can be prepared from compound X via a dehydrating conditions in protonic and aprotic solvents. Dehydrating conditions can be exemplified by using protonic

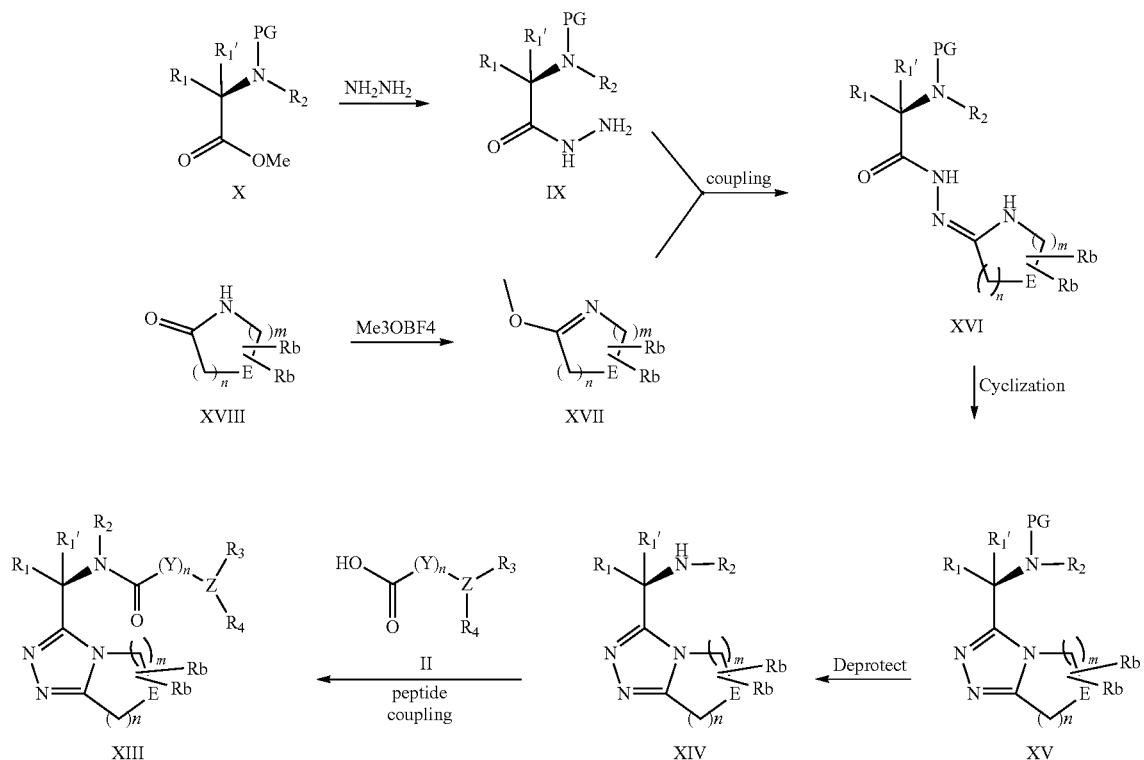

Scheme IIIa describes a general synthetic sequence for the preparation of the compounds of formula XIII (where E can be $CH_2$, CRaRb, NRa, O, S, $SO_2$, SO, CO, C(O)O, C(O)NRa, solvent along or by using combinations with dehydrating agents include HOAc, PPTS or by using Mitsunobu reactions in the inert solvents.

Compound XVI can be prepared from coupling compounds Ix and compound XVII in inert solvent.

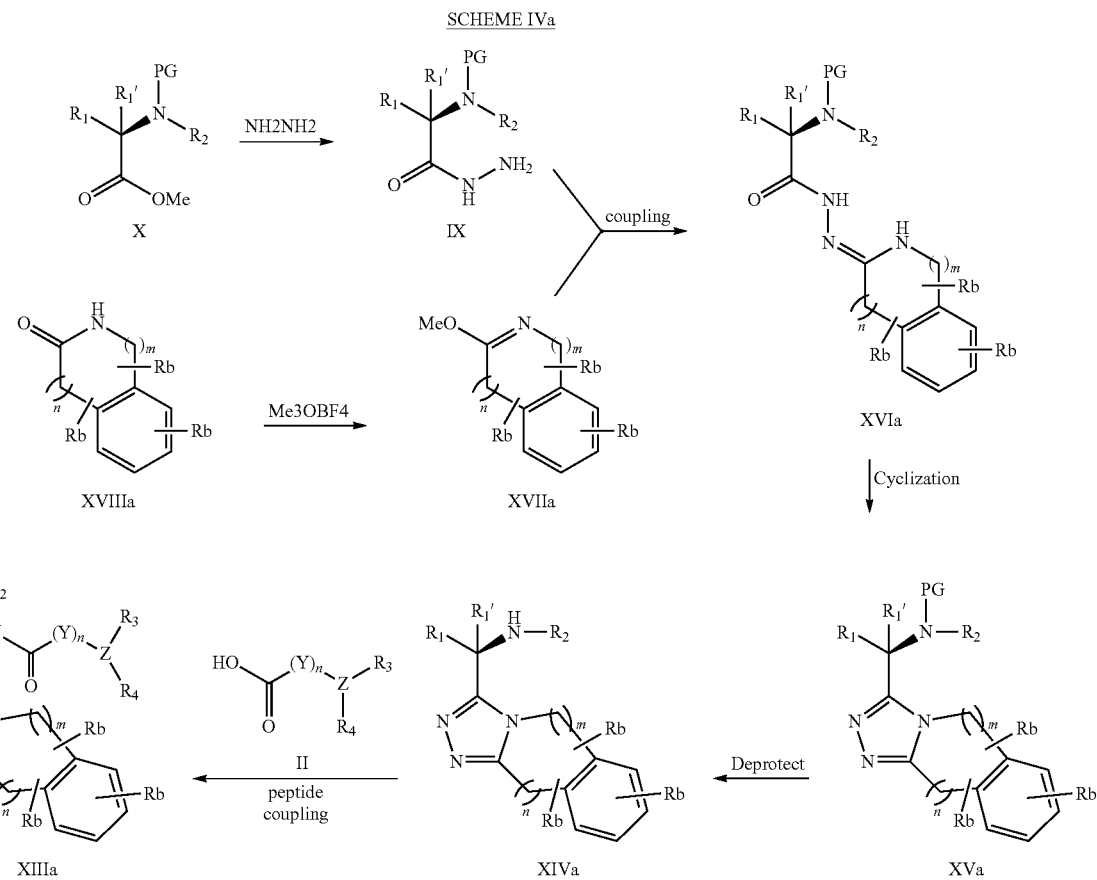

SCHEME IVa

Schemes IVa-IVc can be carried out using similar general procedures as described for Scheme IIIa, where intermediates XVIIIa, XVIIIb and XVIIIc are utilized in place of intermediate XVIII. m and n can independently be an integer from 0 to 5, with the caveat that m and n together form a 6-12 membered ring structure.

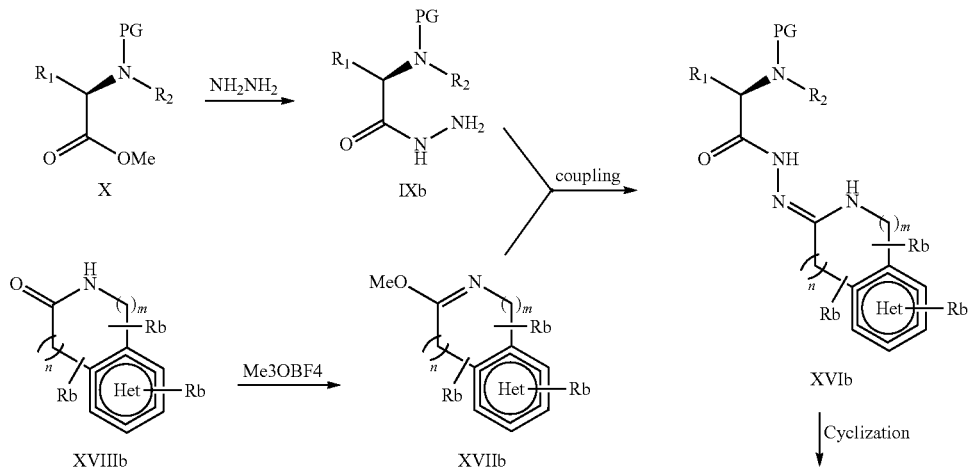

SCHEME IVb

-continued
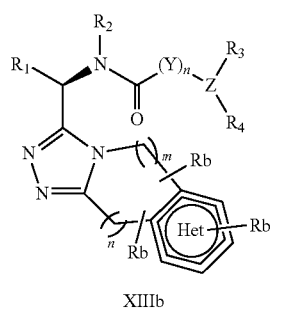 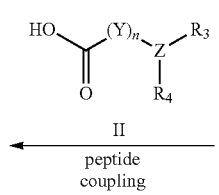 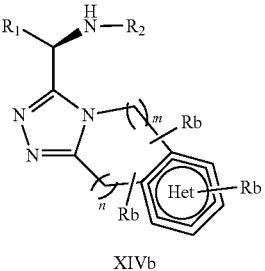 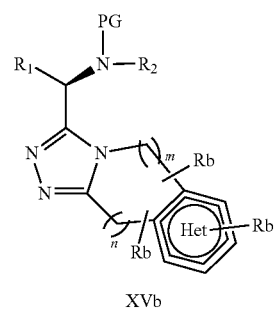
SCHEME IVc
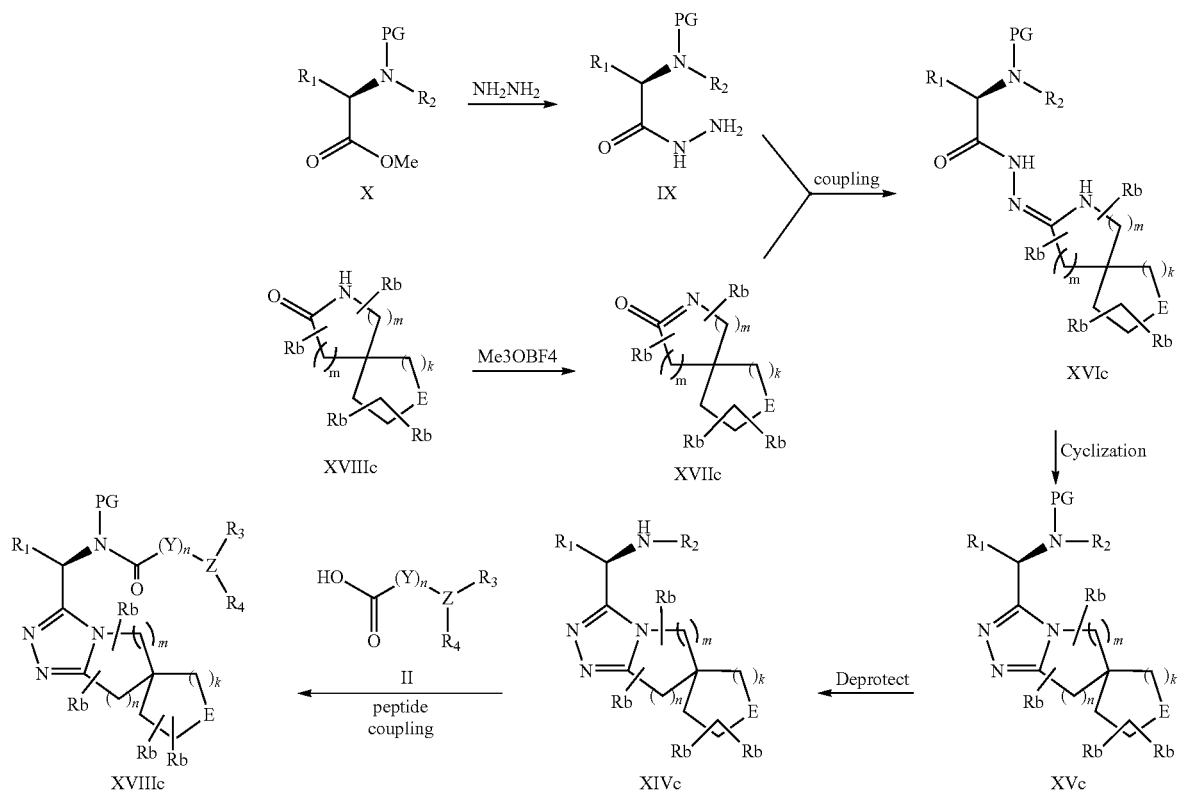
SCHEME V
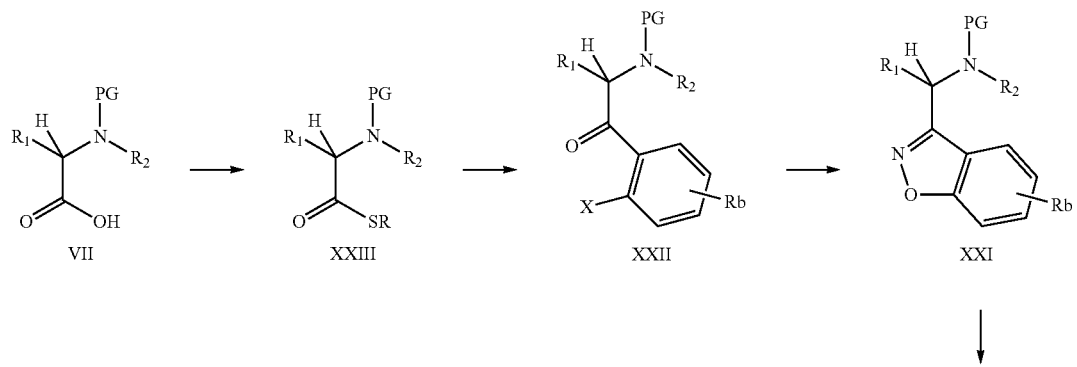

-continued

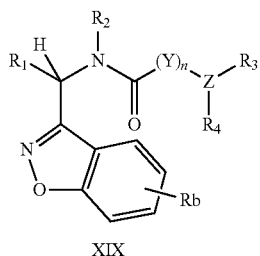
XIX

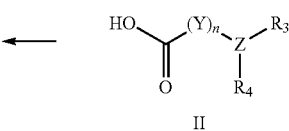
II

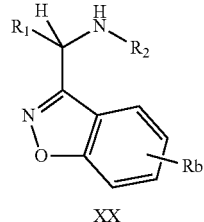
XX

Compounds of formula XIX can be prepared from a compound of formula II and amine XX using an appropriate carboxylic acid activating reagent in an inert solvent. Exemplary carboxylic acid activating agents include isobutylchloroformate, carbonyldiimidazole, dicyclohexylcarbodiimide, pentofluorophenol trifluoroacetate or 1-(3-dimethylaminopropyl)-3-ethylcarbodiimide. Exemplary inert solvents include ethers, dioxane, tetrahydrofuran, N,N-dimethylformamide, acetonitrile or methylene chloride. If $R_3$ and/or $R_4$ are an amine-protecting group, such as Boc-, CBZ or Trityl, they will be deprotected to afford the final products. Reaction conditions for deprotection may be founds in the 'Protective Groups in. Organic Synthesis" Greene et al., John Wiley and Sons Inc, 1991, or other methods used by one of ordinary skill in the art.

Compound XX can be prepared by the deprotection of compound XXI where PG is an appropriate amino protecting group such as Boc-, CBZ or Trityl, etc. Reaction conditions for deprotection may be founds in the 'Protective Groups in Organic Synthesis" Greene et al., John Wiley and Sons Inc, 1991, or other methods used by one of ordinary skill in the art. Exemplary deprotection reagents for Boc- are hydrogen chloride in dioxane, TFA in dichloromethane, etc.; exemplary deprotection for CBZ is catalytic hydrogenation, exemplary deprotection for Trityl is hydrogen chloride in acetone or tetrahydrofuran.

Compound XXI can be prepared from compound XXII (X=Cl or F). Compound XXII first react with hydroxyamine to give an oxime intermediate, then followed by cyclization under basic condition or other methods used by one of ordinary skill in the art.

Compound XXII can be prepared from compound XXIII via treatment of appropriate organic zinc reagents in an inert solvent such as ethers, tetrahydrofuran or toluene. Organic zinc reagents can be prepared via treatment of arylbromide or aryliodide with Rieke®zinc metal as described in *J. Org. Chem.* (1991), 56, 1445 or *Tetrahedron* (1997), 53, 1925. Alternatively, it can also be prepared via treatment of arylbromide or aryliodide with n-BuLi or tert-BuLi followed by addition of zinc bromide or zinc iodide.

Compounds XXIII can be prepared from a compound of formula VII and a mercapto compound such as thiophenol using an appropriate carboxylic acid activating reagent in an inert solvent. Exemplary carboxylic acid activating agents include isobutykhloroformate, carbonyldiimidazole, dicyclohexylcarbodiimide, pentofluorophenol trifluoroacetate, or 1-(3-dimethylaminopropyl)-3-ethylcarbodiimide. Exemplary inert solvents include ethers, dioxane, tetrahydrofuran, N,N-dimethylformamide, acetonitrile, or methylene chloride.

SCHEME VI

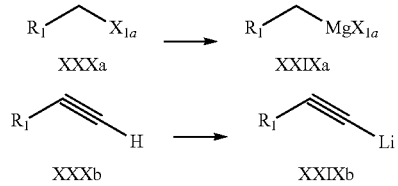

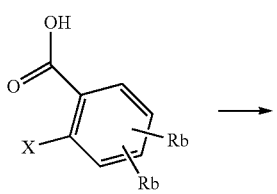
XXVIII

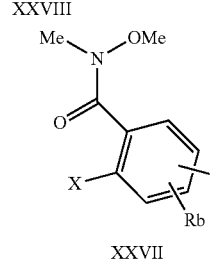
XXVII

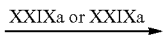
XXIXa or XXIXa

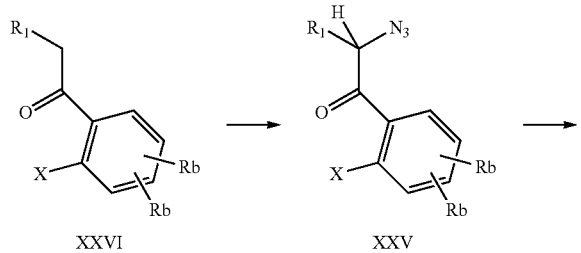
XXVI
XXV

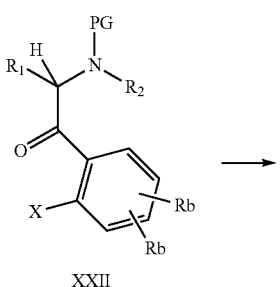
XXII

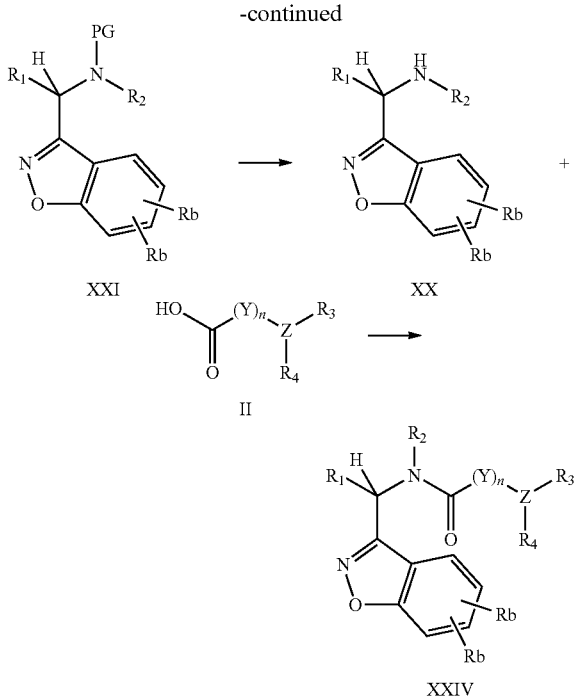

XXIV can be prepared from a compound of formula II and amine XX using an appropriate carboxylic acid activating reagent in an inert solvent. Exemplary carboxylic acid activating agents include isobutylchloroformate, carbonyldiimidazole, dicyclohexylcarbodiimide, pentofluorophenol trifluoroacetate, or 1-(3-dimethylaminopropyl)-3-ethylcarbodiimide. Exemplary inert solvents include ethers, dioxane, tetrahydrofuran, N,N-dimethylformamide, acetonitrile, or methylene chloride. If R3 and/or R4 are an amine-protecting group, such as Boc-, CBZ or Trityl, they will be deprotected to afford the final products. Reaction conditions for deprotection may be founds in the 'Protective Groups in Organic Synthesis" Greene et al., John Wiley and Sons Inc, 1991, or other known methods used by one of ordinary skill in the art.

Compound XX can be prepared by the deprotection of compound XXI where PG is an appropriate amino protecting group such as Boc-, CBZ or Trityl, etc. Reaction conditions for deprotection may be founds in the 'Protective Groups in Organic Synthesis" Greene et al., John Wiley and Sons Inc, 1991, or other known methods used by one of ordinary skill in the art. Exemplary deprotection reagents for Boc- are hydrogen chloride in dioxane, TFA in dichloromethane, etc.; exemplary deprotection for CBZ is catalytic hydrogenation, exemplary deprotection for Trityl is hydrogen chloride in acetone or tetrahydrofuran.

Compound XXI can be prepared from compound XXII (X=Cl or F). Compound XXII first react with hydroxyamine to give an oxime intermediate, then followed by cyclization under basic condition or other methods used by one of ordinary skill in the art.

Compound XXII can be prepared by reduction of azido compound XXV followed by protection of the resulting amine intermediate by an amine protecting group such as Boc, CBz or Trityl, etc. Exemplary reduction reaction include hydrogenation or with triphenylphosphine in aqueous tetrahydrofuran. Reaction conditions for protection of the resulting amine intermediate may be founds in the 'Protective Groups in Organic Synthesis" Greene et al., John Wiley and Sons Inc, 1991, or other methods used by one of ordinary skill in the art.

Compounds XXV can be prepared from a compound of formula XXVI in a two step sequence or other known methods in the art. Treatment of compound XXVI with bromine resulted in a α-bromoketone intermediate, which was followed by treatment with azide ion such as sodium azide.

Compounds XXVI can be prepared from a compound of formula XXVII with an organic metal reagent XXIXa or XXIXb.

Compound XXVII can be prepared from an acid XXVIII and N,O-dimethyl-amine hydrochloride using an appropriate carboxylic acid activating reagent and base in an inert solvent. Exemplary carboxylic acid activating agents include isobutylchloroformate, carbonyldiimidazole, dicyclohexylcarbodiimide, pentofluorophenol trifluoroacetate, or 1-(3-dimethylaminopropyl)-3-ethylcarbodiimide. Exemplary inert solvents include ethers, dioxane, tetrahydrofuran, N,N-dimethylformamide, acetonitrile, or methylene chloride. Alternatively, acid XXVIII can be converted to the corresponding acid chloride using oxalyl chloride, thionyl chloride or other known methods in the art. The resulting acid chloride can then reacted with N,O-dimethyl-amine hydrochloride in the presence of a base such as trimethylamine in an inert solvent.

Compound XXIXa is commonly known as Grignard reagents, and can be prepared by known methods used by one of ordinary skill in the art.

Compound XXIX'b can be prepared by treatment of compound XXXb with MeLi or n-BuLi or by known methods used by one of ordinary skill in the art.

UTILITIES AND COMBINATIONS

A. Utilities

The growth hormone releasing compounds of formula I can be administered to animals, including man, to release growth hormone in vivo. For example, the compounds can be administered to commercially important animals such as swine, cattle, sheep and the like to accelerate and increase their rate and extent of growth, and to increase milk production in such animals.

The present invention includes within its scope pharmaceutical compositions comprising, as an active ingredient, at least one of the compounds of formula I in association with a pharmaceutical carrier or diluent. Optionally, the active ingredient of the pharmaceutical compositions can comprise a growth promoting agent in addition to at least one of the compounds of formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239, 345, e.g., zeranol, and compounds disclosed in U.S. Pat. No. 4,036,979, e.g., sulbenox or peptides disclosed in U.S. Pat. No. 4,411,890.

A still further use of the disclosed compounds of formula I of the invention is in combination with other growth hormone secretagogues such as GHRP-6, GHRP-1 as described in U.S. Pat. No. 4,411,890; and publications WO 89/07110 and WO 89/07111 and B-HT920 or growth hormone releasing factor and its analogs or growth hormone and its analogs or somatomedins including IGF-1 and IGF-2. A still further use of the disclosed compounds of formula I of the invention is in combination with parathyroid hormone or bisphosphonates, such as MK-217 (alendronate), in the treatment of osteoporosis.

A still further use of the disclosed compounds of formula I is in combination with estrogen, testosterone, a selective estrogen receptor modulator, such as tamoxifen or raloxifene, or a selective androgen receptor modulator, such as disclosed in Edwards, J. P. et al., *Bio. Med. Chem. Let.*, 9, 1003-1008 (1999) and Hamann, L. G. et al., *J. Med. Chem.*, 42, 210-212 (1999), for the treatment of aspects of Metabolic Syndrome, maintenance of muscle strength and function in elderly humans, reversal or prevention of frailty in elderly humans, stimulation and increase in muscle mass and muscle strength, attenuation of protein catabolic response after a major operation or trauma; reducing cachexia and protein loss due to chronic illness such as cancer or AIDS; improvement in muscle mobility, and maintenance of skin thickness.

A further use of the compounds of this invention is in combination with progestin receptor agonists ("PRA").

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself.

To those skilled in the art, it is well known that the current and potential uses of growth hormone are varied and multitudinous. Thus, compounds of formula I can be administered for purposes stimulating release of endogenous growth hormone and would thus have similar effects or uses as growth hormone itself. Compounds of formula I are useful for stimulation of growth hormone release (e.g., in the elderly); maintenance of muscle strength and function (e.g., in the elderly); reversal or prevention of frailty or age-related functional decline ("ARM") in the elderly; prevention of catabolic side effects of glucocorticoids; prevention and treatment of osteoporosis; treatment of chronic fatigue syndrome (CFS); treatment of acute fatigue syndrome and muscle loss following election surgery; stimulation of the immune system, including improvement of immune response to vaccination; acceleration of wound healing; accelerating bone fracture repair (such as accelerating the recovery of hip fracture patients); accelerating healing of complicated fractures, e.g. distraction osteogenesis; acceleration of tooth repair or growth; maintenance of sensory function (e.g., hearing, sight, olefaction and taste); treatment of wasting secondary to fractures; treatment of growth retardation; treatment of growth retardation resulting from renal failure or insufficiency; treatment of cardiomyopathy; treatment of wasting in connection with chronic liver disease; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colits; treatment of wasting in connection with chronic obstructive pulmonary disease (COPD); treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of growth retardation associated with the Prader-Willi syndrome and Turner's syndrome; increasing the growth rate of a patient having partial growth hormone insensitive syndrome; accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients; treatment of osteochondrodysplasias; treatment of Noonan's syndrome; treatment of schizophrenia; treatment of depression; improvement of cognitive function (e.g., treatment of dementia; treatment of Alzheimer's disease; treatment of delayed wound healing and psychosocial deprivation; treatment of catabolism in connection with pulmonary dysfunction and ventilator dependency; treatment of cardiac dysfunction (e.g. associated with valvular disease, myocarial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; adjuvant treatment for ovulation induction; stimulation of thymic development and prevention of the age-related decline of thymic function; treatment of immunosuppressed patients; treatment of sarcopenia; treatment of wasting in connection with AIDS; treatment of wasting in connection with multiple sclerosis or other neurodegenerative disorders; improvement in muscle strength, mobility, maintenance of skin thickness; hair/nail growth; treatment of metabolic homeostasis and renal homeostasis (e.g., in the frail elderly); stimulation of osteoblasts, bone remodelling and cartilage growth; regulation of food intake; stimulation of the immune system in companion animals and treatment of disorders of aging in companion animals; promoting growth in livestock; stimulation of wool growth in sheep; increasing milk production in livestock; treatment of insulin resistance including NIDDM, in mammals (e.g. humans); treatment of insulin resistance in the heart; improvement of sleep quality and correction of the relative hyposomatotropism of senescence due to high increase in REM sleep and a decrease in REM latency; treatment of hypothermia; treatment of frailty such as that associated with aging; treatment of congestive heart failure; treatment of hip fractures; treatment of immune deficiency in individuals with a depressed T4/T8 cell ratio; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in elderly); enhancing the activity of protein kinase B (PKB); improvement of the overall pulmonary function; treatment of sleep disorders; and the treatment of the catabolic state of prolonged critical illness. The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727-34 (1997), may be treated employing the compounds of the invention.

B. Combinations

The compounds of the present invention may be employed alone or in combination with each other and/or other growth hormone secretagogues or other suitable therapeutic agents useful in the treatment of the aforementioned disorders including: anti-diabetic agents; anti-osteoporosous agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phosphodiesterase inhibitors; protein tyrosine kinase inhibitors; thyroid mimetics (including thyroid receptor antagonists); anabolic agents; HIV or AIDS therapies; therapies useful in the treatment of Alzheimer's disease and other cognitive disorders; therapies useful in the treatment of sleeping disorders; anti-proliferative agents; anti-tumor agents; and/or anti-ulcer and gastroespheageal reflux disease agents.

Examples of suitable anti-diabetic agents for use in combination with the compounds of the present invention include biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 (attorney docket LA27), glucagon-like peptide-1 (GLP-1), and dipeptidyl peptidase IV (DP4) inhibitors.

Examples of suitable anti-osteoporosous agents for use in combination with the compounds of the present invention include alendronate, risedronate, raloxifene, calcitonin, non-steroidal progestin receptor agonists, RANK ligand agonists, calcium sensing receptor antagonists, TRAP inhibitors, selective estrogen receptor modulators (SERM), estrogen and AP-1 inhibitors;

Examples of suitable anti-obesity agents for use in combination with the compounds of the present invention include aP2 inhibitors such as those disclosed in U.S. Ser. No. 09/519,079 filed Mar. 6, 2000 (attorney docket LA27), PPAR gamma antagonists, PPAR delta agonists, and orlistat.

Examples of suitable antinflammatory agents for use in combination with the compounds of the present invention include prednisone, dexamethasone, Enbrel, cyclooxygenase inhibitors (i.e., COX-1 and/or COX-2 inhibitors such as NSAIDs, aspirin, indomethacin, ibuprofen, piroxicam, Naproxen, Celebrex, Vioxx), CTLA4-Ig agonists/antagonists, CD40 ligand antagonists, integrin antagonists, alpha4 beta7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., zelmac and Maxi-K openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, choesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phosphodiesterase inhibitiors for use in combination with the compounds of the present invention include PDEIII inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone and SARMs.

Examples of suitable HIV or AIDS therapies for use in combination with the compounds of the present invention include indinavir sulfate, saquinavir, saquinavir mesylate, amprenavir, ritonavir, lopinavir, ritonavir/lopinavir combinations, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, taxol, FK 506, and adriamycin.

Examples of suitable anti-tumor agents for use in combination with the compounds of the present invention include taxol, adriamycin, epothilones, cisplatin and carboplatin.

Compounds of the present invention may further be used in combination with nutritional supplements such as those described in U.S. Pat. No. 5,179,080, especially in combination with whey protein or casin, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatine, and coenzyme Q-10.

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the present invention are agents that are growth hormone secretagogues and can be administered to various mammalian species, such as monkeys, dogs, cats, rats, humans, etc., in need of treatment. These agents can be administered systemically, such as orally or parenterally.

The compounds of the invention can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), anti-oxidants (ascorbic acid or sodium bisulfite) or the like. Oral dosage forms are preferred, although parenteral, intranasal or aerosol forms are quite satisfactory as well.

The dose administered must be carefully adjusted according to the age, weight, and condition of the patient, as well as the route of administration, dosage form and regimen, and the desired result. In general, the dosage forms described above may be administered in amounts from about 0.0001 to about 100 mg/kg or body weight or in an amount within the range from about 1 to about 1000 mg per day, preferably, from about 5 to about 500 mg per day in single or divided doses of one to four times daily.

EXAMPLES

The following Examples represent preferred embodiments of the invention. All temperatures are in ° C. unless indicated otherwise.

General Experimental

Method A: The term HPLC refers to a Shimadzu high performance liquid chromatography using a 4 minute gradient of 0-100% solvent B [MeOH:H2O:0.2% H3PO4] with a 1 min. hold, an ultra violet (uv) detector set at 220 nM and using a column (4.6×50 mm) packed with YMC C18 5 micron resin.

A mixture of solvent A (10% MeOH/90% H$_2$O/0.2% TFA) and solvent B (90% MeOH/10% H2O/0.2% TFA) are used for preparative reverse phase HPLC in an automated Shimadzu system. The preparative columns are packed with YMC ODS C18 5 micron resin.

Method B: The term HPLC refers to a Shimadzu high performance liquid chromatography using an 8 minute gradient of 0-100% solvent B [acetonitrile:H2O:0.1% TFA] with a 3 min. hold, an ultra violet (uv) detector set at 220 nM, and using a column (4.6×75 mm) packed with Zorbax C18 5 micron resin. A mixture of solvent A (10% acetonitrile/90% H$_2$O/0.1% TFA) and solvent B (90% acetonitrile/10% H2O/ 0.1% TFA) are used for preparative reverse phase HPLC in an automated Shimadzu system. The preparative columns are packed with YMC ODS C18 5 micron resin.

Method C: The term HPLC refers to a Shimadzu high performance liquid chromatography using an 8 minute gradient of 0-100% solvent B [MeOH:H2O:0.2% H3PO4] with a 2 min. hold, an ultra violet (uv) detector set at 220 nM, and using a column (4.6×75 mm) packed with Zorbax C18 5 micron resin.

The preparative column for the chiral preparative HPLC was packed with Chiralpak AD 2 μM (5×50 cm) using Isopropyl alcohol and hexane as the solvents.

Example 1

2-Amino-N-[1-(6-bromo-[1,2,4]triazolo[4,3-a]pyridin-3-yl)-3-phenyl-propyl]-2-methyl-propionamide

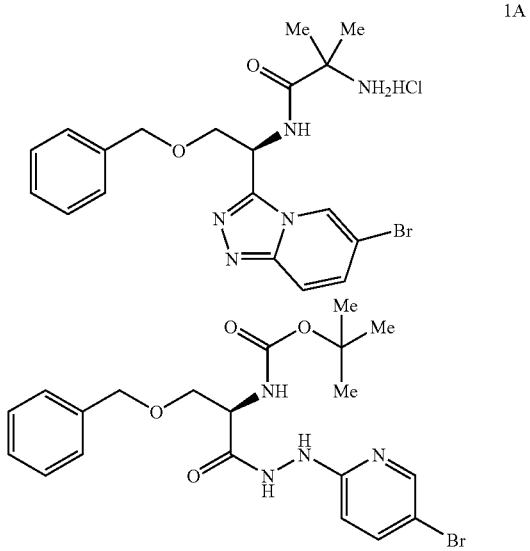

To a THF (100 ml) solution of 3-benzyloxy-2-tert-butoxycarbonylamino -propionic acid (20.0 g, 67.8 mmol) was added N-methyl morpholine (11.2 ml, 101.7 mmol), followed by the addition of iso-butyl chloroformate (11.1 ml, 74 mmol) dropwise. A White suspension was formed. This suspension was stirred at r.t. For 10 min and then 5-bromo-pyridin-2-yl hydrazine (14.1 g, 74.6 mmol) was added in three portions. The resulting suspension was stirred at r.t. for 1 h and then the solvent was removed under reduced pressure until a thick slurry was formed. Water was added and the suspension was stirred to ensure the solid was finely dispersed. The off-white solid was filtered and washed with NaOH (1N, 100 ml), water (100 ml) and HCl(1N, 100 ml) and then water (200 ml) dried to give 1A (31.5 g, 100%).

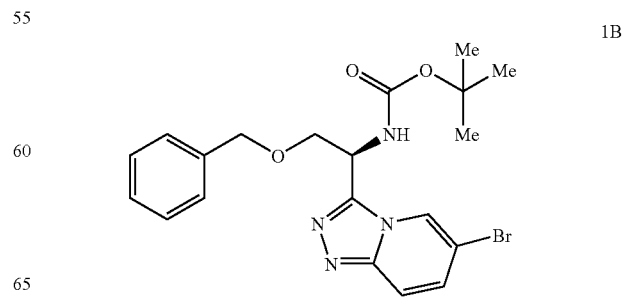

To a THF (100 ml) solution of 1A (30 g, 64.3 mmol) was added triphenylphosphine (20.2 g, 77.2 mmol), and trimethylsilylazide (10.2 ml, 77.2 mmol). To this solution was added diethyl diazacarboxylate (DEAD, 15.2 ml, 96.5 mmol) in rapid drops. The solution became hot. After the addition was complete, the solution was allowed to stir at r.t. until all starting material was consumed (<2 h). The solvent was removed under reduced pressure to give 1B

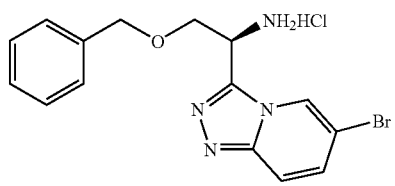

1B (64.3 mmol) was suspended in HCl-dioxane (160 ml, 4 MHCl in dioxane). The suspension was stirred at r.t. until all of the starting material was consumed. The suspension was concentrated to a thick slurry and then diluted with THF (100 ml). The solid was collected by filtration and rinsed with excess $CH_2Cl_2$, diethyl ether, and dried to give 1C (24.5 g, 99%).

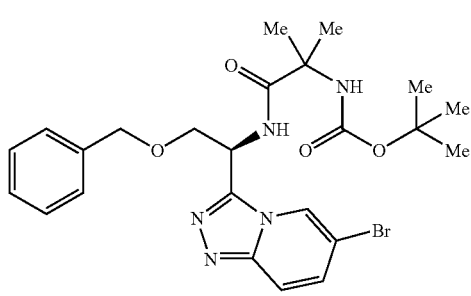

To a THF (100 ml) solution of 2-tert-butoxycarbonylamino-2-methyl-propionic acid (9.5 g, 47.9 mmol) was added EDAC (11.2 g, 58.8 mmol) and HOBT (8.0 g, 58.8 mmol), DMAP (4.8 g, 39.2 mmol), and (i-Pr)$_2$NEt (20.5 ml, 117.6 mmol). This solution was stirred at r.t. for 10 min before the addition of 1C (15 g, 39.2 mmol). The reaction was completed in <1 h. The solvent was then removed under reduced pressure and the residue was dissolved in EtOAc (200 ml). The organic solution was washed with water (200 ml), NaOH (0.5N, 200 ml), HCl (0.5N, 200 ml), and water (200 ml). The organic layer was dried over $Na_2SO_4$ and concentrated to give a white solid 1D (20.0 g, 90%)

1D (1.0 g, 1.8 mmol) was dissolved in 4 M HCl-dioxane (5 ml). The solution was stirred at r.t. until all starting material was consumed. The solvent was evaporated under reduced pressure and the white solid was triturated with diethyl ether to afford pure product of the title compound (0.84 g, <99%). MS (M+H) 433, HPLC retention time 2.07 min.

Examples 2 to 15

Examples 2-15 in Table 1 have been synthesized utilizing the procedures described in Example 1, utilizing the appropriate starting materials.

TABLE 1

| Compound number | R | HPLC Purity (%) | HPLC Retention (mm) | Mass M + H |
|---|---|---|---|---|
| 2 | (triazolopyridine-CF3) | 100 | 2.53 | 422 |
| 3 | (triazolopyridine-NO2) | 90 | 1.93 | 399 |

TABLE 1-continued

| Compound number | R | HPLC Purity (%) | HPLC Retention (mm) | Mass M + H |
|---|---|---|---|---|
| 4 | [3-(6-chloro-[1,2,4]triazolo[4,3-a]pyridin-3-yl)] | 90 | 1.92 | 388 |
| 5 | [3-(6-fluoro-[1,2,4]triazolo[4,3-a]pyridin-3-yl)] | 91 | 1.60 | 372 |
| 6 | [3-([1,2,4]triazolo[4,3-a]pyridin-3-yl)] | 90 | 1.29 | 354 |
| 7 | [3-(6-cyano-[1,2,4]triazolo[4,3-a]pyridin-3-yl)] | 99 | 1.60 | 379 |
| 8 | [3-(7-trifluoromethyl-[1,2,4]triazolo[4,3-a]pyridin-3-yl)] | 94 | 2.46 | 422 |
| 9 | [3-(8-bromo-[1,2,4]triazolo[4,3-a]pyridin-3-yl)] | 96 | 1.80 | 432 |
| 10 | [3-(5-chloro-[1,2,4]triazolo[4,3-a]pyridin-3-yl)] | 94 | 1.73 | 388 |
| 11 | [3-(8-nitro-[1,2,4]triazolo[4,3-a]pyridin-3-yl)] | 89 | 1.73 | 399 |

TABLE 1-continued

| Compound number | R | HPLC Purity (%) | HPLC Retention (mm) | Mass M + H |
|---|---|---|---|---|
| 12 | triazolopyridine with CF₃ and Cl | 91 | 2.37 | 456 |
| 13 | triazolopyridine with Me and CF₃ | 100 | 2.40 | 435 |
| 14 | pyrazolo-triazolopyridine with 3× Me | 100 | 2.12 | 435 |
| 15 | triazolopyridine with OMe | 88 | 1.97 | 384 |

Example 16

2-Amino-2-methyl-N-[3-phenyl-1-(6-trifluoromethyl-[1,2,4]-triazolo[4,3-a]pyridin-3-yl)-propyl]-propionamide

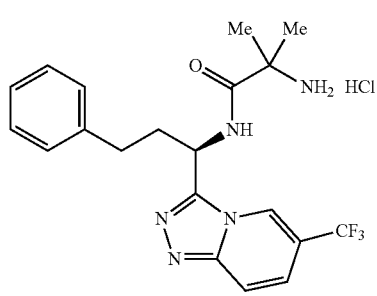

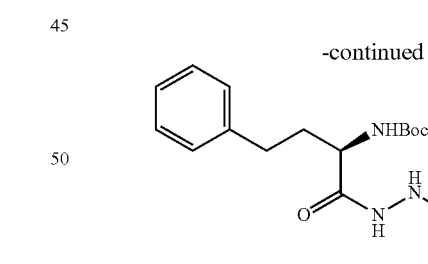

16A

To a THF (100 ml) solution of 2-tert-Butoxycarbony-lamino-4-phenyl-butyric acid (2.0 g, 7.1 mmol) was added TEA (0.98 ml, 7.1 mmol), followed by the addition of iso-butyl chloroformate (0.98 g, 7.1 mmol) dropwise. A White suspension was formed. This suspension was stirred at r.t. for 10 min and then (5-Trifluoromethyl-pyridin-2-yl)-hydrazine (1.3 g, 7.1 mmol) was added in three portions. The resulting suspension was stirred at r.t. for 1 h and then the solvent was removed under reduced pressure until a thick slurry was formed. Water (200 ml) was added and the suspension was stirred to ensure the solid was finely dispersed. The off-white solid was filtered and washed with NaOH (1N, 100 ml), water (100 ml) and HCl (1N, 100 ml) and then water (200 ml) dried to give 16A (1.9 g, 100%).

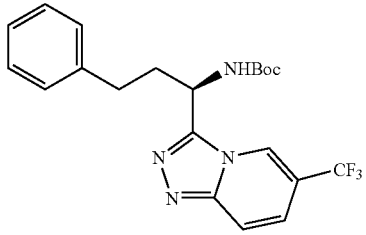

16B

To a THF (100 ml) solution of 16A (1.9 g, 4.3 mmol) was added triphenylphosphine (1.3 g, 5.2 mmol), and trimethylsilyl azide (0.6 g, 5.2 mmol). To this solution was added diethyl diazacarboxylate (DEAD, 1.8 g, 10.8 mmol) in rapid drops. The solution became hot. After the addition was complete, the solution was allowed to stir at r.t. until all starting material was consumed (<2 h). The solvent was removed under reduced pressure to give 16B

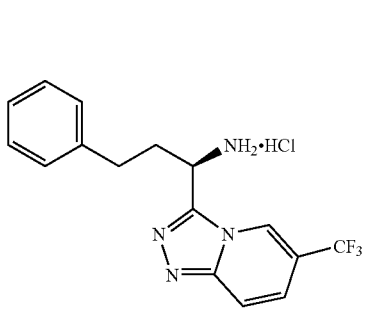

16C 16B was suspended in HCl-dioxane (160 ml, 4M HCl in dioxane). The suspension was stirred at r.t. until all of the starting material was consumed. The suspension was concentrated to a thick slurry and then diluted with THF (100 ml). The solid was collected by filtration and rinsed with excess CH₂Cl₂, diethyl ether, and dried to give 16C

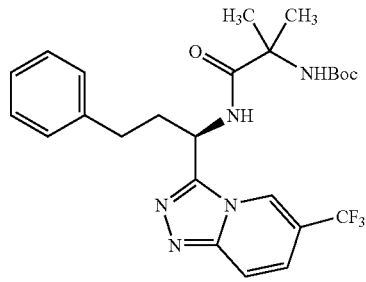

16D

To a THF (100 ml) solution of 2-tert-butoxycarbonylamino-2-methyl-propionic acid (27.5 mg, 0.135 mmol) was added EDAC (29.2 mg, 0.15 mmol) and HOBT (20 mg, 0.15 mmol), DMAP (1.5 mg, 0.01 mmol), and pyridine. This solution was stirred at r.t. for 10 min before the addition of 16C (52 mg, 0.123 mmol). The reaction was completed in <1 h. The solvent was then removed under reduced pressure and the residue was dissolved in EtOAc (200 ml). The organic solution was washed with water (200 ml), NaOH (0.5 N, 200 ml), HCl (0.5 N, 200 ml), and water (200 ml). The organic layer was dried over Na₂SO₄ and concentrated to give a white solid 16D Example 16

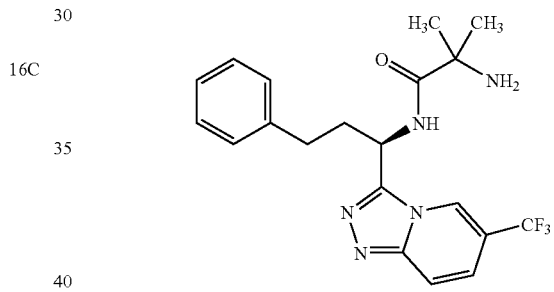

16D was dissolved in 4 M HCl-dioxane (5 ml). The solution was stirred at r.t. until all starting material was consumed. The solvent was evaporated under reduced pressure and the white solid was triturated with diethyl ether to afford pure product (29 mg, 94%). MS (M+H) 406, HPLC retention time 2.3 min.

The following compounds have been prepared utilizing the procedures described in Example 16, which started with the corresponding acids (step A), hydrazines (step A) and amines (Step D) as depicted in Table 2.

TABLE 2

| Compound number | | HPLC Purity (%) | HPLC Retention (min) | Mass |
|---|---|---|---|---|
| 17 | 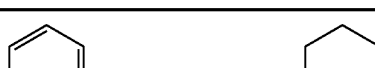 | 98 | 2.28 | 432 |

TABLE 2-continued
| Compound number | | HPLC Purity (%) | HPLC Retention (min) | Mass |
|---|---|---|---|---|
| 18 | 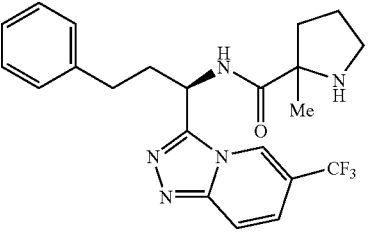 | 91 | 2.28 | 432 |
| 19 | 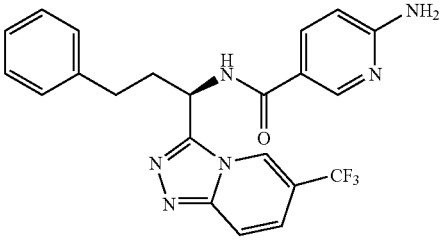 | 95 | 2.47 | 441 |
| 20 | 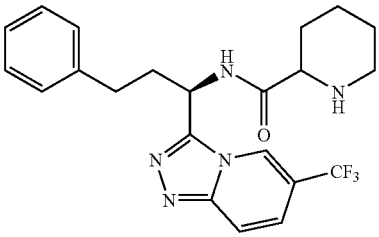 | 98 | 2.26, 2.42 | 432 |
| 21 | 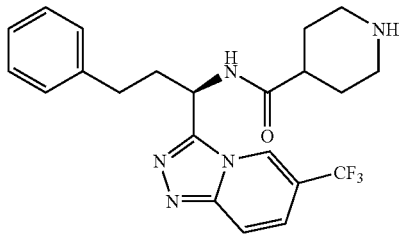 | 98 | 2.35 | 432 |
| 22 | 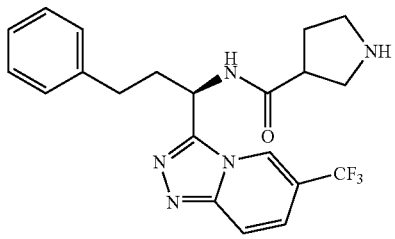 | 94 | 2.31 | 418 |
| 23 | 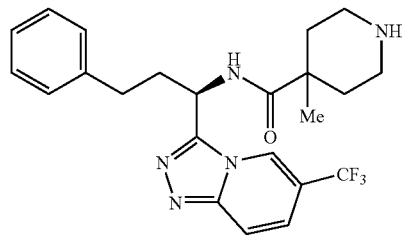 | 93 | 2.47 | 446 |

TABLE 2-continued

| Compound number | | HPLC Purity (%) | HPLC Retention (min) | Mass |
|---|---|---|---|---|
| 24 | (structure) | 95 | 2.39 | 420 |
| 25 | (structure) | 88 | 2.34 | 420 |

Example 26

6-Amino-N-[2-phenyl-1-(6-trifluoromethyl-[1,2,4]triazolo[4,3-a]pyridin-3-yl)-ethyl]-nicotinamide

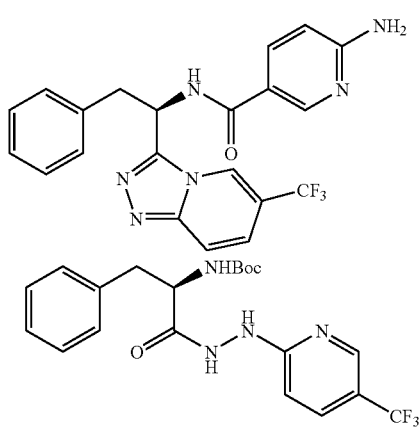

26A

To a THF (100 ml) solution of 2-tert-Butoxycarbonylamino-3-phenyl-propionic acid (2.0 g, 7.1 mmol) was added TEA(0.98 ml, 7.1 mmol), followed by the addition of isobutyl chloroformate (0.98 g, 7.1 mmol) dropwise. A White suspension was formed. This suspension was stirred at r.t. for 10 min and then (5-Trifluoromethyl-pyridin-2-yl)-hydrazine (1.3 g, 7.1 mmol) was added in three portions. The resulting suspension was stirred at r.t. for 1 h and then the solvent was removed under reduced pressure until a thick slurry was formed. Water (200 ml) was added and the suspension was stirred to ensure the solid was finely dispersed. The off-white solid was filtered and washed with NaOH (1N, 100 ml), water (100 ml) and HCl (1N, 100 ml) and then water (200 ml) dried to give 26A(1.9,100%).

Example 26 was prepared utilizing the procedures described in Example 16, substituting with 26A for 16A, 26B for 16B, 26C for 16C, 26D for 16D. Example 26 was obtained as a white foam. MS (M+H) 427, HPLC retention time 2.23 min.

The following compounds have been prepared utilizing the procedures described in Example 26 as depicted in Table 3.

TABLE 3

| Compound number | | HPLC Purity (%) | HPLC Retention (min) | Mass |
|---|---|---|---|---|
| 27 | (structure) | 95 | 2.03 | 418 |

TABLE 3-continued

| Compound number | Structure | HPLC Purity (%) | HPLC Retention (min) | Mass |
|---|---|---|---|---|
| 28 | | 93 | 2.02 | 418 |
| 29 | | 98 | 2.00 | 392 |
| 30 | | 98 | 2.02, 2.16 | 418 |
| 31 | | 80 | 2.08 | 418 |
| 32 | | 88 | 2.06 | 404 |
| 33 | | 90 | 2.15 | 432 |

TABLE 3-continued

| Compound number | | HPLC Purity (%) | HPLC Retention (min) | Mass |
|---|---|---|---|---|
| 34 | (structure) | 88 | 2.14 | 406 |
| 35 | (structure) | 76 | 2.07 | 406 |

Example 36

6-Amino-N-[2-benzyloxy-1-(6-trifluoro methyl-[1,2,4]triazolo[4,3-a]pyridin-3-yl)-ethyl]-nicotinamide

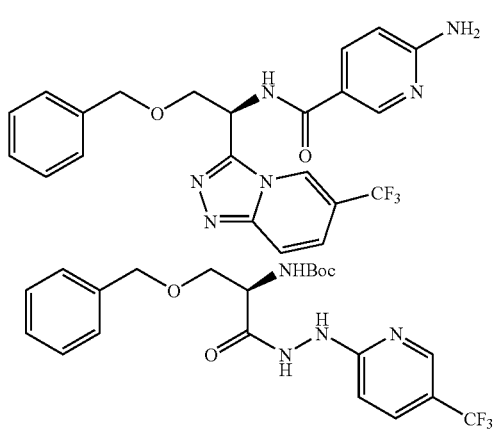

To a THF (100 ml) solution of 3-Benzyloxy-2-tert-butoxycarbonylamino-propionic acid (2.0 g, 7.1 mmol) was added TEA (0.98 ml, 7.1 mmol), followed by the addition of iso-butyl chloroformate (0.98 g, 7.1 mmol) dropwise. A White suspension was formed. This suspension was stirred at r.t. for 10 min and then (5-Trifluoromethyl-pyridin-2-yl)-hydrazine (1.3 g, 7.1 mmol) was added in three portions. The resulting suspension was stirred at r.t. for 1 h and then the solvent was removed under reduced pressure until a thick slurry was formed. Water (200 ml) was added and the suspension was stirred to ensure the solid was finely dispersed. The off-white solid was filtered and washed with NaOH (1N, 100 ml), water (100 ml) and HCl (1N, 100 ml) and then water (200 ml) dried to give 36A(1.9,100%).

Example 36 was prepared utilizing the procedures described in Example 16, substituting with 36A for 16A 36B for 16B, 36C for 16C, 36D for 16D. Example 36 was obtained as a white foam. MS (M+H) 456,HPLC retention time 2.4 in.

The following compounds have been prepared utilizing the procedures described in Example 36 as depicted in Table 4.

TABLE 4

| Compound number | | HPLC Purity (%) | HPLC Retention (min) | Mass |
|---|---|---|---|---|
| 37 | (structure) | 98 | 2.38 | 447 |

TABLE 4-continued

| Compound number | | HPLC Purity (%) | HPLC Retention (min) | Mass |
|---|---|---|---|---|
| 38 | | 100 | 2.29 | 447 |
| 39 | | 97 | 2.31 | 447 |
| 40 | | 95 | 2.08 | 445 |
| 41 | | 95 | 2.22 | 473 |
| 42 | | 97 | 2.11 | 447 |
| 43 | | 90 | 2.09 | 447 |

TABLE 4-continued

| Compound number | | HPLC Purity (%) | HPLC Retention (min) | Mass |
|---|---|---|---|---|
| 44 | 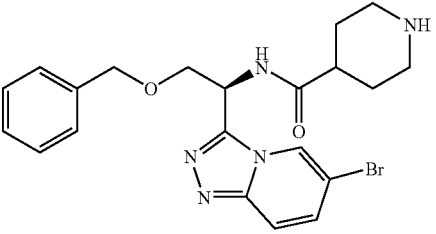 | 96 | 2.09 | 459 |

Example 45

2-Amino-N-{2-benzyloxy-1-[6-(2-fluoro-phenyl)-1,2,4]-triazolo[4,3-a]pyridin-3-yl]-ethyl}-2-methyl-propionamide

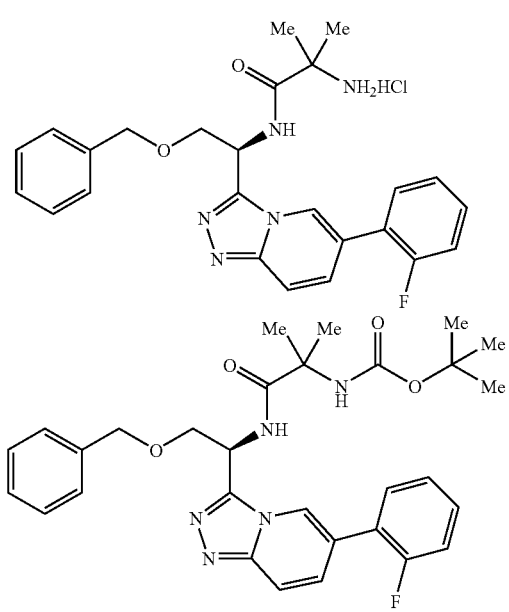

45A

Compound 1D (300 mg, 0.56 mmol), 2-fluorophenylboronic acid (120 mg, 0.86 mmol), Pd(OAc)$_2$ (5 mg, 0.022 mmol), triphenyl phosphine (100 mg, 0.38 mmol), and Et$_3$N (0.24 ml, 1.72 mmol) were dissolved in DMF (2 ml). This solution was heated at 110° C. for 12 h. The resulted mixture was diluted with water (10 ml) and was extracted with EtOAc. The combined organic portion was washed with NH$_4$OH (10%) and brine and dried over anhydrous MgSO$_4$. The solvent was evaporated under reduced pressure to afford a stick liquid. The products were not purified and used directly for the next step.

Example 45

45A was dissolved in 4 M HCl-dioxane (2 ml). The solution was stirred at r.t. until all starting material was consumed. The solvent was evaporated under reduced pressure. The product was purified by preparative HPLC to give the title compound (129 mg, 50%). MS (M+H) 447, HPLC retention time 2.47 min.

The following compounds has been prepared by utilizing the intermediates generated in Example 1 with chemical sequences described in Example 45, utilizing the appropriate starting materials as depicted in Table 5.

TABLE 5

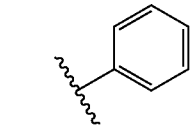

| Compound number | Ar | HPLC Purity (%) | HPLC Retention (min) | Mass |
|---|---|---|---|---|
| 46 | 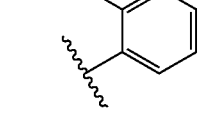 | 100 | 2.45 | 430 |
| 47 | 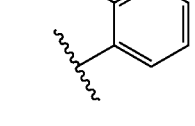 CH$_3$O | 100 | 2.47 | 460 |
| 48 | 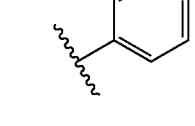 Cl | 98 | 2.63 | 464 |
| 49 | CF$_3$ | 99 | 2.66 | 497 |

TABLE 5-continued

| Compound number | Ar | HPLC Purity (%) | HPLC Retention (min) | Mass |
|---|---|---|---|---|
| 50 | (CF₃O, F-substituted phenyl) | 100 | 2.56 | 477 |

Example 51

2-Amino-N-[2-benzyloxy-1-(6-methanesulfony-lamino-1,2,41-triazolo[4,3-a]pyridin-3-yl)-ethyl]-2-methyl-propionamide

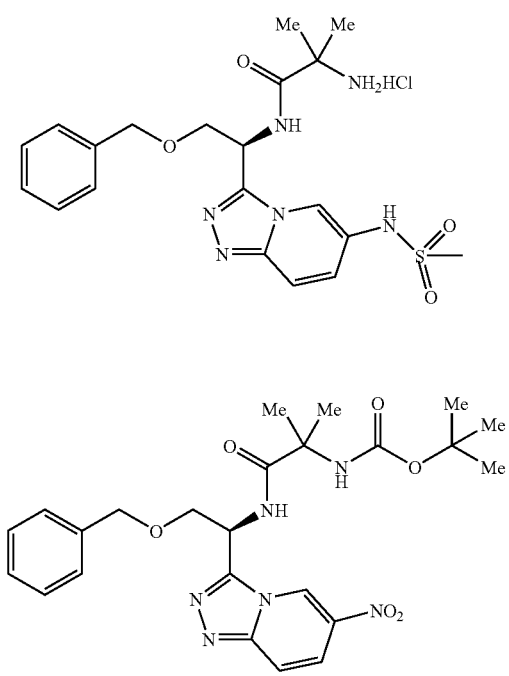

Compound 51A was obtained using the same procedures described for the synthesis of 1D with 5-nitro-2-hydrazinopyridine in place of 5-bromo-2-hydrazinopyridine.

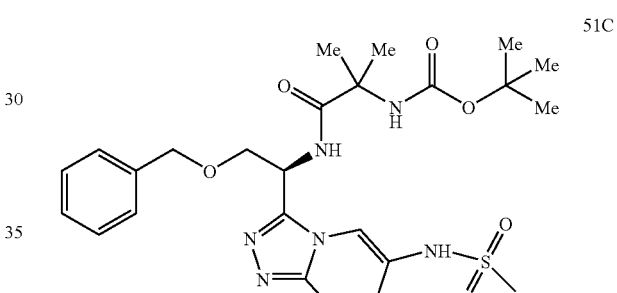

Compound 51A (1.3 g, 2.6 mmol) was dissolved in EtOH (60 ml). Pd/C (35 mg, 10% Pd by weight) was added under $N_2$. This mixture was then subjected to hydrogenation at 50 Psi for 3 h to afford 51B. Solvent was removed under reduced pressure and the product was pure enough (>90%) and was used directly for the next reactions.

Compound 51B (200 mg, 0.43 mmol) was dissolved in $CH_2Cl_2$ (5 ml) and pyridine (0.14 ml, 2.1 mmol) was added. To this solution was added the corresponding methyl sulfonyl chloride (0.05 ml, 0.65 mmol). Reactions were completed in 1.5 h. The reactions were then diluted with $CH_2Cl_2$ (25 ml) and washed with HCl (1N, 20 ml), aqueous saturated $NaHCO_3$ (20 ml), and water (20 ml). Purification by flash chromatography on silica gel (5% $CH_3OH$/ as elutant) gave 51C (90 mg, 40%).

Example 51

Compound 51C was dissolved in HCl (4 ml, 4M in dioxane) and was stirred at r.t. until the reaction was completed. The solvent was removed under reduced pressure. The products were purified by preparative HPLC to give the title compound as a foam (60 mg, 82%). MS (M+H) 447, HPLC retention time 1.73 min.

The following compounds in Table 6 have been synthesized utilizing the procedures described in Example 51, utilizing the appropriate starting materials.

TABLE 6

[Structure shown: 2-amino-2-methyl-propionamide derivative of benzyloxy-ethyl-triazolo[4,3-a]pyridine with NHR substituent, as HCl salt]

| Compound number | R | HPLC Purity (%) | HPLC Retention (min) | Mass |
|---|---|---|---|---|
| 52 | -S(O)₂-Ph | 90 | 2.32 | 509 |
| 53 | -S(O)₂-CH(Me)₂ | 97 | 2.02 | 475 |
| 54 | -S(O)₂-(2-thienyl) | 97 | 2.23 | 515 |

Example 55

N-[1-(6-Acetylaminol-[1,2,4]triazolo[4,3-a]pyridin-3-yl)-2-benzyloxy-ethyl]-2-amino-2-methyl-propionamide

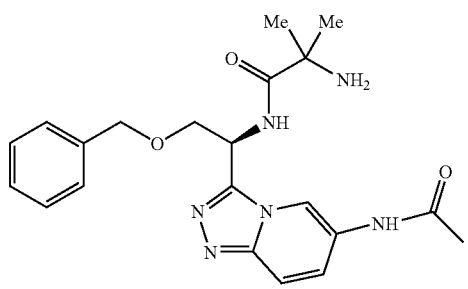

55A

Compound 51B (130 mg, 0.28 mmol) was dissolved in CH₂Cl₂ (2 ml) and Et₃N (0.2 ml, 1.4 mmol) was added. To this solution was added acetyl chloride (0.026 ml, 0.36 mmol). After stirring overnight at r.t, the reaction was then diluted with CH₂Cl₂ (25 ml) and washed with HCl (1N, 20 ml), NaHCO₃ (sat. 20 ml), and water (20 ml). The crude product were purified with flash chromatography (5% CH₃OH/CH₂Cl₂) to give 55A (80 mg, 56%).

Example 55

Compound 55A was dissolved in HCl (4 ml, 4M in dioxane) and was stirred at r.t. until the reaction was completed. The solvent was removed under reduced pressure. The products were purified by preparative HPLC to give the title compound as a foam. MS (M+H) 411, HPLC retention time 1.86 min.

The following compounds in Table 7 have been synthesized utilizing the procedures described in Example 55, utilizing the appropriate starting materials.

TABLE 7

[Structure shown: similar triazolo[4,3-a]pyridine scaffold with NH-R substituent]

| Compound number | R | HPLC Purity (%) | HPLC Retention (min) | Mass |
|---|---|---|---|---|
| 56 | -C(O)-CH(Me)₂ | 88 | 2.24 | 439 |

Example 57

2-Amino-N-[2-benzyloxy-1-(6-chloro-5-dimethylamino-[1,2,4]triazolo[4,3-a]pyridin-3-yl)-ethyl]-2-methyl-propionamide

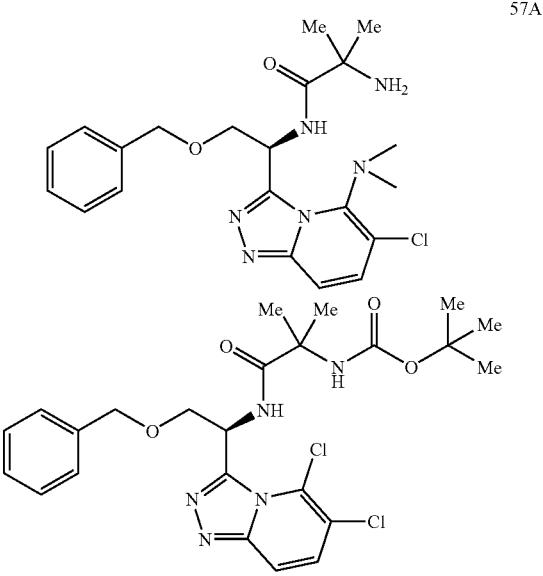

57A

Compound 57A was obtained using the same procedures described for the synthesis of 1D with the corresponding 2-hydrazinopyridine.

57B

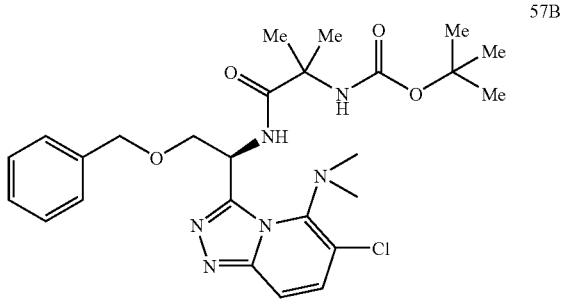

Compound 57A (250 mg, 0.48 mmol) in Dimethylamine (3 ml) was heated at 100° C. for 1.5 h. The reaction was diluted with water (10 ml) and extracted with EtOAc. The combined organic portions were dried over $Na_2SO_4$ and the solvent was evaporated under reduced pressure. The crude product was purified with flash chromatography (2% $CH_3OH/CH_2Cl_2$) to give 57B (140 mg, 55%).

Example 57

57A (140 mg, 0.26 mmol) was dissolved in HCl (5 ml, 4 M HCl in dioxane) and stirred at r.t. until all the starting materials was consumed. Purification by preparative HPLC gave the title compound (51 mg). MS (M+H) 431, HPLC retention time 2.35 min.

The following compounds in Table 8 have been synthesized utilizing the procedures described in Example 57, utilizing the appropriate starting materials.

TABLE 8

| Compound number | Substituted Triazolopyridine (R) | HPLC Purity (%) | HPLC Retention (min) | Mass |
|---|---|---|---|---|
| 58 | | 96 | 1.51 | 397 |
| 59 | | | | |
| 60 | | | | |

TABLE 8-continued

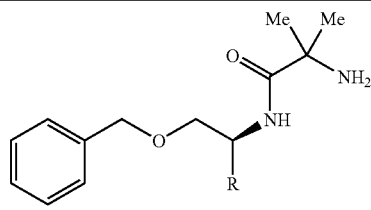

| Compound number | Substituted Triazolopyridine (R) | HPLC Purity (%) | HPLC Retention (min) | Mass |
|---|---|---|---|---|
| 61 | 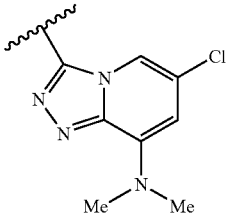 | 98 | 2.51 | 431 |
| 62 | 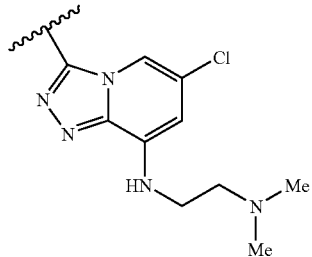 | 97 | 1.34 | 475 |

Example 63

2-Amino-N-{2-benzyloxy-1-[6-chloro-5-(2-methoxy-ethoxy)-[1,2,4]triazolo[4,3-a]pyridin-3-yl]-ethyl}-2-methyl-propionamide

63A

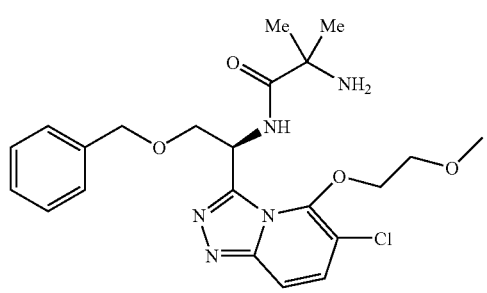

-continued

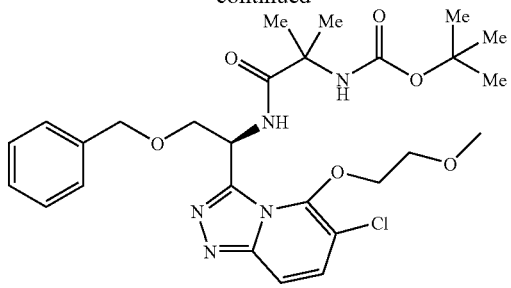

Compound 57A (250 mg, 0.48 mmol) in 2-Methoxy-ethanol (1 ml) and Cesium carbonate (155 mg, 0.48 mmol) was heated at 100° C. for 1.5 h. The reaction was diluted with water (10 ml) and extracted with EtOAc. The combined organic portions were dried over $Na_2SO_4$ and the solvent was evaporated under reduced pressure to give 63A.

Example 63

63A was dissolved in HCl (5 ml 4 M HCl in dioxane) and stirred at r.t. until all the starting materials was consumed. Purification by preparative HPLC gave the title compound (18.6 mg). MS (M+H) 462, HPLC retention time 2.23 min.

The following compounds in Table 9 have been synthesized utilizing the procedures described in Example 63, utilizing the appropriate starting materials.

TABLE 9

| Compound number | R | HPLC Purity (%) | HPLC Retention (min) | Mass |
|---|---|---|---|---|
| 64 | | 90 | 1.97 | 420 |
| 65 | | | | |
| 66 | | | | |
| 67 | | | | |
| 68 | | | | |

Example 69

3-[1-(2-Amino-2-methyl-propionylamino)-2-benzyloxy-ethyl]-1,2,41-triazolo[4,3-a]pyridine-6-carboxylic acid methylamide

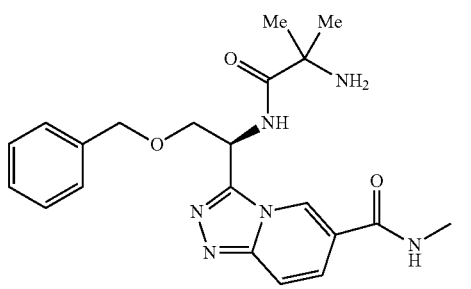
69A

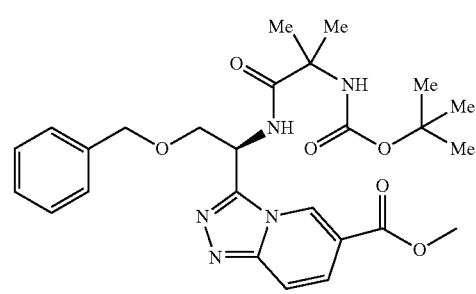

To 1D (0.7 g, 1.32 mmol) in DMF (10 ml) and MeOH (5 ml) was added 1,3-Bis(diphenylphosphino)-propane (217 mg, 0.53 mmol), DBU (240 mg, 1.58 mmol) and palladium acetate (148 mg, 0.66 mmol). The mixture was degassed and the flushed with carbon monoxide and kept at 20 psi. The reaction was heated at 85° C. overnight. The catalyst was filtered and the solution concentrated. The residue was taken in EtOAc, washed with water, brine, dried and concentrated. The crude product was purified with flash chromatography to give 69A as a white foam.

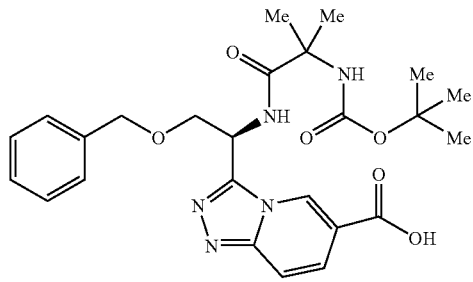
69B

To 69A (2.3 g, 4.5 mmol) in THF (20 ml) was added lithium hydroxide (40 ml of 2N solution). The mixture was stirred for 3 h at r.t. 1NHCl was added to adjust the pH to 2. The solution was extracted with $CH_2Cl_2$, washed, dried and concentrated to give 69B.

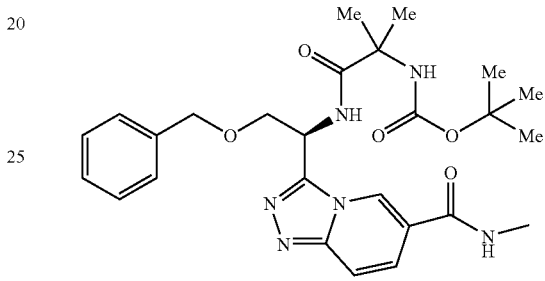
69C

To a $CH_2Cl_2$(2 ml) solution of 69B(150 mg, 0.3 mmol) was added EDAC (86 mg, 0.45 mmol) and HOBT (60 mg, 0.45 mmol) and (i-Pr)$_2$NEt (58 mg, 0.45 mmol) and then 2M solution of methylamine in THF (0.225 ml, 0.45 mmol) The reaction was stirred overnight and then extracted with EtOAc. The organic solution was washed with water, brine, dried and concentrated to give a white solid 69C.

Example 69

69C was dissolved in HCl (5 ml 4 M HCl in dioxane) and stirred at r.t. until all the starting materials was consumed. Purification by preparative HPLC gave the title compound as an oil. MS (M+H) 410, HPLC retention time 2.4 min.

The following compounds in Table 10 have been synthesized utilizing the procedures described in Example 69, utilizing the appropriate starting materials.

TABLE 10

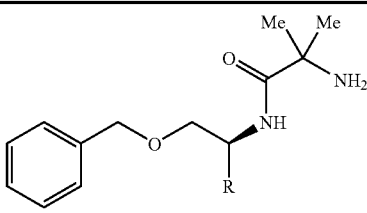

| Compound number | R | HPLC Purity (%) | HPLC Retention (min) | Mass |
|---|---|---|---|---|
| 70 | NH-(CH$_2$)$_4$OH) | 93 | 2.56 | 468 |

TABLE 10-continued

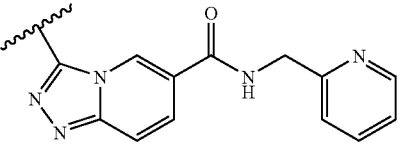

| Compound number | R | HPLC Purity (%) | HPLC Retention (min) | Mass |
|---|---|---|---|---|
| 71 | 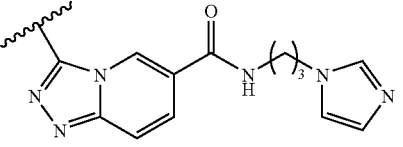 | 90 | 2.13 | 487 |
| 72 | 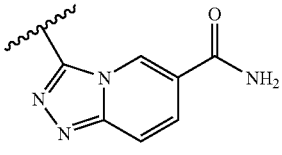 | 90 | 2.00 | 505 |
| 73 | 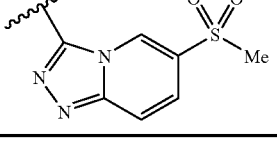 | 93 | 1.39 | 396 |
| 74 | 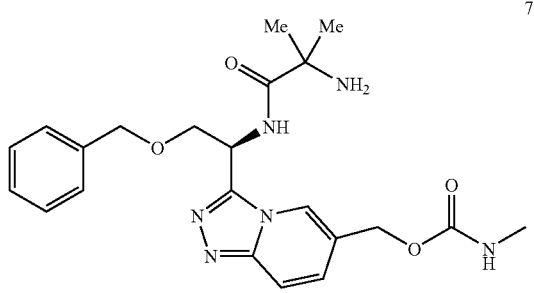 | 95 | 2.39 | 432 |

Example 75

Methyl-carbamic acid 3-[1-(2-amino-2-methyl-propionylamino)-2-benzyloxy-ethyl]-[1,2,4]-triazolo[4,3-a]pyridin-6-ylmethyl ester

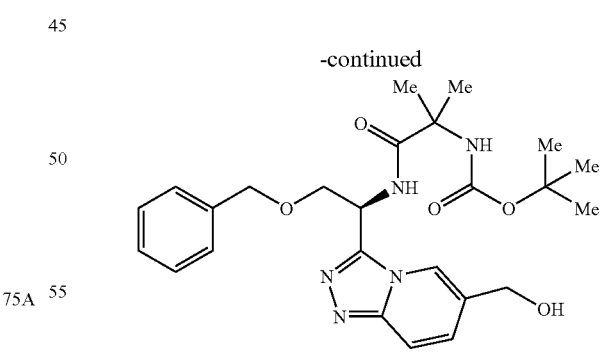

75A

-continued

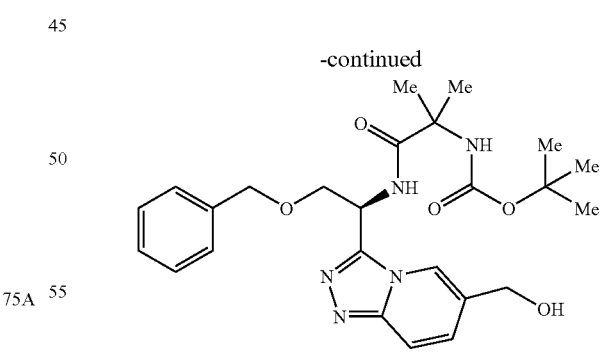

To a stirred solution of 59A (50 mg, 0.098 mmol) in CH$_2$Cl$_2$ at −78° C. was added 1.5M solution of DIBAL in toluene (0.4 ml, 0.58 mmol) and stirred at r.t. overnight. The solution was cooled to 0° C. and then a 1M solution of sodium potassium tartarate was added slowly. Stirred for 1.5 h at r.t. The precipitate formed is filtered off through a pad of celite. And then extracted with CH$_2$Cl$_2$, washed, dried and concentrated to give 75A.

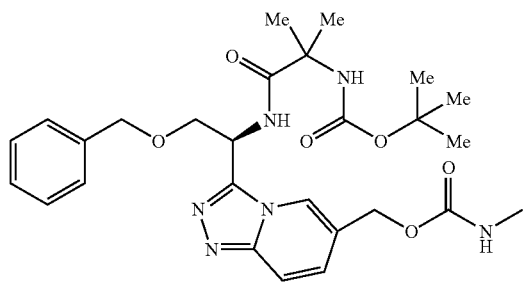
75B

To 75A (180 mg, 0.2 mmol) in CH$_2$Cl$_2$ (2 ml) 0° C. was added TEA (60 mg, 0.6 mmol) and methyl isocyanate (24 mg, 0.4 mmol). Reaction was warmed to r.t. and stirred overnight. The solution was concentrated to give 75B Example 75

75B was dissolved in HCl (5 ml 4 M HCl in dioxane) and stirred at r.t. until all the starting materials was consumed. Purification by preparative HPLC gave the title compound as oil. MS (M+H) 441, HPLC retention time 2.48 min.

Example 76

3-[1-(2-Amino-2-methyl-propionylamino)-2-benzyloxy-ethyl]-5,6,7,8-tetrahydro-[1,2,4]triazolo[4,3-a]pyridine-8-carboxylic acid ethyl ester

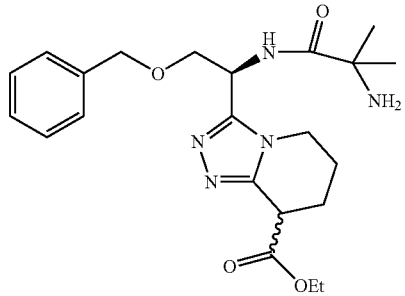
76A

To a cooled solution of potassium hydroxide (100 ml, 40% in water) in ether (500 ml) at 0° C. was added 1-methyl-3-nitro-1-nitoroguanidine(15 g, 0.102 mol) slowly over 15 min. The upper organic phase was poured into a flask containing 30 g potassium hydroxide. After 5 min. the ether solution was slowly added to 3-Benzyloxy-2-tert-butoxycarbonylamino-propionic acid (20.5 g, 0.069 mol) in THF/CH$_2$Cl$_2$(200 ml). After stirring for 5 min the solution was concentrated to give 76A.

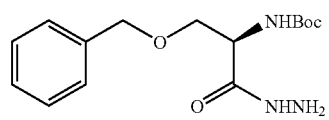
76B

To a solution of 76A (22.8 mg, 74.8 mmol) in 250 ml MeOH was added hydrazine (4.8 g, 149.8 mmol) and the mixture refluxed for 2 days. The solution was concentrated to give crude 76B.

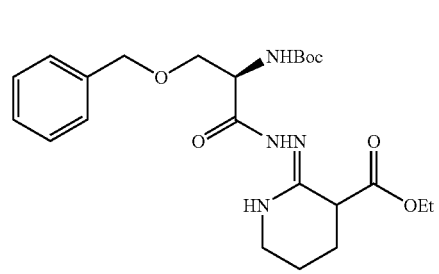
76C

To a solution of 2-Oxo-piperidine-3-carboxylic acid ethyl ester (0.86 g, 5 mmol) in CH$_2$Cl$_2$ (10 ml) was added trimethyloxonium tetrafluoroborate (0.74 g, 5 mmol) and stirred overnight followed by addition of 76B (1.5 g, 5 mmol). The mixture was stirred for 24 h. The solution was diluted with CH$_2$Cl$_2$, washed with water, brine, dried and concentrated to give 76C as a white foam (2.5 g, <99%).

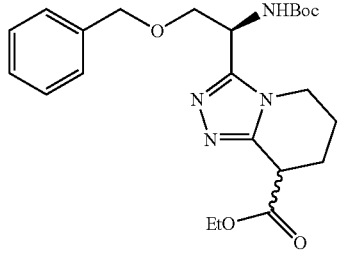
76D

The solution of 76C (1.3 g, 2.8 mmol) in MeOH (27 ml) was refluxed for 4 days. The mixture was concentrated to give 76D.

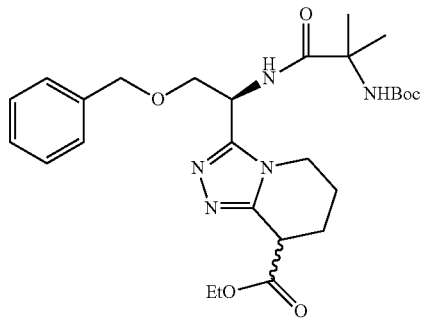
76E

To 76D (1.2 g, 2.8 mmol) in CH$_2$Cl$_2$ was added HCl (5 ml 4 M HCl in dioxane) and stirred at r.t. until all the starting materials was consumed. The solution was concentrated. To a CH$_2$Cl$_2$ (15 ml) solution of the residue was added EDAC (0.8 g, 0.4.16 mmol) and HOBT (0.56 g, 4.16 mmol) and (i-Pr)$_2$NEt (7.15 g, 55.4 mmol) and 2-tert-butoxycarbonylamino-2-methyl-propionic acid (0.68 g, 3.32 mmol). The reaction was stirred overnight and then extracted with EtOAc. The organic solution was washed with water, brine, dried and concentrated. Purification by flash chromatography on silica gel (5% CH$_3$OH/CH$_2$Cl$_2$ as elutant) gave 76E.

Example 76

76E (50 mg, 0.1 mmol) in CH$_2$Cl$_2$ (5 ml) was treated with HCl (2 ml 4 M HCl in dioxane) and stirred at r.t. until all the starting materials was consumed. Purification by preparative HPLC gave the title compound as a salt (22 mg, 55%). MS (M+H) 430, HPLC retention time 2.63 min.

Example 77

2-Amino-N-[2-benzyloxy-1-(5,6,7,8-tetrahydro-[1,2,4]triazolo[4,3-a]pyridin-3-yl)-ethyl]-2-methyl-propionamide

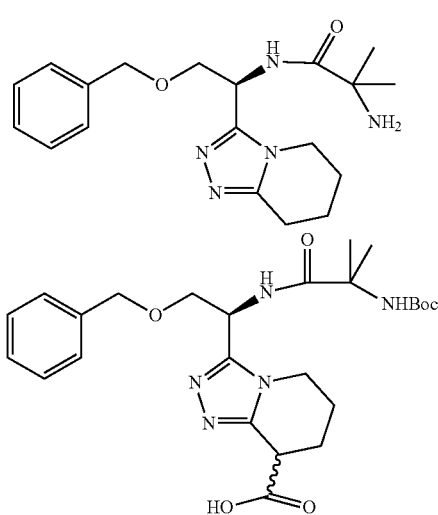

77A

To a solution of 76E (0.32 g, 0.6 mmol) in THF (1 ml) was added H$_2$O (4 ml), MeOH (0.5 ml) and Lithium hydroxide (6 ml of 4N solution). The mixture was stirred at r.t. for 1.5 h. The pH of the solution was adjusted to 2 with the slow addition of 1N HCl, followed by extraction with CH$_2$Cl$_2$ washed with water, brine, dried and concentrated to give 77A (270 mg, 89%)

Example 77

To 77A (135 mg, 0.27 mmol) in ether (2.5 ml) was added methylamine (0.27 ml, 0.54 mmol, 2M in THF), HOBT (73 mg, 0.54 mmol) and EDAC (103 mg, 0.54 mmol). After stirring for 24 h, the solution was extracted with CH$_2$Cl$_2$, washed with water, brine, dried and concentrated. The residue in CH$_2$Cl$_2$ (2 ml) was treated with HCl (1 ml 4 M HCl in dioxane) and stirred at r.t. until all the starting materials was consumed. Purification by preparative HPLC gave the title compound as a foam (61 mg, 65%). MS (M+H) 358, HPLC retention time 1.86 min.

Example 78

3-[1-(2-Amino-2-methyl-propionylamino)-2-benzyloxy-ethyl]-5,6,7,8-tetrahydro-[1,2,4]triazolo[4,3-a]pyridine-7-carboxylic acid ethyl ester

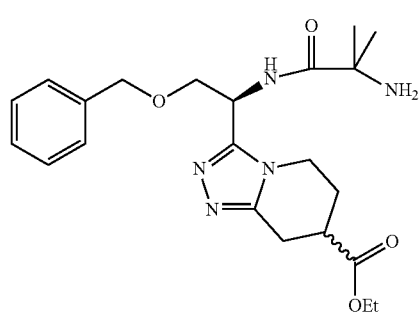

78A

To a solution of ethyl isonipecotate (20.4 g, 0.13 mmol) in CH$_2$Cl$_2$ (120 ml) was added di-tert-butyl dicarbonate (31.1 g, 0.13 mol). After 5 h of stirring at r.t, the reaction was quenched with water and extracted with CH$_2$Cl$_2$, washed with water, brine, dried and concentrated. Purification by flash chromatography on silica gel (1:6 EtOAc/hexane as elutant) gave 78A.

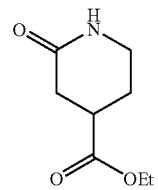

78B

To a solution of 78A (10.38 g, 40.4 mmol) in water (120 ml) and acetonitrile (25 ml) at r.t. was added sodium periodate (25.9 g, 121.1 mmol) and ruthinium oxide (0.5 g, 3.63 mmol). After stirring for 6 h the mixture was filtered. The residue was washed with CH$_2$Cl$_2$ and the aqueous layer was extracted with CH$_2$Cl$_2$, dried and concentrated. The residue in CH$_2$Cl$_2$ (100 ml) was treated with HCl (14 ml 4 M HCl in dioxane) and stirred at r.t. until all the starting materials was consumed. Purification by flash chromatography on silica gel (5% CH$_3$OH/CH$_2$Cl$_2$ as elutant) gave 78B.

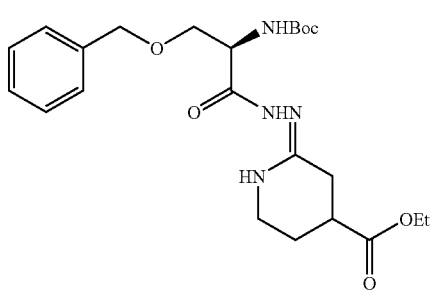

78C

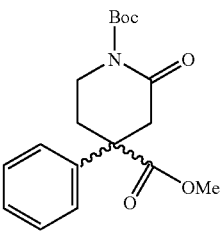

79B 79B was prepared using the method described in 78B substituting 78A with 79A (4 g, 12.5 mmol) and. 7913 was obtained as a colorless oil (3.1 g, 75%).

78C was prepared using the method described in 76C substituting 2-Oxo-piperidine-3-carboxylic acid ethyl ester with 78B (1.2 g, 7.1 mmol) and 76B(2.9 g, 7.1 mmol). 78C was obtained as a colorless oil (3.4 g, <99%).

Example 78 was prepared by using the same methods as described to prepare 76D substituting 76C with 78C to provide the title compound as a foam (17 mg). MS (M+H) 430, HPLC retention time 2.56 min.

Preparative HPLC separation of Example 78 gave the two diastereomers as Example 78a MS (M+H) 430, HPLC retention time 2.55 min and Example 78b MS (M+H) 430, HPLC retention time 1.89 min.

Example 79

3-[1-(2-Amino-2-methyl-propionylamino)-2-benzyloxy-ethyl]-7-phenyl-5,6,7,8-tetrahydro-[1,2,4]triazolo[4,3-a]pyridine-7-carboxylic acid methyl ester

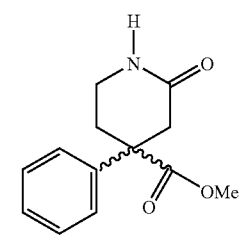

79C 79B (3.1 g, 9.3 mmol) in $CH_2Cl_2$/MeOH (6 ml/6 ml) was treated with HCl (5 ml 4 M HCl in dioxane) and stirred at r.t. until all the starting materials was consumed. Purification by flash chromatography on silica gel (5% $CH_3OH/CH_2Cl_2$ as elutant) gave 79C.

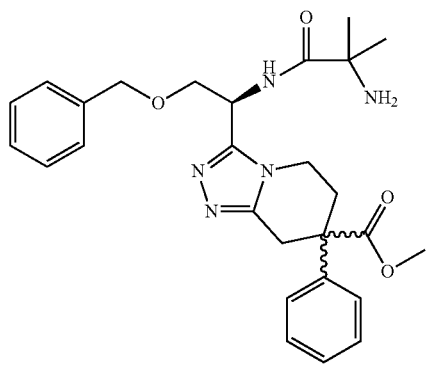

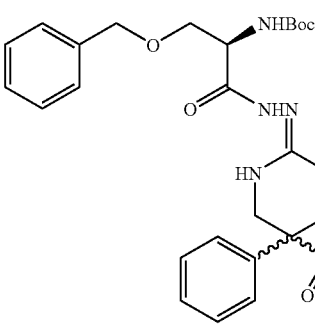

79D

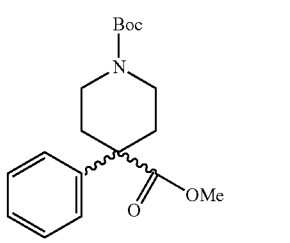

79A

To a cooled solution of potassium hydroxide (15 ml, 40% in water) in ether (100 ml) at 0° C. was added 1-methyl-3-nitro-1-nitoroguanidine(5 g, 34 mmol) slowly over 15 min. The upper organic phase was poured into a flask containing 30 g potassium hydroxide. After 5 min the ether solution was slowly added to 4-formyl-4-phenyl-piperidine-1-carboxylic acid tert-butyl ester (4.15 g, 13.6 mmol) in THF (20 ml). After stirring for 5 min the solution was concentrated to give 79A (4.4 g, <99%).

79D was prepared using the method described in 76C substituting 2-Oxo-piperidine-3-carboxylic acid ethyl ester with 79C (830 mg, 35.6 mmol) and 76B(2.9 g, 7.1 mmol). 79D was obtained as a colorless oil (2.2 g, <99%).

Example 79 was prepared by using the same methods for 76D, 76E and example 76 substituting 76C with 79D 76B with 79E, 76E with 79F to provide the title compound as a foam (8.5 mg). MS (M+H) 492, HPLC retention time 2.91 min.

Example 80 and Example 81

Example 79 was subjected to preparative HPLC to separate the diastereomers to give 24 mg of Example 80 (MS (M+H) 492, HPLC retention time 2.89 min) & 34 mg of Example 81 (MS (M+H) 492, HPLC retention time 3.01 min)

Example 82

3-[1-(2-Amino-2-methyl-propionylamino)-2-benzyloxy-ethyl]-5,6,7,8-tetrahydro-1,2,41-triazolo[4,3-a]pyridine-7-carboxylic acid ethylamide

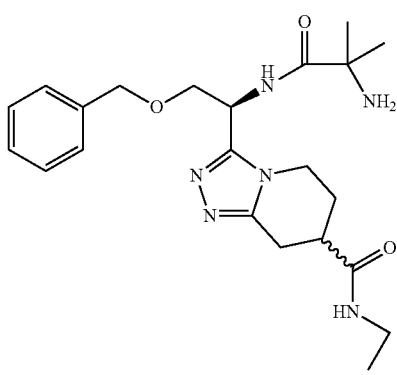

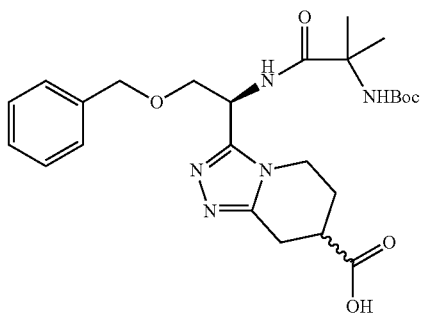

82A 82A was prepared using the method described in 77A substituting 76E with 78D (200 mg, 0.38 mmol) and. 82A was obtained as a colorless oil (168 mg, 89%).

Example 82

To a solution of 82A (89 mg, 0.18 mmol) in $CH_2Cl_2$ (2 ml) at −40° C. was added N-methyl morpholine and isobutyl chloroformate (24.3 mg, 0.18 mmol). The mixture was stirred for 1 h at −40° C. Then 2M solution of ethylamine in THF (90 μl, 0.18 mmol) was added. The reaction was slowly warmed up to r.t. and concentrated. The residue was redissolved in $CH_2Cl_2$ (2 ml) was treated with HCl (1 ml 4 M HCl in dioxane) and stirred at r.t. until all the starting materials was consumed. Purification by preparative HPLC gave the title compound as a salt (14 mg, 20%). MS (M+H) 429, HPLC retention time 1.89 min.

Compounds 83 and 83a were synthesized utilizing the procedures described in Example 82, utilizing the appropriate starting materials.

| 83 | 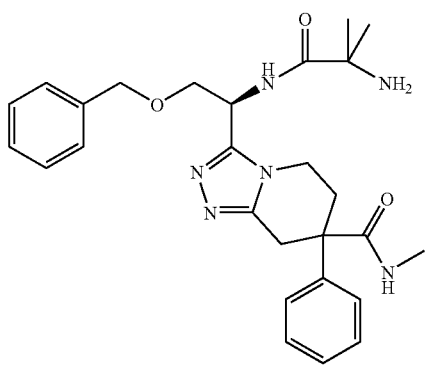 | 90 | 2.42 | 491 |

| 83a<br>Other diastereomer | 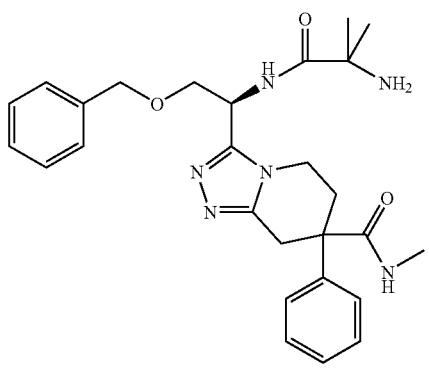 | 95 | 2.73 | 491 |

Example 84

2-Amino-N-[1-(6-chloro-benzo[d]isoxazol-3-yl)-4-phenyl-butyl]-2-methyl-propionamide

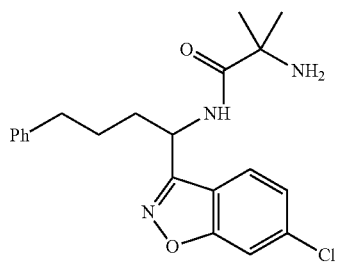
84A

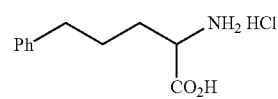

To 60 ml of EtOH was added Na metal (2.3 g, 100 mmol) slowly & stirred for 30 min. until all the Na metal had dissolved. 2-Acetyl amino-malonic acid diethyl ester (21.7 g, 100 mmol) was then added. After stirring for 1 h at r.t, (3-bromo-propyl)-benzene (15.2 ml, 100 mmol) was added & then heated at 75° C. overnight. The mixture was quenched with water extracted with EtOAc, dried over Na₂SO₄, filtered & concentrated. The residue was triturated with hexane to give a white solid 84A (18.7 g, 81%)

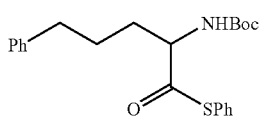
84B

To a stirred solution of A (4.3 g, 18.7 mmol) in 1N NaOH (56 ml) and THF (50 ml), Di-tert-butyl dicarbonate (4.9 g, 22.5 mmol) was added at RT. After 3 h of stirring benzenethiol (3.1 g, 28.1 mmol), EDAC (7.1 g, 37 mmol) and HOBT (5.1 g, 37 mmol) were added and the reaction mixture was stirred at r.t. overnight. The mixture was extracted with EtOAc washed with water, dried over Na₂SO₄, filtered & concentrated. Purification by flash chromatography on silica gel (1:9 EtOAc/hexane as elutant) gave a white solid 84B (3.8 g, 53%).

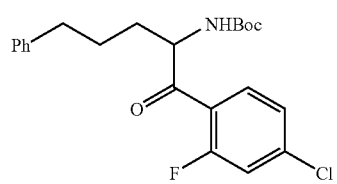
84C

To 84B (1.1 g, 3.8 mmol) in THF (10 ml) under nitrogen was added dichlorobis(triphenylphosphine) Palladium (II) (200 mg, 0.28 mmol) at 0° C. followed by 3-chloro-4-fluoro phenylzinc iodide (17 ml, 8.5 mmol) 0.5M in THF via syringe. After stirring the mixture at r.t. for 3 h it was quenched with water extracted with EtOAc, dried over Na₂SO₄, filtered and concentrated. Purification by flash chromatography on silica gel (1:9 EtOAc/hexane as elutant) gave a white solid 84C (710 mg, 45%)

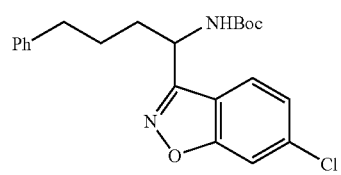
84D

To a stirred solution of 84C (700 mg, 1.7 mmol) in pyridine (5 ml) was added Hydroxylamine hydrochloride (240 mg, 3.4 mmol) & heated in a sealed tube for 2 h. The mixture was concentrated, the residue dissolved in DMF (5 ml) and potassium hydroxide (450 mg, 6.8 mmol) added. The mixture was heated at 85° C. overnight, quenched with water extracted with EtOAc, dried over Na₂SO₄, filtered and concentrated. Purification by flash chromatography on silica gel (1:9 EtOAc/hexane as elutant) gave a white solid 84D (390 mg, 57%)

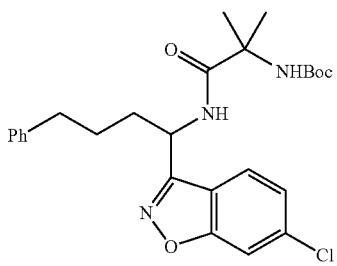
84E

To a stirred solution of 84D (390 mg, 0.97 mmol) was added 5 ml of 20% TFA/CH₂Cl₂ and stirred at r.t. for 2 h. The mixture was concentrated, the residue dissolved in 1N NaOH, water brine, dried and concentrated. The residue was taken in 5 ml CH₂Cl₂ & Boc-2-Aminoisobutyric acid (390 mg, 1.9 mmol), 1-Hydroxybenzotriazole hydrate (270 mg, 2 mmol), EDAC (380 mg, 2 mmol) were added. The mixture was stirred at r.t. overnight, extracted with EtOAc washed with water, dried over Na₂SO₄, filtered & concentrated. Purification by flash chromatography on silica gel (1:9 EtOAc/hexane as elutant) gave a white solid 84E (360 mg, 76%).

Example 84

A solution of 84E (13 mg, 0.03 mmol) in 1 ml of 20% TFA/CH₂Cl₂ was stirred for 1 h and then concentrated. The residue was purified by preparative HPLC to give the title compound as a white solid (34.5 mg, 53%). MS (M+H) 386, HPLC retention time 3.32 min.

Example 85

2-Amino-N-[1-(5-chloro-benzo[d]isoxazol-3-yl)-4-phenyl-butyl]-2-methyl-propionamide

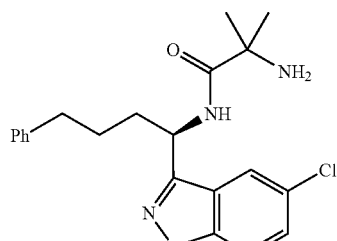

85A

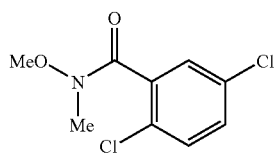

To a stirred solution of 2,5-Dichloro-benzoic acid (3.5 g, 18.3 mmol) in CH$_2$Cl$_2$ (5 ml) was added Oxalyl chloride (18.3 ml, 2M in CH$_2$Cl$_2$) followed by several drops of DMF. The mixture was stirred at r.t. for 2 h and concentrated. The residue was dissolved in CH$_2$Cl$_2$ (20 ml) & TEA (7.6 ml, 55 mmol) was added followed by N,O-Dimethylhydroxyamine hydrochloride (3.6 g, 36.6 mmol). The mixture was stirred at r.t. overnight & extracted with EtOAc washed, dried, filtered & concentrated. Purification by flash chromatography on silica gel (EtOAc/hexane as elutant) gave a pale brown solid 85A (3 g, 67%).

85B

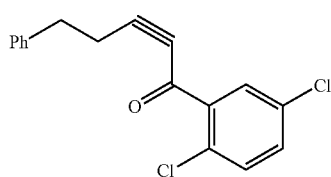

To But-3-ynyl-benzene (1.5 g, 11.5 mmol) in THF (15 ml) at 0° C. was added nbuLi (5.3 ml, 2.5M in hexane) via syringe. After stirring for 30 min. 85A (2.4 g, 10.3 mmol) in 5 ml THF was added followed by additional 1 h of stirring at 0° C. The mixture was quenched with water, extracted with EtOAc, dried over Na$_2$SO$_4$, filtered & concentrated. Purification by flash chromatography on silica gel (1:9 EtOAc/hexane as elutant) gave a yellow liquid 85B (1.3 g, 42%)

85C

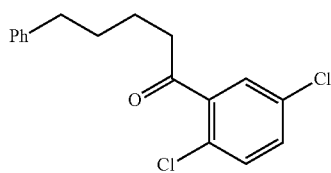

To C (1.3 g, 4.3 mmol) in MeOH (15 ml) and EtOAc (5 ml) was added Pd—C catalyst (260 mg, 5% by weight of palladium) and stirred at r.t. with a hydrogen balloon for 6 h. The catalyst was filtered and concentrated. Purification by flash chromatography on silica gel (5:95 EtOAc/hexane as elutant) gave a yellow liquid 85C (1.1 g, 85%).

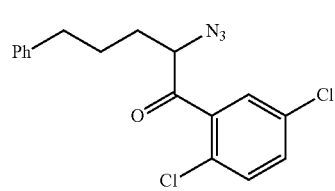

85D

To a stirred solution of 85C (900 mg, 2.9 mmol) in dioxane (5 ml) was added bromine (470 mg, 2.9 mmol) in dioxane (5 ml) slowly at r.t. via syringe & then stirred overnight. The mixture was quenched with water extracted with EtOAc, dried over Na$_2$SO$_4$, filtered & concentrated & the residue passed through a silica pad to give a pale yellow oil as the intermediate. The intermediate was dissolved in acetone (10 ml) and sodium azide (200 mg, 3.1 mmol) in 2 ml water was added. The mixture was stirred at r.t. for 30 min and concentrated, extracted with EtOAc, dried over Na$_2$SO$_4$, filtered & concentrated. Purification by flash chromatography on silica gel (1:9 EtOAc/hexane as elutant) gave 85D (710 mg, 70%).

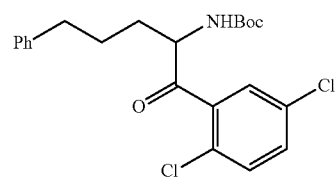

85E

To 85D (710 mg, 2 mmol) in MeOH (10 ml) was added di-tert-butyl dicarbonate (1.3 g, 6 mmol) and Pd—C catalyst (70 mg, 5% by weight of palladium) and stirred at r.t. with a hydrogen balloon overnight. The catalyst was filtered & concentrated. Purification by flash chromatography on silica gel (1:9 EtOAc/hexane as elutant) gave a white solid 85E (250 mg, 89%).

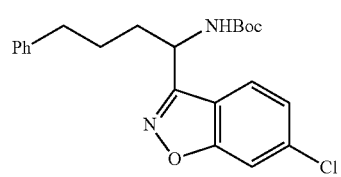

85F 85F was prepared using the method described in 84D substituting 84C with 85E (650 mg, 1.5 mmol) and hydroxylamine hydrochloride (210 mg, 3 mmol) & potassium hydroxide (400 mg, 6 mmol). 85F was obtained as a colorless oil (490 mg, 81%).

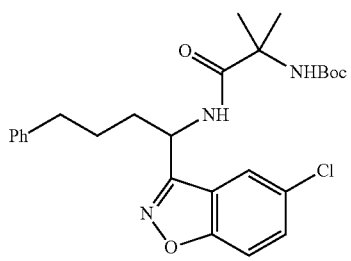

85G 85G was prepared using the method described in 84E substituting 84D with 85F (490 mg, 1.2 mmol) and Boc-2-Aminoisobutyric acid (490 mg, 2.4 mmol). 85G was obtained as a colorless oil (540 mg, 91%).

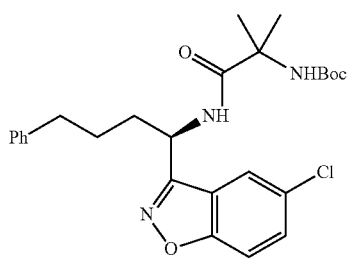

85H 85G was subjected to chiral separation using chiral prep HPLC (Chiralpak AD 5 cm×50 cm 2 μm) & 20% IPA/hexane as elutant) to give 265 mg of 85H (rt=6.54 min)) & 265 mg of 85I (rt=12.85 min).

Example 85

85I (265 mg, 0.55 mmol) was treated with 3 ml of 20% TFA/CH2Cl2 according to the method for Example 84 to give the title compound as a white solid (245 mg) with 99% purity. MS (M+H) 387, HPLC retention time 3.34 min.

Example 86

2-Amino-N-[1-(5-chloro-benzo[d]isoxazol-3-yl)-4-phenyl-butyl]-2-methyl-propionamide

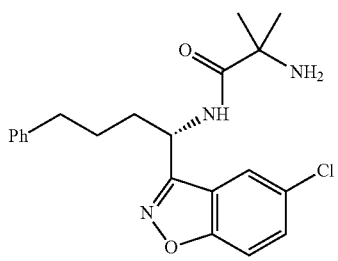

86H (10 mg, 0.02 mmol) was treated with 20% TFA/CH2Cl2 (0.7 ml) according to the method for Example 84 to give the title compound as a white solid (7.4 mg) with 97% purity. MS (M+H) 386, HPLC retention time 3.37 min.

Example 87

2-Amino-N-[1-(6-methanesulfonyl-[1,2,4]triazolo[4,3-a]pyridin-3-yl)-3-phenyl-propyl]-2-methyl-propionamide

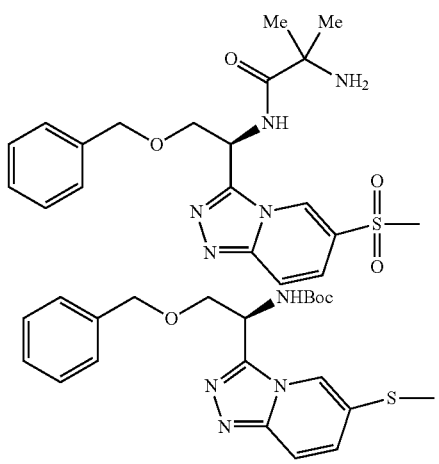

87A

To 1C (200 mg, 0.447 mmol) in THF (3 ml) was added isopropyl magnesium chloride (1.34 ml, 2.68 mmol, 2M solution) at r.t. After 1 h of stirring, dimethyldisulphide (94.2 mg) was added and stirred overnight. Diluted with water and extracted with CH2Cl2, dried and concentrated. Purification by flash chromatography on silica gel (1:1 EtOAc/hexane as elutant) gave a white solid 87A.

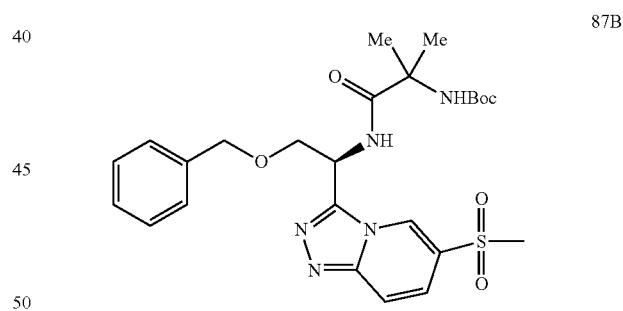

87B

To 87A (15 mg, 0.03 mmol) in CH2Cl2 (1 ml) was added m-chloro perbenzoic acid (21 mg, 0.07) and stirred for 2 h. The mixture was concentrated and redissolved in CH2Cl2 washed with 1N NaOH, brine, dried and concentrated. The residue in MeOH (1 ml) was treated with 4NHCl (1 ml) for 3 h at r.t. and then concentrated. The residue was taken in 1.5 ml CH2Cl2 & Boc-2-Aminoisobutyric acid (390 mg, 1.9 mmol), 1-HOAT (10 mg, 0.07 mmol), EDAC (14 mg, 0.072 mmol) and TEA (20 μl, 0.144 mmol) were added. The mixture was stirred at r.t. overnight, extracted with EtOAc washed with water, dried over Na2SO4, filtered & concentrated to give 87B Example 87

A solution of 87B in MeOH (1 ml) was treated with 4N HCl (1 ml) and stirred for 1 h and then concentrated. The residue was purified by preparative HPLC to give the title compound as a white solid (15 mg). MS (M+H) 432, HPLC retention time 2.4 min.

Example 88

Methyl-carbamic acid 3-[1-(2-amino-2-methyl-propionylamino)-2-benzyloxy-ethyl]-7-phenyl-5,6,7,8-tetrahydro-[1,2,4]triazolo[4,3-a]pyridin-7-ylmethyl ester

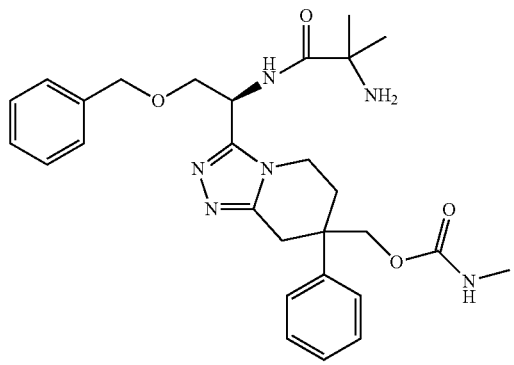

88A

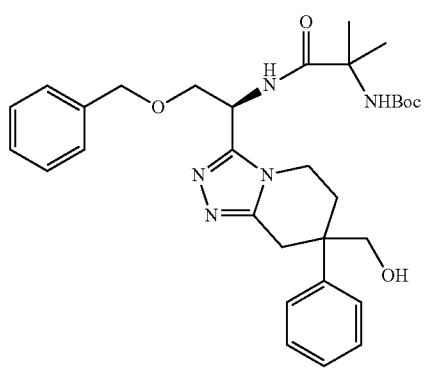

To a solution of 79E (350 mg, 0.6 mmol) in CH$_2$Cl$_2$ (6 ml) was added lithium borohydride (1.2 ml, 2.4 mmol, 2M solution) at 0° C. The mixture was warmed to r.t. and stirred overnight. The reaction was quenched with pH 3 buffer, stirred for 30 min and extracted with CH$_2$Cl$_2$, washed with brine, dried, filtered and concentrated to give crude product 88A (336 mg, <99%)

Example 88

To a solution of 88A in CH$_2$Cl$_2$ (3 ml) at 0° C. was added TEA (127 μl, 0.91 mmol) and methylisocyanate (35 mg, O_61 mmol). The mixture was warmed to r.t. and stirred overnight. The residue in CH$_2$Cl$_2$ (3 ml) was treated with HCl (1.5 ml 4 M HCl in dioxane) and stirred at r.t. until all the starting materials was consumed. Purification and separation by Preparative HPLC gave the two diastereomers as Example 88a MS (M+H) 521, HPLC retention time 2.55 min and Example 88b MS (M+H) 521, HPLC retention time 2.92 min.

Example 89

2-Amino-N-[2-benzyloxy-1-(6-chloro-[1,2,4]-triazolo[4,3-b]pyridazin-3-yl)-ethyl]-2-methyl-propionamide

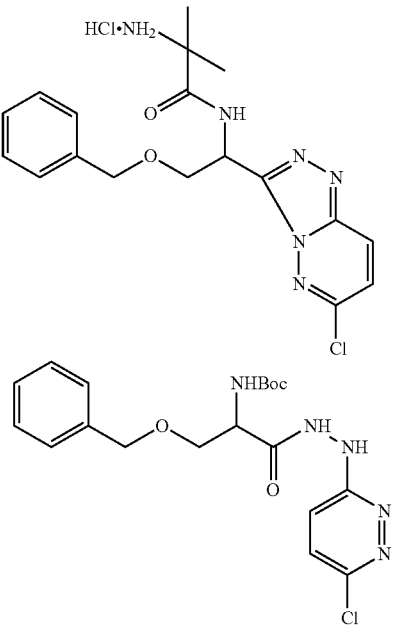

To a slurry of 3-Benzyloxy-2-butoxycarbonylamino-propionic acid (740 mg, 2.5 mmol) in CH$_2$Cl$_2$ (10 mL) was added EDAC (475 mg, 2.5 mmol) at r.t. After stirring for 1 h (6-chloropyridazin-3-yl)hydrazine (362 mg, 2.5 mmol) was added. After 2 h, the reaction was quenched with saturated aqueous NaHCO$_3$. The mixture was extracted with EtOAc, dried, filtered and concentrated. Purification by flash chromatography on silica gel (1:2 EtOAc/hexane as elutant) gave 89A (730 mg, 69%) as a yellow foam.

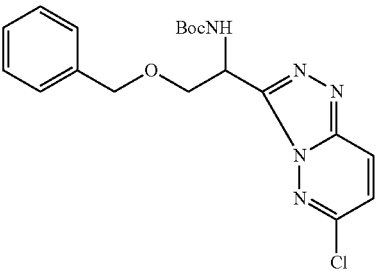

89B

To a solution of 89A (210 mg, 0.5 mmol) in acetonitrile (5 mL) at 0° C. was added 1,2-dibromo-1,1,2,2-tetrachloroethane (179 mg, 0.55 mmol) followed by triethylamine (0.31 mL, 2.2 mmol) and triphenylphosphine (289 mg, 1.1 mmol). After stirring for 1 h, the mixture was warmed to r.t. and stirred for 2 h. The solution was concentrated and the residue was redissolved in EtOAc, washed with 1:1 brine/10% citric acid, brine, dried, filtered and concentrated. Purification by preparative HPLC gave 89B as an off-white solid (125 mg, 62%).

89C

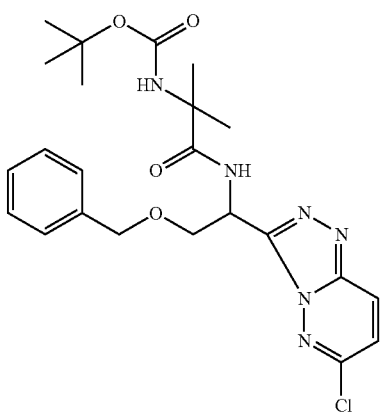

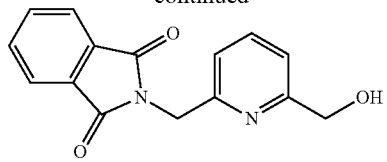

To a stirred solution of potassium phthalimide (1.04 g, 5.15 mmol) at RT under argon in DMF (40 mL) was added a DMF solution (10 mL) of (6-bromomethylpyridin-2-yl)-methanol (1.03 g, 5.11 mmol) over 5 min. The slurry was warmed at 40° C. and stirred overnight. The DMF was then distilled off at 40-55° C. (1 Torr). The powdery residue was stirred rapidly in CH$_2$Cl$_2$ for 20 min and filtered through Celite. The residue was redissolved in CH$_2$Cl$_2$, washed with water, dried and concentrated to give 90A as an off-white solid (1.16 g, 85%)

To MeOH (3.5 ml) at 0° C. was added acetyl chloride (0.8 mL) over 3 min. After stirring the solution for 1 h, the solution was added to 89B (125 mg, 0.31 mmol) in CH$_2$Cl$_2$ (0.3 ml) at r.t. The mixture was stirred at r.t. for 2 h and then concentrated twice from CH$_2$Cl$_2$. The residue was redissolved in CH$_2$Cl$_2$ (1 mL) and added to a slurry of Boc-2-aminoisobutyric acid (94.4 mg, 0.46 mmol), HOAT (63.6 mg, 0.46 mmol) and N-methyl morpholine (0.051 ml, 0.5 mmol) in CH$_2$Cl$_2$ (2 ml). The solution was stirred for 15 h, diluted with EtOAc, washed with saturated aqueous NaHCO$_3$, dried, filtered and concentrated. Purification by flash chromatography on silica gel (1:99 MeOH/EtOAc as elutant) gave 89C as a colorless foam (69 mg, 46%).

90B

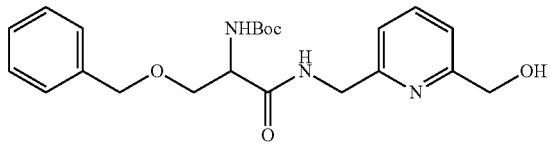

To a stirred solution of 90A (1.2 g, 4.32 mmol) in EtOH (60 ml) was added hydrazine (0.41 mL, 13.1 mmol) and the reaction mixture was refluxed for 14 h under argon. The solution was cooled, filtered through Celite and the filtrate concentrated. The residue was redissolved in MeOH, cooled, filtered and concentrated to give (6-aminomethyl-pyridin-2-yl)methanol. To a stirred solution of Boc-(O-benzyl)serine (1.3 g, 4.32 mmol) and N-methyl morpholine (0.484 mL, 4.4 mmol) in THF (10 mL) at −12° C. was added isobutylchloroformate (0.56 mL, 4.35 mmol). After 30 min stirring, a slurry of (6-aminomethylpyridin-2-yl)-methanol in THF was added over 1 min. The solution was stirred at r.t. for 1 h. The reaction was diluted with EtOAc, washed with saturated aqueous sodium bicarbonate solution, dried and concentrated to give 90B as a yellow oil (1.9 g). The material was used without purification in the following reaction.

Example 89

To MeOH (3.5 mL) at 0° C. was added acetyl chloride (0.8 mL) over 3 min. After stirring the solution for 1 h, the solution was added to 89C (69 mg, 0.14 mmol) in CH$_2$Cl$_2$ (0.3 ml) at r.t. The mixture was stirred at r.t. for 2 h and then concentrated.

The residue was dissolved in water, filtered through a 0.45μ nylon filter and lyophilized to give the title compound as a white amorphous solid. MS (M+H) 389, HPLC retention time 2.92 mm.

Example 90

(4-Hydroxy-butyl)-carbamic acid 3-[1-(2-amino-2-methyl-propionylamino)-2-benzyloxy-ethyl]-imidazo[1,5-a]pyridin-5-ylmethyl ester

90A

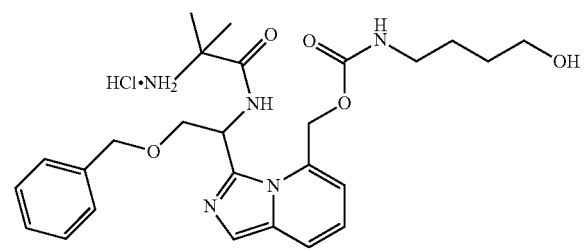

90C

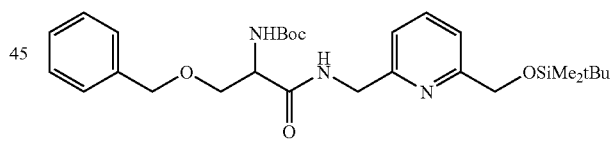

To a solution of 90B (1.9 g, 4.3 mmol) in DMF (10 ml) was added imidazole (410 mg, 6.02 mmol) and t-butyldimethyl-silylchloride (750 mg, 4.98 mmol). The solution was stirred for 20 h. The reaction was quenched with water, extracted with EtOAc, dried, filtered and concentrated. Purification by flash chromatography on silica gel (19:81 EtOAc/CH$_2$Cl$_2$ as elutant) gave 90C (1.4 g, 53%)as a colorless oil.

90D

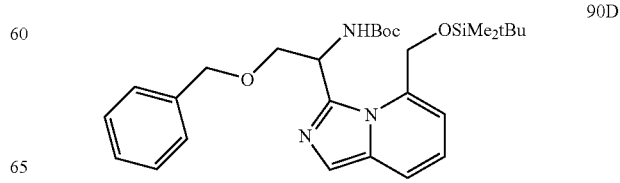

To a stirred slurry of 90C (1.4 g, 2.6 mmol) and 1,2-dibromo-1,1,2,2-tetrachloroethane (1.9 g, 5.8 mmol) in acetonitrile (15 mL) at 0° C. was added triphenylphosphine (1.5 g, 5.8 mmol) and TEA (1.60 mL, 11.6 mmol). After 30 min, the resulting yellow slurry was stirred at r.t. for 16 h. A red solution had formed. This was concentrated, partitioned between water and EtOAc, dried, filtered and concentrated. Purification by flash chromatography on silica gel (3:17 EtOAc/CH$_2$Cl$_2$ as elutant) gave 90D as a tan oil (625 mg, 46%).

To a solution of 90E (279 mg, 0.58 mmol) and pyridine (0.12 mL, 1A mmol) in THF (3 mL) 0° C. was added 4-nitrophenyl chloroformate (256 mg, 1.3 mmol) in CH$_2$Cl$_2$ (3 mL). The solution was stirred for 1 h and concentrated. The residue was dissolved in THF (5 mL) and 4-aminobutanol (0.5 mL) was added. The solution was stirred for 30 min, diluted with EtOAc, washed with 1N NaOH, dried and concentrated. Purification by flash chromatography on silica gel (EtOAc as elutant) gave 90F as a yellow oil (207 mg, 60%).

Example 90

90E

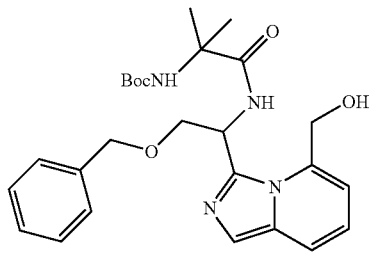

To MeOH (8 mL) at 0° C. was added acetyl chloride (2.0 mL) over 3 min. After stirring the solution for 1 h, it was added to 90F (204 mg, 0.342 mmol) at 0° C. The solution was stirred for 2 h and concentrated. The residue was lyophilized to give the title compound as a yellow solid. MS (M+H) 498, HPLC retention time 2.64 min.

The following compound has been synthesized utilizing the procedures described in Example 90, utilizing the appropriate starting materials. Example 263 was also prepared by this method.

| Compound number | Structure | Mass M + H | HPLC Purity (%) | HPLC Retention (min) |
|---|---|---|---|---|
| 91 | 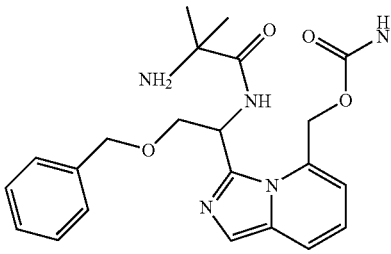 | 584 | 98 | 2.6 |

To MeOH (8 mL) at 0° C. was added acetyl chloride (2.0 mL) over 3 min. After stirring the solution for 1 h, it was added to 90D (620 mg, 1.2 mmol) at 0° C. The solution was stirred for 2 h and concentrated. The residue was dissolved in CH$_2$Cl$_2$ (5 mL) and added to a stirred slurry of Boc-2-aminoisobutyric acid (370 mg, 1.82 mmol), HOAt (249 mg, 1.82 mmol) and EDAC (346 mg, 1.82 mmol) followed by addition of N-methylmorpholine (0.3 mL, 2.7 mmol). The mixture was stirred for 15 h, diluted with CH$_2$Cl$_2$, washed with saturated aqueous NaHCO$_3$, dried and concentrated. Purification by flash chromatography on silica gel (3:17 EtOAc/CH$_2$Cl$_2$ as elutant) gave 90E as a colorless foam (450 mg, 77%).

Example 92

3-[1-(2-Amino-2-methyl-propionylamino)-2-benzyloxy-ethyl]-5,6-dihydro-5H-[1,2,4]-triazolo[4,3-a]pyrazine-7-carboxylic acid benzyl ester

90F

92A

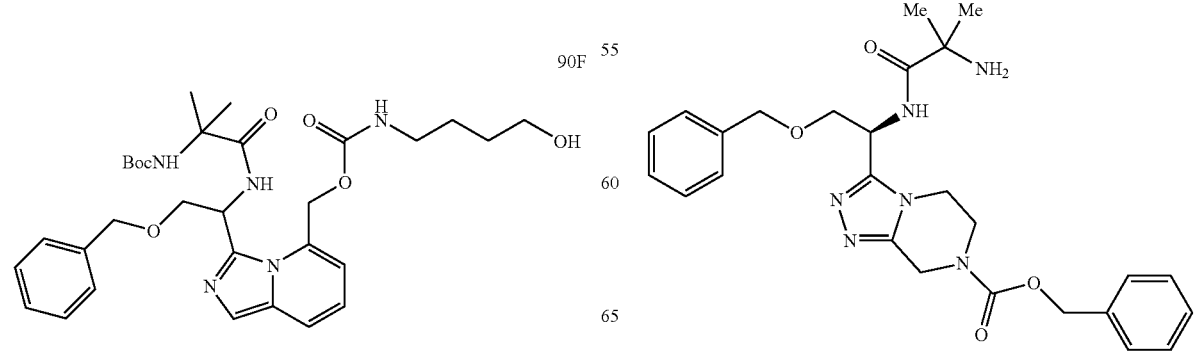

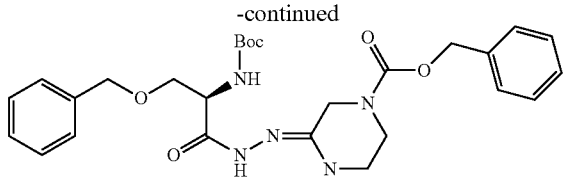

To a solution of 3-Oxo-piperazine-1-carboxylic acid benzyl ester (1.5 g, 6.4 mmol) in CH$_2$Cl$_2$(20 ml) was added trimethyloxonium tetrafluoroborate (0.99 g, 6.72 mmol). The solution was stirred for 60 h. A solution of (2-Benzyloxy-1-hydrazinocarbonyl-ethyl)-carbamic acid tert-butyl ester (2.07 g, 309.7 mmol) in CH$_2$Cl$_2$(20 ml) was added to give a clear solution. After 2 h of stirring the solution was diluted with CH$_2$Cl$_2$, washed with water, dried and concentrated to give 92A as a white foam (3.2 g, 95%).

92B

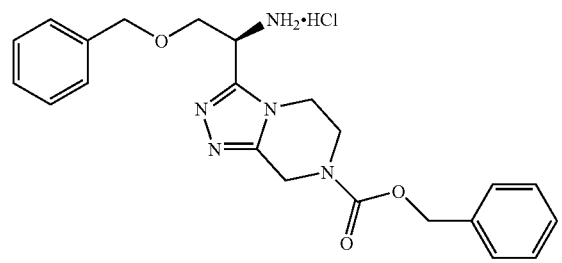

A solution of 92A (2.6 g, 4.9 mmol) in EtOH (26 ml) was treated by microwave at 120° C., 60W for 10 min. The mixture was treated with 4NHCl in dioxane (30 ml) for 30 min. the solution was concentrated and coevaporated with ethanol to 92B (2.8 g).

92C

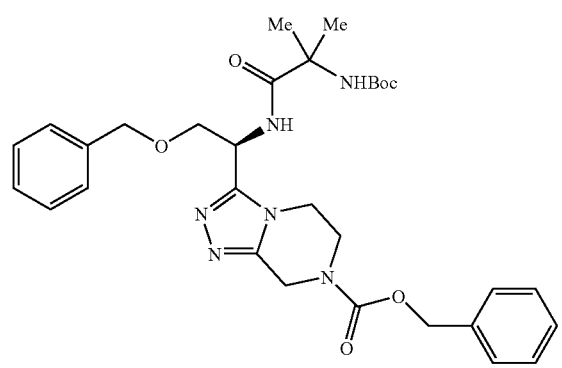

To a CH$_2$Cl$_2$ (100 ml) solution of 2-tert-butoxycarbonylamino-2-methyl-propionic acid (1.34 g, 66.1 mmol) was added EDAC (1.8 g, 9.45 mmol) and HOBT (1.27 g, 9.45 mmol), DMAP (0.77 g, 6.3 mmol), and TEA (2.63 ml, 18.9 mmol). This solution was stirred at r.t. for 10 min before the addition of 92B (2.8 g, 6.3 mmol). The reaction was completed in 2 h. The solution was diluted with CH$_2$Cl$_2$, washed with water, 1NHCl, 1N NaOH, dried and concentrated. Purification by flash chromatography on silica gel (5:95 MeOH/CH$_2$Cl$_2$ as elutant) gave 92C as a foam(3 g).

Example 92

To a solution of 92C (250 mg) in CH$_2$Cl$_2$ was treated with HCl (30 ml 4 M HCl in dioxane) and stirred at r.t for 1 h. The solution was concentrated and the residue crystallized using MeOH/EtOAc to give the title compound as a solid (130 mg). MS (M+H) 493, HPLC retention time 2.33 min.

Example 93

3-[1-(2-Amino-2-methyl-propionylamino)-2-benzyloxy-ethyl]-5,6-dihydro-8H-[1,2,4]triazolo[4,3-a]pyrazine-7-carboxylic acid naphthalen-2-ylmethyl ester

93A

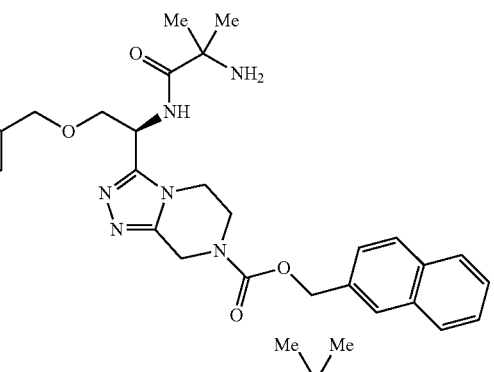

To a solution of 92C (2.6 g, 4.4 mmol) and catalyst palladium on carbon (30 mg) in MeOH (70 ml) under nitrogen was added ammonium formate (1.3 g, 20.9 mmol). The solution was stirred for 3 h and filtered through celite and concentrated to give 93A(2.45 g)

93B

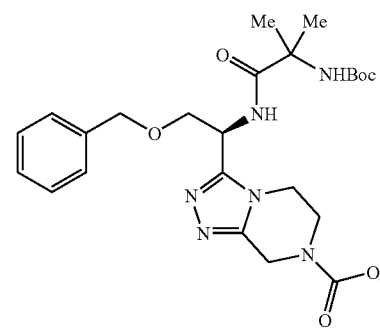

To a solution of 2-naphthalenmethanol (11 mg, 0.07 mmol) in CH$_2$Cl$_2$ (0.25 ml) was added n-methylmorpholine (12 μl, 0.1 mmol) and 4-nitrophenyl chloroformate (15 mg, 0.0735 mmol) in CH$_2$Cl$_2$ (0.25 ml). The solution was stirred overnight followed by addition of 93A (32 mg, 0.07 mmol) in CH$_2$Cl$_2$(0.08 ml) and TEA (0.1 ml, 0.7 mmol). The solution was stirred overnight and diluted with $CH_2Cl_2$, washed with 1NHCl, 1NaOH, water, dried and concentrated to give 93B.

Example 93

To a solution of 93B in $CH_2Cl_2$ was treated with TFA in $CH_2Cl_2$ and stirred at r.t for 1 h. The solution was concentrated. The residue was purified by preparative HPLC to give the title compound. MS (M+H) 543, HPLC retention time 2.82 min.

The following compounds were synthesized utilizing the procedures as described in Example 93, utilizing the appropriate starting materials as know to those skilled in the art.

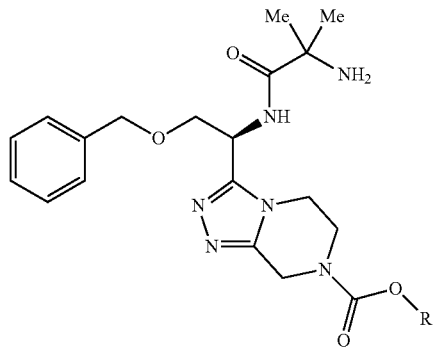

| Compound number | R | Mass M + H | HPLC Purity (%) | HPLC Retention (min) |
|---|---|---|---|---|
| 94 | 2,5-dimethylphenyl | 523 | 80 | 2.77 |
| 95 | 3-methylphenyl | 507 | 90 | 2.57 |
| 96 | 3,5-dimethylphenyl | 521 | 90 | 2.8 |
| 97 | 4-fluorophenyl | 511 | 85 | 2.4 |
| 98 | 4-tert-butylphenyl | 549 | 81 | 3.04 |
| 99 | 3,5-difluorophenyl | 529 | 85 | 2.5 |
| 100 | 3,4-difluorophenyl | 529 | 90 | 2.48 |

-continued
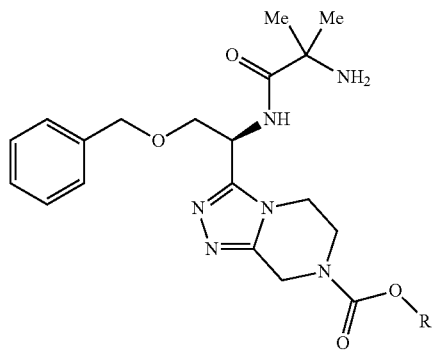
| Compound number | R | Mass M + H | HPLC Purity (%) | HPLC Retention (min) |
|---|---|---|---|---|
| 101 | 4-ethynylphenyl | 518 | 97 | 2.08 |
| 102 | 2,5-difluorophenyl | 529 | 80 | 2.42 |
| 103 | 2-fluorophenyl | 511 | 90 | 2.4 |
| 104 | 3-fluorophenyl | 511 | 95 | 2.37 |
| 105 | 3-methoxyphenyl | 523 | 90 | 2.37 |
| 106 | 4-isopropylphenyl | 535 | 90 | 2.97 |

The following examples were prepared using procedures as described in the general synthetic schemes and working examples above, utilizing the appropriate starting materials as know to those skilled in the art.

| Compound number | Structure | Mass M + H | HPLC Purity (%) | HPLC Retention (min) |
|---|---|---|---|---|
| 107 | 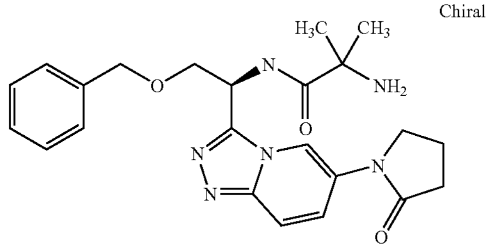 | 437 | 92 | 2.5 |
| 108 | 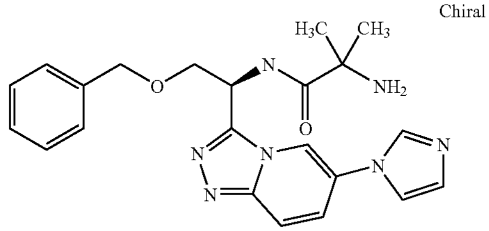 | 420 | 90 | 1.71 |
| 109 | 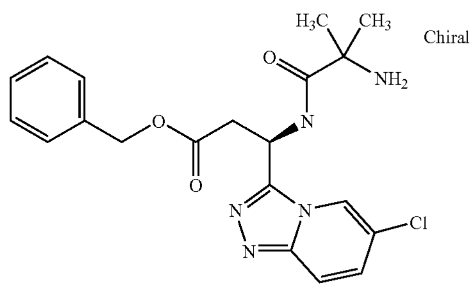 | 416 | 98 | 1.9 |
| 110 | 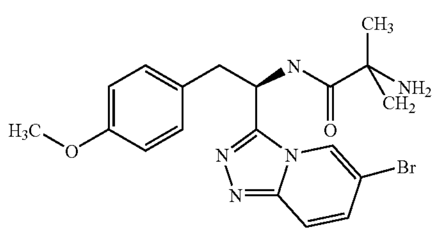 | 433 | 96 | 1.8 |
| 111 | 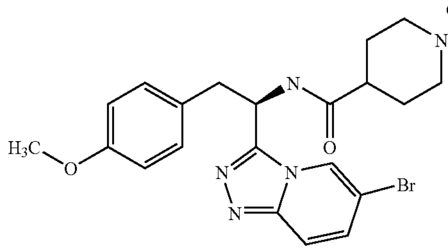 | 459 | 90 | 1.9 |

-continued
| Compound number | Structure | Mass M + H | HPLC Purity (%) | HPLC Retention (min) |
|---|---|---|---|---|
| 112 | 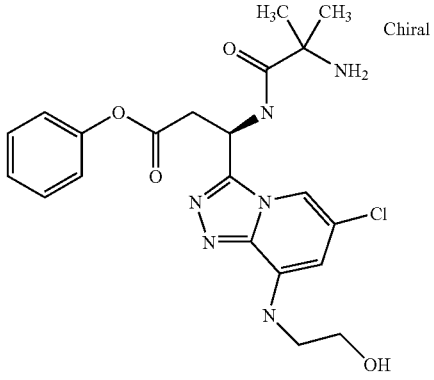 | 448 | 85 | 2.3 |
| 113 | 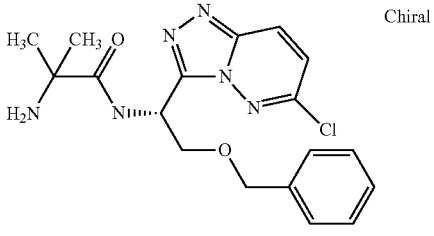 | 390 | 2.7 | 99 |
| 114 | 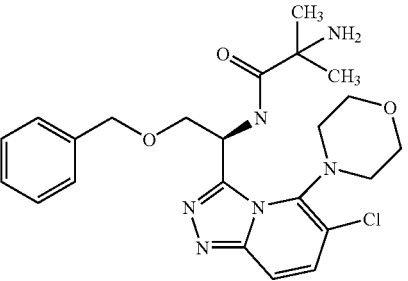 | 473 | 88 | 2.24 |
| 115 | 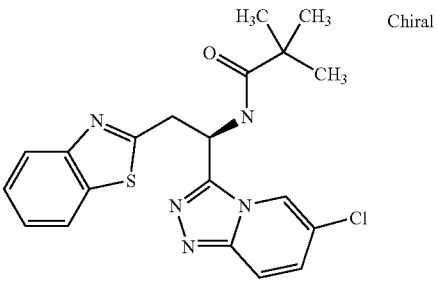 | 416 | 100 | 1.9 |
| 116 | 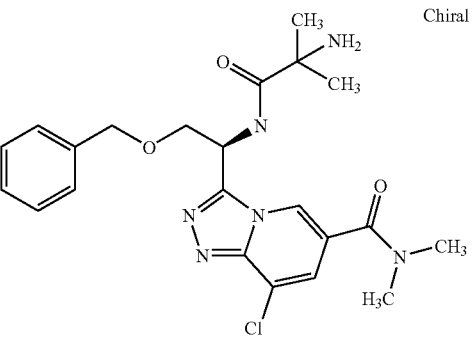 | 459 | 90 | 1.87 |

| Compound number | Structure | Mass M + H | HPLC Purity (%) | HPLC Retention (min) |
|---|---|---|---|---|
| 117 | Chiral | 486 | 100 | 1.23 |
| 118 | Chiral | 434 | 93 | 2.6 |
| 119 | Chiral | 455 | 99 | 4.04 |
| 120 | Chiral | 469 | 97 | 2.73 |

-continued

| Compound number | Structure | Mass M + H | HPLC Purity (%) | HPLC Retention (min) |
|---|---|---|---|---|
| 121 | Chiral | 368 | 92 | 1.5 |
| 122 | 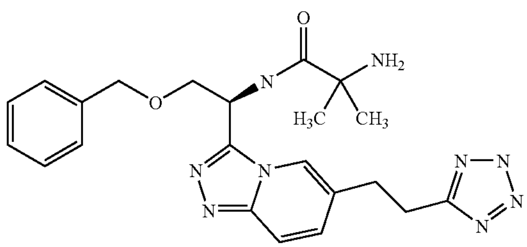 | 450 | 95 | 2.2 |
| 123 | 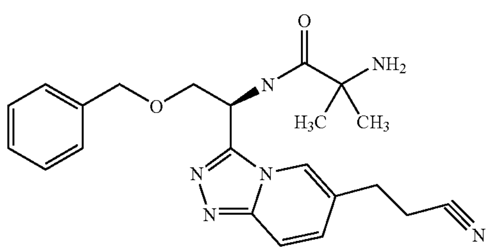 | 407 | 98 | 2.2 |
| 124 | Chiral | 447 | 95 | 2.05 |
| 125 | Chiral | 413 | 95 | 1.9 |

| Compound number | Structure | Mass M + H | HPLC Purity (%) | HPLC Retention (min) |
| --- | --- | --- | --- | --- |
| 126 | 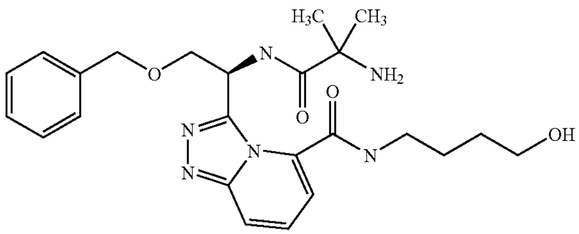 | 469 | 90 | 2.52 |
| 127 | 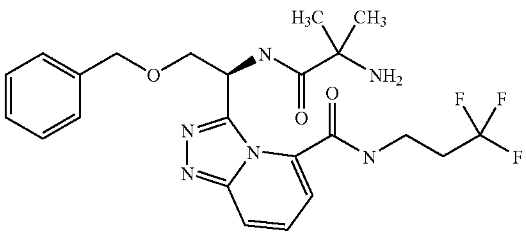 | 493 | | 2.98 |
| 128 | 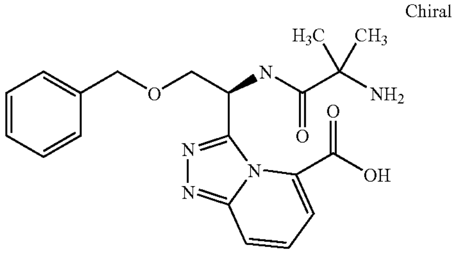 | 398 | 90 | 2.26 |
| 129 | 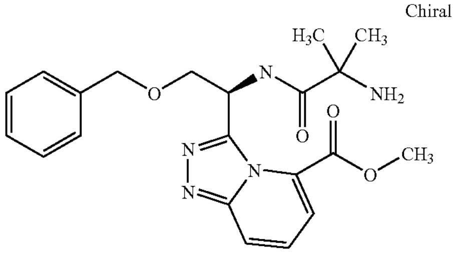 | 412 | 98 | 2.71 |
| 130 | 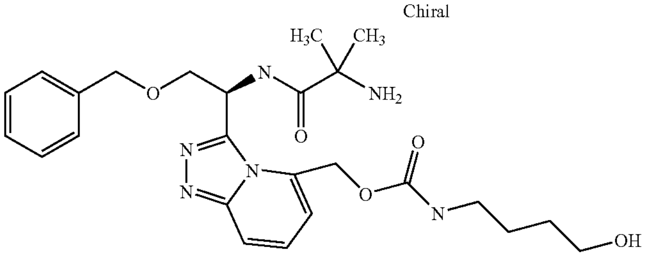 | 499 | 97 | 2.6 |

-continued

| Compound number | Structure | Mass M + H | HPLC Purity (%) | HPLC Retention (min) |
|---|---|---|---|---|
| 131 | Chiral | 483 | 85 | 3.1 |
| 132 | Chiral | 473 | 95 | 2.4 |
| 133 | Chiral | 399 | 93 | 1.7 |
| 134 | Chiral | 502 | 94 | |

-continued
| Compound number | Structure | Mass M + H | HPLC Purity (%) | HPLC Retention (min) |
|---|---|---|---|---|
| 135 | 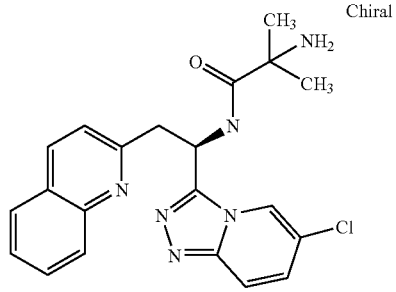 | 409 | 86 | 1.14 |
| 136 | 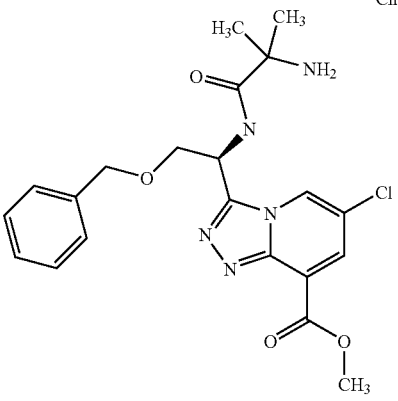 | 446 | 99 | 2.3 |
| 137 | 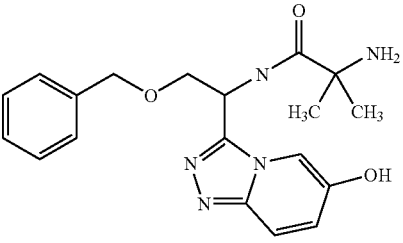 | 370 | 95 | 2.07 |
| 138 | 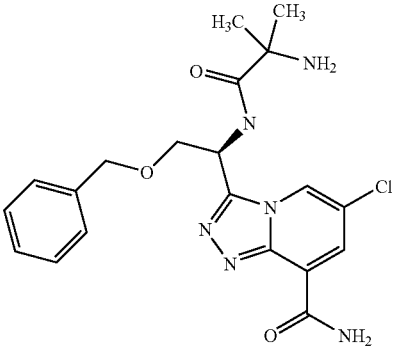 | 431 | 99 | 2.3 |

123                                                                                           124

-continued

| Compound number | Structure | Mass M + H | HPLC Purity (%) | HPLC Retention (min) |
|---|---|---|---|---|
| 139 | Chiral | 380 | 90 | |
| 140 | Chiral | 432 | 97 | 2.2 |
| 141 | Chiral | 413 | 95 | 2.4 |
| 142 | Chiral | 467 | 93 | 2.9 |
| 143 | Chiral | 467 | 97 | 2.86 |

-continued
| Compound number | Structure | Mass M + H | HPLC Purity (%) | HPLC Retention (min) |
|---|---|---|---|---|
| 144 | 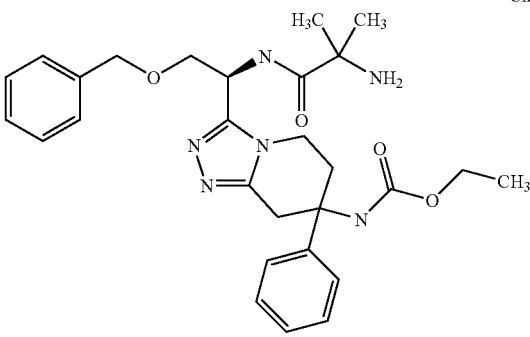 Chiral | 521 | 89 | 2.8 |
| 145 | 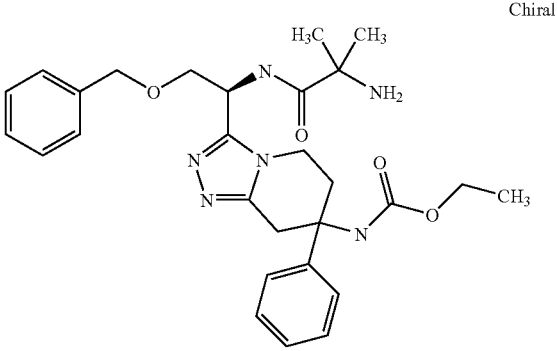 Chiral | 521 | 85 | 2.96 |
| 146 | 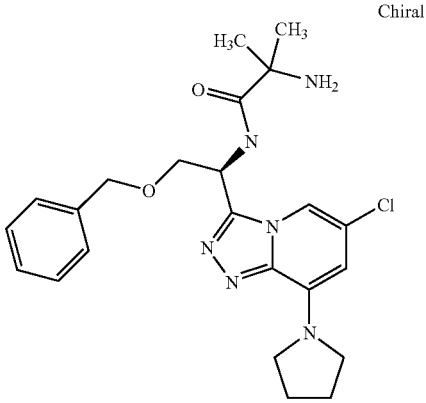 Chiral | 457 | 100 | 2.9 |
| 147 | 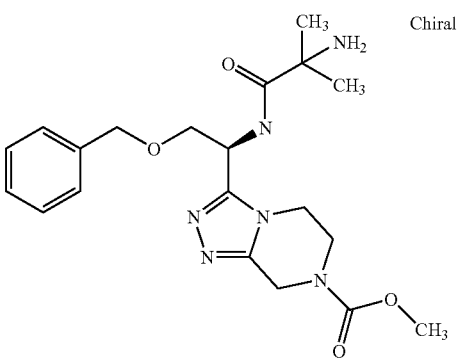 Chiral | 417 | 85 | 1.37 |

-continued

| Compound number | Structure | Mass M + H | HPLC Purity (%) | HPLC Retention (min) |
|---|---|---|---|---|
| 148 | 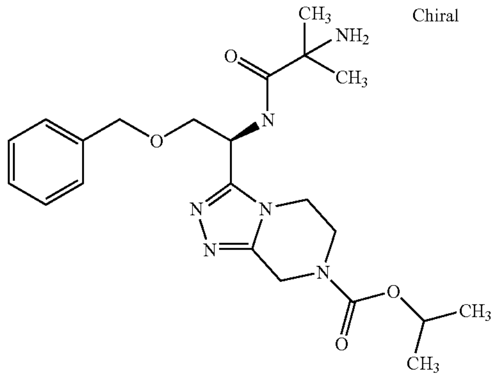 | 445 | 90 | 1.95 |
| 149 | 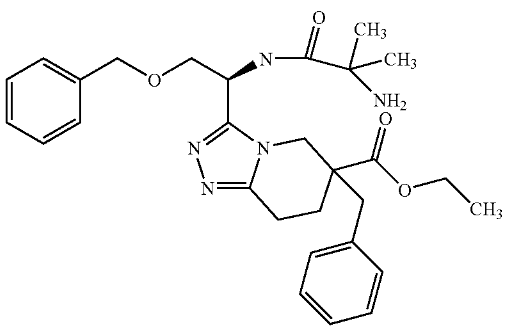 | 520 | 95 | 3.2 |
| 150 | 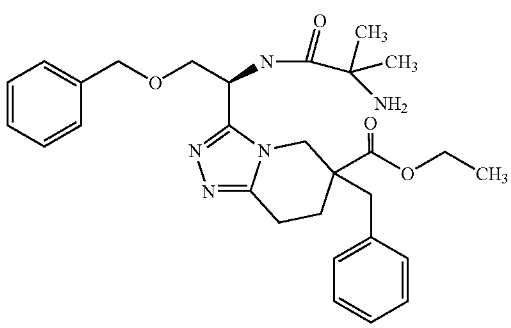 | 520 | 90 | 3.26 |
| 151 | 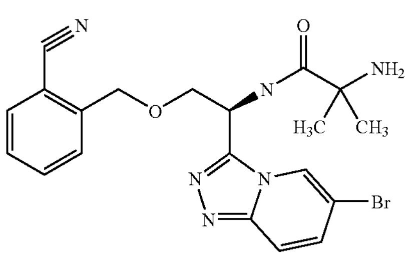 | 458 | 97 | 2.4 |

-continued

| Compound number | Structure | Mass M + H | HPLC Purity (%) | HPLC Retention (min) |
|---|---|---|---|---|
| 152 | 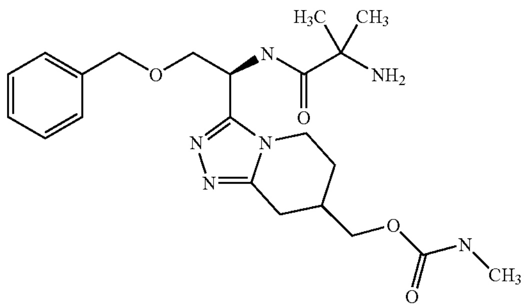 | 445 | 90 | 2.22 |
| 153 | Chiral | 359 | 90 | 0.4 |
| 154 | Chiral | 463 | 95 | 1.81 |
| 155 | Chiral | 539 | 95 | 2.9 |

-continued
| Compound number | Structure | | Mass M + H | HPLC Purity (%) | HPLC Retention (min) |
|---|---|---|---|---|---|
| 156 | 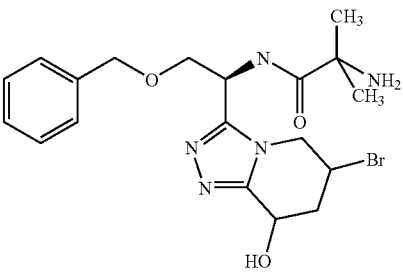 | Chiral | 445 | 95 | 2.08 |
| 157 | 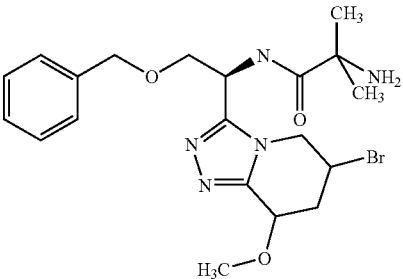 | Chiral | 463 | 95 | 2.17 |
| 158 | 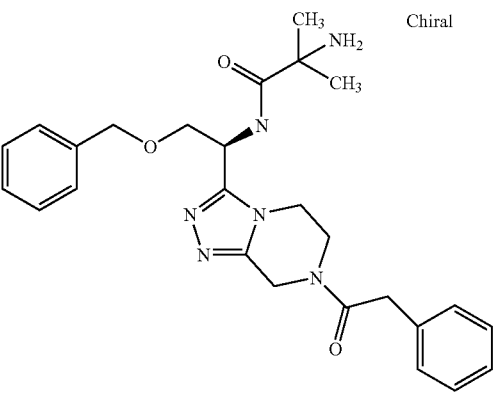 | Chiral | 477 | 85 | 1.95 |
| 159 | 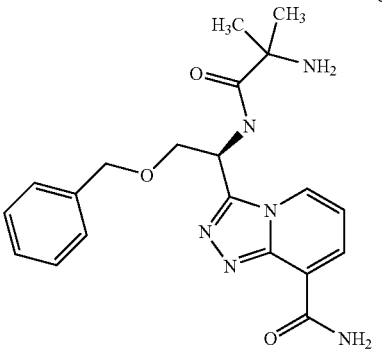 | Chiral | 397 | 98 | 1.5 |

-continued

| Compound number | Structure | | Mass M + H | HPLC Purity (%) | HPLC Retention (min) |
|---|---|---|---|---|---|
| 160 | 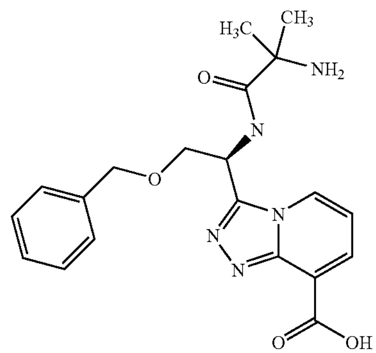 | Chiral | 397 | 94 | 1.13 |
| 161 | 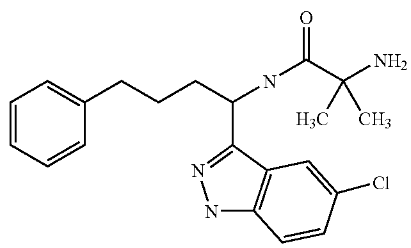 | Chiral | 385 | 95 | |
| 162 | 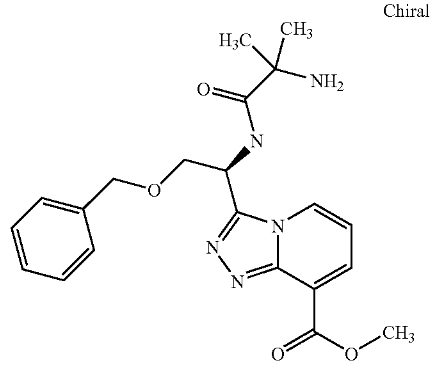 | Chiral | 412 | 100 | 1.6 |
| 163 | 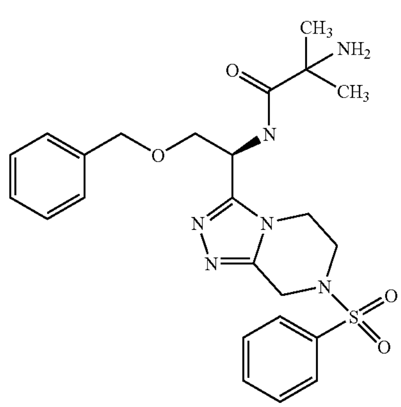 | Chiral | 499 | 95 | 2.85 |

-continued

| Compound number | Structure | Mass M + H | HPLC Purity (%) | HPLC Retention (min) |
|---|---|---|---|---|
| 164 | Chiral | 549 | 94 | 2.56 |
| 165 | Chiral | 379 | 98 | 1.5 |
| 166 | Chiral | 497 | 96 | 2.58 |
| 167 | 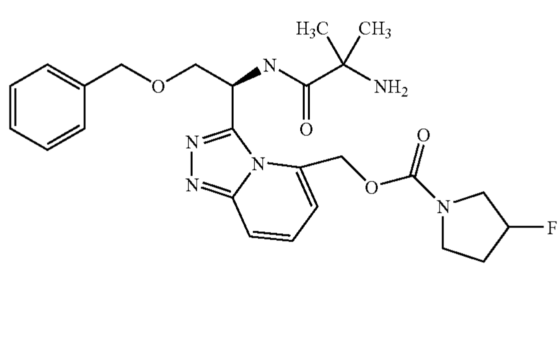 | 499 | 96 | 2.85 |

-continued

| Compound number | Structure | | Mass M + H | HPLC Purity (%) | HPLC Retention (min) |
|---|---|---|---|---|---|
| 168 | 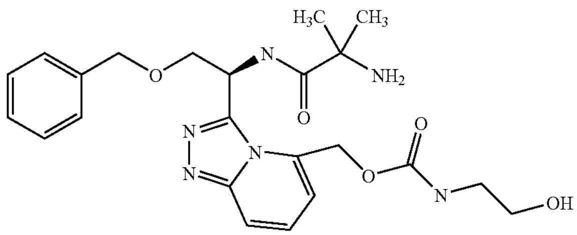 | Chiral | 471 | 95 | 2.43 |
| 169 | 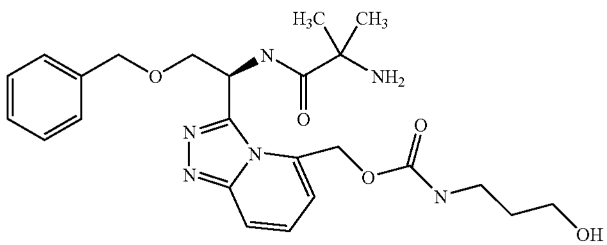 | Chiral | 485 | 95 | 2.5 |
| 170 | 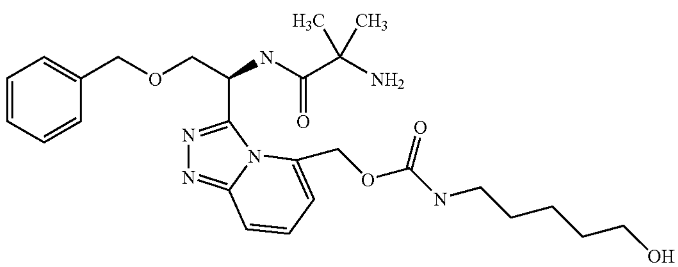 | Chiral | 513 | 94 | 2.7 |
| 171 | 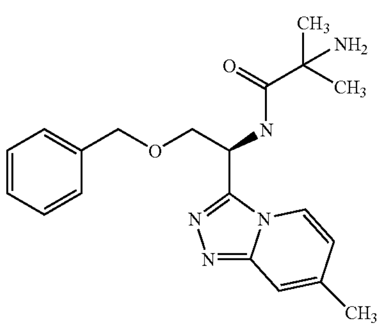 | Chiral | 368 | 98 | 1.21 |
| 172 | 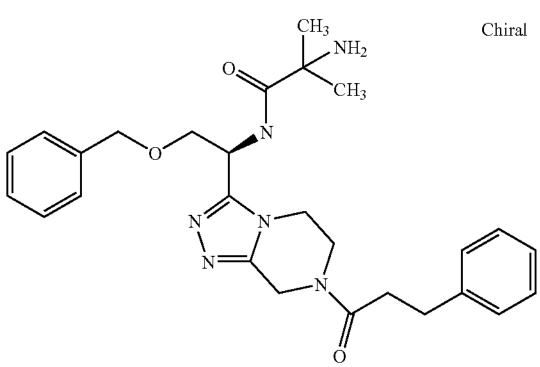 | Chiral | 491 | 95 | 2.21 |

| Compound number | Structure | Mass M + H | HPLC Purity (%) | HPLC Retention (min) |
| --- | --- | --- | --- | --- |
| 173 | 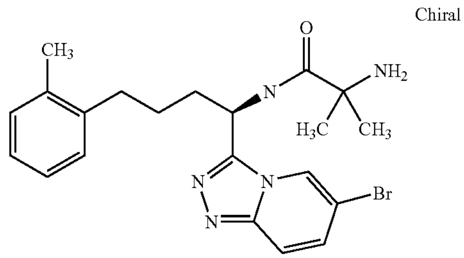 | 447 | 97 | 2.8 |
| 174 | 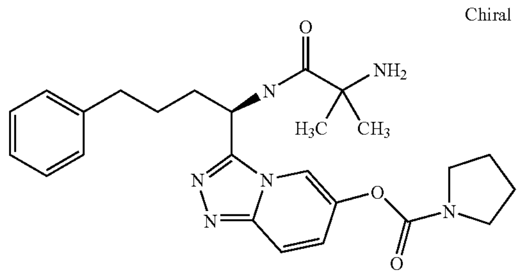 | 467 | 95 | 2.8 |
| 175 | 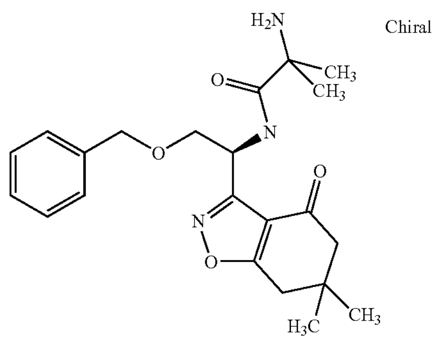 | 400 | 95 | 2.34 |
| 176 | 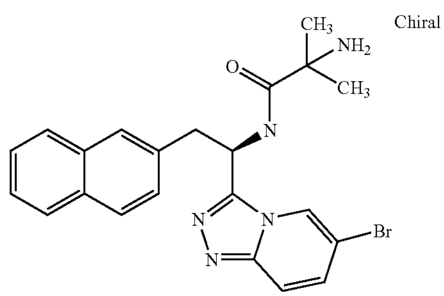 | 453 | 90 | 2.37 |
| 177 | 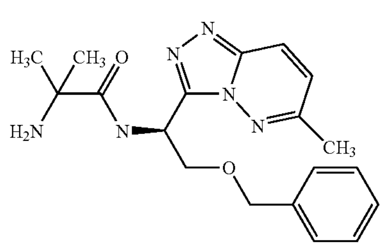 | 369 | 98 | 2.58 |

-continued

| Compound number | Structure | | Mass M + H | HPLC Purity (%) | HPLC Retention (min) |
|---|---|---|---|---|---|
| 178 | 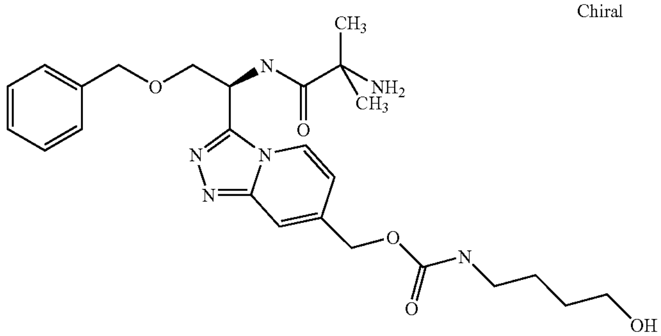 | Chiral | 499 | 95 | 1.75 |
| 179 | 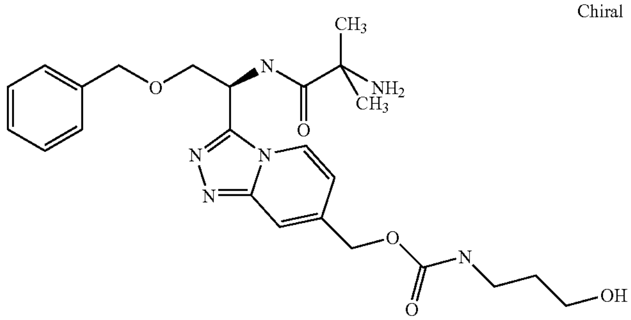 | Chiral | 485 | 90 | 1.6 |
| 180 | 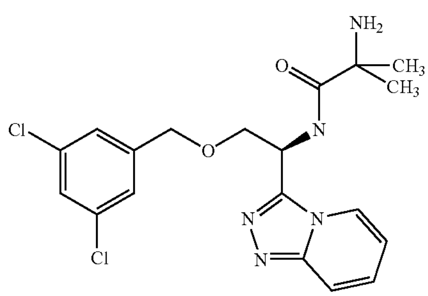 | | 423 | 97 | 5.80 |
| 181 | 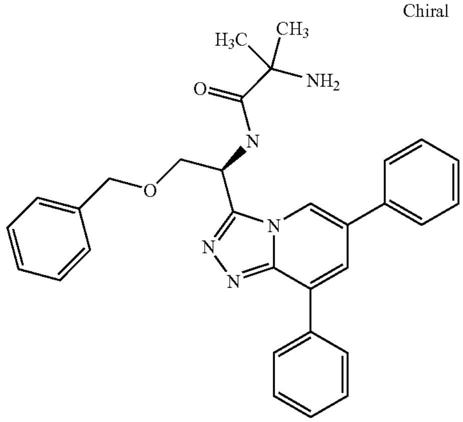 | Chiral | 506 | 94 | 3.2 |

-continued

| Compound number | Structure | Mass M + H | HPLC Purity (%) | HPLC Retention (min) |
|---|---|---|---|---|
| 182 | Chiral | 465 | 100 | 2.8 |
| 183 | Chiral | 430 | 88 | 2.4 |
| 184 | 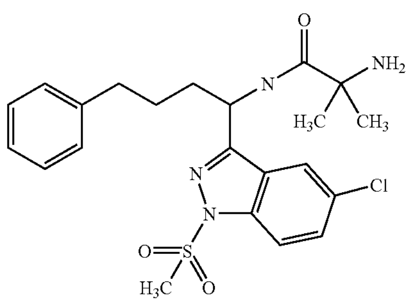 | 463 | 94 | 3.4 |
| 185 | Chiral | 414 | 94 | 2.23 |

-continued

| Compound number | Structure | Mass M + H | HPLC Purity (%) | HPLC Retention (min) |
|---|---|---|---|---|
| 186 | 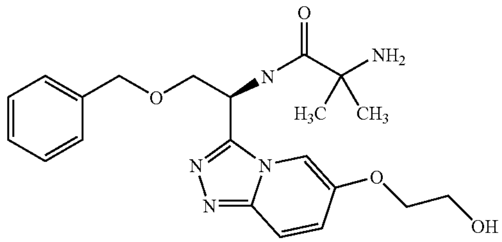 | 414 | 94 | 2.23 |
| 187 | 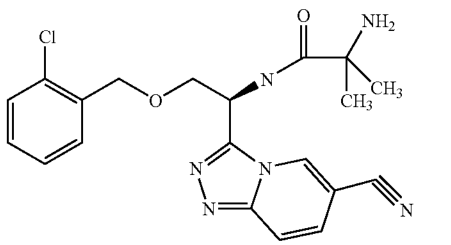 | 413 | 97 | 2.6 |
| 188 | 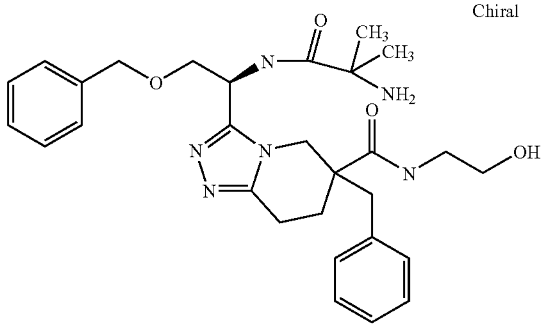 | 535 | 90 | 2.62 |
| 189 | 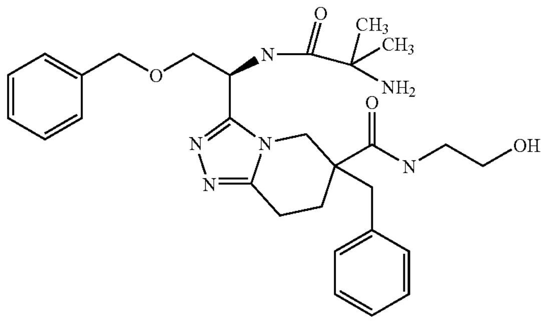 | 535 | 95 | 2.8 |
| 190 | 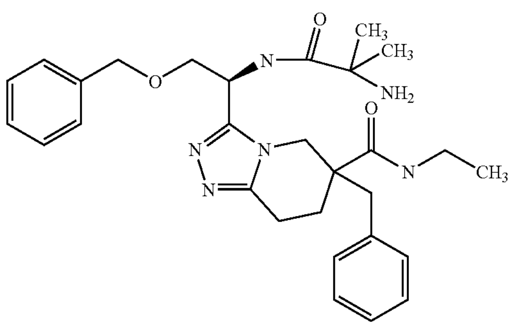 | 519 | 96 | 2.88, 2.91 |

-continued

| Compound number | Structure | Mass M + H | HPLC Purity (%) | HPLC Retention (min) |
|---|---|---|---|---|
| 191 | Chiral | 563 | 90 | 2.76 |
| 192 | Chiral | 563 | 90 | 2.87 |
| 193 | Chiral | 442 | 98 | 2.5 |
| 194 | Chiral | 497 | 98 | |
| 195 | Chiral | 485 | 98 | |

-continued

| Compound number | Structure | Mass M + H | HPLC Purity (%) | HPLC Retention (min) |
|---|---|---|---|---|
| 196 | 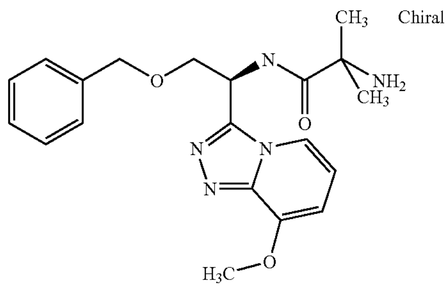 | 384 | 95 | 1.67 |
| 197 | 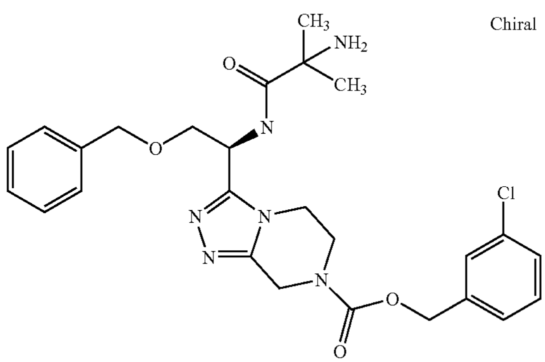 | 527 | 90 | 2.64 |
| 198 | 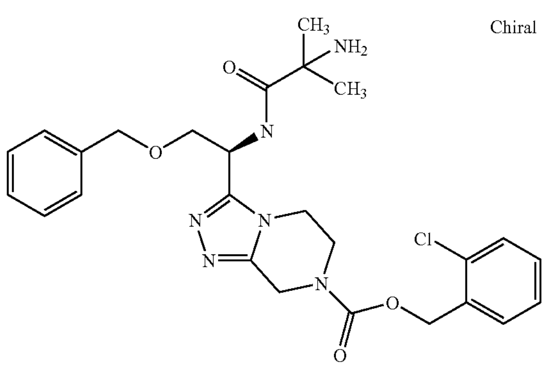 | 527 | 84 | 2.56 |
| 199 | 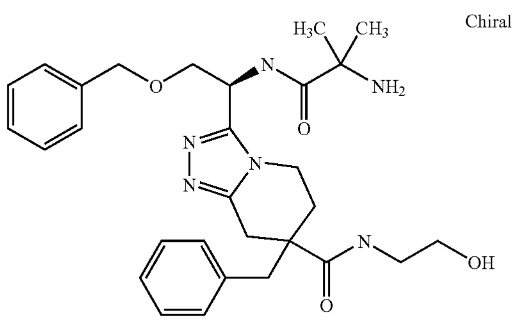 | 535 | 98 | 2.5 |

-continued

| Compound number | Structure | | Mass M + H | HPLC Purity (%) | HPLC Retention (min) |
|---|---|---|---|---|---|
| 200 | 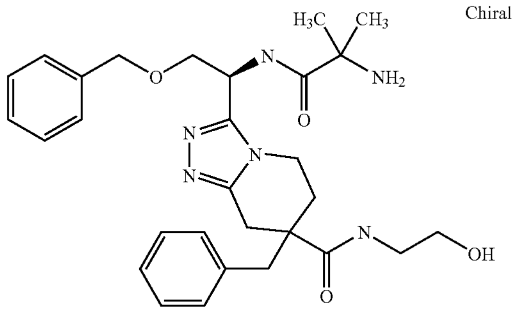 | Chiral | 535 | 95 | 2.8 |
| 201 | 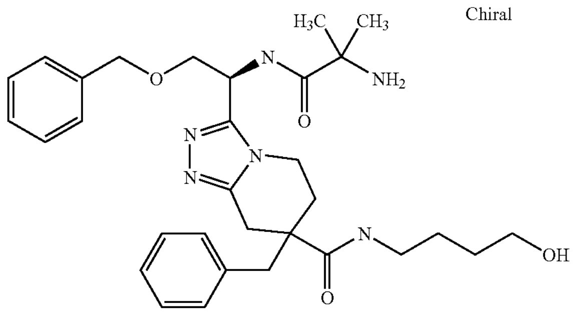 | Chiral | 563 | 98 | 2.68 |
| 202 | 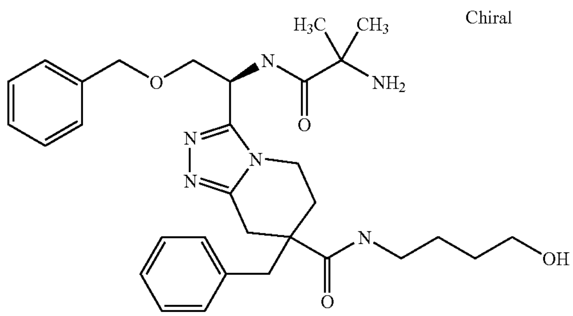 | Chiral | 563 | 98 | 2.9 |
| 203 | 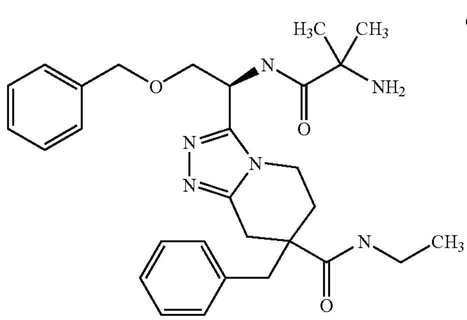 | Chiral | 519 | 90 | 2.86 |

-continued
| Compound number | Structure | | Mass M + H | HPLC Purity (%) | HPLC Retention (min) |
|---|---|---|---|---|---|
| 204 | 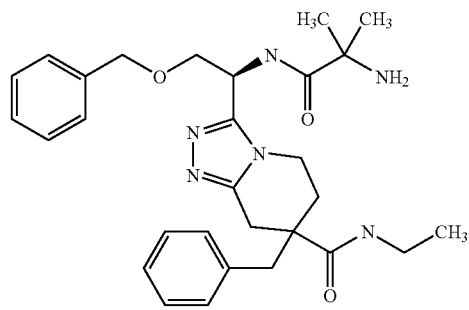 | Chiral | 519 | 90 | 2.94 |
| 205 | 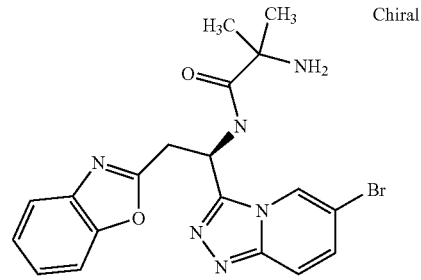 | Chiral | 444 | 90 | 1.77 |
| 206 | 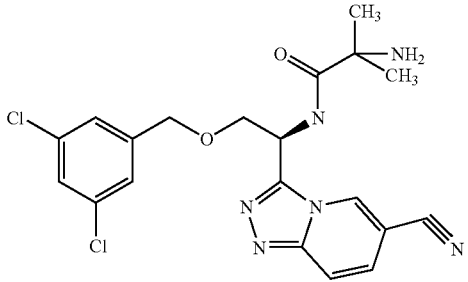 | Chiral | 448 | 95 | 6.04 |
| 207 | 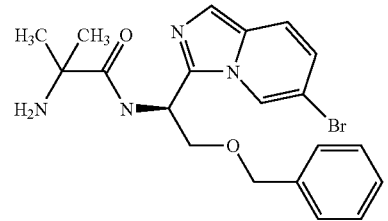 | | 432 | 98 | 2.94 |
| 208 | 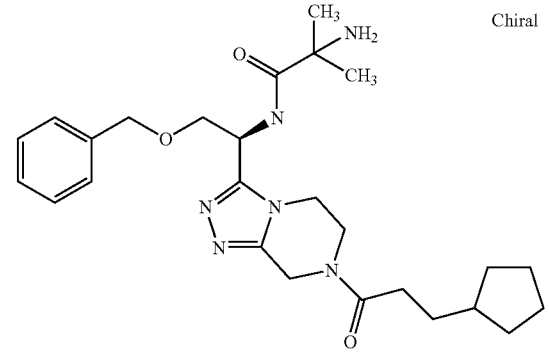 | Chiral | 483 | 90 | 2.53 |

-continued
| Compound number | Structure | Mass M + H | HPLC Purity (%) | HPLC Retention (min) |
|---|---|---|---|---|
| 209 | 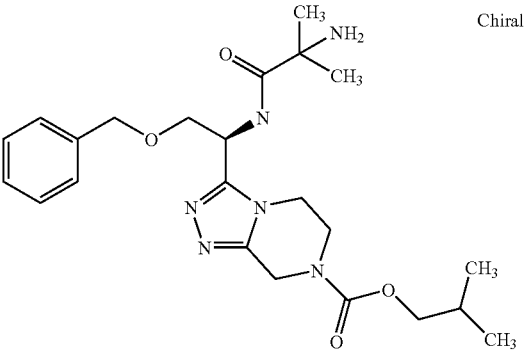 Chiral | 459 | 90 | 2.25 |
| 210 | 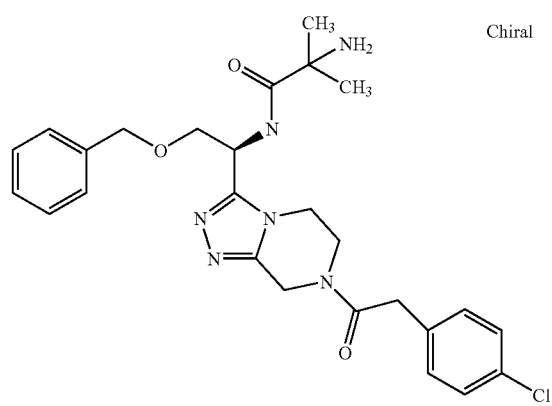 Chiral | 512 | 95 | 2.36 |
| 211 | 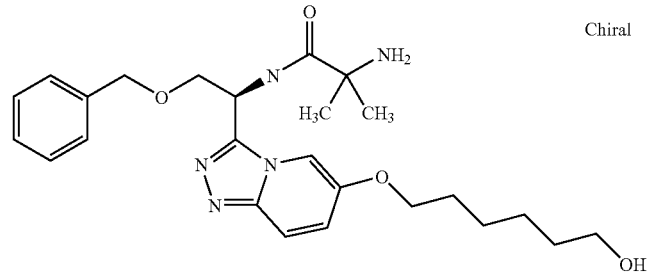 Chiral | 470 | 98 | 3.07 |
| 212 | 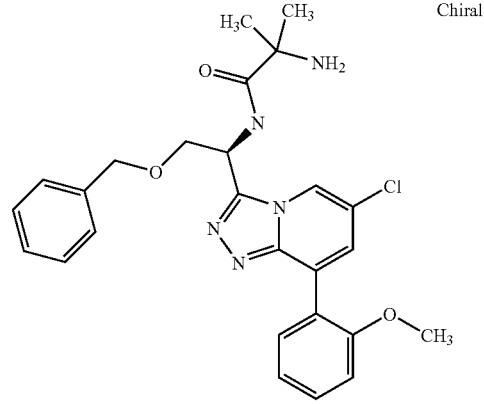 Chiral | 495 | 100 | 2.82 |

-continued

| Compound number | Structure | Mass M + H | HPLC Purity (%) | HPLC Retention (min) |
|---|---|---|---|---|
| 213 | Chiral | 512 | 100 | 2.87 |
| 214 | Chiral | 499 | 100 | 2.87 |
| 215 | Chiral | 482 | 100 | 2.78 |

-continued

| Compound number | Structure | Mass M + H | HPLC Purity (%) | HPLC Retention (min) |
|---|---|---|---|---|
| 216 | Chiral | 532 | 100 | 2.92 |
| 217 | Chiral | 475 | 95 | 1.61 |
| 218 | Chiral | 505 | 85 | 2.41 |
| 219 | Chiral | 528 | 90 | 2.62 |

-continued

| Compound number | Structure | Mass M + H | HPLC Purity (%) | HPLC Retention (min) |
|---|---|---|---|---|
| 220 | Chiral | 521 | 90 | 2.32 |
| 221 | Chiral | 527 | 90 | 2.49 |
| 222 | Chiral | 521 | 90 | 2.7 |
| 223 | Chiral | 561 | 90 | 2.63 |

| Compound number | Structure | Mass M + H | HPLC Purity (%) | HPLC Retention (min) |
|---|---|---|---|---|
| 224 | 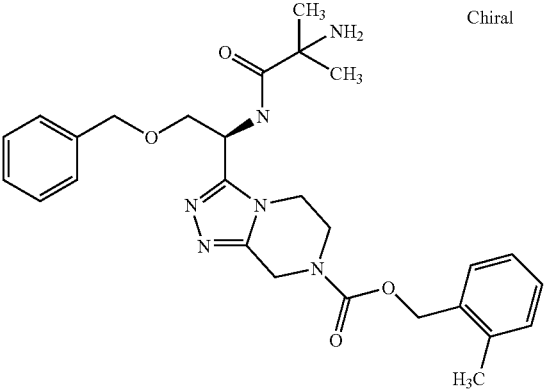 Chiral | 547 | 90 | 2.9 |
| 225 | 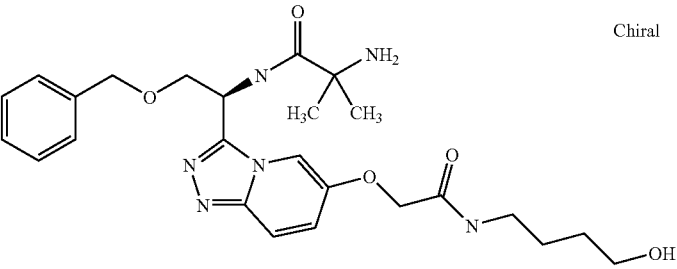 Chiral | 499 | 94 | 2.4 |
| 226 | 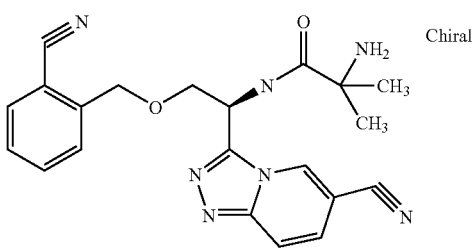 Chiral | 404 | 95 | 1.45 |
| 227 | 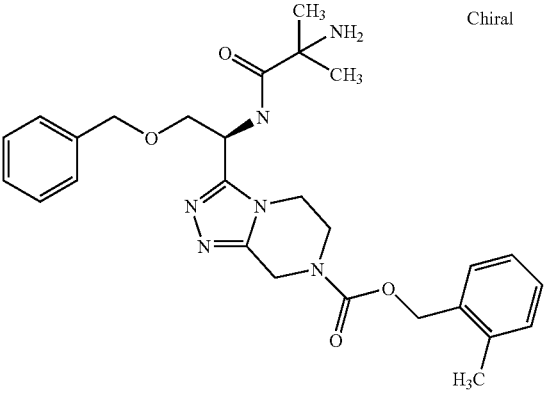 Chiral | 507 | 92 | 2.5 |

-continued
| Compound number | Structure | Mass M + H | HPLC Purity (%) | HPLC Retention (min) |
|---|---|---|---|---|
| 228 | 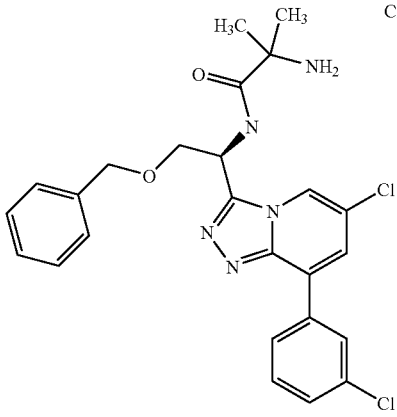 Chiral | 499 | 100 | 3.05 |
| 229 | 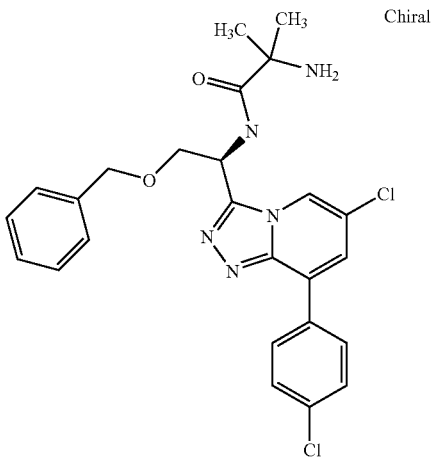 Chiral | 499 | 100 | 3.06 |
| 230 | 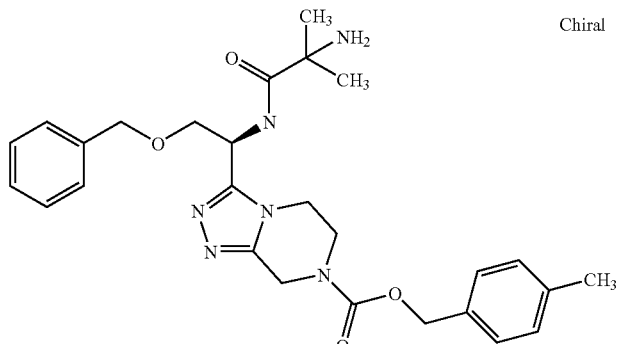 Chiral | 507 | 97 | 2.51 |

-continued
| Compound number | Structure | Mass M + H | HPLC Purity (%) | HPLC Retention (min) |
|---|---|---|---|---|
| 231 | 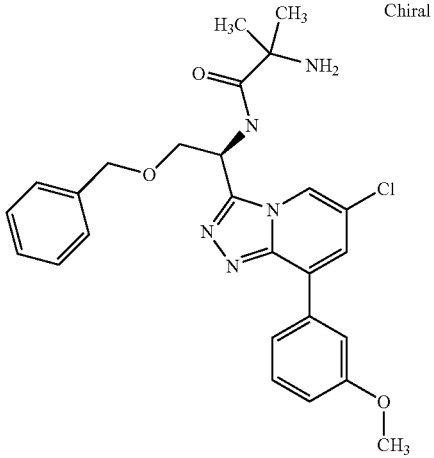 Chiral | 495 | 94 | 2.9 |
| 232 | 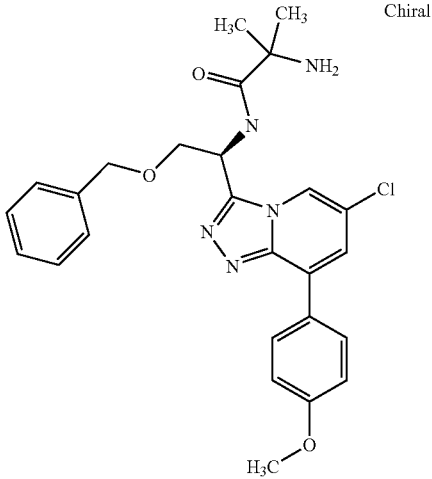 Chiral | 495 | 95 | 2.9 |
| 233 | 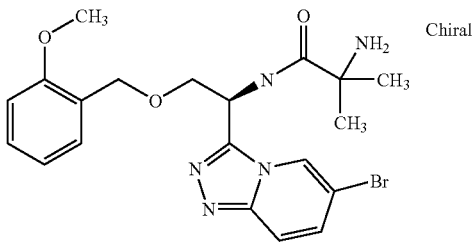 Chiral | 463 | 97 | 2.85 |

-continued

| Compound number | Structure | Mass M + H | HPLC Purity (%) | HPLC Retention (min) |
|---|---|---|---|---|
| 234 | Chiral | 482 | 93 | 2.85 |
| 235 | Chiral | 482 | 99 | 2.85 |
| 236 | Chiral | 500 | 97 | 2.9 |

-continued

| Compound number | Structure | Mass M + H | HPLC Purity (%) | HPLC Retention (min) |
|---|---|---|---|---|
| 237 | Chiral | 509 | 97 | 3.06 |
| 238 | Chiral | 557 | 92 | 3.4 |
| 239 | Chiral | 495 | 87 | 2.68 |

-continued

| Compound number | Structure | | Mass M + H | HPLC Purity (%) | HPLC Retention (min) |
|---|---|---|---|---|---|
| 240 | 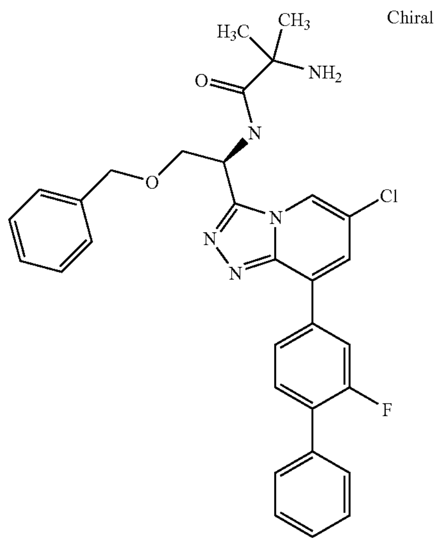 | Chiral | 559 | 98 | 3.4 |
| 241 | 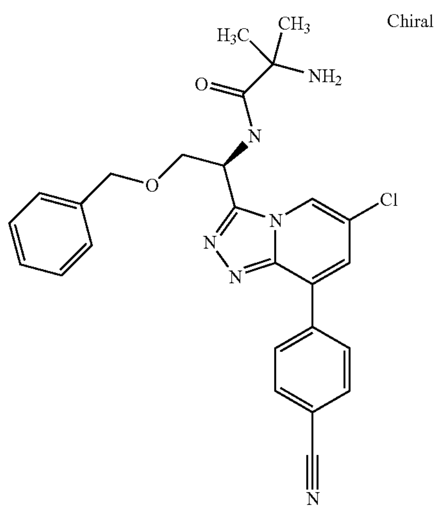 | Chiral | 489 | 80 | 2.6 |
| 242 | 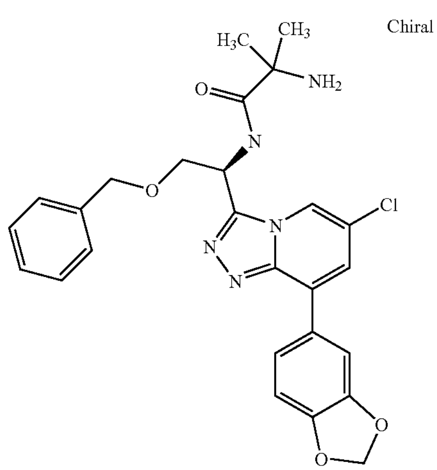 | Chiral | 508 | 90 | 2.85 |

-continued
| Compound number | Structure | Mass M + H | HPLC Purity (%) | HPLC Retention (min) |
|---|---|---|---|---|
| 243 | 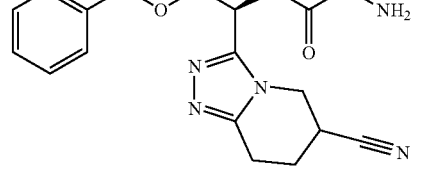 | 383 | 90 | 1.96 |
| 244 | 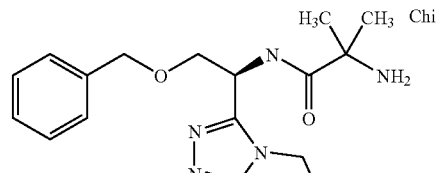 | 383 | 88 | 2.19 |
| 245 | 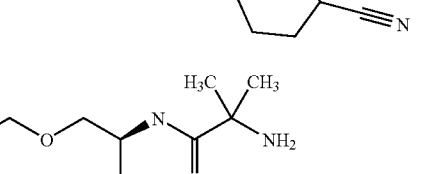 | 527 | 96 | 2.8 |
| 246 | 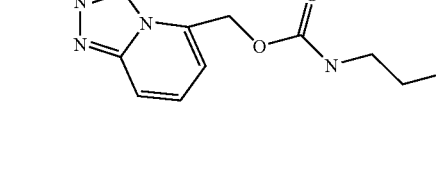 | 584 | 90 | 2.44 |
| 247 | 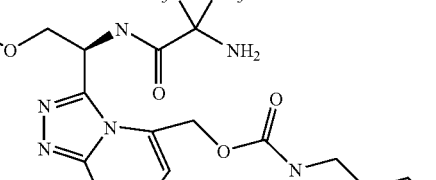 | 500 | 98 | 2.94 |

-continued
| Compound number | Structure | Mass M + H | HPLC Purity (%) | HPLC Retention (min) |
|---|---|---|---|---|
| 248 | 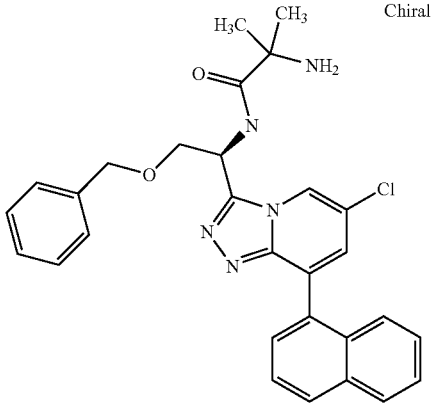 Chiral | 514 | 100 | 3.1 |
| 249 | 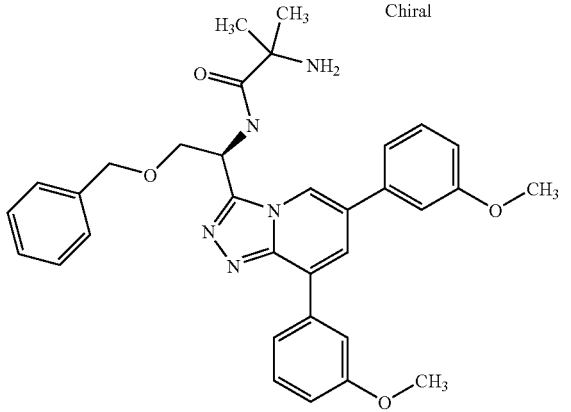 Chiral | 566 | 94 | 3.28 |
| 250 | 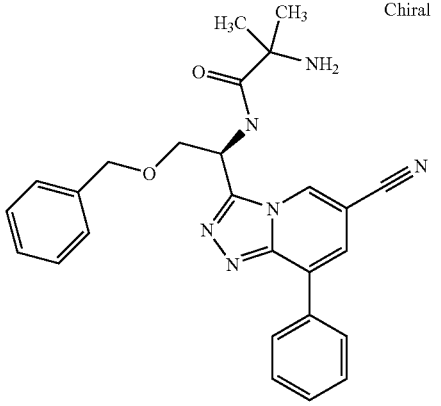 Chiral | 455 | 98 | 2.55 |

-continued

| Compound number | Structure | Mass M + H | HPLC Purity (%) | HPLC Retention (min) |
|---|---|---|---|---|
| 251 | 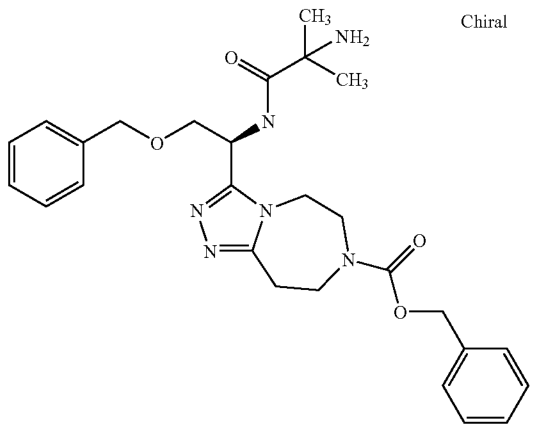 | 507 | 82 | 2.2 |
| 252 | 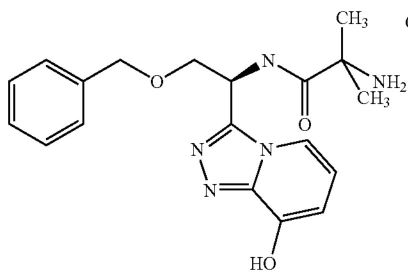 | 370 | 95 | 1.38 |
| 253 | 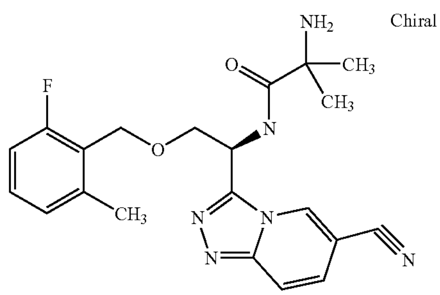 | 411 | 96 | 5.19 |
| 254 | 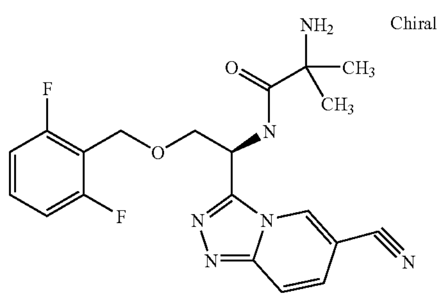 | 415 | 95 | 4.67 |

-continued
| Compound number | Structure | | HPLC Mass Purity M + H (%) | HPLC Retention (min) |
|---|---|---|---|---|
| 255 | 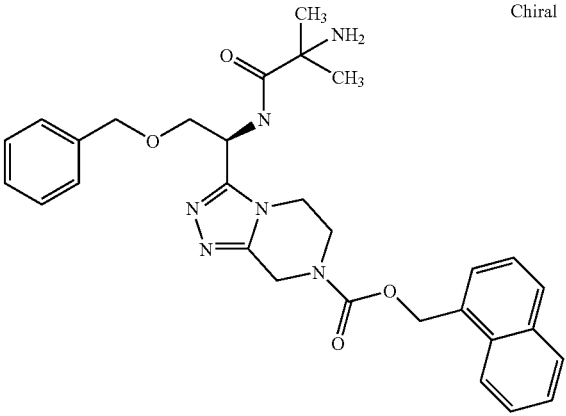 | Chiral | 543 91 | 2.76 |
| 256 | 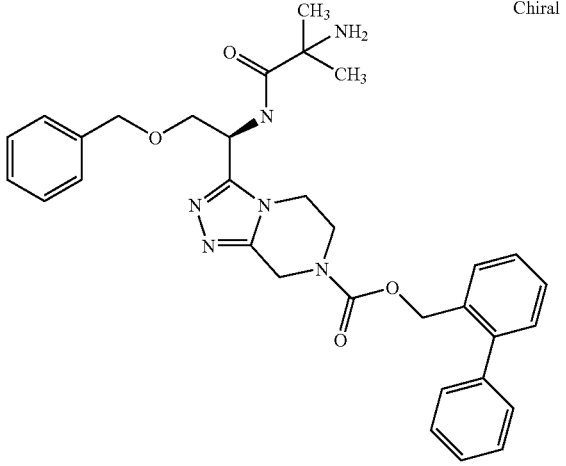 | Chiral | 569 94 | 2.88 |
| 257 | 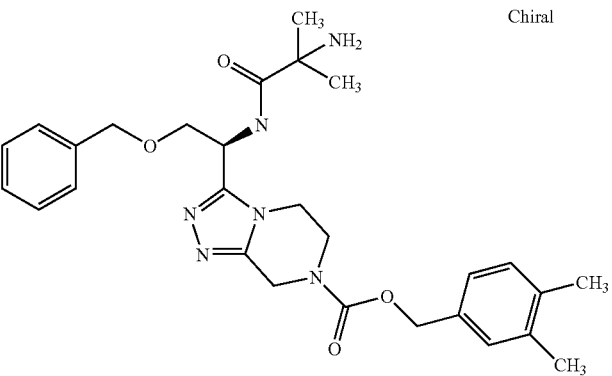 | Chiral | 521 93 | 2.74 |

-continued

| Compound number | Structure | Mass M + H | HPLC Purity (%) | HPLC Retention (min) |
|---|---|---|---|---|
| 258 | 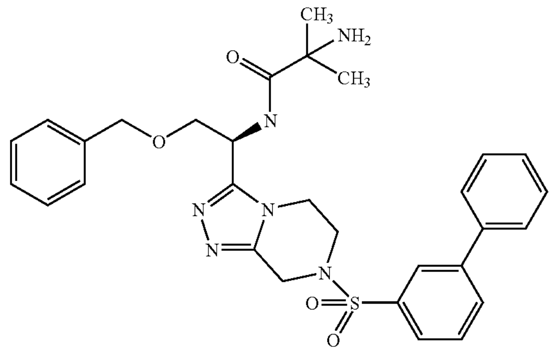 | 575 | 98 | 2.79 |
| 259 | 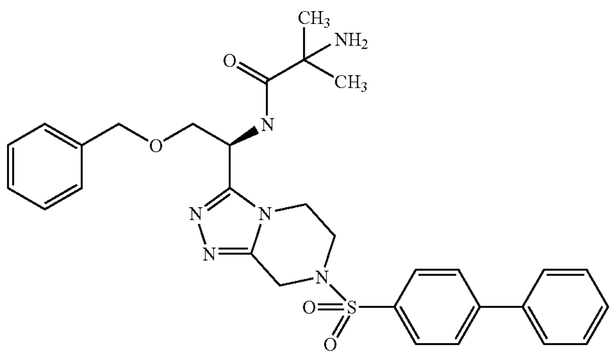 | 575 | 92 | 2.74 |
| 260 | 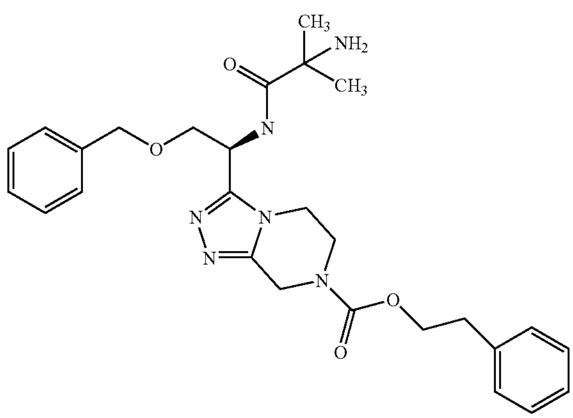 | 507 | 90 | 2.43 |
| 261 | Chiral | 496 | 98 | 2.62 |

-continued

| Compound number | Structure | Mass M + H | HPLC Purity (%) | HPLC Retention (min) |
|---|---|---|---|---|
| 262 | Chiral | 471 | 98 | 2.38 |
| 263 | Chiral | 499 | 95 | 2.58 |
| 264 | Chiral | 515 | 98 | 2.50 |
| 265 | Chiral | 531 | 92 | 2.62 |
| 266 | Chiral | 547 | 92 | 2.93 |

-continued

| Compound number | Structure | | Mass M + H | HPLC Purity (%) | HPLC Retention (min) |
|---|---|---|---|---|---|
| 267 | 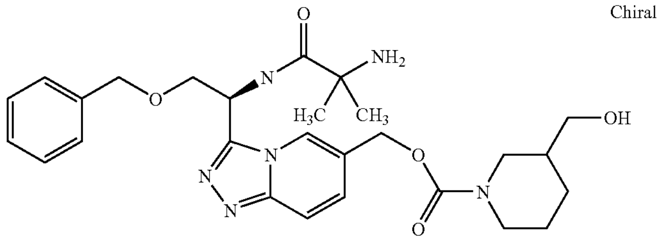 | Chiral | 525 | 98 | 2.84 |
| 268 | 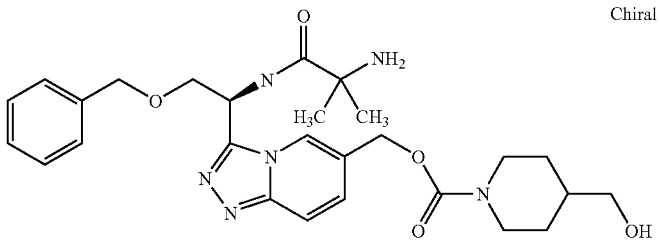 | Chiral | 525 | 96 | 2.76 |
| 269 | 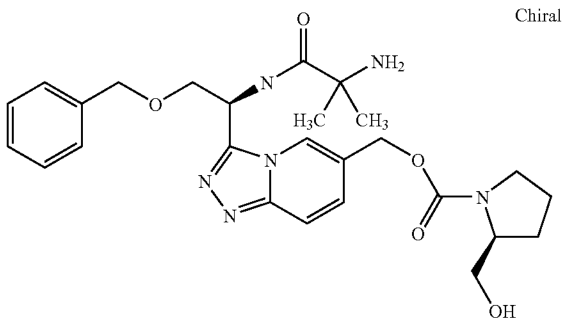 | Chiral | 511 | 99 | 2.73 |
| 270 | 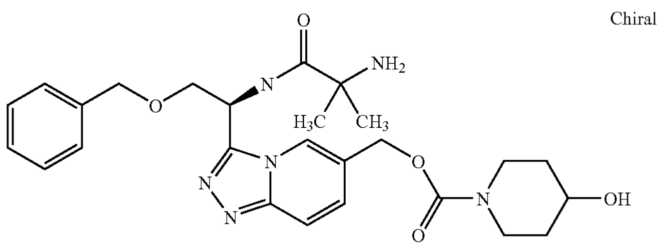 | Chiral | 511 | 98 | 2.62 |
| 271 | 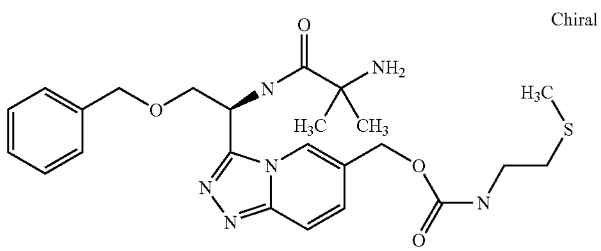 | Chiral | 501 | 95 | 2.83 |
| 272 | 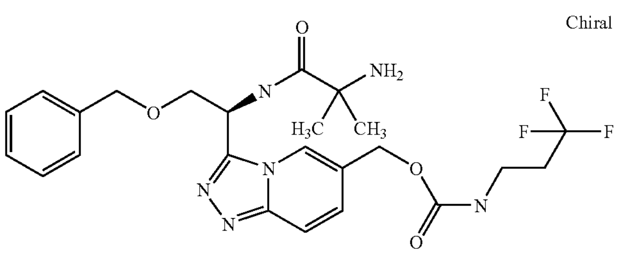 | Chiral | 523 | 96 | 2.93 |

-continued

| Compound number | Structure | Mass M + H | HPLC Purity (%) | HPLC Retention (min) |
|---|---|---|---|---|
| 273 | 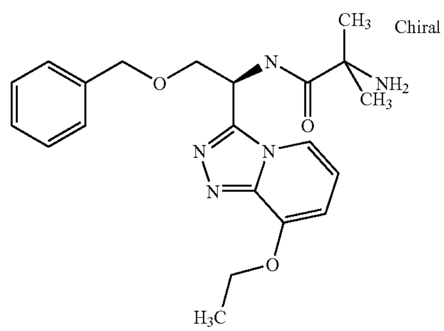 | 398 | 93 | 1.90 |
| 274 | 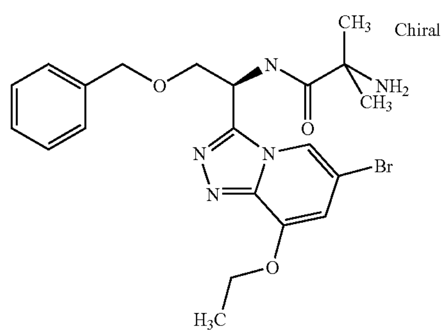 | 477 | 95 | 2.41 |
| 275 | 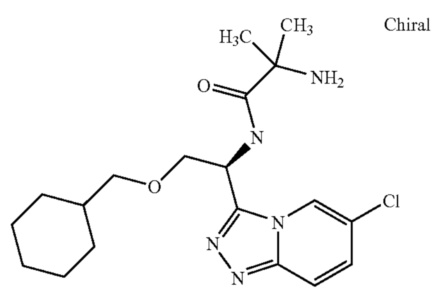 | 394 | 95 | 2.57 |
| 276 | 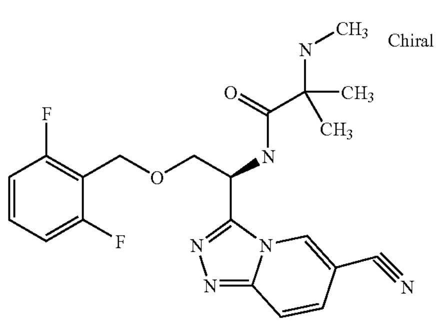 | 429 | 94 | 4.73 |

-continued

| Compound number | Structure | Mass M + H | HPLC Purity (%) | HPLC Retention (min) |
|---|---|---|---|---|
| 277 | 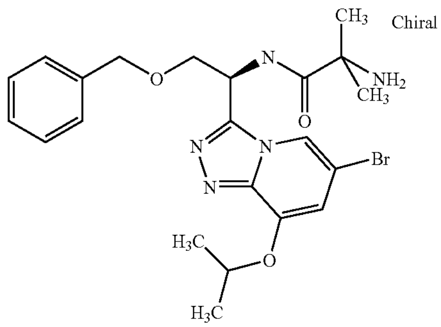 | 491 | 95 | 2.17 |
| 278 | 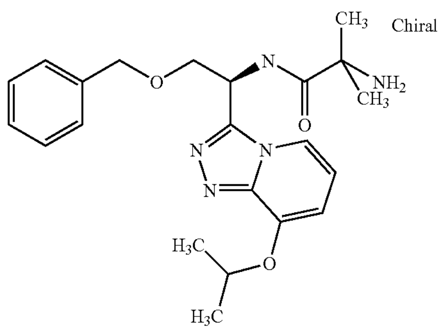 | 412 | 95 | 2.07 |
| 279 | 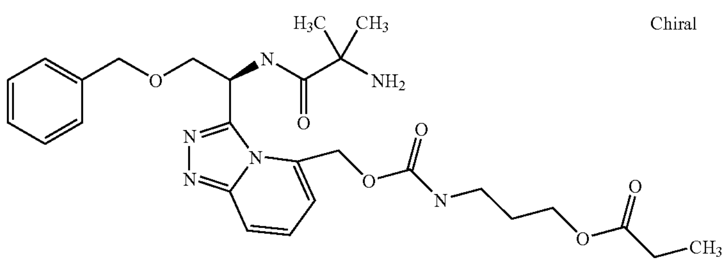 | 541 | 95 | 3.13 |
| 280 | 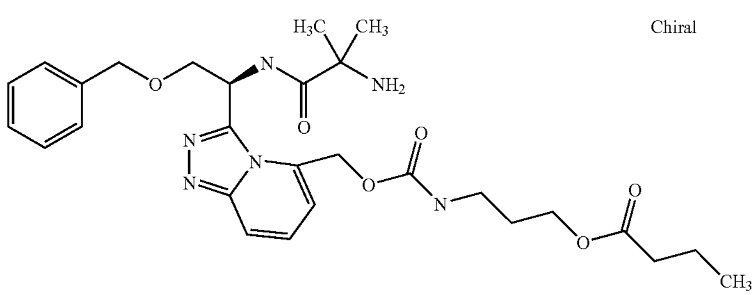 | 555 | 95 | 3.18 |
| 281 | 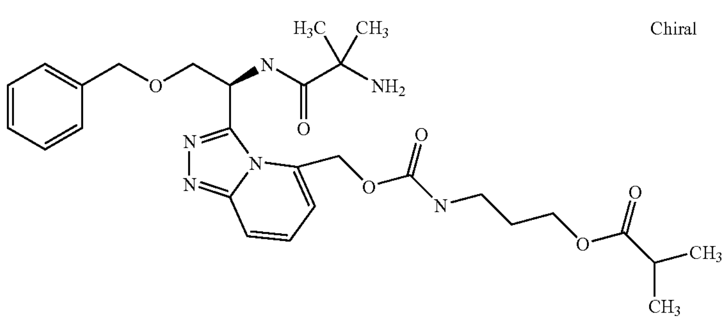 | 555 | 95 | 3.13 |

| Compound number | Structure | | Mass M + H | HPLC Purity (%) | HPLC Retention (min) |
|---|---|---|---|---|---|
| 282 | (structure) | Chiral | 542 | 90 | 2.16 |
| 283 | (structure) | Chiral | 556 | 90 | 2.22 |
| 284 | (structure) | Chiral | 556 | 90 | 2.22 |
| 285 | (structure) | Chiral | 460 | 95 | 2.54 |

| Compound number | Structure | Mass M + H | HPLC Purity (%) | HPLC Retention (min) |
|---|---|---|---|---|
| 286 | 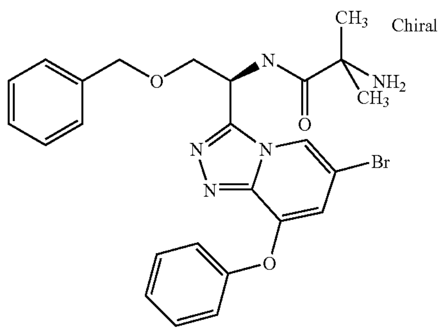 | 525 | 90 | 2.07 |
| 287 | 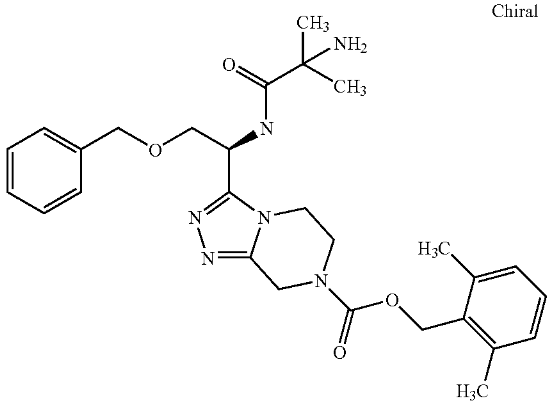 | 521 | 90 | 2.72 |
| 288 | 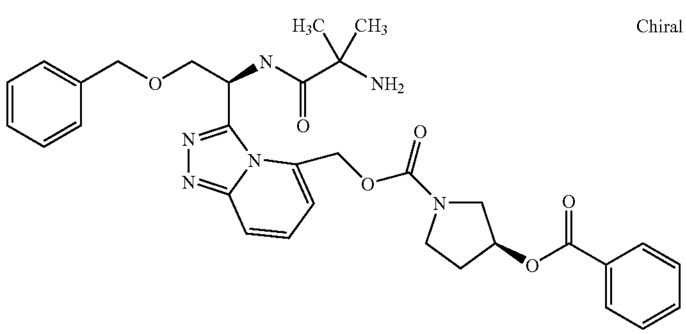 | 601 | 90 | 3.34 |
| 289 | 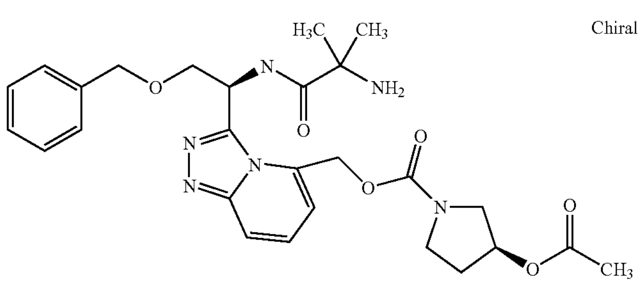 | 539 | 90 | 2.85 |

| Compound number | Structure | Mass M + H | HPLC Purity (%) | HPLC Retention (min) |
|---|---|---|---|---|
| 290 | Chiral | 581 | 90 | 3.33 |
| 291 | Chiral | 507 | 90 | 2.42 |
| 292 | Chiral | 383 | 97 | 1.47 |
| 293 | Chiral | 359 | 100 | 0.22 |

-continued
| Compound number | Structure | Mass M + H | HPLC Purity (%) | HPLC Retention (min) |
|---|---|---|---|---|
| 294 | 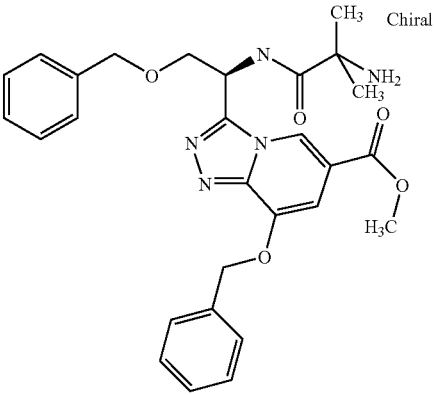 | 518 | 95 | 2.80 |
| 295 | 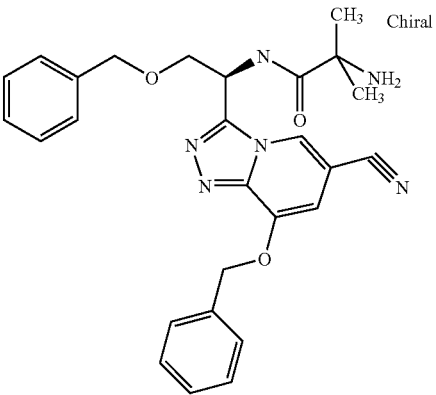 | 485 | 93 | 2.61 |
| 296 | 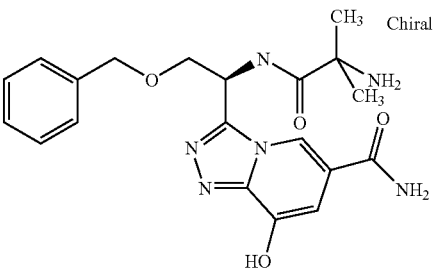 | 413 | 91 | 1.39 |
| 297 | 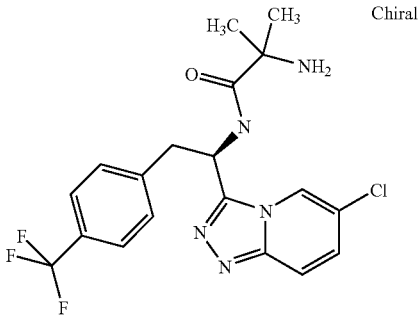 | 426 | 100 | 2.59 |

-continued

| Compound number | Structure | Mass M + H | HPLC Purity (%) | HPLC Retention (min) |
|---|---|---|---|---|
| 298 | 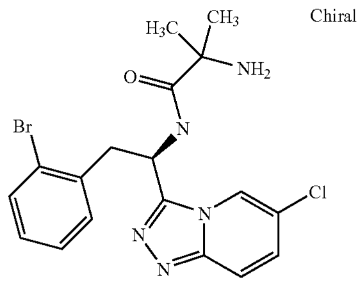 | 437 | 98 | 2.11 |
| 299 | 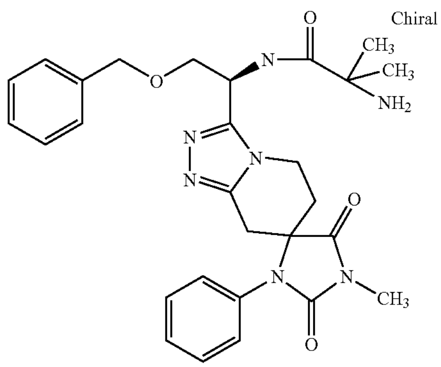 | 532 | 80 | 2.50 |
| 300 | 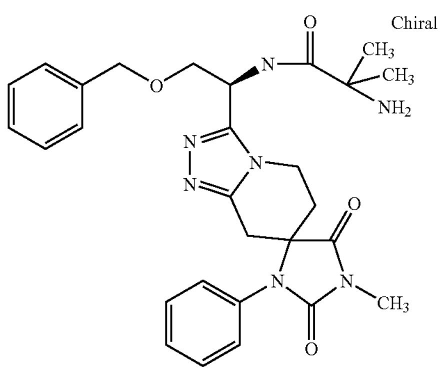 | 532 | 100 | 2.64 |
| 301 | 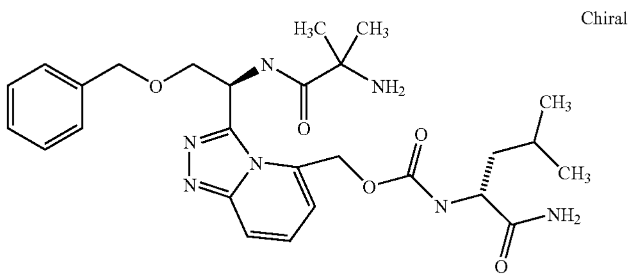 | 540 | 93 | 2.89 |

-continued

| Compound number | Structure | Mass M + H | HPLC Purity (%) | HPLC Retention (min) |
|---|---|---|---|---|
| 302 | Chiral | 477 | 86 | 1.89 |
| 303 | Chiral | 540 | 95 | 3.01 |
| 304 | Chiral | 498 | 82 | 2.37 |
| 305 | 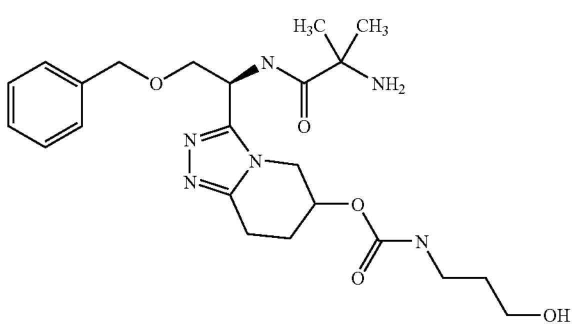 | 475 | 75 | 2.30 |

-continued

| Compound number | Structure | Mass M + H | HPLC Purity (%) | HPLC Retention (min) |
|---|---|---|---|---|
| 306 | 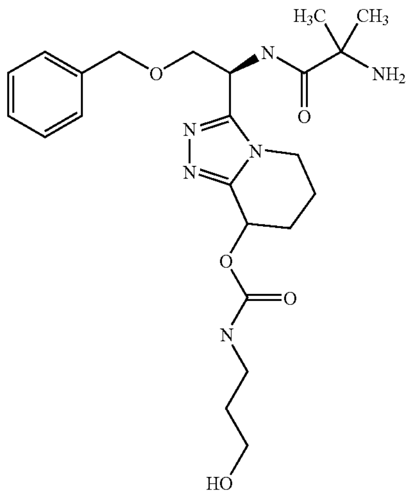 | 475 | 85 | 2.30 |
| 307 | 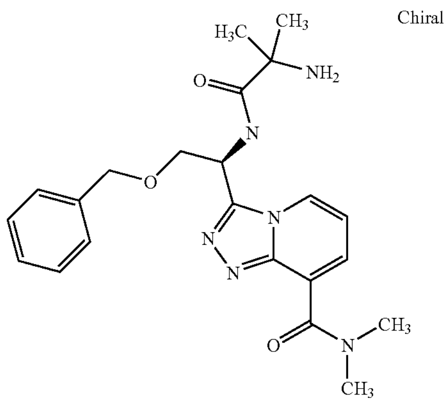 | 425 | 99 | 1.56 |
| 308 | 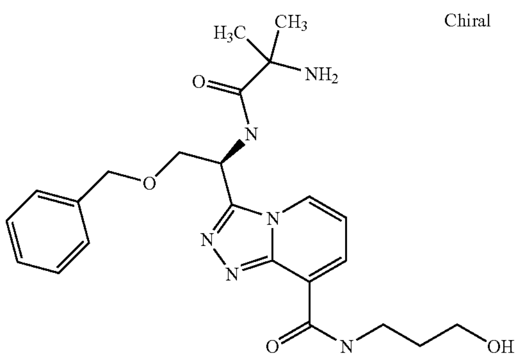 | 455 | 93 | 1.86 |
| 309 | 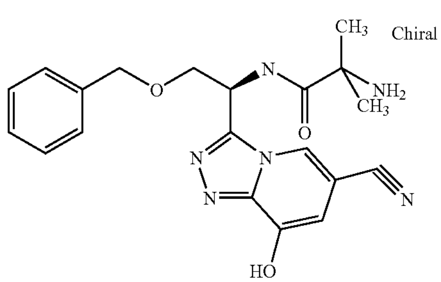 | 395 | 90 | 1.73 |

-continued

| Compound number | Structure | Mass M + H | HPLC Purity (%) | HPLC Retention (min) |
|---|---|---|---|---|
| 310 | 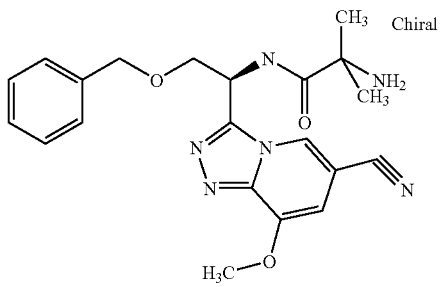 | 409 | 93 | 1.82 |
| 311 | 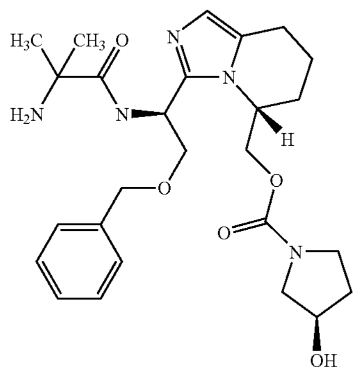 | 500 | 96 | 2.64 |
| 312 | 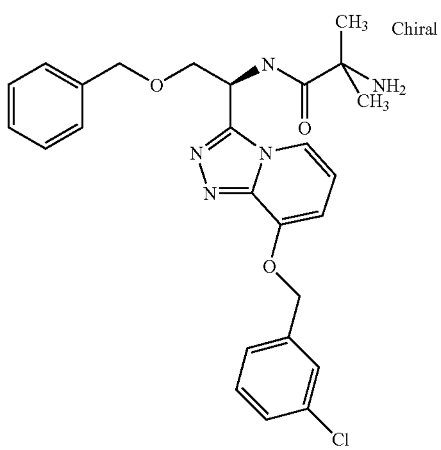 | 495 | 96 | 2.78 |
| 313 | 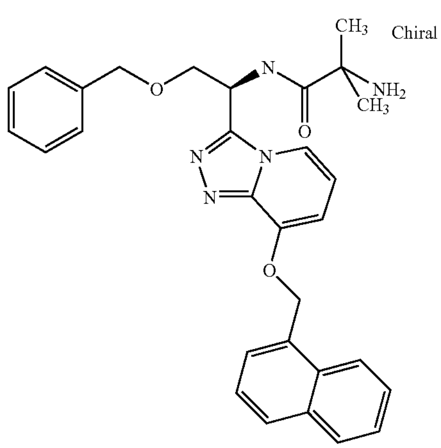 | 510 | 98 | 2.92 |

-continued
| Compound number | Structure | Mass M + H | HPLC Purity (%) | HPLC Retention (min) |
|---|---|---|---|---|
| 314 | 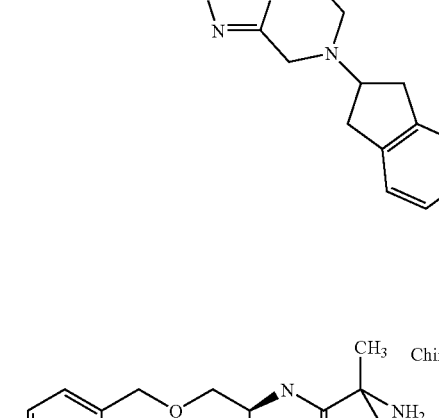 | 475 | 89 | 1.99 |
| 315 | 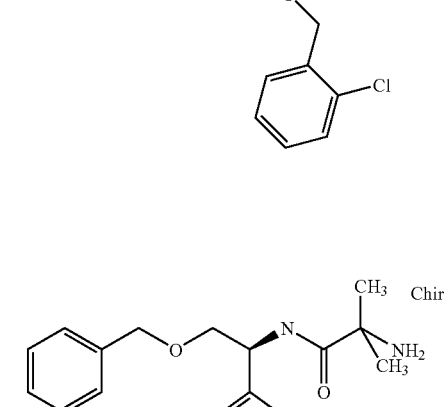 | 495 | 95 | 2.79 |
| 316 | 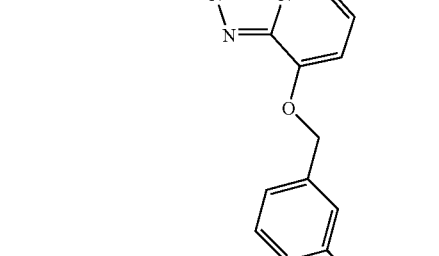 | 525 | 96 | 2.92 |

-continued

| Compound number | Structure | Mass M + H | HPLC Purity (%) | HPLC Retention (min) |
|---|---|---|---|---|
| 317 | Chiral | 437 | 100 | 2.11 |
| 318 | Chiral | 467 | 97 | 1.37 |
| 319 | Chiral | 439 | 98 | 2.26 |
| 320 | Chiral | 468 | 98 | 1.13 |

-continued
| Compound number | Structure | | Mass M + H | HPLC Purity (%) | HPLC Retention (min) |
|---|---|---|---|---|---|
| 321 | 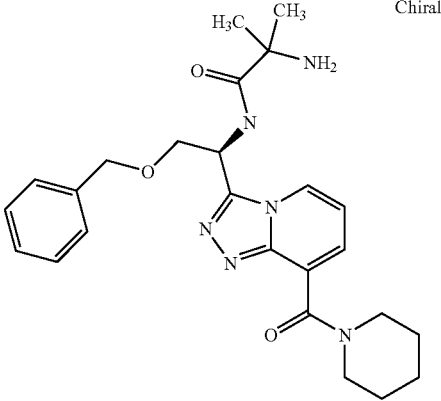 | Chiral | 465 | 94 | 1.90 |
| 322 | 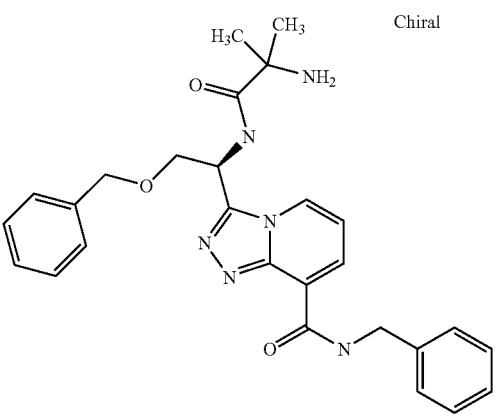 | Chiral | 487 | 99 | 2.57 |
| 323 | 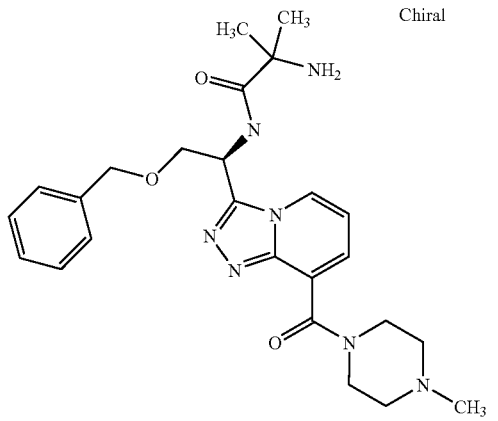 | Chiral | 480 | 83 | 0.73 |

| Compound number | Structure | Mass M + H | HPLC Purity (%) | HPLC Retention (min) |
|---|---|---|---|---|
| 324 | Chiral | 411 | 99 | 1.74 |
| 325 | Chiral | 524 | 96 | 2.56 |
| 326 | Chiral | 574 | 95 | 2.93 |
| 327 | Chiral | 498 | 93 | 1.64 |

-continued

| Compound number | Structure | Mass M + H | HPLC Purity (%) | HPLC Retention (min) |
|---|---|---|---|---|
| 328 | Chiral | 568 | 95 | 3.05 |
| 329 | Chiral | 602 | 93 | 3.08 |
| 330 | 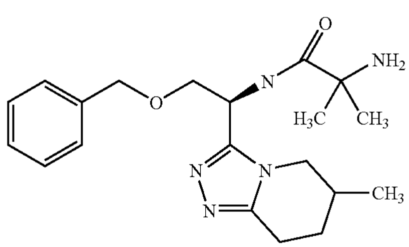 | 372 | 80 | 1.75 |
| 331 | Chiral | 423 | 98 | 1.14 |
| 332 | Chiral | 371 | 90 | 2.14 |

-continued
| Compound number | Structure | Mass M + H | HPLC Purity (%) | HPLC Retention (min) |
|---|---|---|---|---|
| 333 | 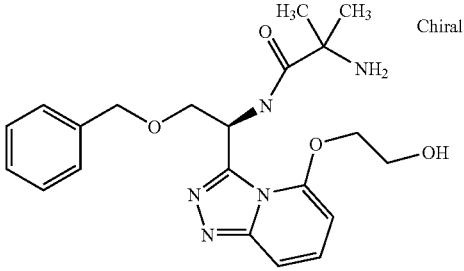 | 414 | 83 | 2.29 |
| 334 | 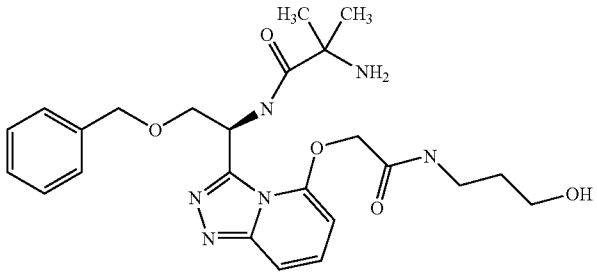 | 485 | 93 | 2.25 |
| 335 | 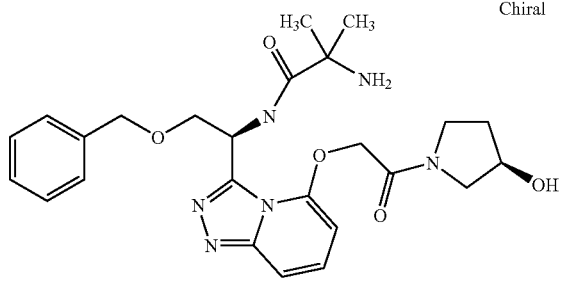 | 497 | 98 | 2.63 |
| 336 | 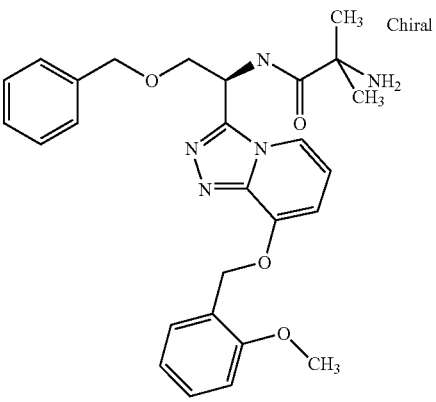 | 490 | 98 | 3.01 |

| Compound number | Structure | Mass M + H | HPLC Purity (%) | HPLC Retention (min) |
|---|---|---|---|---|
| 337 | 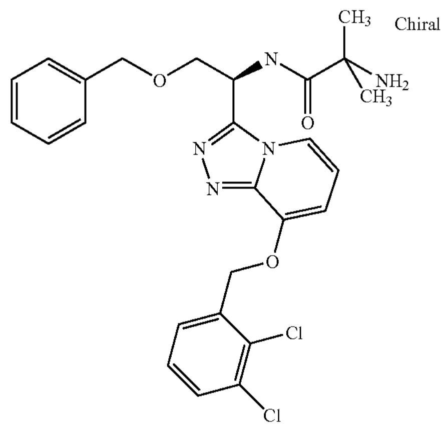 | 529 | 98 | 3.01 |

Example 338

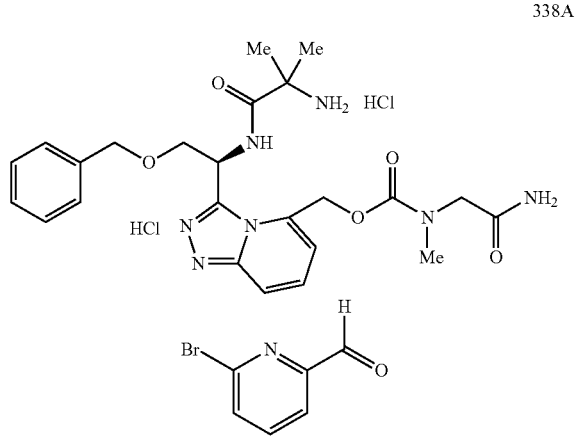

338A

To a solution n-BuLi (2.5 Min THF, 84 ml, 0.21 mol) in toluene (200 mL) at −10° C. was added n-BuMgCl (2.0 M in THF, 52.5 ml, 0.105 mol) over 10 min. The mixture was stirred at −10° C. for 30 min, then 2,6-dibromopyridine (71.07 g, 0.3 mol) in toluene (500 mL) was added via an additional funnel over 30 min. The resulting suspension was stirred at −10° C. for 2.5 hours, then transferred via a canula to a cooled solution of DMF in toluene (200 mL). The solution was stirred at −10° C. for 30 min, then 30% citric acid (300 mL) was added. After stirring for 30 min, the organic phase was washed with water (300 mL), brine (200 mL), and dried over sodium sulfate. After filtration the filtrate was concentrated to give 338A as light yellow colored solid (54.2 g). HPLC(A) retention time 1.88 min.

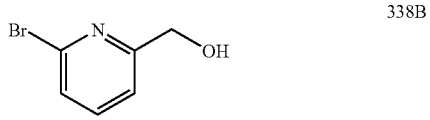

338B

To a stirred soln of 338A (29.0 g, 0.151 mol) in methanol (600 mL) cooled to 12° C. in a water bath is added sodium borohydride (5.89 g, 0.16 mol) in small batches over 20 min. The temperature is not allowed to rise above 23° C. The reaction mixture was stirred 1 h more and then cautiously quenched with ice cold 10% HCl to pH2 (total of 64 mL). The reaction mixture was concentrated in vacuo, generating considerable foaming. The residue was redissolved in methylene chloride (250 mL) and stirred with a 5% potassium carbonate solution (150 mL, at pH 8). The aqueos layer was extracted twice with methylene chloride (250 mL each). The combined organics were dried with sodium sulfate, filtered through magnesium sulfate, and concentrated in vacuo to give 338B as a yellow colored oil, (27.65 g). The compound slowly crystallizes to a yellow colored solid. MS (M+H+) 188, 190; HPLC(A) retention time 1.99 min.

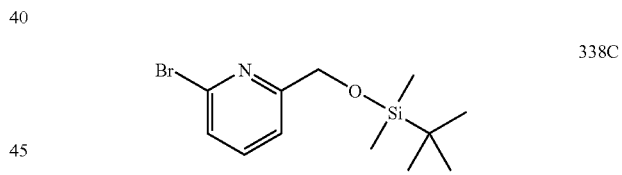

338C

To a stirred solution of 338B (25.0 g, 0.129 mol) in DMF (200 mL) at room temperature under argon is added imidazole (17.56 g, 0.258 mol) and then, after the imidazole had dissolved, tert-butyldimethylsilyl chloridel (23.27 g, 0.155 mol) in one portion. A slight endotherm is noted. After stirring for 16 h., the reaction mixture was quenched with ice water (500 mL) and extracted 3×250 mL hexanes. The hexane extracts were combined, washed twice with water (150 mL) and once with brine. After drying the organics over sodium sulfate, they were filtered through magnesium sulfate, and stripped to give 338C as a light yellow colored oil (39.15 g). MS (M+H) 302, 304; HPLC(A) retention time 4.56 min.

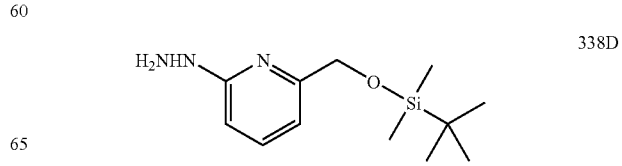

338D

A 1 L 3-necked flask is charged with a solution of 338C (38.5 g, 0.127 mol) in pyridine (500 ml) and treated with hydrazine (40 ml, 1.28 mol) in one portion. A slight endotherm is noted. The reaction mixture is stirred and heated to reflux under argon (pot temperature 109-111° C.) for 45 h. After cooling to room temp in an ice bath, solid sodium bicarbonate (11 g) is added. The mixture is stirred for 1 h and stripped to give a yellow oil. Addition of water (200 mL) leads to formation of a solid with the aid of seed crystals. The solid mass is broken up, collected, and washed with water (5×100 mL). In order to expedite drying, the solid is dissolved in ether (500 mL), washed once with brine, dried over sodium sulfate, and filtered through magnesium sulfate. The organics were concentrated in vacuo to give 338D as an off-white solid (31.5 g). MS (M+H$^+$) 254; HPLC(A) retention time 2.53 min.

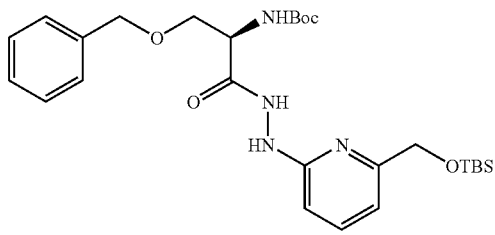

338E

A 1 L 3-necked flask (oven-dried) is charged with N-(tert-butoxycarbonyl)-D-serine (35.74 g, 0.12 mol) in THF (250 mL) and cooled to −13° C. (isopropanol/ice bath) under argon. N-Methylmorpholine (13.74 ml, 0.125 mol) is added in one portion (temperature temporarily rises to 2° C.). After the temperature cools again to −13° C., isobutylchloroformate (15.69 ml, 0.12 mol) is added at such a rate as to keep the temperature below −10° C. The reaction mixture is stirred 20 min and then a solution of 338D (30.4 g, 0.12 mol) in THF (100 mL) is added over 15 min, not allowing the temperature to rise above −5.5° C. during this addition process. The addition funnel is rinsed with THF (25 mL) and the yellow reaction slurry is stirred for 90 min. The reaction is quenched at −10° C. with saturated sodium bicarbonate (100 mL) and the aqueous layer is extracted twice with ethyl acetate (500 mL). The combined organics were washed once with brine, 10% citric acid, saturated sodium bicarbonate, and dried over sodium sulfate. After filtering through magnesium sulfate, the volatiles were removed in vacuo, and the residue restripped from methylene chloride/hexanes to give 338E as a yellow foam (63.97 g). MS (M+H+) 531; HPLC(A) retention time 3.91 min.

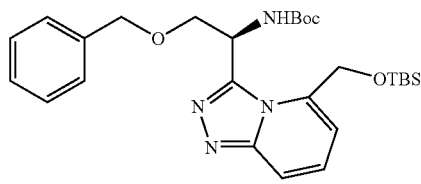

338F

To a stirred solution of 338E (93.6 g, 0.177 mol) in THF (800 mL) at −78° C. under nitrogen is added triethylamine (196 ml, 1.41 mol). After 10 min, dichlorotriphenylphosphine (194.2 g, 0.583 mol) is added portion wise over 10 min. The mixture was stirred and slowly warmed to room temperature overnight (~20 h). The volatiles were removed and the residue was filtered through a short silicon gel column, rinsing the column with hexane/ethyl acetate (1:2). The combined filtrates were evaporated to give the crude 338F (200 g, mixed with triphenylphosphine oxide). MS: (M+H+) 513; HPLC (A) retention time 4.30 min.

An alternative procedure: To a stirred solution of 338E (63.95 g, 0.12 mol) in THF (800 ml) at −73° C. under argon is added triethylamine (134 ml, 0.964 mol). After 15 min, dichlorotriphenylphosphine (132.49 g, 0.398 mol) is added portion wise over 30 min, stirred 1 h and then brought to −10° C. by displacing the acetone cold bath with room temperature water. The reaction mixture is allowed to warm from −10° C. to room temperature in situ overnight, then filtered through Celite and concentrated in vacuo. The resulting solid was dissolved in methylene chloride (750 mL), cooled to 0° C. and treated with ice-cold 10% citric acid (100 mL). The mixture was stirred rapidly for 5 min, the organics washed once with water, saturated sodium bicarbonate, dried (magnesium sulfate), filtered and restripped to give 338F as a light tan colored solid (167.74 g, contaminated with triphenylphosphine oxide).

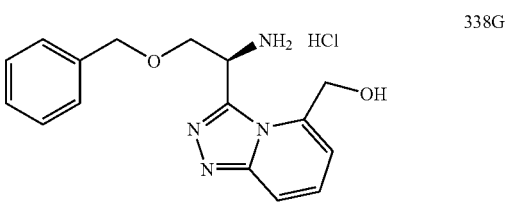

338G

To methanol (400 ml) at 2° C. was added acetyl chloride (100 g) dropwise over 20 min. After stirring 30 min, the solution was brought to room temperature for 45 min. The methanol solution was added directly to crude 338F (<167 g, ~0.12 mol) and the mixture was stirred for 3 h, concentrated in vacuo at temperatures below 30° C., and then the brown colored residue was suspended in THF (500 mL) for 30 min. The resulting solid was collected by filtration, and re-suspended in THF (500 mL) for 30 min. After filtration, the solid was dried in vacuo at 40° C. to give 338G as light yellow colored solid (38.6 g). MS (M+H) 299; HPLC(A) retention time 1.65 min.

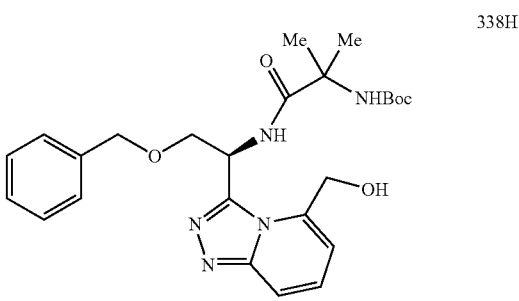

338H

To a stirred slurry of N-(tert-butoxycarbonyl)-α-methylalanine (24.39 g, 0.120 mol) and HOBt (18.37 g, 0.120 mol) in methylene chloride at room temperature under argon is added EDAC (22.83 g, 0.120 mol) as a solid over 10 min. The resulting solution is stirred 1 h and then added (filtering through a cotton plug) to a solution of 338G (~0.120 mol) and N-methylmorpholine (19.79 ml, 0.18 mol) in methylene chloride at room temperature. After stirring 45 h, the reaction mixture was stirred with saturated sodium bicarbonate (200 mL) for 30 min. The phases were separated and the organic extract was washed once with brine, 10% citric acid (at pH3) and once again with brine. The organics were dried over sodium sulfate, filtered, and the filtrate was partially evaporated (to ~250 mL volume) and ether (~100 mL) was added. The resulting solids were filtered to give 338H as a colorless solid (30.10. The mother liquors were concentrated and recrystallized from chloroform (50 mL) and hexanes (sufficient to cause cloudiness in the boiling solution) to obtain an additional 3.45 g. Both solids were combined to give 338H (33.55 g). mp 155-157 deg° C. MS (M+H+) 484; HPLC(A) retention time 2.85 min.

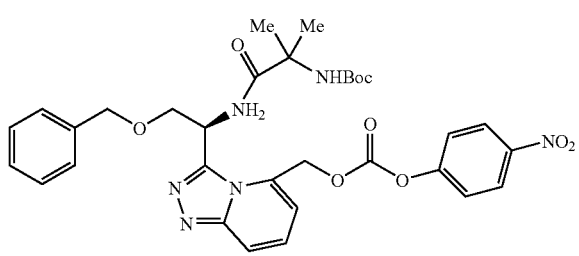

338I

To a suspension of 338H (25.63 g, 0.053 mol) in methylene chloride (300 mL) at 0° C. was added pyridine (9.0 mL, 0.111 mol). After 10 min, para-nitrophenyl chloroformate (21.4 g, 0.106 mol) was added slowly under nitrogen and the reaction was slowly warmed to room temperature overnight. The mixture was filtered and the solid cake was rinsed with methylene chloride (100 mL). The filtrate was concentrated in vacuo, ethyl acetate and ether (200 mL, 1:1) were added and the mixture was stirred at room temperature for 30 min. The solids were filtered and the crude solid product was collected. The solid was re-suspended in ethyl acetate and ether (200 mL, 1:1) three times to give 338I as a colorless solid (38.5 g). MS (M+H+) 649; HPLC(A) retention time 3.68 min.

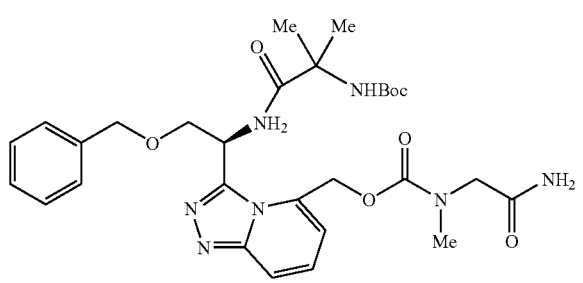

338J

To a suspension of sarcosinamide (2.61 g, 29.6 mmol) in anhydrous THF (250 mL) at 2° C. was added solid 338I (16.0 g, 24.7 mmol) over 10 min. The yellow mixture was stirred at room temperature for 24 h. After concentration, the resulting yellow foamy residue was diluted with ethyl acetate (600 mL) and washed with cold 1N NaOH (7×100 ml), water (100 ml) and dried over magnesium sulfate. The organic layer was concentrated in vacuo to give crude 338J as colorless solid (14.38 g). The material could be further purified by column chromatography, eluting with 10% methanol/methylene chloride to give pure 338J (10.47 g). MS (M+H+) 531; HPLC (A) retention time 3.91 min.

Example 338

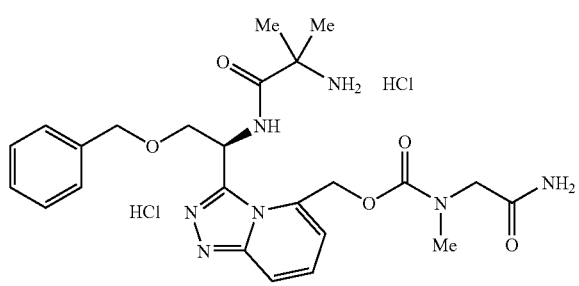

HCl gas (67.8 g, 1.86 mol) was bubbled into ice-cold isopropanol (200 mL). The resulting solution was cooled to 5° C. and solid 338J (13.8 g, 23.1 mmol) was added in portions over 5 min. After 30 min at 0° C., the reaction mixture was stirred at room temperature an additional 30 min before concentration in vacuo. The resulting viscous liquid was stirred with isopropanol (100 mL) and the resulting colorless solid was collected by filtration to give 338 (12.65 g). mp 151.4-152.6° C.; MS (M+H+) 498; HPLC(A) retention time 1.723 min.

Example 339

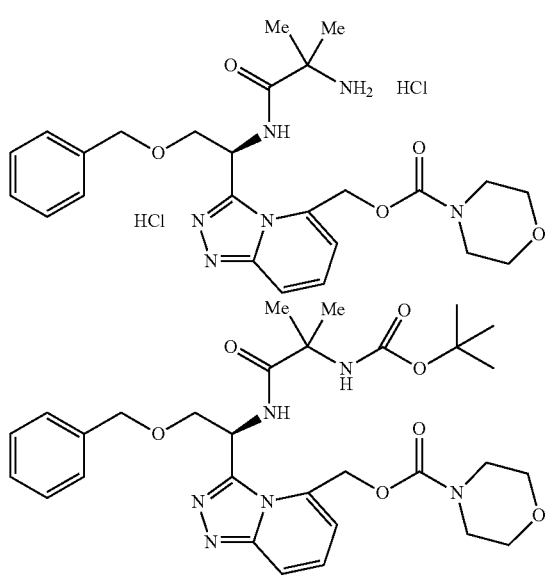

339A

To a stirred slurry of intermediate 338I (37.41 g, 0.058 mol) and triethylamine (12.06 ml, 0.087 mol) in THF (300 ml) at room temperature under argon was added morpholine (5.53 ml, 0.063 mol) over 2 minutes. A yellow solution forms within 5 min and the reaction was stirred overnight. After 15 h, the reaction solution was concentrated in vacuo and re-dissolved in EtOAc (800 mL). The organic layer was washed with saturated sodium bicarbonate (5×125 mL), once with 5% potassium hydrogensulfate (200 mL), brine and once with saturated sodium bicarbonate (100 mL). The organic layer was dried over magnesium sulfate, filtered and concentrated to give a colorless foam, 37.5 g. This material is recrystallized twice from 5:4 ethyl acetate:hexane to give 339A as a colorless solid (30.95 g). mp 104-106° C., MS (M+H+) 597; HPLC (A) retention time 3.58 min.

Example 339

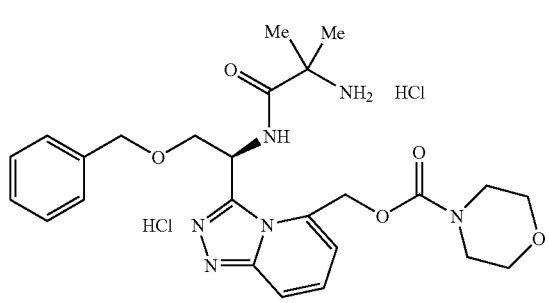

Acetyl chloride (50 ml, 0.637 mol) was added dropwise over 30 min to dry methanol (200 mL) at 0° C. After 30 min, the mixture was warmed to room temperature, stirred 1 h, then added to solid 339A (30.2 g, 0.051 mol). After 4 h, the reaction mixture was concentrated and the resulting colorless amorphous solid was suspended in THF and sonicated for 30 min. Filtration gave a colorless amorphous solid which was dried at 45° C. for 15 h to give 339 (25.75 g). MS (M+H) 497; HPLC(A) retention time 2.73 min. CHN elemental analysis: C25H32N6O5̃2HCl The following examples were prepared using procedures as described in the general synthetic schemes and working examples above, utilizing the appropriate starting materials as known to those skilled in the art.

| Compound number | Structure | Mass M + H | HPLC Purity (%) | HPLC Retention (min) |
| --- | --- | --- | --- | --- |
| 340 | Chiral | 512 | 95 | 1.73 |
| 341 | Chiral | 511 | 95 | 2.07 |
| 342 | Chiral | 524 | 96 | 2.56 |
| 343 | Chiral | 455 | 95 | 3.33 |
| 344 | Chiral | 534 | 97 | 1.85 |

-continued
| Compound number | Structure | Mass M + H | HPLC Purity (%) | HPLC Retention (min) |
|---|---|---|---|---|
| 345 | 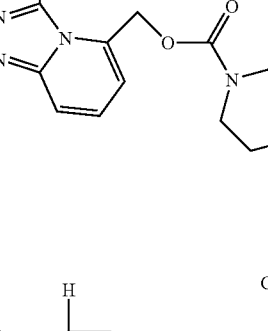 Chiral | 533 | 98 | 2.3 |
| 346 | 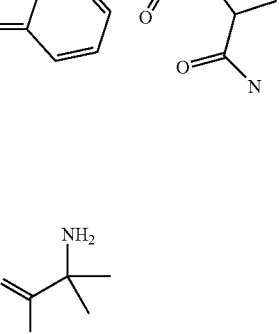 Chiral | 523 | 96 | 4.10 |
| 347 | 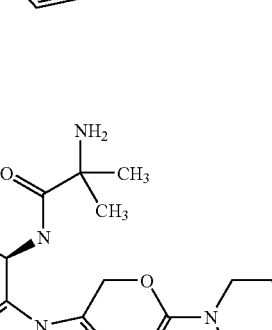 Chiral | 497 | 97 | 4.73 |
| 348 | 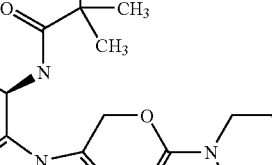 Chiral | 534 | 97 | 4.73 |
The following examples were prepared using procedures as described in the general synthetic schemes and working examples above, utilizing the appropriate starting materials as known to those skilled in the art.

| Compound number | Structure | Mass M + H | HPLC Purity (%) | HPLC Retention (min) |
|---|---|---|---|---|
| 349 | Chiral | 414 | 94 | 2.67 |
| 350 | Chiral | 437 | 97 | 2.13 |
| 351 | Chiral | 384 | 99 | 1.28 |
| 352 | Chiral | 538 | 95 | 2.53 |
| 353 | Chiral | 552 | 92 | 2.70 |

-continued

| Compound number | Structure | | Mass M + H | HPLC Purity (%) | HPLC Retention (min) |
|---|---|---|---|---|---|
| 354 | 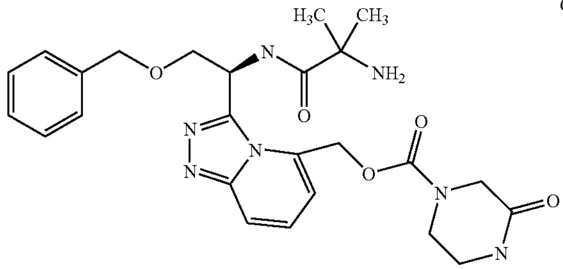 | Chiral | 510 | 92 | 2.47 |
| 355 | 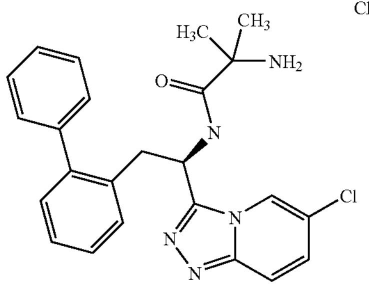 | Chiral | 434 | 99 | 2.60 |
| 356 | 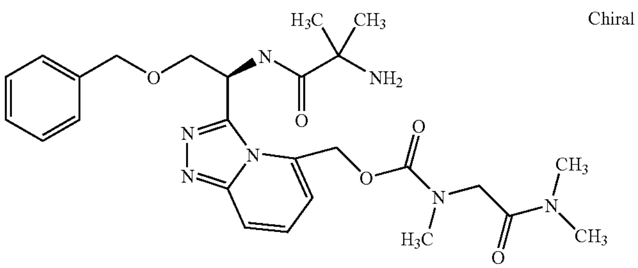 | Chiral | 526 | 95 | 2.60 |
| 357 | 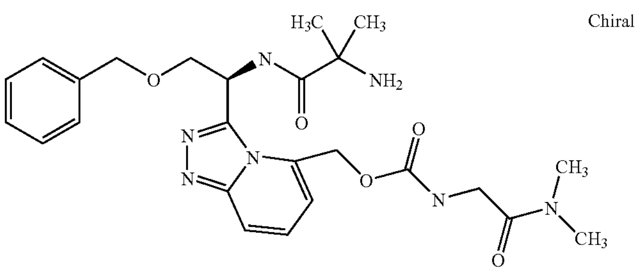 | Chiral | 512 | 95 | 2.54 |
| 358 | 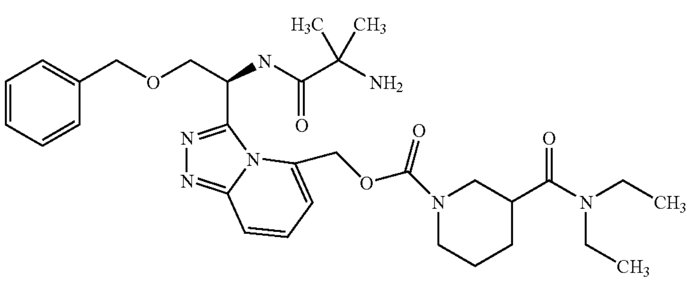 | | 594 | 95 | 3.07 |

-continued

| Compound number | Structure | Mass M + H | HPLC Purity (%) | HPLC Retention (min) |
| --- | --- | --- | --- | --- |
| 359 | 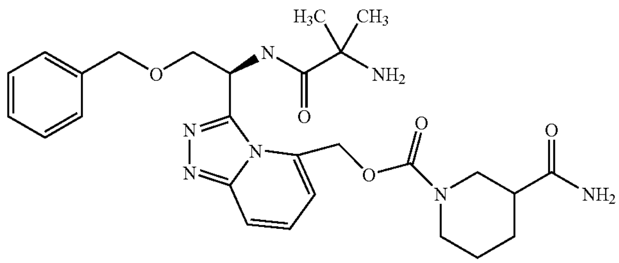 | 538 | 95 | 2.68 |
| 360 | 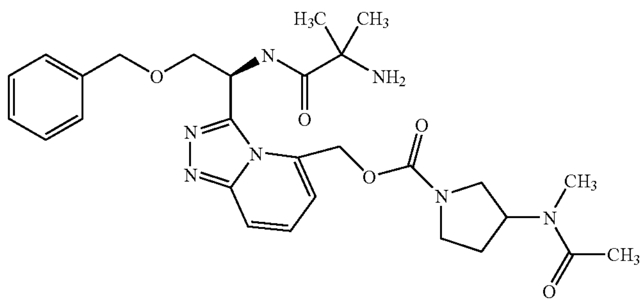 | 552 | 95 | 2.64 |
| 361 | Chiral | 568 | 95 | 3.06 |
| 362 | Chiral | 495 | 97 | 2.35 |
| 363 | 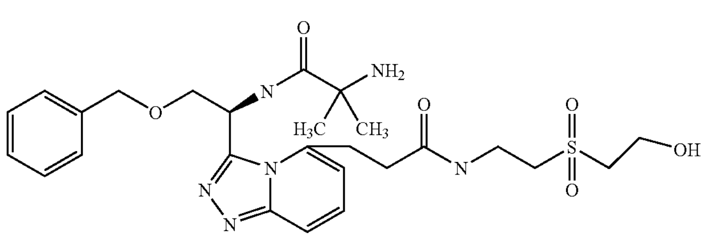 | 561 | 90 | 2.28 |

-continued

| Compound number | Structure | Mass M + H | HPLC Purity (%) | HPLC Retention (min) |
|---|---|---|---|---|
| 364 | Chiral | 483 | 98 | 2.36 |
| 365 | Chiral | 384 | 95 | 1.96 |
| 366 | Chiral | 512 | 95 | 2.48 |
| 367 | Chiral | 538 | 95 | 2.63 |
| 368 | Chiral | 511 | 95 | 2.71 |
| 369 | Chiral | 497 | 95 | 2.63 |

-continued

| Compound number | Structure | | Mass M + H | HPLC Purity (%) | HPLC Retention (min) |
|---|---|---|---|---|---|
| 370 | 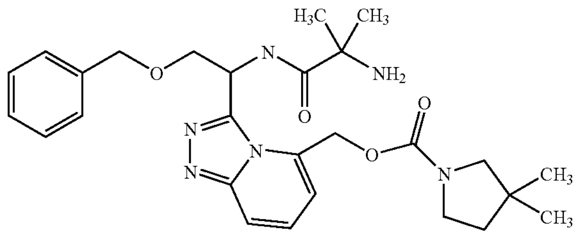 | | 511 | 95 | 2.74 |
| 371 | 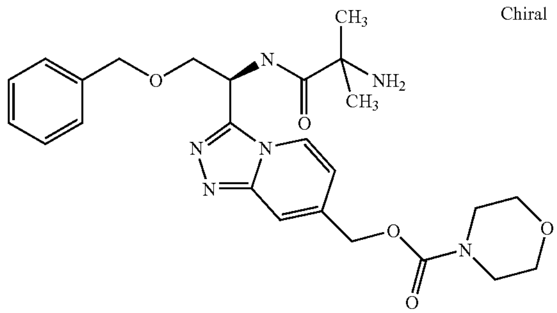 | Chiral | 497 | 98 | 1.87 |
| 372 | 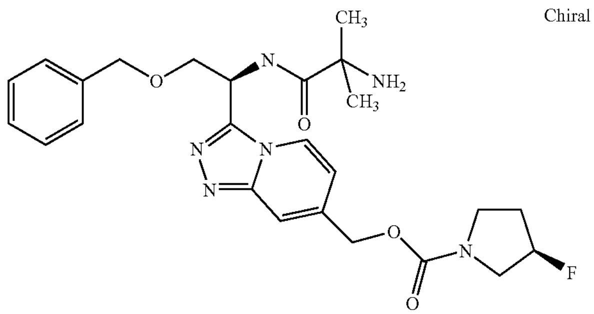 | Chiral | 499 | 95 | 2.13 |
| 373 | 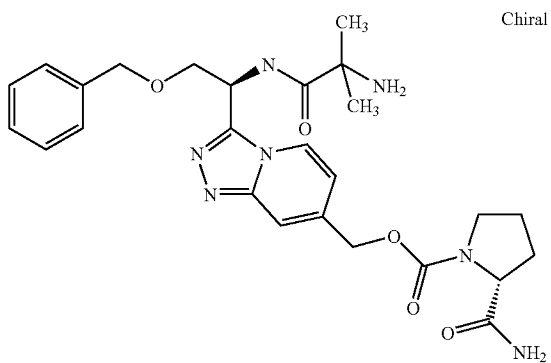 | Chiral | 524 | 95 | 1.73 |
| 374 | 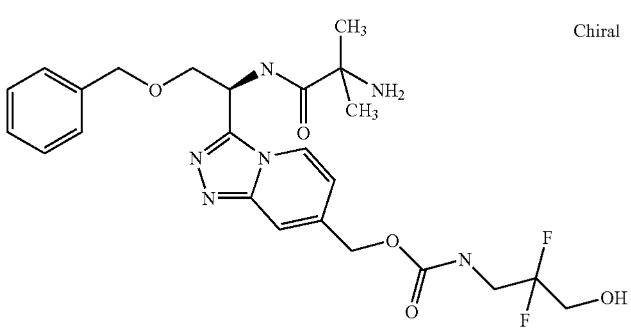 | Chiral | 521 | 90 | 1.77 |

-continued

| Compound number | Structure | | Mass M + H | HPLC Purity (%) | HPLC Retention (min) |
|---|---|---|---|---|---|
| 375 | 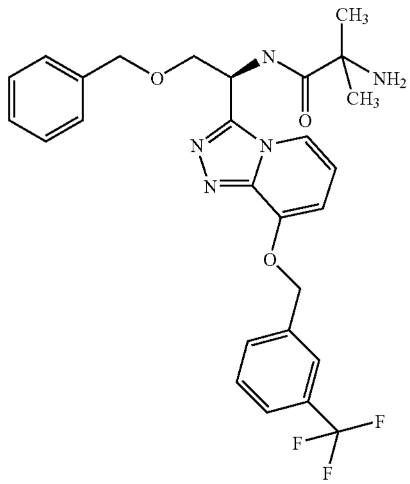 | Chiral | 528 | 98 | 2.93 |
| 376 | 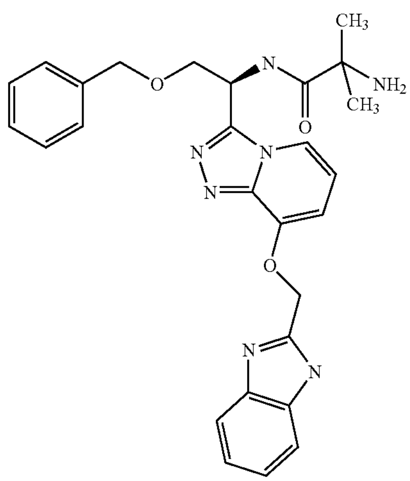 | Chiral | 500 | 95 | 1.85 |
| 377 | 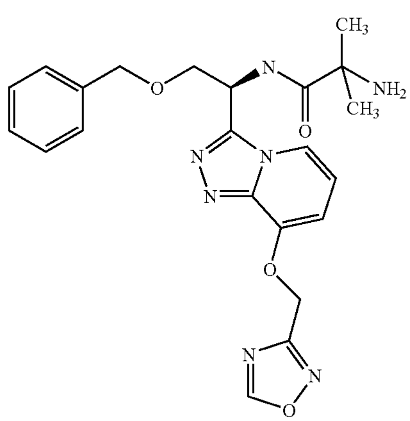 | Chiral | 452 | 90 | 1.78 |

| Compound number | Structure | Mass M + H | HPLC Purity (%) | HPLC Retention (min) |
|---|---|---|---|---|
| 378 | Chiral | 465 | 95 | 2.15 |
| 379 | Chiral | 461 | 95 | 1.47 |
| 380 | Chiral | 404 | 96 | 2.74 |
| 381 | Chiral | 404 | 97 | 2.65 |

-continued

| Compound number | Structure | Mass M + H | HPLC Purity (%) | HPLC Retention (min) |
| --- | --- | --- | --- | --- |
| 382 | Chiral | 430 | 98 | 2.77 |
| 383 | Chiral | 513 | 95 | 3.12 |
| 384 | 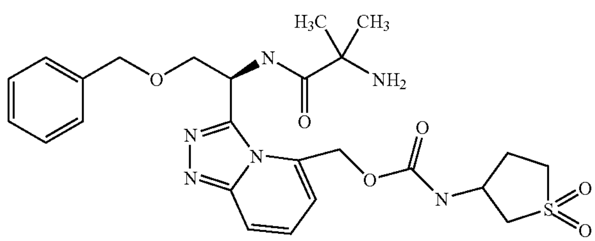 | 545 | 95 | 2.49 |
| 385 | Chiral | 485 | 92 | 2.56 |
| 386 | Chiral | 485 | 93 | 2.55 |

-continued

| Compound number | Structure | Mass M + H | HPLC Purity (%) | HPLC Retention (min) |
|---|---|---|---|---|
| 387 | 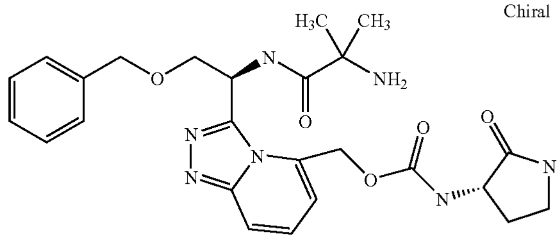 | 510 | 92 | 2.42 |
| 388 | 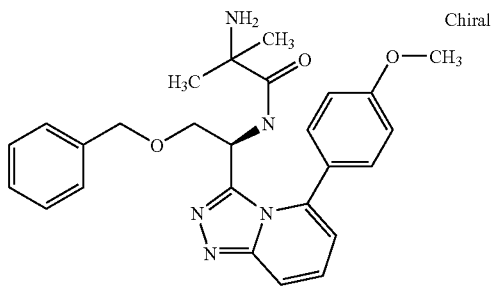 | 460 | 100 | 2.87 |
| 389 | 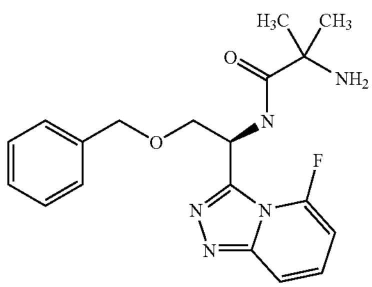 | 372 | 80 | 1.51/1.64 |
| 390 | 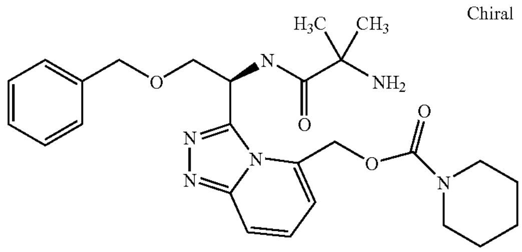 | 495 | 95 | 3.19 |
| 391 | 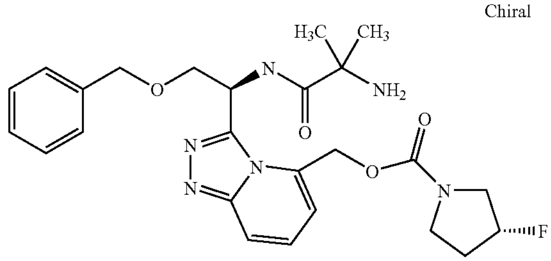 | 499 | 95 | 2.86 |

-continued
| Compound number | Structure | | Mass M + H | HPLC Purity (%) | HPLC Retention (min) |
|---|---|---|---|---|---|
| 392 | 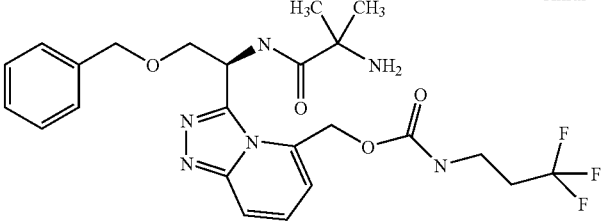 | Chiral | 523 | 95 | 2.97 |
| 393 | 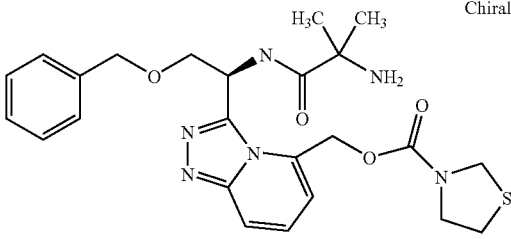 | Chiral | 499 | 93 | 2.99 |
| 394 | 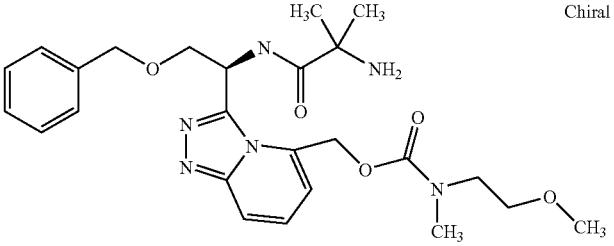 | Chiral | 499 | 95 | 2.81 |
| 395 | 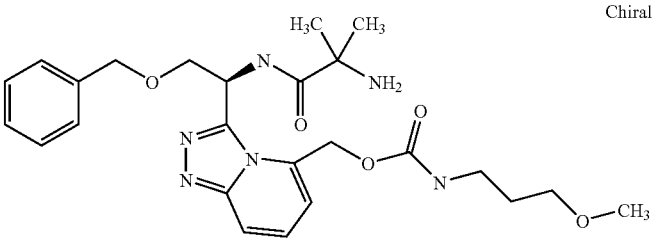 | Chiral | 499 | 95 | 2.75 |
| 396 | 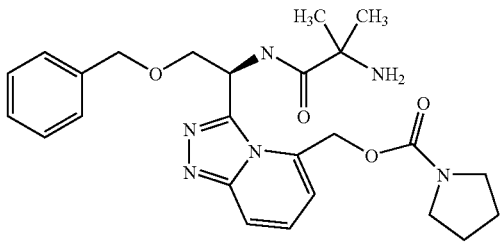 | Chiral | 481 | 95 | 3.01 |
| 397 | 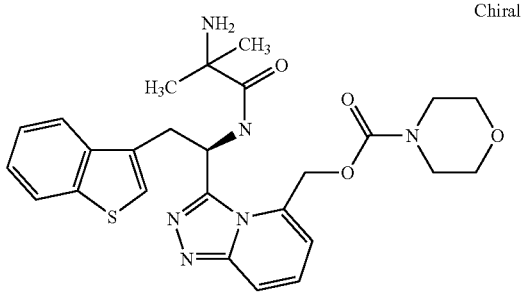 | Chiral | 523 | 93 | 2.20 |

-continued

| Compound number | Structure | | Mass M + H | HPLC Purity (%) | HPLC Retention (min) |
|---|---|---|---|---|---|
| 398 | 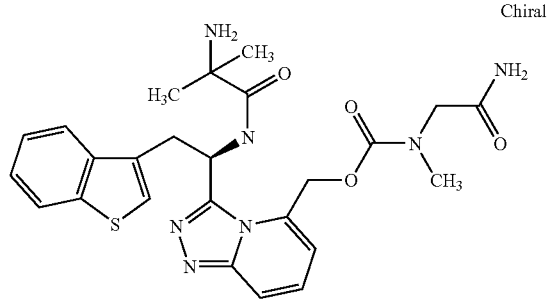 | Chiral | 524 | 97 | 1.89 |
| 399 | 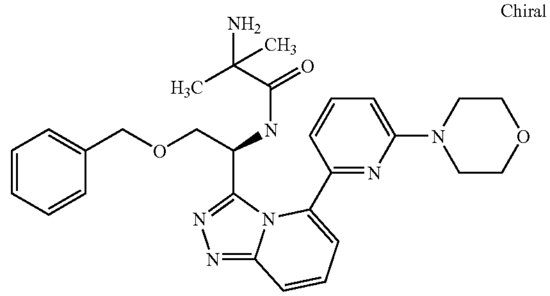 | Chiral | 516 | 99 | 2.21 |
| 400 | 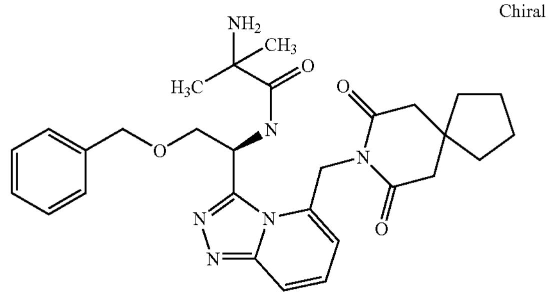 | Chiral | 533 | 100 | 2.40 |
| 401 | 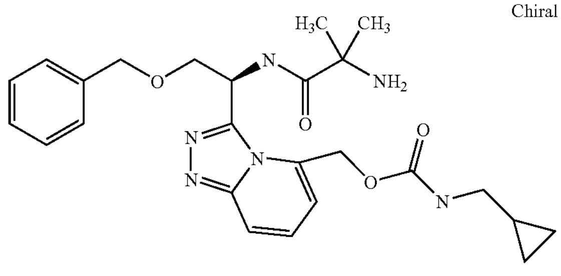 | Chiral | 481 | 95 | 3.52 |
| 402 | 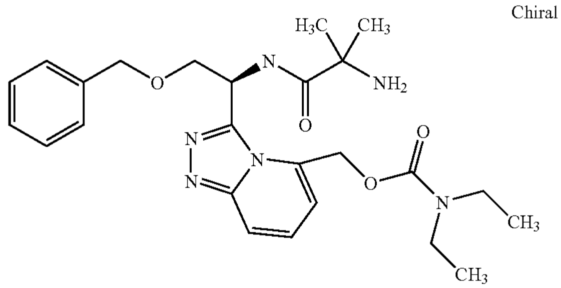 | Chiral | 483 | 95 | 3.72 |

-continued

| Compound number | Structure | | Mass M + H | HPLC Purity (%) | HPLC Retention (min) |
|---|---|---|---|---|---|
| 403 | 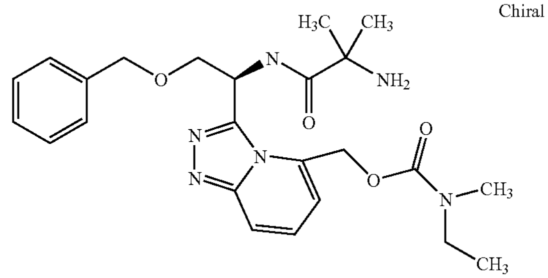 | Chiral | 469 | 95 | 3.59 |
| 404 | 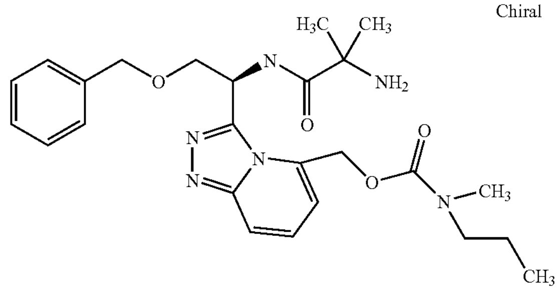 | Chiral | 483 | 95 | 2.56 |
| 405 | 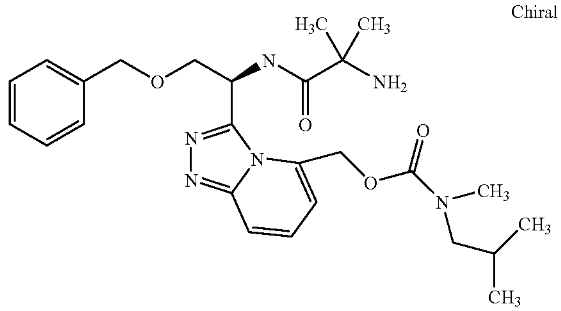 | Chiral | 497 | 90 | 2.74 |
| 406 | 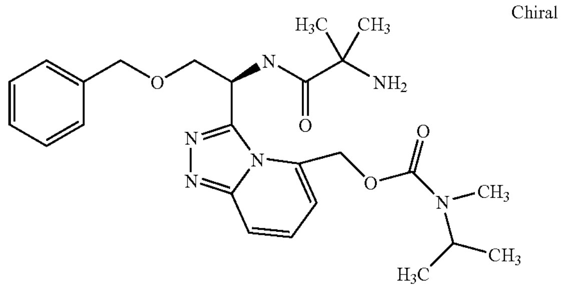 | Chiral | 483 | 90 | 2.56 |
| 407 | 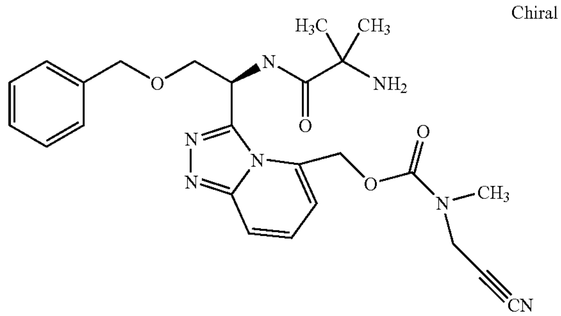 | Chiral | 479 | 90 | 2.28 |

-continued

| Compound number | Structure | Mass M + H | HPLC Purity (%) | HPLC Retention (min) |
|---|---|---|---|---|
| 408 | Chiral | 479 | 92 | 1.57 |
| 409 | Chiral | 507 | 99 | 2.04 |
| 410 | Chiral | 393 | 98 | 4.84 |
| 411 | Chiral | 461 | 89 | 2.32 |
| 412 | Chiral | 502 | 96 | 2.34 |

-continued

| Compound number | Structure | Mass M + H | HPLC Purity (%) | HPLC Retention (min) |
|---|---|---|---|---|
| 413 | Chiral | 567 | 90 | 3.78 |
| 414 | Chiral | 549 | 90 | 3.60 |
| 415 | Chiral | 499 | 90 | 3.08 |
| 416 | Chiral | 441 | 90 | 2.64 |
| 417 | Chiral | 455 | 90 | 2.91 |

-continued
| Compound number | Structure | | Mass M + H | HPLC Purity (%) | HPLC Retention (min) |
|---|---|---|---|---|---|
| 418 | 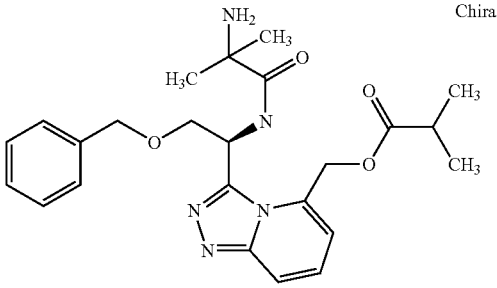 | Chiral | 454 | 93 | 2.37 |
| 419 | 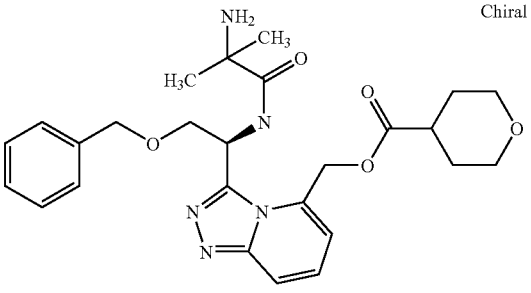 | Chiral | 496 | 94 | 2.03 |
| 420 | 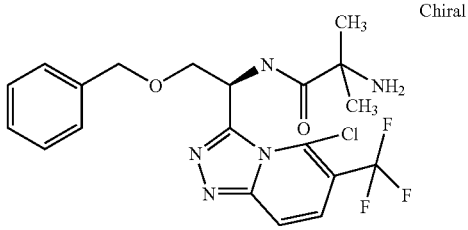 | Chiral | 456 | 93 | 2.44 |
| 421 | 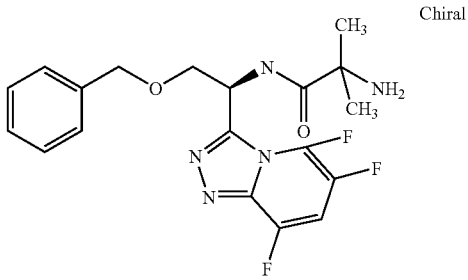 | Chiral | 408 | 95 | 1.87 |
| 422 | 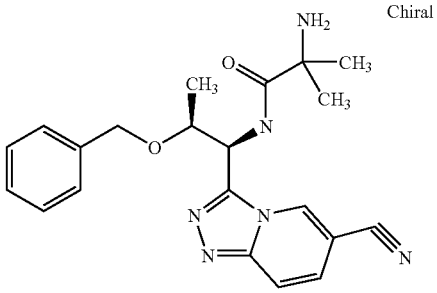 | Chiral | 393 | 97 | 4.93 |

-continued

| Compound number | Structure | Mass M + H | HPLC Purity (%) | HPLC Retention (min) |
|---|---|---|---|---|
| 423 | Chiral | 480 | 75 | 2.01 |
| 424 | Chiral | 494 | 80 | 2.00 |
| 425 | Chiral | 466 | 80 | 1.80 |
| 426 | Chiral | 495 | 97 | 1.62 |
| 427 | 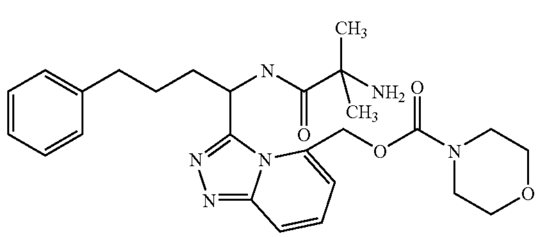 | 495 | 98 | 2.31 |

-continued

| Compound number | Structure | Mass M + H | HPLC Purity (%) | HPLC Retention (min) |
|---|---|---|---|---|
| 428 | 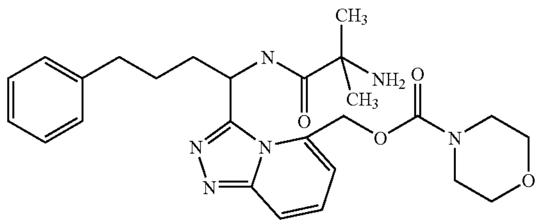 | 495 | 98 | 2.31 |
| 429 | Chiral | 497 | 95 | 2.17 |
| 430 | Chiral | 467 | 90 | 2.00 |
| 431 | Chiral | 455 | 93 | 2.43 |
| 432 | Chiral | 495 | 98 | 2.06 |

-continued

| Compound number | Structure | | Mass M + H | HPLC Purity (%) | HPLC Retention (min) |
|---|---|---|---|---|---|
| 433 | 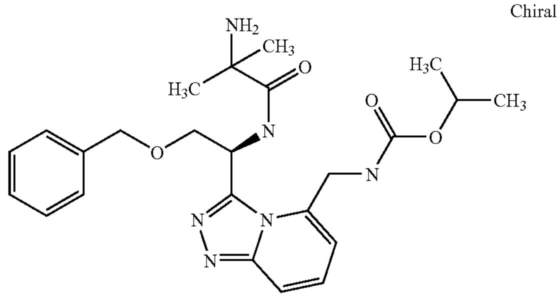 | Chiral | 469 | 98 | 2.07 |
| 434 | 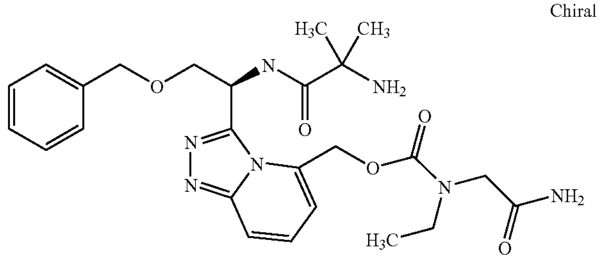 | Chiral | 512 | 90 | 1.94 |
| 435 | 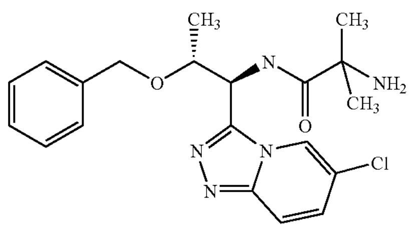 | Chiral | 402 | 95 | 2.12 |
| 436 | 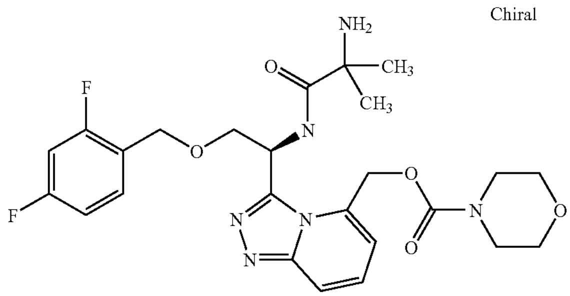 | Chiral | 533 | 99 | 4.18 |
| 437 | 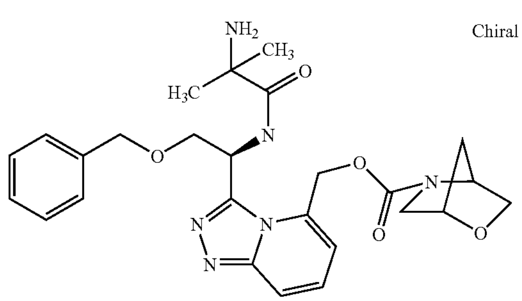 | Chiral | 509 | 98 | 3.02 |

-continued

| Compound number | Structure | Mass M + H | HPLC Purity (%) | HPLC Retention (min) |
|---|---|---|---|---|
| 438 | Chiral | 533 | 98 | 4.13 |
| 439 | 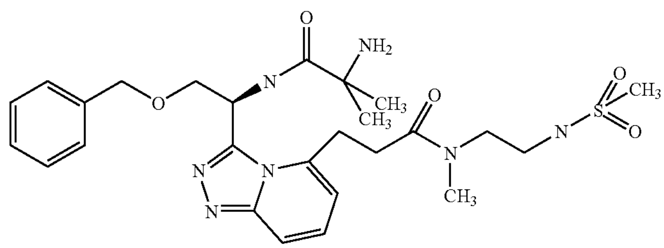 | 562 | 98 | 1.98 |
| 440 | Chiral | 534 | 96 | 1.96 |
| 441 | Chiral | 523 | 98 | 3.08 |
| 442 | Chiral | 496 | 85 | 1.45 |

-continued

| Compound number | Structure | Mass M + H | HPLC Purity (%) | HPLC Retention (min) |
|---|---|---|---|---|
| 443 | 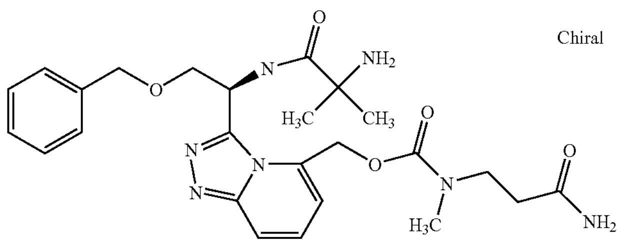 | 512 | 96 | 1.89 |
| 444 | 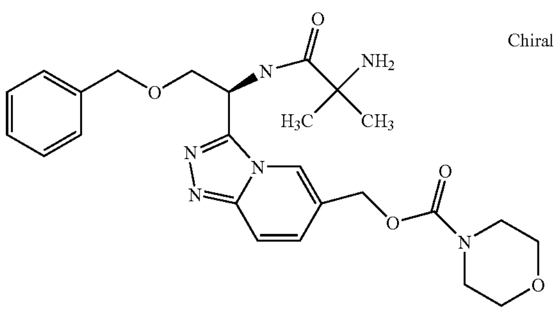 | 497 | 95 | 2.09 |
| 445 | 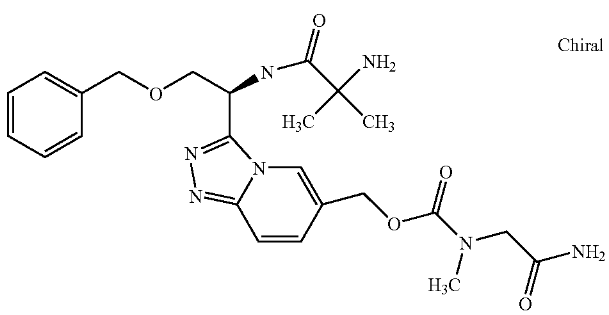 | 498 | 97 | 1.75 |
| 446 | 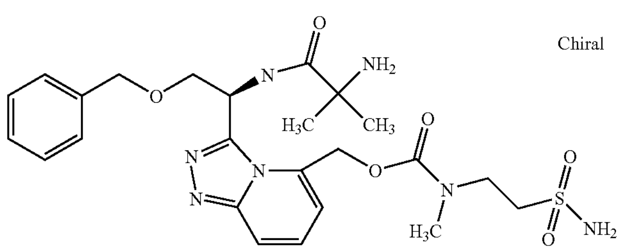 | 548 | 98 | 1.89 |
| 447 | 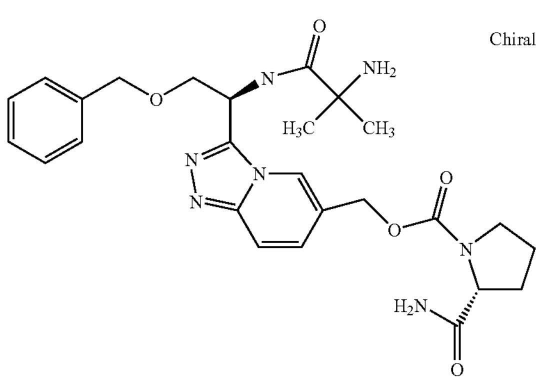 | 524 | 96 | 1.88 |

-continued

| Compound number | Structure | Mass M + H | HPLC Purity (%) | HPLC Retention (min) |
|---|---|---|---|---|
| 448 | 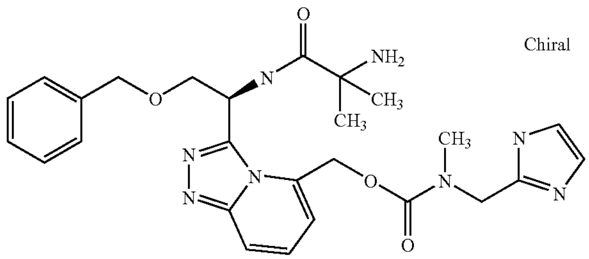 | 521 | 97 | 1.38 |
| 449 | 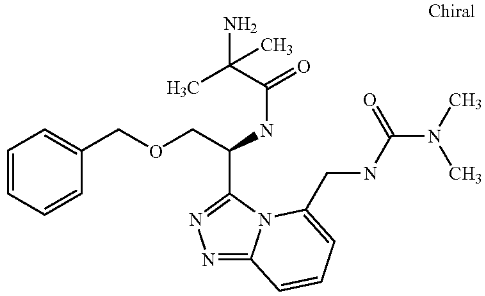 | 454 | 96 | 1.39 |
| 450 | 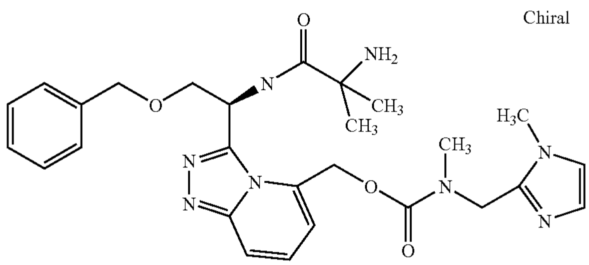 | 535 | 95 | 1.34 |
| 451 | 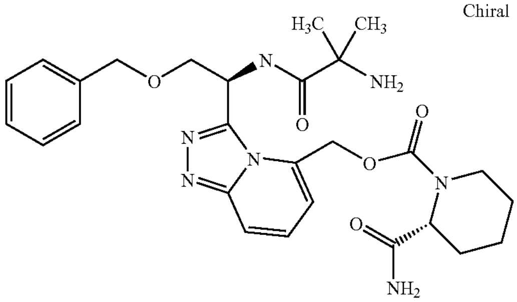 | 538 | 92 | 2.26 |
| 452 | 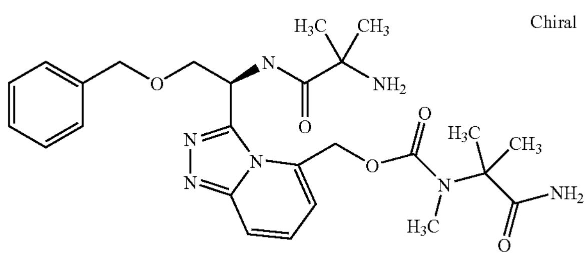 | 526 | 94 | 2.11 |

-continued

| Compound number | Structure | | Mass M + H | HPLC Purity (%) | HPLC Retention (min) |
|---|---|---|---|---|---|
| 453 | 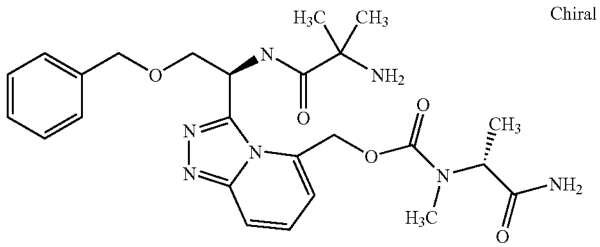 | Chiral | 512 | 90 | 2.04 |
| 454 | 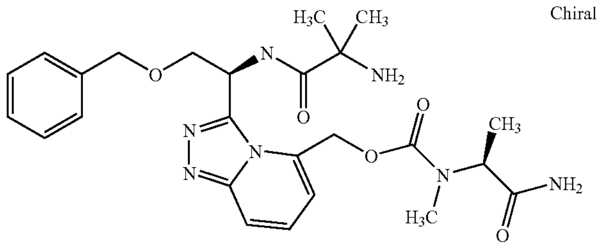 | Chiral | 512 | 94 | 2.02 |
| 455 | 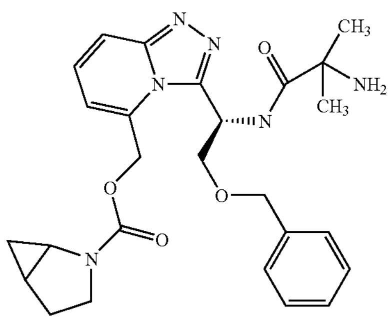 | | 493 | 98 | 2.62 |
| 456 | 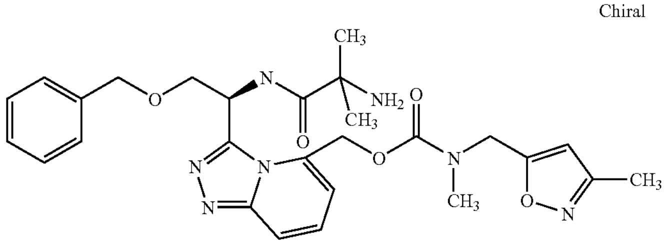 | Chiral | 536 | 98 | 2.20 |
| 457 | 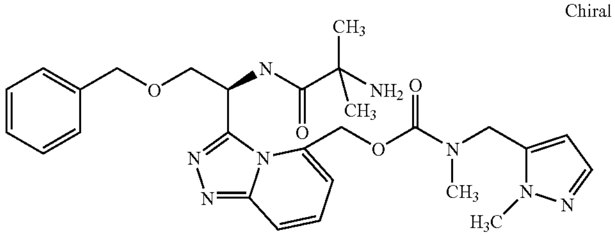 | Chiral | 535 | 98 | 2.19 |
| 458 | 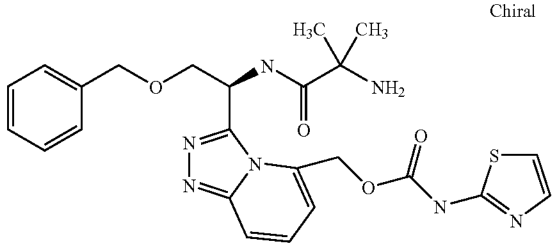 | Chiral | 510 | 90 | 2.40 |

-continued

| Compound number | Structure | Mass M + H | HPLC Purity (%) | HPLC Retention (min) |
|---|---|---|---|---|
| 459 | Chiral | 521 | 97 | |
| 460 | Chiral | 511 | 99 | 3.11 |
| 461 | Chiral | 512 | 99 | 2.76 |
| 462 | Chiral | 536 | 96 | 2.92 |
| 463 | Chiral | 499 | 96 | 2.07 |

-continued
| Compound number | Structure | Mass M + H | HPLC Purity (%) | HPLC Retention (min) |
|---|---|---|---|---|
| 464 | 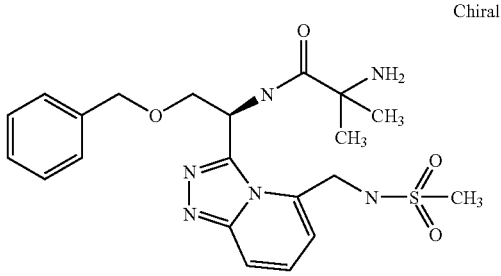 Chiral | 461 | 97 | 1.58 |
| 465 | 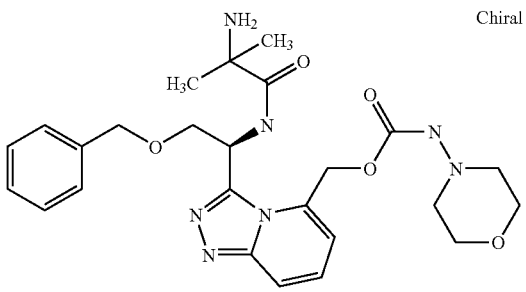 Chiral | 512 | 89 | 1.65 |
| 466 | 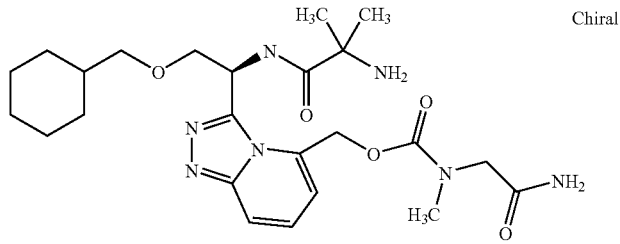 Chiral | 504 | 92 | 2.33 |
| 467 | 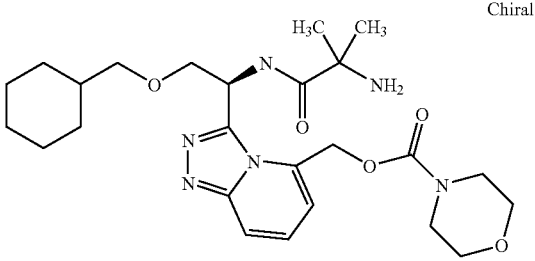 Chiral | 503 | 92 | 2.66 |
| 468 | 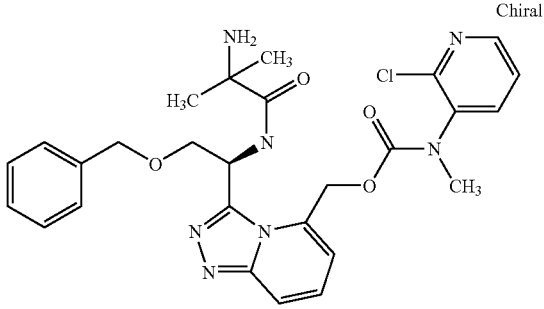 Chiral | 553 | 94 | 2.16 |

| Compound number | Structure | Mass M + H | HPLC Purity (%) | HPLC Retention (min) |
|---|---|---|---|---|
| 469 | Chiral | 523 | 89 | 1.69 |
| 470 | Chiral | 469 | 97 | 5.71 |
| 471 | Chiral | 511 | 97 | 5.53 |
| 472 | Chiral | 512 | 97 | 4.97 |
| 473 | Chiral | 526 | 99 | 2.09 |

| Compound number | Structure | Mass M + H | HPLC Purity (%) | HPLC Retention (min) |
|---|---|---|---|---|
| 474 | Chiral | 511 | 98 | 2.55 |
| 475 | Chiral | 512 | 97 | 2.18 |
| 476 | Chiral | 469 | 97 | 2.62 |
| 477 | Chiral | 425 | 97 | 1.43 |
| 478 | Chiral | 533 | 95 | 2.03 |
| 479 | Chiral | 512 | 95 | 1.71 |

-continued

| Compound number | Structure | Mass M + H | HPLC Purity (%) | HPLC Retention (min) |
|---|---|---|---|---|
| 480 | 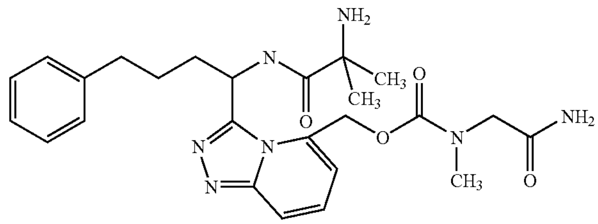 | 496 | 95 | 1.96 |
| 481 | 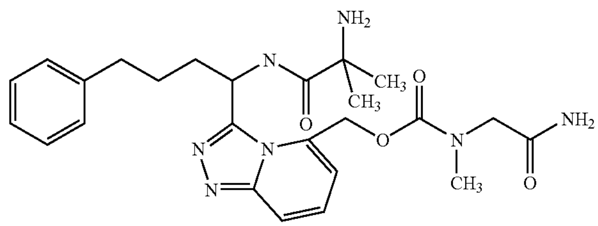 | 496 | 98 | 1.96 |
| 482 | Chiral | 435 | 96 | 4.41 |
| 483 | Chiral | 449 | 99 | 4.66 |
| 484 | Chiral | 555 | 92 | 3.14 |

-continued

| Compound number | Structure | | Mass M + H | HPLC Purity (%) | HPLC Retention (min) |
|---|---|---|---|---|---|
| 485 | 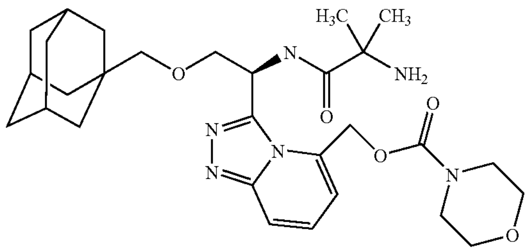 | Chiral | 555 | 92 | 3.12 |
| 486 | 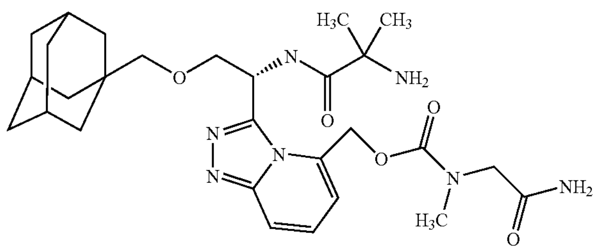 | Chiral | 556 | 92 | 2.86 |
| 487 | 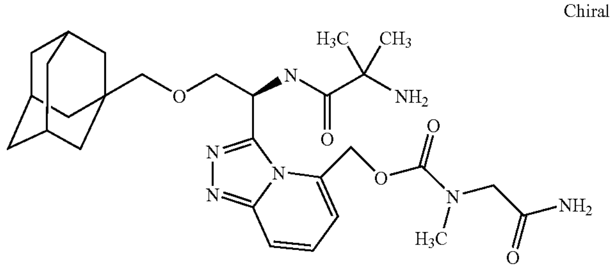 | Chiral | 556 | 93 | 2.88 |
| 488 | 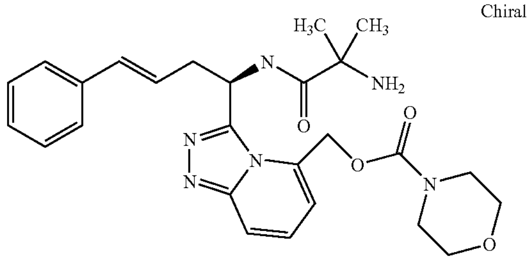 | Chiral | 493 | 99 | 2.26 |
| 489 | 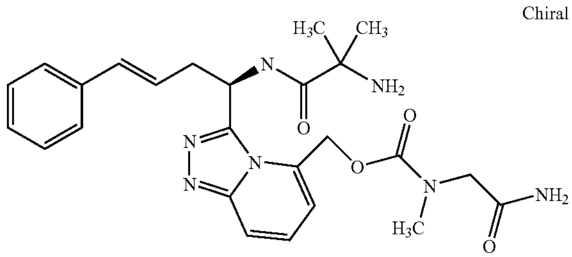 | Chiral | 494 | 99 | 1.92 |

-continued

| Compound number | Structure | Mass M + H | HPLC Purity (%) | HPLC Retention (min) |
|---|---|---|---|---|
| 490 | Chiral | 498 | 96 | 1.41 |
| 491 | Chiral | 497 | 89 | 1.79 |
| 492 | 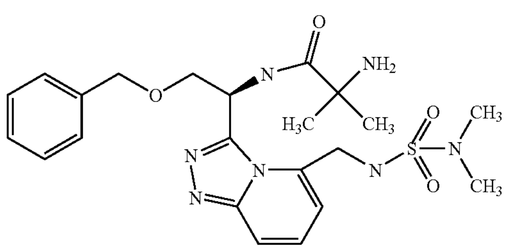 | 490 | 99 | 1.92 |
| 493 | 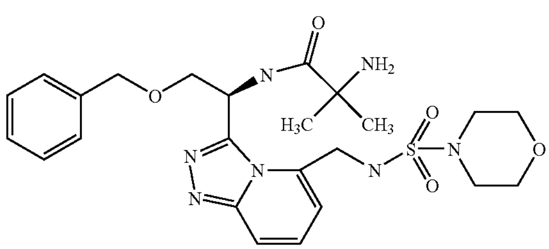 | 532 | 99 | 1.94 |
| 494 | Chiral | 485 | 97 | 5.83 |

-continued

| Compound number | Structure | Mass M + H | HPLC Purity (%) | HPLC Retention (min) |
|---|---|---|---|---|
| 495 | Chiral | 532 | 99 | 5.69 |
| 496 | Chiral | 533 | 98 | 5.07 |
| 497 | Chiral | 518 | 96 | 1.97 |
| 498 | Chiral | 517 | 90 | 2.25 |
| 499 | 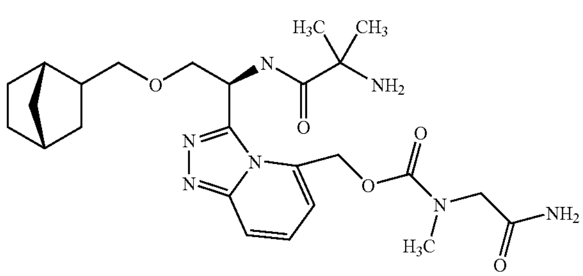 | 516 | 90 | 2.37 |

-continued

| Compound number | Structure | | Mass M + H | HPLC Purity (%) | HPLC Retention (min) |
|---|---|---|---|---|---|
| 500 | 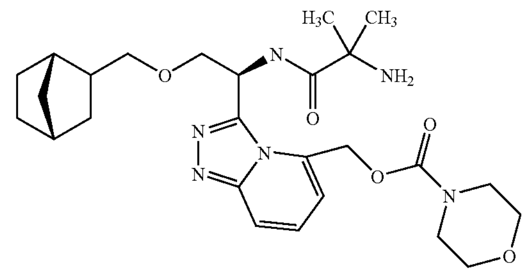 | | 515 | 95 | 2.68 |
| 501 | 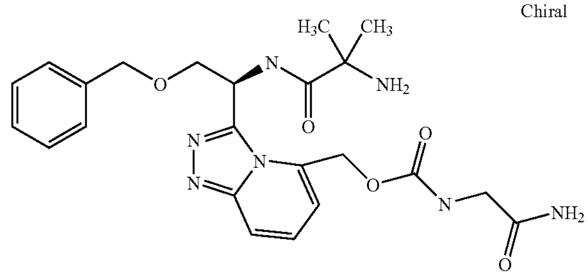 | Chiral | 484 | 95 | 1.69 |
| 502 | 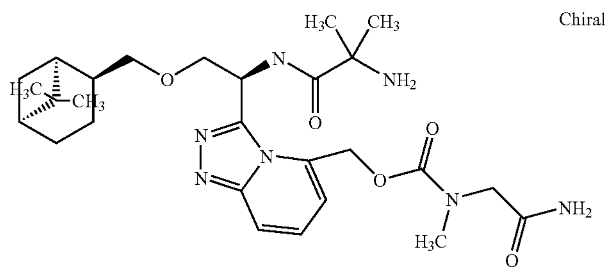 | Chiral | 544 | 95 | 2.79 |
| 503 | 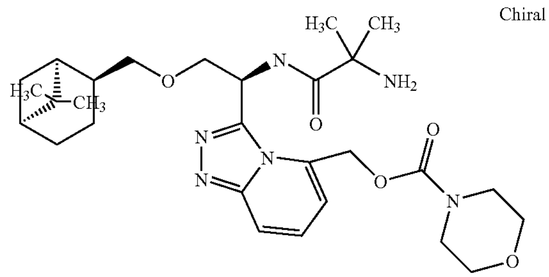 | Chiral | 543 | 92 | 3.01 |
| 504 | 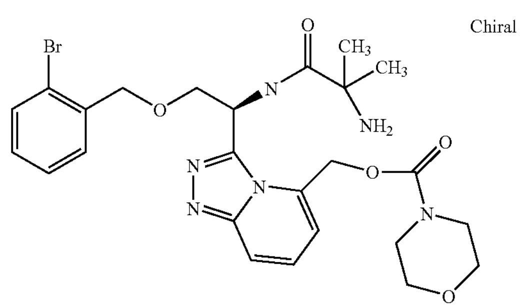 | Chiral | 576 | 96 | 2.44 |

-continued

| Compound number | Structure | Mass M + H | HPLC Purity (%) | HPLC Retention (min) |
|---|---|---|---|---|
| 505 | Chiral | 577 | 88 | 2.13 |
| 506 | Chiral | 427 | 90 | 1.76 |
| 507 | Chiral | 460 | 100 | 2.56 |
| 508 | Chiral | 464 | 95 | 1.84 |
| 509 | Chiral | 525 | 91 | 1.59 |

| Compound number | Structure | Mass M + H | HPLC Purity (%) | HPLC Retention (min) |
| --- | --- | --- | --- | --- |
| 510 | Chiral | 524 | 90 | 1.96 |
| 511 | Chiral | 511 | 94 | 2.21 |
| 512 | Chiral | 540 | 98 | 4.73 |
| 513 | Chiral | 511 | 99 | 3.28 |

-continued

| Compound number | Structure | Mass M + H | HPLC Purity (%) | HPLC Retention (min) |
|---|---|---|---|---|
| 514 | 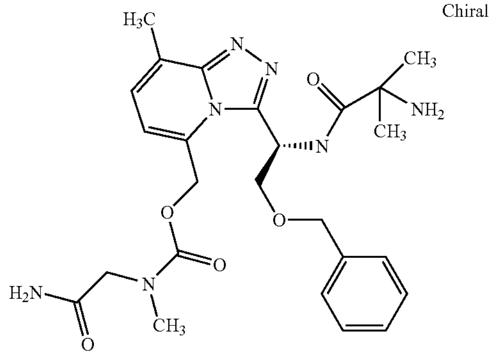 | 512 | 94 | 2.91 |
| 515 | 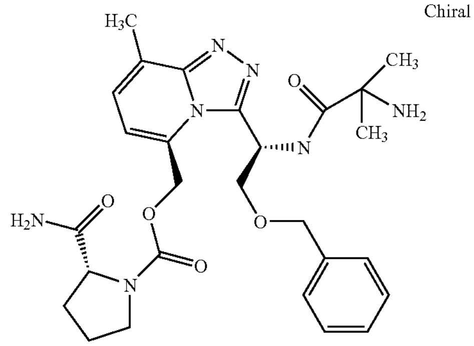 | 538 | 97 | 3.10 |
| 516 | 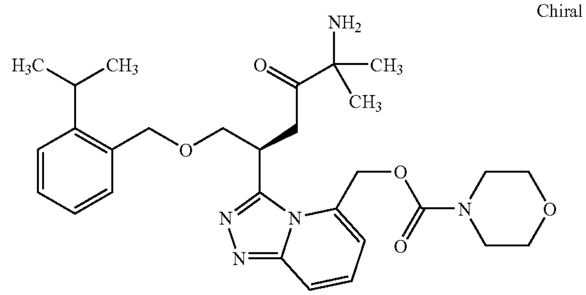 | 539 | 99 | 5.35 |
| 517 | 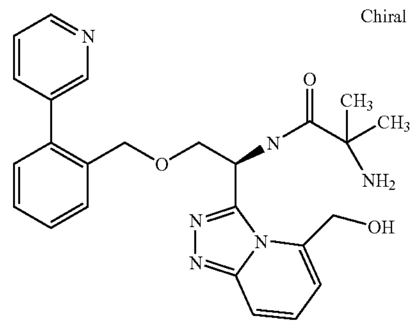 | 461 | 95 | 0.197/0.97 |

-continued

| Compound number | Structure | Mass M + H | HPLC Purity (%) | HPLC Retention (min) |
|---|---|---|---|---|
| 518 | 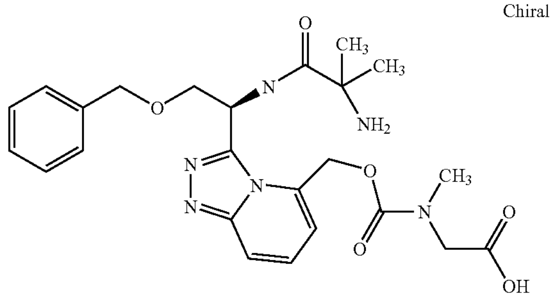 | 499 | 99 | 2.03 |
| 519 | 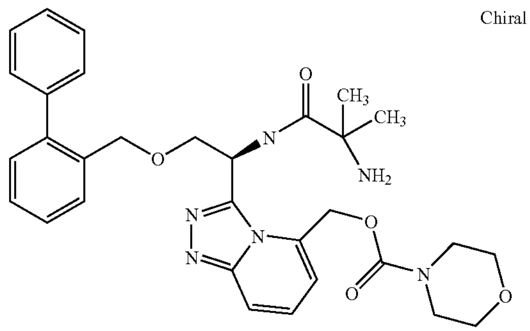 | 573 | 97 | 2.79 |
| 520 | 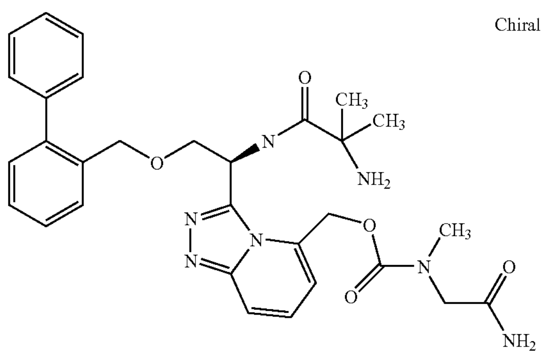 | 574 | 95 | 2.58 |
| 521 | 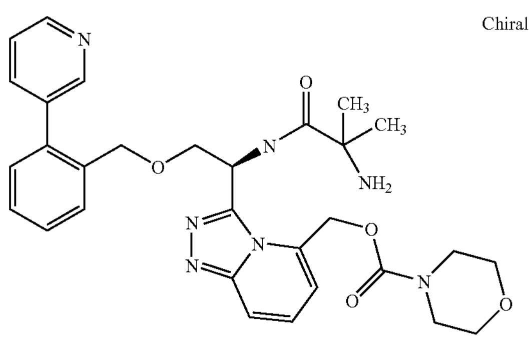 | 574 | 93 | 1.59 |

-continued

| Compound number | Structure | Mass M + H | HPLC Purity (%) | HPLC Retention (min) |
|---|---|---|---|---|
| 522 | Chiral | 575 | 95 | 0.197/1.21 |
| 523 | Chiral | 520 | 95 | 2.80 |
| 524 | Chiral | 519 | 95 | 3.00 |
| 525 | Chiral | 490 | 95 | 2.00 |
| 526 | Chiral | 489 | 95 | 2.40 |

-continued

| Compound number | Structure | | Mass M + H | HPLC Purity (%) | HPLC Retention (min) |
|---|---|---|---|---|---|
| 527 | 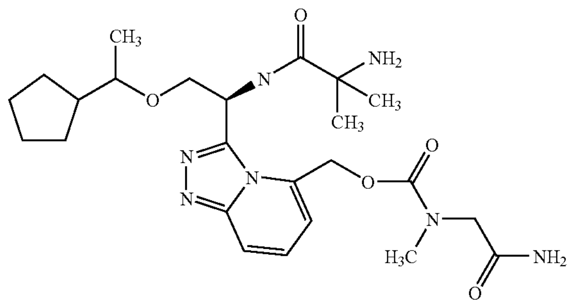 | | 504 | 95 | 2.16 |
| 528 | 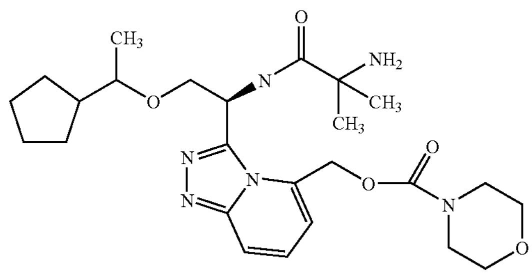 | | 503 | 95 | 2.45 |
| 529 | 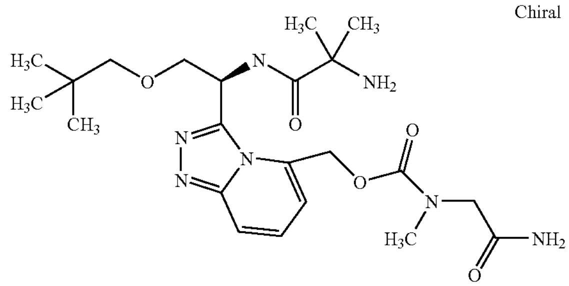 | Chiral | 478 | 92 | 2.03 |
| 530 | 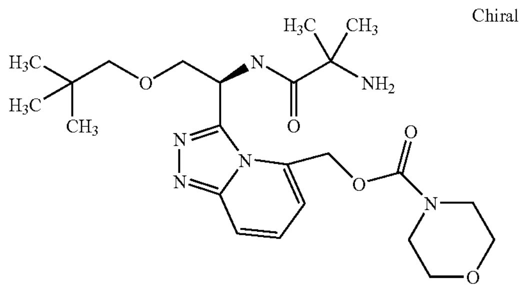 | Chiral | 477 | 93 | 2.39 |
| 531 | 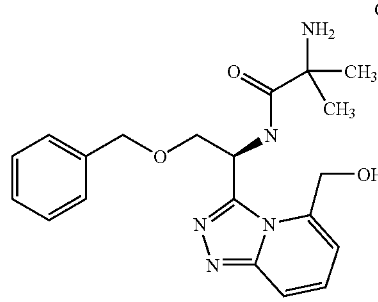 | Chiral | 384 | 97 | 3.21 |

-continued

| Compound number | Structure | Mass M + H | HPLC Purity (%) | HPLC Retention (min) |
|---|---|---|---|---|
| 532 | Chiral | 411 | 98 | 2.74 |
| 533 | Chiral | 393 | 98 | 3.85 |
| 534 | Chiral | 513 | 95 | 2.17 |
| 535 | Chiral | 517 | 95 | 2.67 |
| 536 | Chiral | 518 | 97 | 2.38 |

-continued

| Compound number | Structure | | Mass M + H | HPLC Purity (%) | HPLC Retention (min) |
|---|---|---|---|---|---|
| 537 | 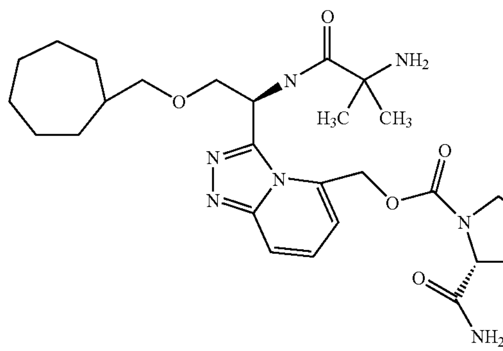 | Chiral | 544 | 95 | 2.47 |
| 538 | 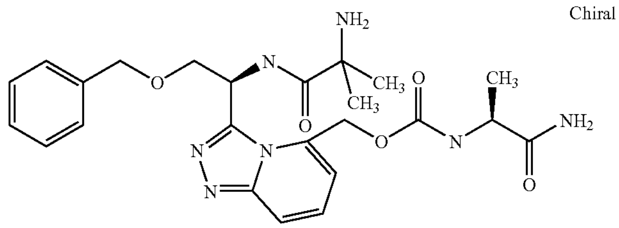 | Chiral | 498 | 92 | 1.71 |
| 539 | 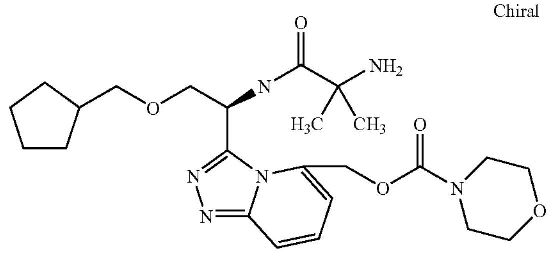 | Chiral | 489 | 95 | 3.05 |
| 540 | 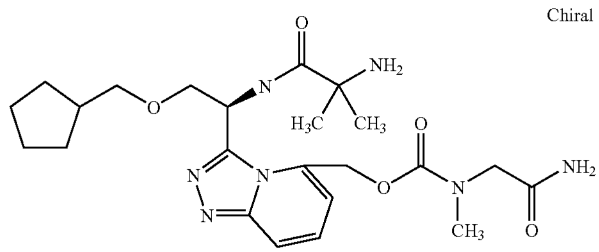 | Chiral | 490 | 97 | 2.67 |
| 541 | 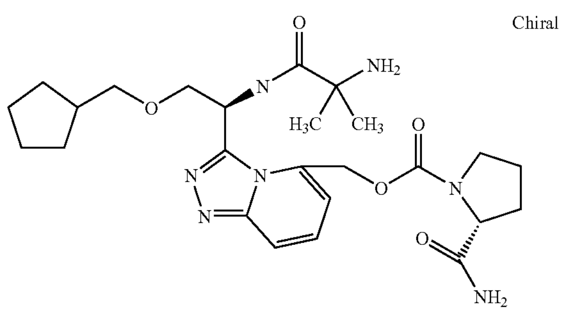 | Chiral | 516 | 97 | 2.83 |

-continued

| Compound number | Structure | Mass M + H | HPLC Purity (%) | HPLC Retention (min) |
|---|---|---|---|---|
| 542 | Chiral | 513 | 95 | 2.31 |
| 543 | Chiral | 514 | 99 | 1.87 |
| 544 | Chiral | 512 | 90 | 3.80 |

The following examples were prepared using procedures as described in Example 90, as well as described in the general synthetic schemes and working examples above, utilizing the appropriate starting materials as known to those skilled in the art.

| Compound number | Structure | Mass M + H | HPLC Purity (%) | HPLC Retention (min) |
|---|---|---|---|---|
| 545 | Chiral 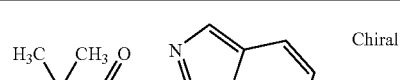 | 378 | 97 | 3.03 |

-continued

| Compound number | Structure | | Mass M + H | HPLC Purity (%) | HPLC Retention (min) |
|---|---|---|---|---|---|
| 546 | 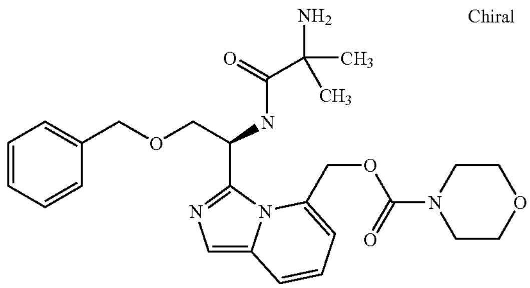 | Chiral | 496 | 94 | 5.67 |
| 547 | 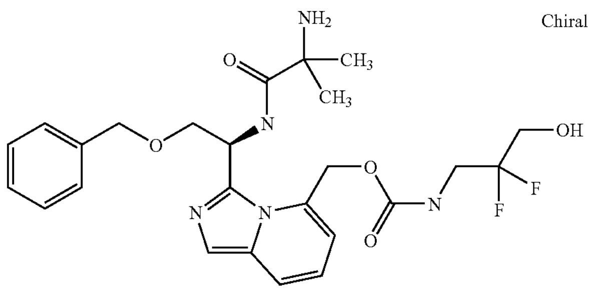 | Chiral | 520 | 94 | 5.08 |
| 548 | 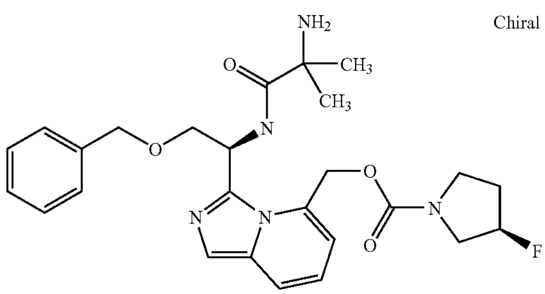 | Chiral | 498 | 99 | 5.88 |
| 549 | 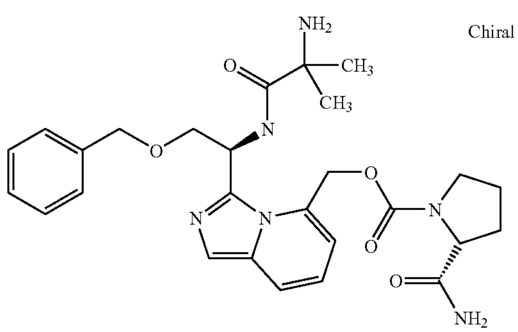 | Chiral | 523 | 96 | 4.10 |
| 550 | 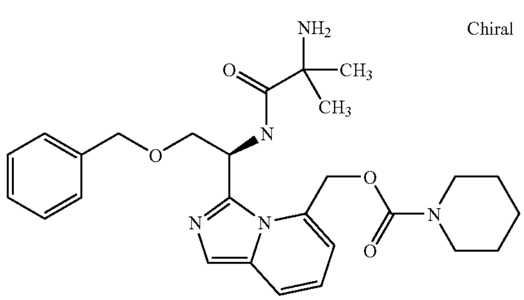 | Chiral | 494 | 98 | 6.78 |

-continued

| Compound number | Structure | | Mass M + H | HPLC Purity (%) | HPLC Retention (min) |
|---|---|---|---|---|---|
| 551 | 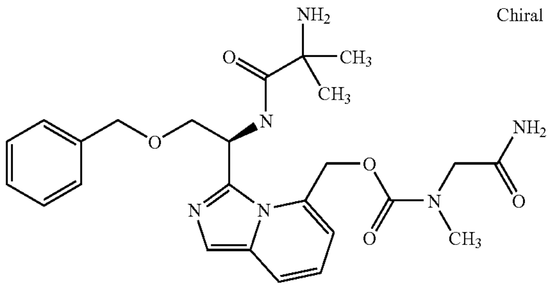 | Chiral | 497 | 91 | 4.73 |
| 552 | 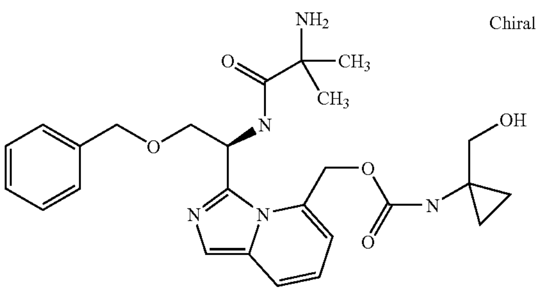 | Chiral | 496 | 95 | 5.19 |
| 553 | 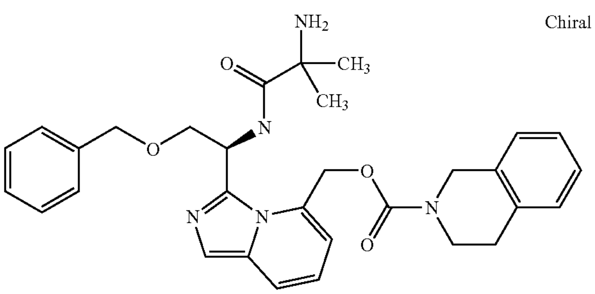 | Chiral | 542 | 96 | 7.27 |
| 554 | 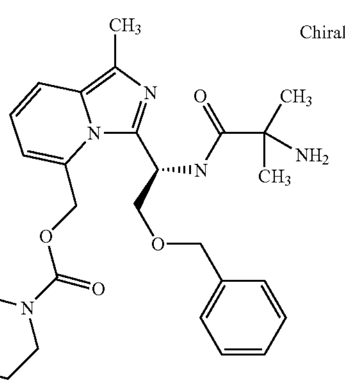 | Chiral | 510 | 97 | 3.10 |

-continued

| Compound number | Structure | Mass M + H | HPLC Purity (%) | HPLC Retention (min) |
|---|---|---|---|---|
| 555 | 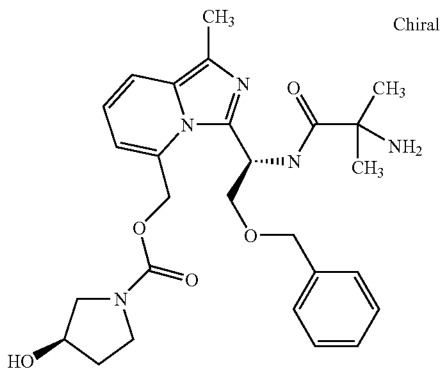 | 510 | 96 | 2.85 |
| 556 | 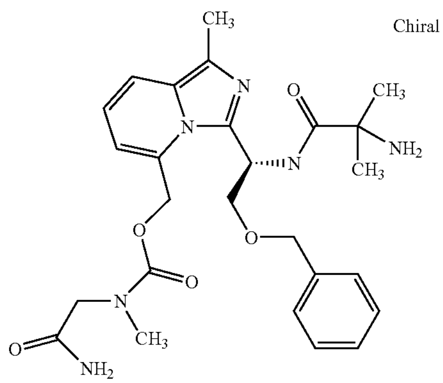 | 511 | 98 | 2.84 |
| 557 | 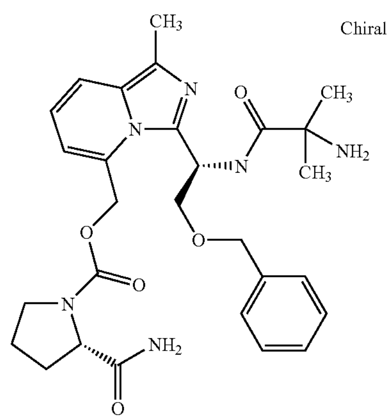 | 537 | 98 | 2.84 |
| 558 | 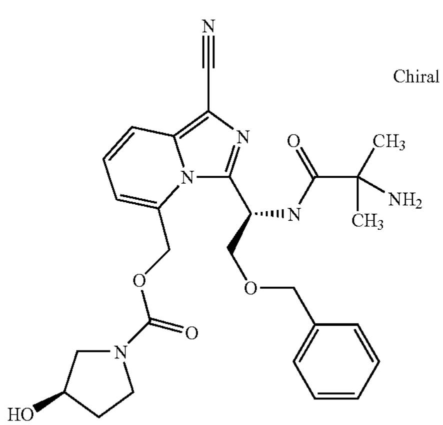 | 521 | 98 | 3.56 |

| Compound number | Structure | Mass M + H | HPLC Purity (%) | HPLC Retention (min) |
|---|---|---|---|---|
| 559 | 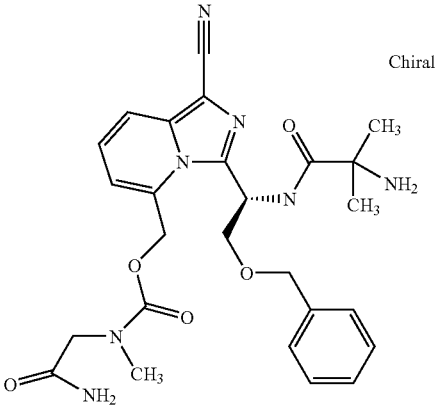 Chiral | 522 | 97 | 3.38 |
| 560 | 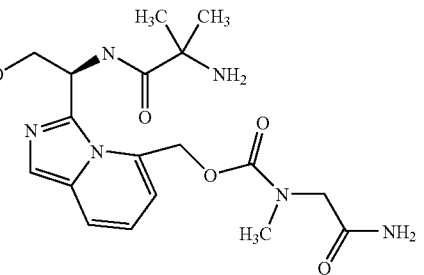 Chiral | 573 | 98 | 2.75 |
| 561 | 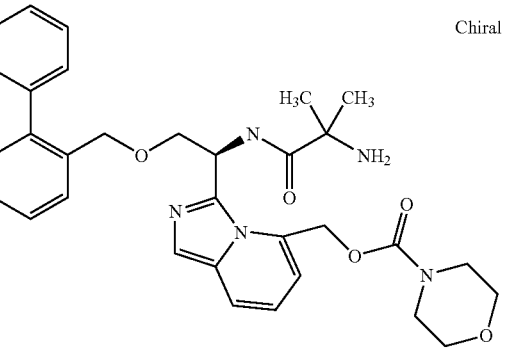 Chiral | 572 | 98 | 2.97 |
| 562 | 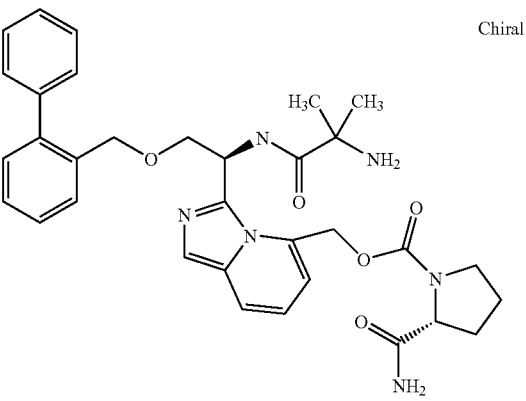 Chiral | 599 | 97 | 2.80 |

The following examples were prepared using procedures as described in Example 92 and Example 93 above, and as described in the general synthetic schemes and working examples above, utilizing the appropriate starting materials as known to those skilled in the art.
| Compound number | Structure | | Mass M + H | HPLC Purity (%) | HPLC Retention (min) |
|---|---|---|---|---|---|
| 563 | 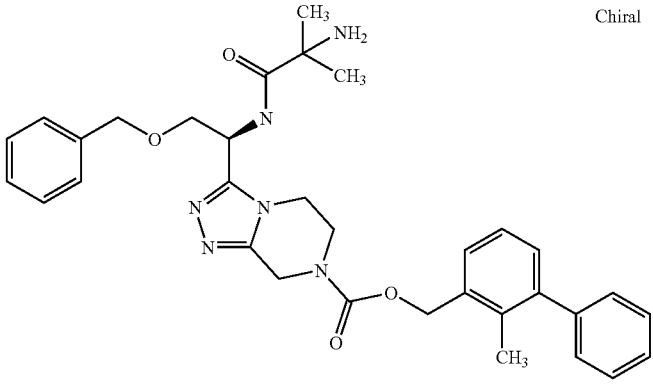 | Chiral | 583 | 95 | 3.09 |
| 564 | 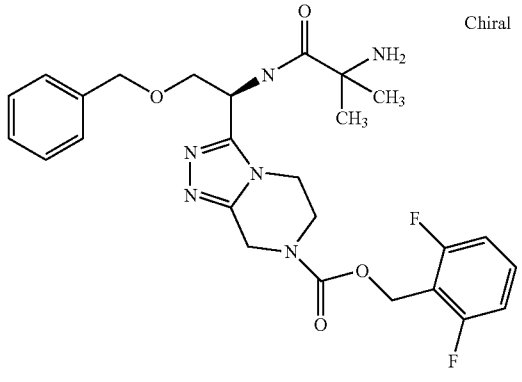 | Chiral | 529 | 95 | 3.10 |
| 565 | 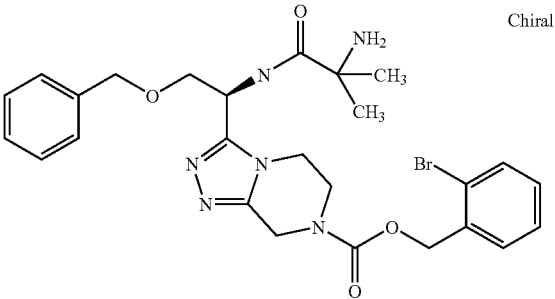 | Chiral | 572 | 95 | 3.20 |

-continued
| Compound number | Structure | | Mass M + H | HPLC Purity (%) | HPLC Retention (min) |
|---|---|---|---|---|---|
| 566 | 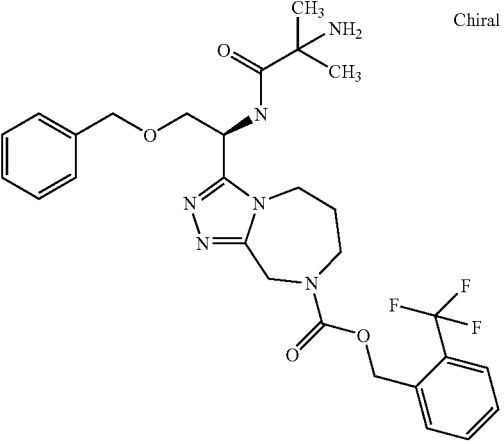 | Chiral | 575 | 90 | 2.61 |
| 567 | 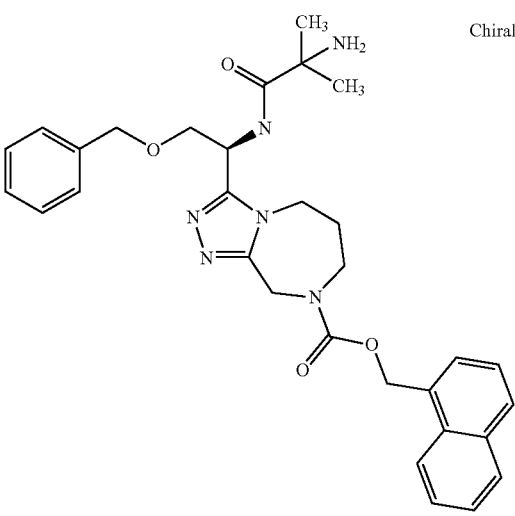 | Chiral | 557 | 84 | 3.42 |
| 568 | 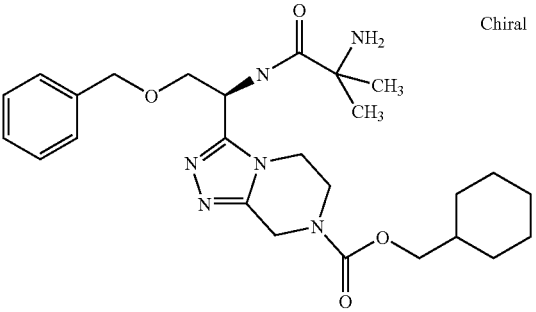 | Chiral | 499 | 95 | 2.77 |

-continued

| Compound number | Structure | Mass M + H | HPLC Purity (%) | HPLC Retention (min) |
|---|---|---|---|---|
| 569 | 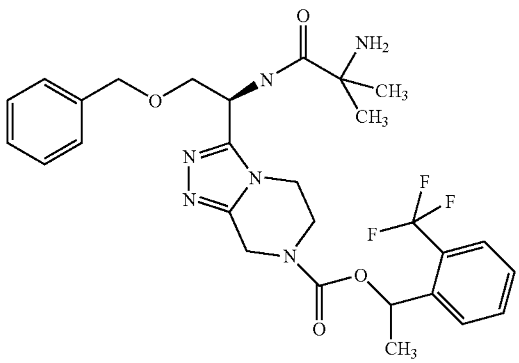 | 575 | 95 | 3.40 |
| 570 | Chiral | 529 | 97 | 3.21 |
| 571 | Chiral | 509 | 98 | 2.89 |
| 572 | Chiral | 516 | 93 | 0.19 |

-continued

| Compound number | Structure | Mass M + H | HPLC Purity (%) | HPLC Retention (min) |
|---|---|---|---|---|
| 573 | 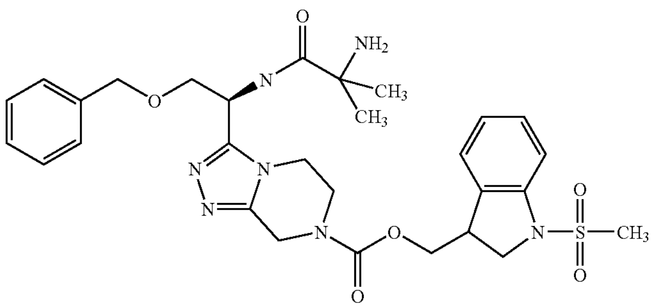 | 612 | 95 | 2.89 |
| 574 | Chiral | 600 | 95 | 2.70 |
| 575 | 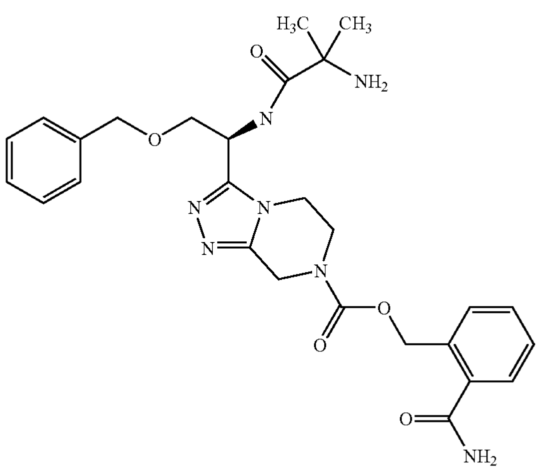 | 536 | 95 | 2.60 |
| 576 | Chiral | 518 | 95 | 2.93 |

-continued
| Compound number | Structure | Mass M + H | HPLC Purity (%) | HPLC Retention (min) |
|---|---|---|---|---|
| 577 | 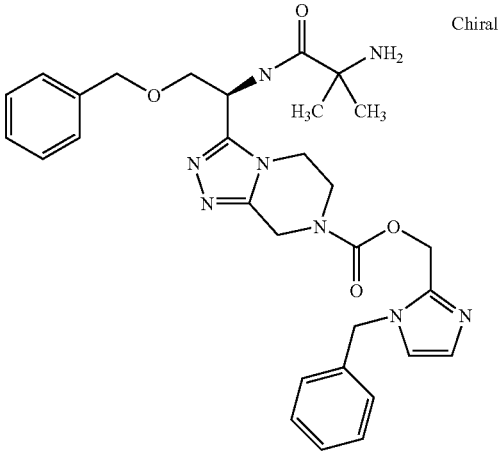 Chiral | 573 | 99 | 2.62 |
| 578 | 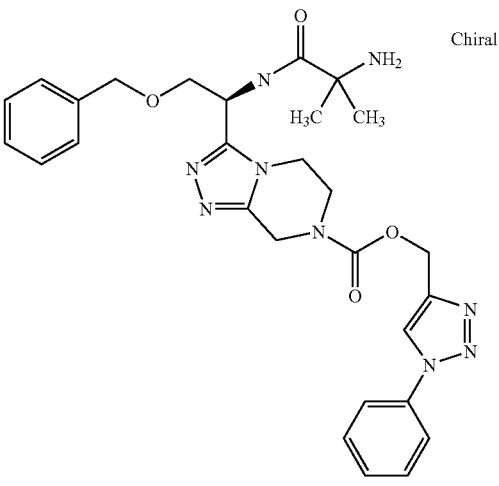 Chiral | 560 | 98 | 3.43 |
| 579 | 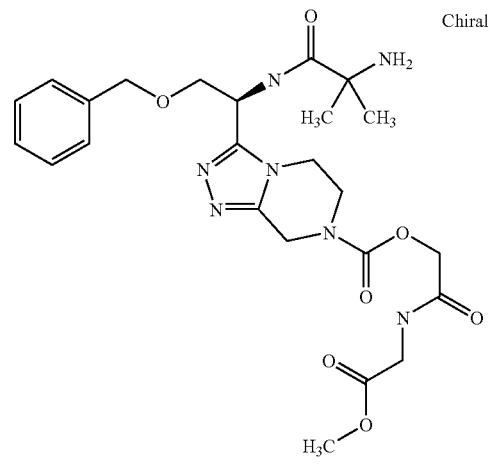 Chiral | 532 | 95 | 2.64 |

| Compound number | Structure | Mass M + H | HPLC Purity (%) | HPLC Retention (min) |
| --- | --- | --- | --- | --- |
| 580 | Chiral | 586 | 97 | 3.20 |
| 581 | Chiral | 545 | 98 | |
| 582 | Chiral | 586 | 95 | 1.99 |

-continued

| Compound number | Structure | | Mass M + H | HPLC Purity (%) | HPLC Retention (min) |
|---|---|---|---|---|---|
| 583 | 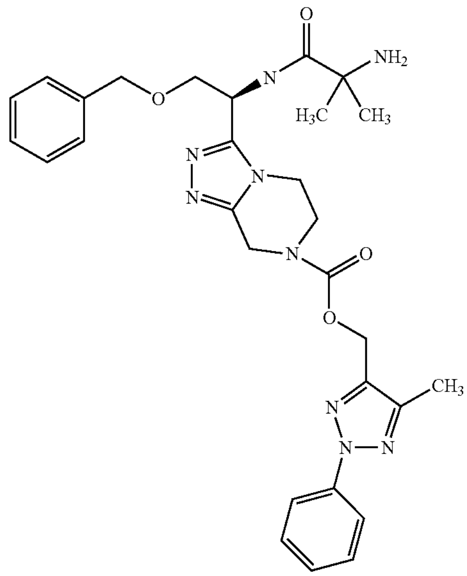 | | 574 | 99 | |
| 584 | 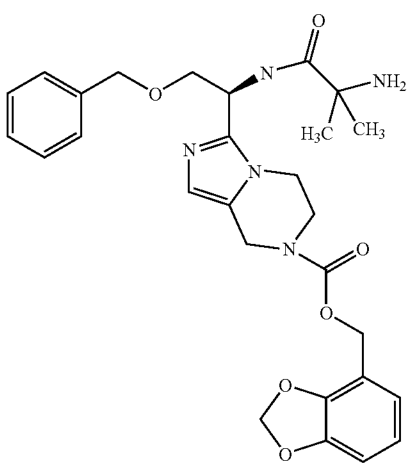 | Chiral | 537 | 90 | 3.64 |
| 585 | 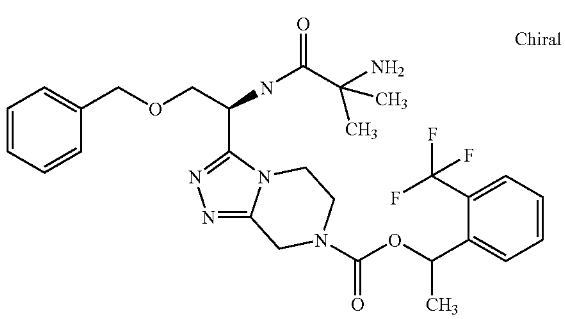 | Chiral | 575 | 95 | 2.79 |

-continued
| Compound number | Structure | Mass M + H | HPLC Purity (%) | HPLC Retention (min) |
|---|---|---|---|---|
| 586 | 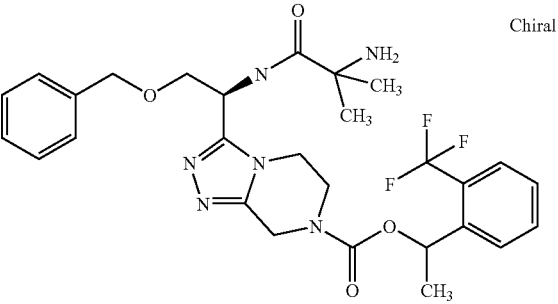 Chiral | 575 | 95 | 2.80 |
| 587 | 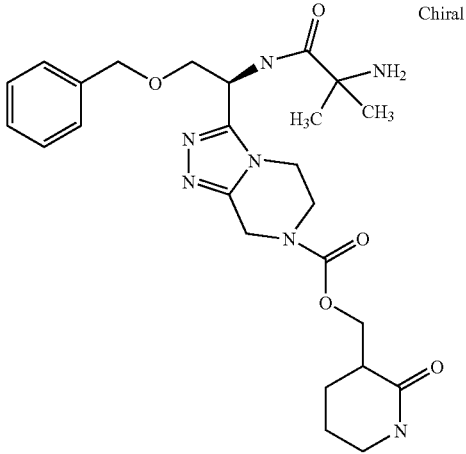 Chiral | 514 | 97 | 1.84 |
| 588 | 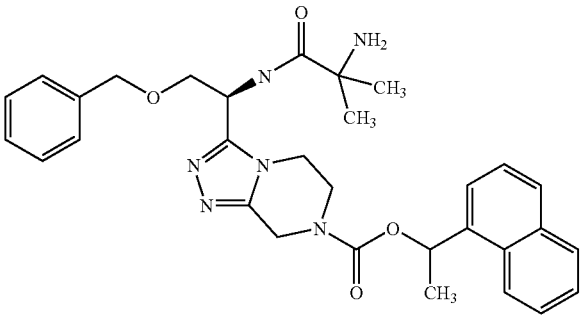 | 557 | 95 | 2.84 |
| 589 | 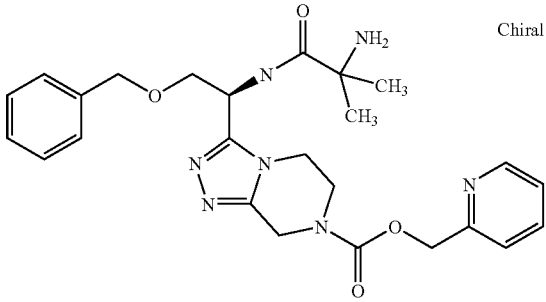 Chiral | 494 | 97 | 2.85 |

| Compound number | Structure | Mass M + H | HPLC Purity (%) | HPLC Retention (min) |
|---|---|---|---|---|
| 590 | 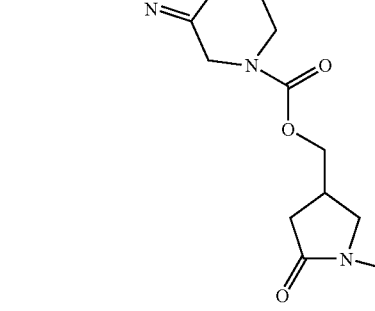 | 590 | 98 | 2.37 |
| 591 | 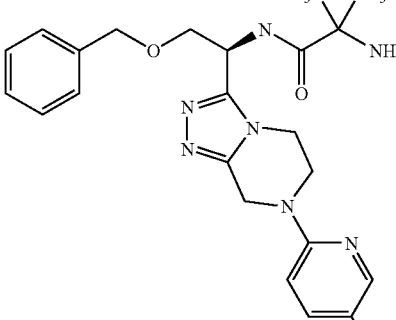 | 515 | 90 | 2.68 |
The following examples were prepared using procedures as described in the general synthetic schemes and working examples above, utilizing the appropriate starting materials as known to those skilled in the art.
| Compound number | Structure | Mass M + H | HPLC Purity (%) | HPLC Retention (min) |
|---|---|---|---|---|
| 592 | 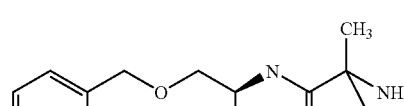 | 461 | 94 | 3.01 |

| Compound number | Structure | Mass M + H | HPLC Purity (%) | HPLC Retention (min) |
|---|---|---|---|---|
| 593 | 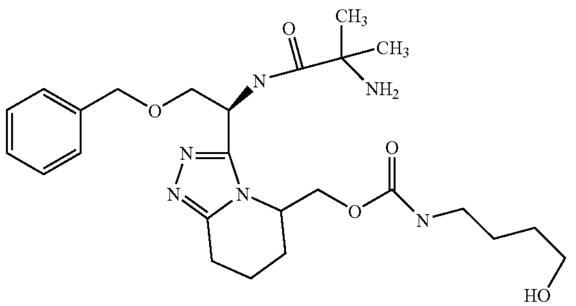 | 503 | 95 | 2.39 |
| 594 | Chiral | 385 | 95 | 1.26 |
| 595 | Chiral | 461 | 96 | 2.52 |
| 596 | Chiral | 371 | 90 | 1.26 |
| 597 | Chiral | 461 | 97 | 2.43 |

-continued
| Compound number | Structure | Mass M + H | HPLC Purity (%) | HPLC Retention (min) |
|---|---|---|---|---|
| 598 | 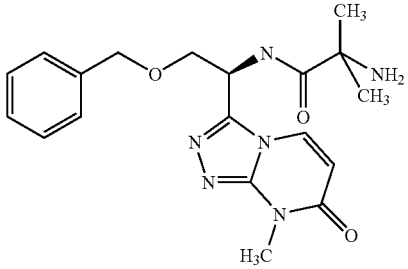 Chiral | 385 | 90 | 1.47 |
| 599 | 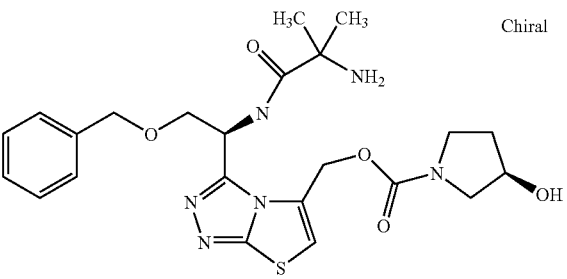 Chiral | 503 | 97 | 2.00 |
| 600 | 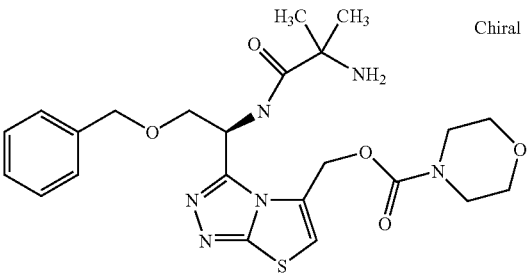 Chiral | 503 | 98 | 2.21 |
| 601 | 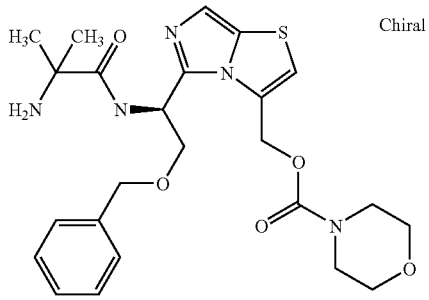 Chiral | 502 | 96 | 2.66 |
| 602 | 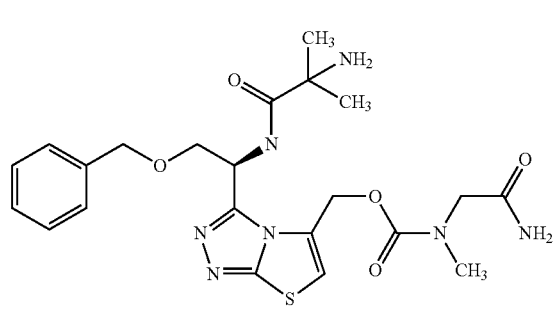 | 504 | 91 | |

-continued

| Compound number | Structure | | Mass M + H | HPLC Purity (%) | HPLC Retention (min) |
|---|---|---|---|---|---|
| 603 | 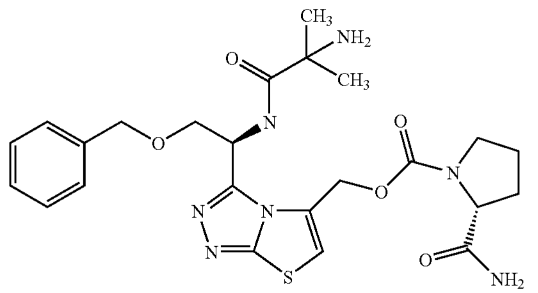 | | 530 | 95 | |
| 604 | 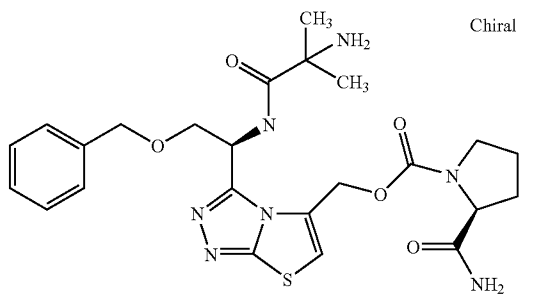 | Chiral | 530 | 91 | |
| 605 | 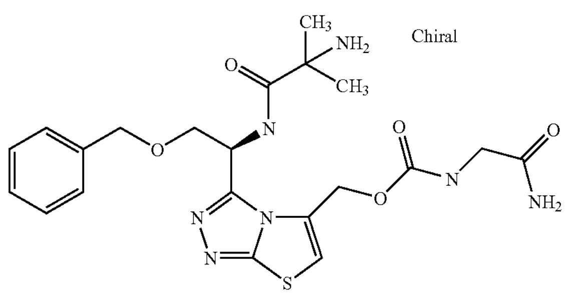 | Chiral | 490 | 90 | |
| 606 | 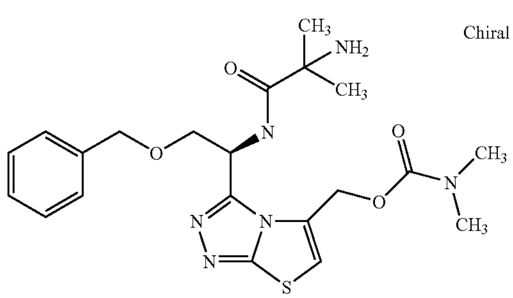 | Chiral | 461 | 91 | |
| 607 | 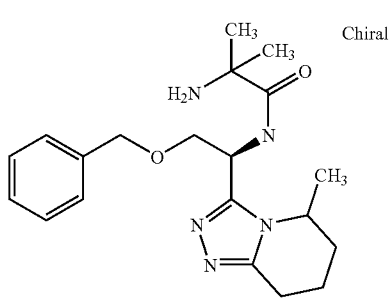 | Chiral | 372 | 97 | 3.03 |

-continued

| Compound number | Structure | | Mass M + H | HPLC Purity (%) | HPLC Retention (min) |
|---|---|---|---|---|---|
| 608 | 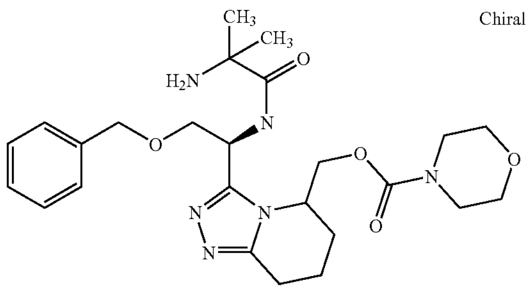 | Chiral | 501 | 98 | 3.28 |
| 609 | 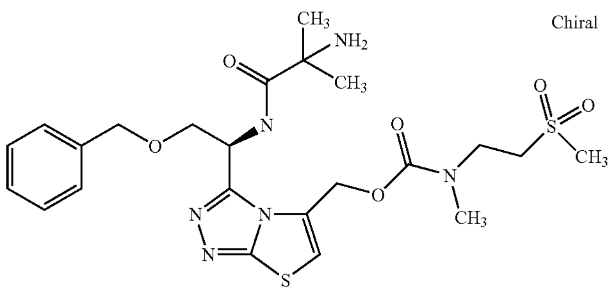 | Chiral | 553 | 95 | |
| 610 | 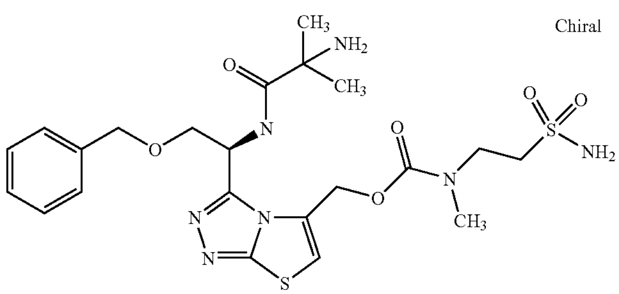 | Chiral | 554 | 90 | |
| 611 | 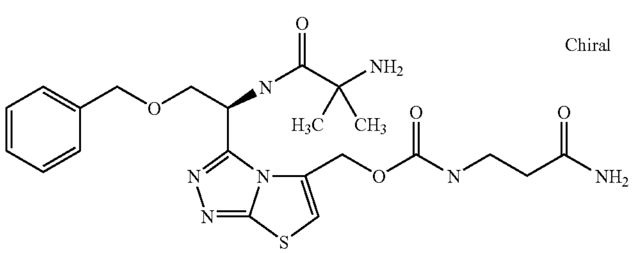 | Chiral | 504 | 96 | 1.77 |
| 612 | 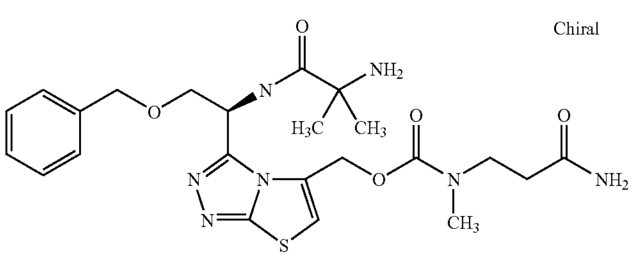 | Chiral | 518 | 96 | 1.85 |

-continued

| Compound number | Structure | Mass M + H | HPLC Purity (%) | HPLC Retention (min) |
|---|---|---|---|---|
| 613 | 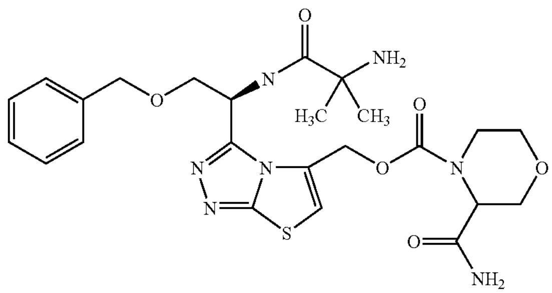 | 546 | 90 | 1.87 |
| 614 | Chiral | 544 | 96 | 2.20 |
| 615 | Chiral | 505 | 95 | 2.26 |
| 616 | Chiral | 519 | 95 | 2.54 |
| 617 | Chiral | 487 | 95 | |

| Compound number | Structure | Mass M + H | HPLC Purity (%) | HPLC Retention (min) |
|---|---|---|---|---|
| 618 | 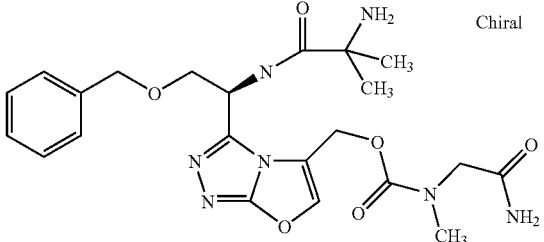 | 488 | 90 | |
The following pro-drug examples were prepared using procedures as described in the general synthetic schemes and working examples above, utilizing the appropriate starting materials as known to those skilled in the art.
| Compound number | Structure | Mass M + H | HPLC Purity (%) | HPLC Retention (min) |
|---|---|---|---|---|
| 619 | 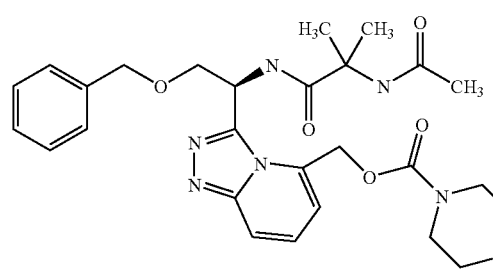 | 539 | 99 | 3.27 |
| 620 | 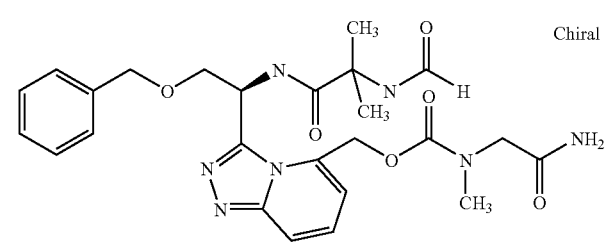 | 526 | 92 | 2.11 |
| 621 | 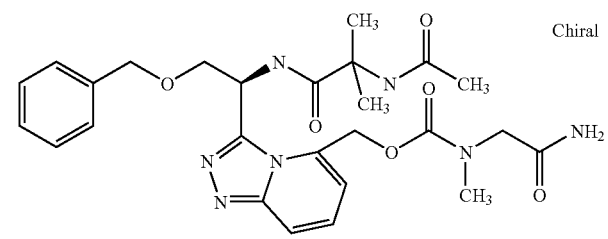 | 540 | 92 | 2.12 |
| 622 | 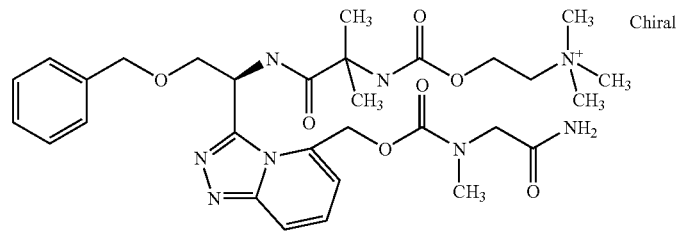 | 628 | 94 | 1.81 |

-continued

| Compound number | Structure | Mass M + H | HPLC Purity (%) | HPLC Retention (min) |
|---|---|---|---|---|
| 623 | Chiral | 570 | 94 | 2.08 |
| 624 | Chiral | 654 | 99 | 3.46 |

What is claimed is:

1. A method for treating diabetes which comprises administering to a mammalian patient in need of treatment a therapeutically effective amount of a compound according to Formula I

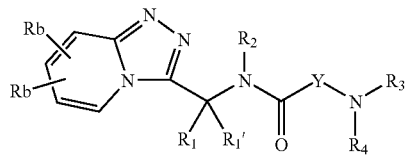

wherein $R_1$ is a substituted or unsubstituted alkyl;

$R_2$ is a substituted or unsubstituted functional group selected from the group consisting of hydrogen, alkyl, aryl, alkenyl, alkynyl, arylalkyl, cycloalkyl, heterocycle, alkoxyalkyl, arylalkyloxyalkyl, aryloxyalkyl, heteroaryl, cycloalkylalkoxyalkyl, heteroarylalkyl and heterocycloalkyl;

$R_3$ and $R_4$ are each independently a substituted or unsubstituted functional group selected from the group consisting of hydrogen and alkyl, or $R_3$ and $R_4$ taken together can form a 4 to 7 membered heterocyclic ring, or one or more of $R_3$ and $R_4$ can be taken together with Y to form a 4 to 7 membered heterocyclic ring;

$R_1'$ is a substituted or unsubstituted functional group selected from the group consisting of hydrogen, alkyl, cycloalkyl, heterocycle, aryl and heteroaryl;

Y is a linking group selected from the group consisting of alkylene, alkenylene, alkynylene, arylene and heteroarylene, said linking group may optionally be substituted with one or more functional group selected from the group consisting of alkyl, aryl, cycloalkyl, heterocycle, alkoxyalkyl, heteroaryl, arylalkyl, aryl alkyloxyalkyl, aryloxyalkyl, cycloalkylalkoxyalkyl, heteroarylalkyl, —$OR_5$, —$OC(O)R_5$, —$CF_3$, —$OCF_3$, —$N(R_5)C(O)R_5'$ and —$NR_5R_5'$;

$R_5$ and $R_5'$ for each occurrence are each independently selected from the group consisting of hydrogen, alkyl, cycloalkyl, heterocycle and aryl, wherein $R_5$ and $R_5'$ for each occurrence may optionally be substituted with one or more Rb;

Rb for each occurrence is independently selected from the group consisting of hydrogen, alkyl, alkenyl, alkynyl, halogen, cyano, —CN, aryl, arylalkyl, arylalkenyl, arylalkynyl, cycloalkyl, alkoxy, alkoxyalkyl, aryloxy, aryloxyalkyl, heterocycle, heteroaryl, heteroarylalkyl, —$OR_2$, —$NR_5R_5'$, —$CF_3$, —$SO_2R_6$, —$OC(O)R_5$, —$SO_2NR_6R_6'$, —$(CH_2)_mR_8$ and $R_9$;

$R_6$ and $R_6'$ for each occurrence are each independently selected from the group consisting of hydrogen, alkyl, alkenyl, alkynyl, alkylthioalkyl, alkoxyalkyl, aryl, arylalkyl, heterocycle, heteroaryl, heteroarylalkyl, heterocycloalkyl and cycloalkyl, wherein $R_6$ and $R_6'$ for each occurrence may optionally be substituted with 1 to 3 substituents selected from the group consisting of halogen, $OR_2$, alkoxy, heterocycloalkyl, —$NR_5C(O)NR_5R_5'$, —$C(O)NR_5R_5'$, —$NR_5C(O)R_5'$, —CN, —$NR_5SO_2R_5'$, —$OC(O)R_5$, —$SO_2NR_5R_5'$, —$SOR_7$, —COON and —$C(O)OR_7$, or $R_6$ and $R_6'$ taken together can be cyclized to form —$(CH_2)_qX(CH_2)_s$—, which may optionally be substituted with 1 to 3 substituents selected from the group consisting of halogen, $OR_2$, alkoxy, heterocycloalkyl, —$NR_5C(O)NR_5R_5'$, —$C(O)NR_5R_5'$, —$NR_5C(O)R_5'$, —CN, —$NR_5SO_2R_5'$, —$OC(O)R_5$, —$SO_2NR_5R_5'$, —$SOR_7$, —COOH and —$C(O)OR_7$;

$R_7$ for each occurrence is independently selected from the group consisting of $C_1$ to $C_6$ alkyl, aryl and heteroaryl, wherein $R_7$ may optionally be substituted with —$(CH_2)_wOH$;

$R_8$ is selected from the group consisting of alkoxy, alkoxycarbonyl, —$C(O)NR_6R_6'$, —$NR_5R_5'$, —$C(O)R_6$, —$NR_5C(O)NR_5R_5'$ and —N-heteroaryl;

R₉ is selected from the group consisting of heterocycloalkyl, heteroaryl, —CN, —(CH₂)ₚN(R₆)C(O)R₆', —(CH₂)ₚCN, —(CH₂)ₚN(R₆)C(O)OR₆', —(CH₂)ₚN(R₆)C(O)NR₆R₆', —(CH₂)ₚN(R₆)SO₂R₆, —(CH₂)ₚC(O)NR₆R₆', —(CH₂)ₚC(O)OR₆, —(CH₂)ₚOC(O)OR₆, —(CH₂)ₚOC(O)R₆, —(CH₂)ₚOC(O)NR₆R₆', —(CH₂)ₚN(R₆)SO₂NR₆R₆', —(CH₂)ₚOR₆, —(CH₂)ₚOC(O)N(R₆)(CH₂)ₘOH, —(CH₂)ₚSOR₆ and —(CH₂)ₚOCH₂C(O)N(R₆)(CH₂)ₘOH;

X is selected from the group consisting of —CR₅R₅'—, —O—, —S—, —SO—, —SO₂—, —NC(O)OR₇—, —NC(O)NR₅— and —NR₅—;

m is an integer between 1 and 6;
p is an integer from 0 to 5;
w is an integer between 0 and 5; and
q and s are each independently an integer between 1 and 3, with the proviso that R₅, R₅', R₆ or R₆' cannot be hydrogen when either is connected to a carbonyl group or sulfone group.

2. The method of claim 1, wherein the compound of Formula I is selected from the group consisting of

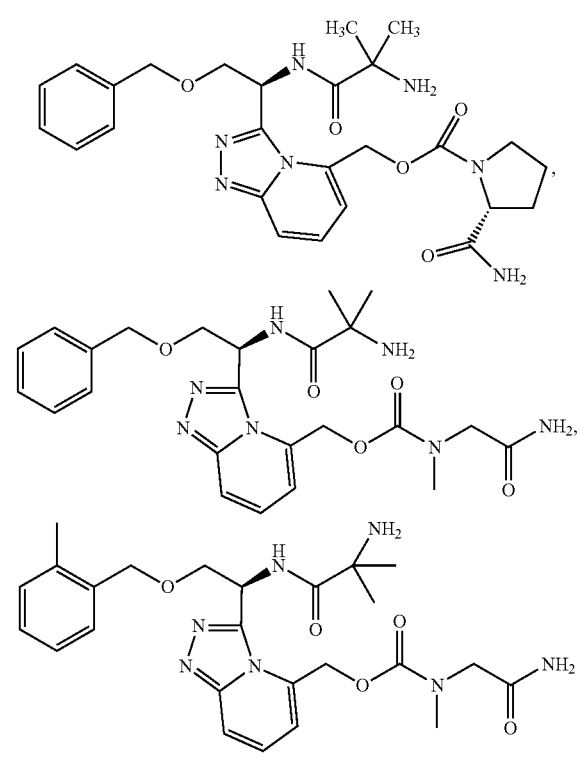

and

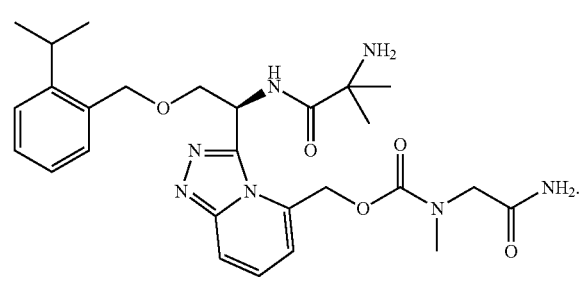

3. The method of claim 1, wherein the compound of Formula I is

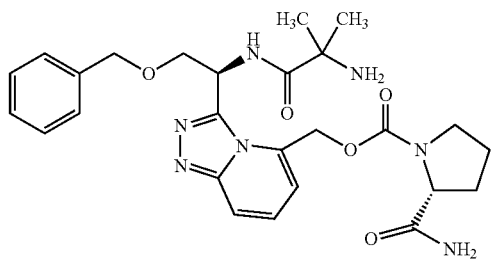

4. The method of claim 1, wherein the compound of Formula I is

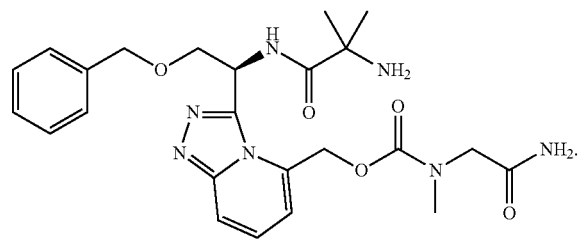

5. The method of claim 1, wherein the compound of Formula I is

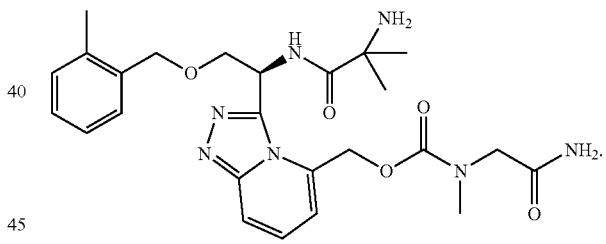

6. The method of claim 1, wherein the compound of Formula I is

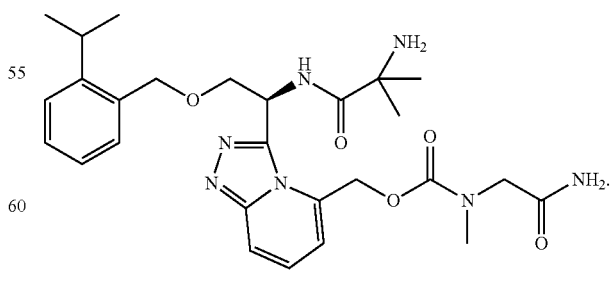

* * * * *

UNITED STATES PATENT AND TRADEMARK OFFICE
CERTIFICATE OF CORRECTION

| | |
|---|---|
| PATENT NO. | : 7,977,353 B2 |
| APPLICATION NO. | : 12/852610 |
| DATED | : July 12, 2011 |
| INVENTOR(S) | : Guixue Yu et al. |

It is certified that error appears in the above-identified patent and that said Letters Patent is hereby corrected as shown below:

COLUMN 349:

Line 64, "aryl alkyloxy-" should read --arylalkyloxy- --.

COLUMN 350:

Line 52, "-COON" should read -- -COOH--.

Signed and Sealed this
Eleventh Day of December, 2012

David J. Kappos
*Director of the United States Patent and Trademark Office*